US010028923B2

(12) United States Patent
Baron et al.

(10) Patent No.: US 10,028,923 B2
(45) Date of Patent: *Jul. 24, 2018

(54) BIGUANIDE COMPOSITIONS AND METHODS OF TREATING METABOLIC DISORDERS

(71) Applicant: Elcelyx Therapeutics, Inc., San Diego, CA (US)

(72) Inventors: Alain D. Baron, San Diego, CA (US); Mark S. Fineman, San Diego, CA (US); Nigel R. A. Beeley, Solana Beach, CA (US)

(73) Assignee: ELCELYX THERAPEUTICS, INC., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/339,378

(22) Filed: Oct. 31, 2016

(65) Prior Publication Data

US 2017/0202790 A1 Jul. 20, 2017

Related U.S. Application Data

(63) Continuation of application No. 14/451,323, filed on Aug. 4, 2014, now Pat. No. 9,481,642, which is a continuation of application No. 13/547,022, filed on Jul. 11, 2012, now Pat. No. 8,796,338, and a continuation-in-part of application No. PCT/US2012/020548, filed on Jan. 6, 2012, and a continuation-in-part of application No. 13/345,135, filed on Jan. 6, 2012, now abandoned.

(60) Provisional application No. 61/649,171, filed on May 18, 2012, provisional application No. 61/430,914, filed on Jan. 7, 2011.

(51) Int. Cl.

| A61P 3/10 | (2006.01) |
|---|---|
| C07C 279/26 | (2006.01) |
| A61K 9/22 | (2006.01) |
| A61K 31/155 | (2006.01) |
| A61K 45/06 | (2006.01) |
| A61K 31/55 | (2006.01) |
| A61K 31/137 | (2006.01) |
| A61K 31/357 | (2006.01) |
| A61K 31/485 | (2006.01) |
| A61K 9/20 | (2006.01) |
| A61K 9/00 | (2006.01) |

(52) U.S. Cl.
CPC .......... *A61K 31/155* (2013.01); *A61K 9/0053* (2013.01); *A61K 9/2086* (2013.01); *A61K 31/137* (2013.01); *A61K 31/357* (2013.01); *A61K 31/485* (2013.01); *A61K 31/55* (2013.01); *A61K 45/06* (2013.01)

(58) Field of Classification Search
None
See application file for complete search history.

(56) References Cited

U.S. PATENT DOCUMENTS

| 4,166,452 A | 9/1979 | Generales, Jr. |
|---|---|---|
| 4,256,108 A | 3/1981 | Theeuwes |
| 4,265,874 A | 5/1981 | Bonsen et al. |
| 6,451,808 B1 | 9/2002 | Cowles |
| 6,475,521 B1 | 11/2002 | Timmins et al. |
| 6,676,966 B1 | 1/2004 | Odidi et al. |
| 6,790,459 B1 | 9/2004 | Cheng et al. |
| 6,830,759 B2 | 12/2004 | Makino et al. |
| 7,060,295 B2 | 6/2006 | Richardson et al. |
| 7,442,720 B2 | 10/2008 | Chan et al. |
| 7,507,768 B2 | 3/2009 | Li et al. |
| 7,799,782 B2 | 9/2010 | Munson et al. |
| 7,829,530 B2 | 11/2010 | Bachovchin et al. |
| 7,919,116 B2 | 4/2011 | Chen et al. |
| 7,964,216 B2 | 6/2011 | Shanghvi et al. |
| 8,389,008 B2 | 3/2013 | Baichwal et al. |
| 8,475,841 B2 | 7/2013 | Cheng et al. |
| 8,796,338 B2 | 8/2014 | Baron et al. |
| 8,846,695 B2 * | 9/2014 | Dugi .................... A61K 31/155 514/263.21 |
| 9,050,292 B2 | 6/2015 | Baron et al. |
| 9,056,134 B2 | 6/2015 | Duarte-Vazquez et al. |
| 9,211,263 B2 | 12/2015 | Baron et al. |
| 9,463,170 B2 | 10/2016 | Baron et al. |
| 9,481,642 B2 | 11/2016 | Baron et al. |

(Continued)

FOREIGN PATENT DOCUMENTS

| CA | 2382098 A1 | 3/2001 |
|---|---|---|
| CA | 2651019 A1 | 11/2007 |

(Continued)

OTHER PUBLICATIONS

Li (Li et al., Meta-Analysis: Pharmacologic Treatment of Obesity, 142 Ann. Intern. Med. 532 (2005).*
CN 1413582, English translation.*
U.S. Appl. No. 13/345,135 (U.S. Publication No. US 2012-0177730-A1), entitled, "Chemosensory Receptor Ligand-Based Therapies," filed Jan. 6, 2012, of Baron, Alain et al. (Abandoned).
U.S. Appl. No. 13/547,022 (U.S. Pat. No. 8,796,338 issued Aug. 5, 2014), entitled, "Biguanide Compositions and Methods of Treating Metabolic Disorders," filed Jul. 11, 2012, of Baron, Alain et al.
U.S. Appl. No. 13/734,966 (U.S. Pat. No. 9,211,263 issued Dec. 15, 2015), entitled, "Compositions and Methods of Treating Metabolic Disorders," filed Jan. 5, 2013, of Elcelyx Therapeutics, Inc.
U.S. Appl. No. 13/978,514 (U.S. Pat. No. 9,050,292 issued Jun. 9, 2015), entitled, "Chemosensory Receptor Ligand-Based Therapies," filed Sep. 18, 2013, of Elcelyx Therapeutics, Inc.

(Continued)

Primary Examiner — H S Park
(74) Attorney, Agent, or Firm — Todd A. Lorenz

(57) ABSTRACT

Provided herein are methods for treating certain conditions, including diabetes, obesity, and other metabolic diseases, disorders or conditions by administrating a composition comprising a biguanide or related heterocyclic compound, e.g., metformin. Also provided herein are biguanide or related heterocyclic compound compositions, and methods for the preparation thereof for use in the methods of the present invention. Also provided herein are compositions comprising metformin and salts thereof and methods of use.

26 Claims, 11 Drawing Sheets

(56) References Cited

U.S. PATENT DOCUMENTS

| | | |
|---|---|---|
| 2002/0177602 A1 | 11/2002 | Piper |
| 2003/0077335 A1 | 4/2003 | Richardson et al. |
| 2003/0113366 A1 | 6/2003 | MacGregor |
| 2004/0081697 A1 | 4/2004 | Lewis et al. |
| 2004/0156900 A1 | 8/2004 | Shanghvi et al. |
| 2005/0037077 A1 | 2/2005 | Legrand et al. |
| 2006/0094782 A9 | 5/2006 | Wong et al. |
| 2006/0222709 A1 | 10/2006 | Devane |
| 2006/0263425 A1 | 11/2006 | Lewis et al. |
| 2007/0141154 A1 | 6/2007 | Li et al. |
| 2007/0172525 A1 | 7/2007 | Sesha |
| 2008/0038739 A1 | 2/2008 | Li et al. |
| 2008/0064701 A1 | 3/2008 | Sesha |
| 2008/0113026 A1 | 5/2008 | McKinney et al. |
| 2008/0166416 A1 | 7/2008 | Lizio et al. |
| 2008/0274180 A1 | 11/2008 | Jathar et al. |
| 2009/0220611 A1 | 9/2009 | Dargelas et al. |
| 2010/0113603 A1 | 5/2010 | Aronne |
| 2010/0184796 A1 | 7/2010 | Behrens et al. |
| 2010/0254916 A1 | 10/2010 | Karanewsky et al. |
| 2010/0256014 A1 | 10/2010 | Tennagels et al. |
| 2010/0267643 A1 | 10/2010 | Baron et al. |
| 2010/0331419 A1* | 12/2010 | Aronne ............. A61K 31/155 514/635 |
| 2010/0331420 A1 | 12/2010 | Aronne |
| 2011/0065731 A1 | 3/2011 | Dugi et al. |
| 2011/0082407 A1 | 4/2011 | Aronne |
| 2011/0250271 A1 | 10/2011 | Shanghvi et al. |
| 2011/0257432 A1 | 10/2011 | DiMauro |
| 2012/0177730 A1 | 7/2012 | Baron et al. |
| 2014/0235558 A1 | 8/2014 | Kim et al. |
| 2014/0235559 A1 | 8/2014 | Kim et al. |
| 2014/0294951 A1* | 10/2014 | Fayad ............. A61K 31/7004 424/463 |

FOREIGN PATENT DOCUMENTS

| | | | |
|---|---|---|---|
| CN | 1413582 A | * | 4/2003 |
| CN | 1561980 A | | 1/2005 |
| CN | 1891229 A | | 1/2007 |
| CN | 101 190 179 B | | 6/2008 |
| CN | 101339178 A | | 1/2009 |
| CN | 101590007 A | | 12/2009 |
| CN | 101 695 575 A | | 4/2010 |
| CN | 101785763 A | | 7/2010 |
| CN | 101978956 A | | 2/2011 |
| CN | 102188429 A | | 9/2011 |
| CN | 102357088 A | | 2/2012 |
| EP | 1591114 A1 | | 12/2005 |
| JP | 2002-326927 A | | 11/2002 |
| KR | 10-2007-0045940 | | 5/2007 |
| WO | WO 98/057634 A1 | | 12/1998 |
| WO | WO 00/28989 A1 | | 5/2000 |
| WO | WO 01/021159 A2 | | 3/2001 |
| WO | WO 03/004009 A1 | | 3/2001 |
| WO | WO 01/032158 A2 | | 5/2001 |
| WO | WO 01/035941 A2 | | 5/2001 |
| WO | WO 03/004498 A1 | | 1/2003 |
| WO | WO 03/026637 A2 | | 4/2003 |
| WO | WO 03/039527 A1 | | 5/2003 |
| WO | WO 03/05133 A1 | | 6/2003 |
| WO | WO 03/045355 A1 | | 6/2003 |
| WO | WO 03/068209 A1 | | 8/2003 |
| WO | WO 03/075933 A1 | | 9/2003 |
| WO | WO 04/012715 A1 | | 2/2004 |
| WO | WO 04/110375 A2 | | 12/2004 |
| WO | WO 04/110422 A1 | | 12/2004 |
| WO | WO 05/023766 A1 | | 3/2005 |
| WO | WO 05/041923 A1 | | 5/2005 |
| WO | WO 05/060942 A1 | | 5/2005 |
| WO | WO 06/078811 A1 | | 7/2006 |
| WO | WO 06/082523 A1 | | 8/2006 |
| WO | WO 06/086727 A2 | | 8/2006 |
| WO | WO 06/104401 A1 | | 10/2006 |
| WO | WO 06/109175 A2 | | 10/2006 |
| WO | WO 08/057470 A2 | | 5/2008 |
| WO | WO 08/057968 A2 | | 5/2008 |
| WO | WO 08/058355 A2 | | 5/2008 |
| WO | WO 08/058358 A2 | | 5/2008 |
| WO | 08/113000 A | | 9/2008 |
| WO | WO 09/111200 A1 | | 9/2009 |
| WO | WO 10/045656 A2 | | 4/2010 |
| WO | WO 10/123930 A2 | | 10/2010 |
| WO | WO 11/002001 A1 | | 1/2011 |
| WO | WO 11/051966 A2 | | 5/2011 |
| WO | WO 11/159100 A2 | | 12/2011 |
| WO | WO 11/160093 A2 | | 12/2011 |
| WO | WO 12/094636 A2 | | 7/2012 |
| WO | WO 13/063527 A1 | | 5/2013 |
| WO | WO 13/103384 A1 | | 7/2013 |
| WO | WO 13/103919 A2 | | 7/2013 |

OTHER PUBLICATIONS

U.S. Appl. No. 14/147,449 (U.S. Publication No. US 2014-0193498-A1), entitled, "Compositions and Methods for Treating Metabolic Disorders," filed Jan. 3, 2014, of Baron, Alain et al.

U.S. Appl. No. 14/370,449 (U.S. Pat. No. 9,480,663 issued Nov. 1, 2016), entitled, "Biguanide Compositions and Methods of Treating Metabolic Disorders," filed Oct. 8, 2014, of Elcelyx Therapeutics, Inc.

U.S. Appl. No. 14/370,450 (U.S. Publication No. US 2015-0065578-A1), entitled, "Compositions and Methods of Treating Metabolic Disorders," filed Jul. 2, 2014, of Elcelyx Therapeutics, Inc.

U.S. Appl. No. 14/414,091, (U.S. Pat. No. 9,572,784 issued Feb. 21, 2017),entitled, "Compositions Comprising Statins, Biguanides and Further Agents for Reducing Cardiometabolic Risk," filed Jan. 1, 2015, of Elcelyx Therapeutics, Inc.

U.S. Appl. No. 14/451,323 (U.S. Pat. No. 9,481,642 issued Nov. 1, 2016), entitled, "Biguanide Compositions and Methods of Treating Metabolic Disorders," filed Aug. 4, 2014, of Elcelyx Therapeutics, Inc.

U.S. Appl. No. 14/733,750 (U.S. Pat. No. 9,463,170 issued Oct. 11, 2016), entitled, "Chemosensory Receptor Ligand-Based Therapies," filed Jun. 8, 2015, of Elcelyx Therapeutics, Inc.

U.S. Appl. No. 14/968,696 (U.S. Publication No. 2016-0095828 A1), entitled, "Compositions and Methods of Treating Metabolic Disorders," filed Dec. 14, 2015, of Elcelyx Therapeutics, Inc.

U.S. Appl. No. 15/289,713 (U.S. Publication No. US 2017-0020829 A1), entitled, "Chemosensory Receptor Ligand-Based Therapies," filed Oct. 10, 2016, of Elcelyx Therapeutics, Inc.

U.S. Appl. No. 15/339,346, entitled, "Biguanide Compositions and Methods of Treating Metabolic Disorders," filed Oct. 31, 2016, of Elcelyx Therapeutics, Inc.

U.S. Appl. No. 15/433,987, entitled, "Compositions Comprising Statins, Biguanides and Further Agents for Reducing Cardiometabolic Risk," filed Feb. 15, 2016, of Elcelyx Therapeutics, Inc.

Ali et al., "Formulation and development of hydrodynamically balanced system for metformin: in vitro and in vivo evaluation," Europ. J. of Pharmaceutics and Biopharmaceutics 67:196-201 (2007).

Bailey CJ, Mynett KJ, Page T., "Importance of the intestine as a site of metformin-stimulated glucose utilization," Br J Pharmacol. 112: 671-675 (1994).

Bailey et al., "Metformin," N Engl J Med , vol. 334, No. 9: 574-9 (1996).

Becker et al., "Pharmacogenetics of Oral Antidiabetic Drug," International Journal of Endocrinology vol. 2013, Article ID 686315, 10 pages.

Bell, David S.H., "Metformin-Induced Vitamin B12 Deficientcy Presenting as a Peripheral Neuropathy," 103 South. Med. J. 265, abstract (2010).

Bhoyar et al., "Formulation and in vitro Evaluation of Sustained Release Dosage Form with Taste Masking of Meformin Hydrochloride," Indian Journal of Pharmaceutical Sciences, Mar.-Apr. 2010: 184-190.

(56) References Cited

OTHER PUBLICATIONS

Blonde et al., "Gastrointestinal tolerability of extended-release metformin tablets compared to immediate-release metformin tablets: results of a retrospective cohort study," Current Medical Research and Opinion, vol. 20, No. 4, pp. 565-572 (2004).
Buler et al., "Metforminreduces hepatic expression of SIRT3, the mitochondrial deacetylase controlling energy metabolism," Plos One, Nov. 2012 vol. 7, Issue 11.
Burcelin, R. "The antidiabetic gutsy role of metformin uncovered?" Gut Online First, published on Jul. 9, 2013.
Campbell et al., "A Clinical Evaluation of a Delayed Release Preparation of Metformin," J INt. Med. Res (1), pp. 551-556 (1973).
Corti et al., "Sustained-release matrix tablets of metformin hydrochloride in combination with triacetyl-β-cyclodextrin," Europ. J. of Pharmaceutics and Biopharmaceutics 68:303-309 (2008).
Davidson et al., "Steady-state pharmacokinetics of a novel extended-release metformin formulation", Br J Diabetes Vasc Dis (2004) 4:273-277.
DeFronzo et al., "Delayed-Release Metformin May be Suitable for Use in Diabetes Patients with Renal Impairment Who are Contrandicated for Currently Available Metformin Formulations," presented at the 73rd Annual Scientific Meeting of the American Diabetes Associaten, Jun. 21-25, 2013, in Chicago, IL.
DeFronzo et al., "Dissociation Between Metformin Plasma Exposure and its Glucose-Lowering Effect: A Novel Gut-Mediated Mechanism of Action," presented at the 73rd Annual Scientific Meeting of the American Diabetes Associaten, Jun. 21-25, 2013, in Chicago, IL.
Di Colo et al., "A site-specific controlled-release system for metformin," J. of Pharmacy and Pharmacology, vol. 57, pp. 565-571 (2005).
Di Colo et al., "In vitro evaluation of a system for pH-controlled peroral delivery of metformin," Europ. J. of Pharmaceutics and Biopharmaceutics 68:303-309 (2008).
Evonik Industries productin formation for Eudragit S 100, printed 2015.
Evonik Industries productin formation for Eudragit S 12,5, printed 2015.
Foretz et al., "Metformin inhibits hepatic gluconeogenesis in mice independently of the LKB1/AMPK pathway via a decrease in hepatic energy state," J. of Clinical Investigation; 120(7):2355-2369 (2010).
Geraedts et al.; "Release of Satiety Hormones Induced by the Five Basic Tastants Is Controlled by the Influx of Calcium," Gastroenterology, Elsevier, Philadelphia, PA, vol. 136, No. 5, May 1, 2009, p. A-25.
Hong et al., "Population exposure-response modeling of metformin in patients with type 2 diabetes mellitus," J Clin Pharmacol. 48: 696-707 (2008).
http://www.agnovel.com/mytag.php?id=46161.
http://www.chem02.com/en/product/hormones/2010/1103/97693.html.
http://www.chemyq.com/En/xz/xz13/122367peabr.htm.
http://www.weiku.com/products/10476375/METFORMIN_HYDROCHLORIDE_ENTERIC_COATED_TABLET.html.
Hu et al., "Preparation and in vitro/in vivo evaluation of sustained-release metformin hydrochloride pellets," Europ. J. of Pharmaceutics and Biopharmaceutics 64:185-192 (2006).
Ibekwe et al., "A comparative in vitro assessment of the drug relase performance pH-responsive polymers for ileo-colonic dlivery," Intl. J. Pharma., 308: pp. 52-60 (2006).
Karlsson et al., "Effects of Metformin and Rosiglitazone Treatment on Insulin Signaling and Glucose Uptake in Patients With Newly Diagnosed Type 2 Diabetes," Diabetes, May 2005, vol. 54, p. 1459.
Karttunen et al., "The influence of pharmaceutical formulation on the gastrointestinal side effect of metformin" Acta Endocrinol.; 94: (Suppl 237) 42 (1980).
Karttunen et al., "The pharmacokinetics of metformin: a comparison of the properties of a rapid-release and a sustained-relese preparation," Int. J. Clin. Pharmacol. Ther. Toxicol. 21:31-36 (1983).
Lee et al., "Metformin Decreases Food Consumption and Induces Weight Loss in Subject with Obesity with Type II Non-Insulin-Dependent Diabetes," Obesity Research, vol. 6, No. 1, pp. 47-53, Jan. 1998.
Levy et al., "Assessment of efficacy and tolerability of once-daily extended release metformin in patients with type 2 diabetes mellitus", Dibetology & Metabolic Syndrome; 2:16 (2010).
Li et al., "Meta-Analysis: Pharmacologic Treatment of Obesity," Ann. Intern Med.; 142:532-546 (2005).
Li et al., "AMPK Phosphorylates and Inhibits SREBP Activity to Attenuate Hepatic Steatosis and Atherosclerosis in Diet-induced Insulin Resistant Mice," Cell Metab. Apr. 6, 2011; 13(4): 376-388.
Mannucci et al., "Effects of metformin on glucagon-like peptide-1 levels in obese patients with and without Type 2 diabetes," Diabetes Nutr Metab;17:336-42 (2004).
Marathe et al., "Effect of altered gastric emptying and gastrointestinal motility on metformin absorption," Br. J. Clin. Pharmacol. 50:325-332 (2000).
Marchetti et al., "Plasma biguanide levels are correlated with metabolic effects in diabetic patients," Clin Pharmacol Ther.; 41: 450-454 (1987).
Miller et al., "Biguanides suppress hepatic glucagon signaling by decreasing production of cyclic AMP," Nature Feb. 14, 2013; 494(7436): 256-260.
Mu et al., "Anti-Diabetic efficacy and impact on amino acid metabolism of GRA1, a novel small-molecule glucagon receptor antagonist," Plos One, Nov. 2012, vol. 7, Issue 11.
Mulherin et al., "Mechanisms Underlying Metformin-Induced Secretion of Glucagon-Like Peptide-1 from the Intestinal L Cell," Endocrinology, Dec. 2011; 152(12):4610-4619.
Natali et al., CAS: 145: 179868 (2006).
Nauck et al., CAS: 154: 426492 (2010).
Neary et al., "Gut homrones: implications for the treatment of obesity," Phrmacol Ther ;124:44-56 (2009).
Nicoluccil et al., "Incretin-based therapies: a new potential treatment approach to overcome clinical inertia in type 2 diabetes," Acta Biomedica; 79(3):184-91 (2008).
Noel et al., "Kinetic study of normal and sustained relase dosage forms of metformin in normal subjects," Res. Clin. Forums 1:35-50 (1979).
Owen et al., "Evidence that metformin exerts its anti-diabetic effects through inhibition of complex 1 of the mitochondrial respiratory chain," Biochem J. 348 Pt 3: 607-614 (2000).
Pentikainen, "Bioavailability of metformin. Comparison of solution, rapidly dissovling tablet, and three sustained release products," Int. J. Clin. Pharmacol. Ther. Toxicol. 24:213-220 (1986).
Perriello, G., "Mechanisms of metformin action in non-insulin-dependent diabetes mellitus," Diabetes Metab Rev.; 11 Suppl 1: S51-56 (1995).
"Prescription Medications for the Treatment of Obesity," NIH Publication No. 07-491, Dec. 2007.
Pyra et al., "Prebiotic Fiber Increases Hepatic Acetyl CoA Carboxylase Phosphorylation and Supresses Glucose-Dependent Insulinotropic Polypeptide Secretion More Effectively When Used with Metformin in Obese Rats[1,2]" J. Nutr. 142:213-220 (2012).
Rena et al., "Molecular mechanism of action of metformin: old or new insights?" Diabetologia; 56:1898-1906 (2013).
Rozengurt, "Taste Receptors in the Gastrointestinal Tract. I. Biter taste receptors and α-gustducin in the mammalia gut," Am J Physiol. Gastrointest Liver Physiol 291: G171-G177 (2006).
Scarpello, JH "Review: Optimal dosing strategies for maximising the clinical response to metformin in type 2 diabets," British J. Diab. Vasc. Disease., 1: 28 (2001).
Scarpello et al., "Metformin therapy and clinical uses," Diabetes Vasc. Dis. Res., vol. 5(3), pp. 157-67 (2008).
Scheen, "Clinical pharmacokinetics of Metformin," Clin. Pharmacokinet. 30(5):359-71 (1996).

(56) References Cited

OTHER PUBLICATIONS

Shaw et al., "The Kinase LKB1 Mediates Glucose Homeostasis in Liver and Therapeutic Effects of Metformin," Science. Dec. 9, 2005; 310(5754): 1642-1646.

Shaw et al., "Metformin trims fats to restore insulin sensitivity," Nature Medicine. Dec. 2013; vol. 19, No. 12: 1570-1572.

Shu et al., Effect of genetic variation in the organic cation transporter 1 (OCT1) on metformin action. J Clin Invest.; 117: 1422-1431 (2007).

Singer et al., "Comparative studies of the effect of N1-n-butylbiguanide hydrochloride (Buformin) and N1-n-butylbiguanide tosylate (Buformin retard)," Z Gesamete Inn Med., 28(16): pp. 504-506 (1973).

Stepensky et al., "Preclinical evaluation of pharmacokinetic-pharmacodynamic rationale for oral CR metformin formulation," J Control Release. Mar. 12, 2001; 71(1):107-15.

Stepensky et al., "Pharmacokinetic-pharmacodynamic analysis of the glucose-lowering effect of metformin in diabetic rats reveals first-pass pharmacodynamic effect", Drug Metabolism and Dispositioin, 30(8): 861-868 (2002).

Tennagels et al., CAS:150:207438 (2009).

Timmins et al., "New prolonged-release metformin improves gastrointestinal tolerability", Clin. Pharmcokinet; 44:721-729 (2005).

Tsilchorozidou, et al., "Metformin increases fasting plasma peptide tyrosine tyrosine (PYY) in women with polycystic ovarian syndrome (PCOS)," Clin Endocrinol (Oxf);69:936-42 (2008).

Tucker et al., "Metformin kinetics in healthy subjects and in patients with diabetes mellitus," Br. J. Clin. Pharmacol. 12:235-246 (1981).

Ubl et al., "Anti-diabetic biguanides inhitib hormone-induced intracellular $Ca^{2+}$ concentration oscillations in rat hepatocytes," Biochem. J; 304, 561-567 (1994).

Vidon et al., "Metformin in the digestive tract," Diabestes Research and Clinical Practice, vol. 4, pp. 223-229 (1988).

Viollet et al., "Revisiting the mechanisms of metformin action in the liver," Annales d'Endocrinologie 74: 123-129 (2013).

Wang, et al., "Involvement of organic cation transporter 1 in hepatic and intestinal distribution of metformin," J Pharmacol Exp Ther.; 302: 510-515 (2002).

Zakeri-Milani et al., "In-vitro bioequivalence study of 8 brands of metformin tablets in Iran market," Journal of Applied Pharmaceutical Science 02 (08): 194-197 (2012).

Zander et al., "Additive glucose-lowering effects of glucagon-like peptide-1 and metformin in type 2 diabetes," Diabetes Care.;vol. 24, No. 1: 720-725 (2001).

Assmus et al.,"Accurate GI Targeting with EUDRAGIT FS 30 D / L 30 D-55 Mixtures," Evonik Rohm GmbH, (https://www.pharmaceuticalonline.com/doc/accurate-gi-targeting-with-eudragitreg-fs-0002), Jan. 16, 2009.

Hashida, M. (ed.), "Design and Evaluation of Oral Formulations," Yakugyo Jiho Co. Ltd., pp. 259-261 (1995).

Huyghebaert et al., "In vitro evaluation of coating polymers for enteric coating and human ileal targeting," International Journal of Pharmaceutics, vol. 298, pp. 26-37 (2005).

Opardy "SURETERIC Product Information," (http://www.colorcon.com/literature/marketing/mr/Delayed%20Release/Sureteric/English/pi)sureteric_recon.pdf) (2011).

Wikipedia, Definition of: "Cellulose acetate phthalate," (https://en.wikipedia.org/wiki/Cellulose_acetate_phthalate), last modified Nov. 17, 2016.

U.S. Appl. No. 15/712,026, entitled, "Compositions and Methods for Treating Metabolic Disorders," filed Sep. 21, 2017, of Elcelyx Therapeutics, Inc.

\* cited by examiner

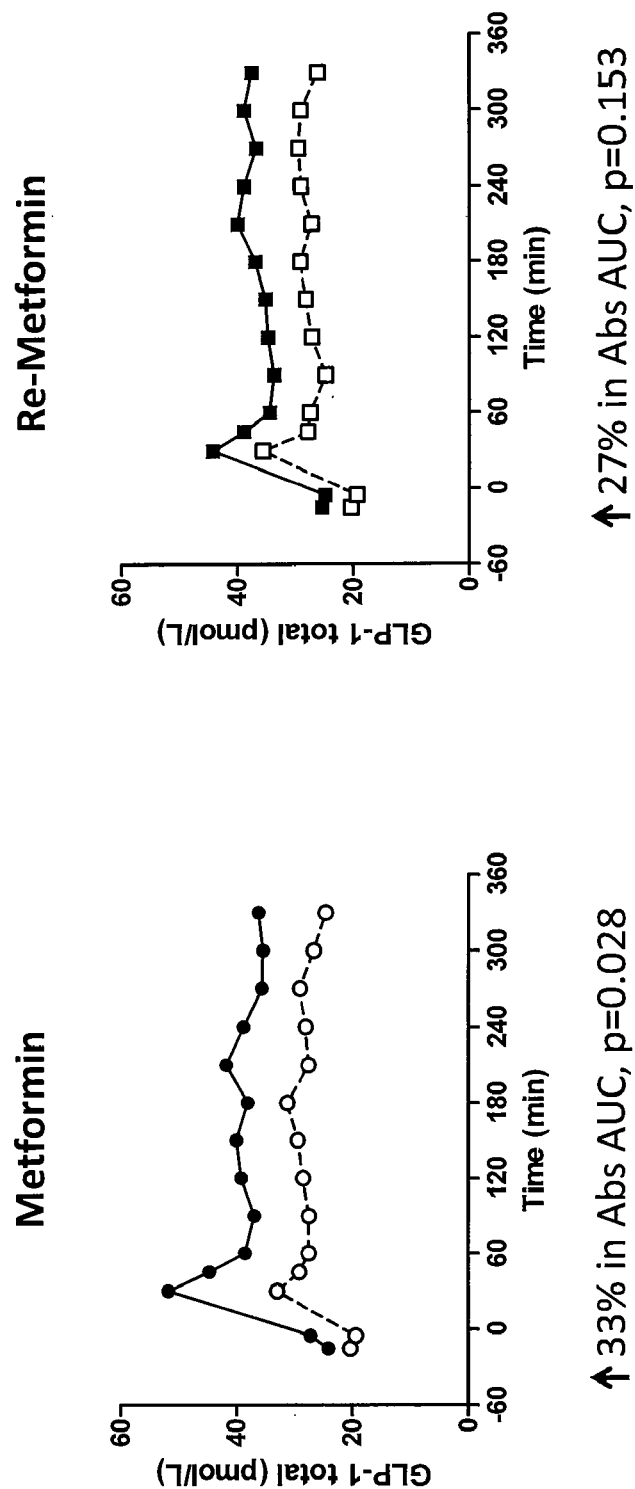

BIGUANIDE COMPOSITIONS AND METHODS OF TREATING METABOLIC DISORDERS

CROSS-REFERENCE

This application is a continuation of U.S. application Ser. No. 14/451,323, filed on Aug. 4, 2014, now patented as U.S. Pat. No. 9,481,642. U.S. application Ser. No. 14/451,323 is a continuation of U.S. application Ser. No. 13/547,022, filed on Jul. 11, 2012, now patented as U.S. Pat. No. 8,796,338. U.S. application Ser. No. 13/547,022, filed on Jul. 11, 2012, now patented as U.S. Pat. No. 8,796,338, claims the benefit of priority of U.S. Provisional Application No. 61/649,171, filed on May 18, 2012; is a continuation-in-part of U.S. application Ser. No. 13/345,135, filed on Jan. 6, 2012, now abandoned; and is a continuation-in-part of International Application No. PCT/US2012/020548, filed on Jan. 6, 2012. U.S. application Ser. No. 13/345,135, filed on Jan. 6, 2012, now abandoned, claims the benefit of priority of U.S. Provisional Application No. 61/430,914, filed on Jan. 7, 2011. International Application No. PCT/US2012/020548, filed on Jan. 6, 2012, claims the benefit of priority of U.S. Provisional Application No. 61/430,914, filed on Jan. 7, 2011.

FIELD OF INVENTION

The present invention relates generally to compositions for targeted administration of biguanide or related heterocyclic compounds to a subject, e.g., in methods of treating metabolic disorders.

BACKGROUND OF THE INVENTION

Despite the longstanding, massive, effort to develop effective treatments for diabetes, metabolic syndrome, obesity, overweight and related metabolic conditions, the number of people worldwide who suffer from them is rapidly growing. These conditions result in numerous medical complications, a lowered quality of life, shortened lifespan, lost work productivity, a strain on medical systems, and a burden on medical insurance providers that translates into increased costs for all. Additionally, maintenance of health, including healthy body weight and healthy blood glucose levels is desirable.

Type II diabetes treatments in use or development are designed to lower blood glucose levels. They include mimetics of GLP-1 (glucagon-like peptide-1), a hormone that plays a key role in regulating insulin, glucose and hunger. Examples of mimetics are the GLP-1 receptor agonist, Exenatide (Byetta®) and the GLP-1 analog Liraglutide. Other drugs inhibit DPP-IV, an enzyme that rapidly degrades endogenous GLP-1. Exenatide is a GLP-1 receptor agonist that is degraded more slowly by DPP-IV. Liraglutide, a GLP-1 analog, is attached to a fatty acid molecule that binds to albumin and slows the rate of GLP-1 release and its degradation. (See, e.g., Nicolucci, et al., 2008, "Incretin-based therapies: a new potential treatment approach to overcome clinical inertia in type 2 diabetes," Acta Biomedica 79(3):184-91 and U.S. Pat. No. 5,424,286 "Exendin-3 and exendin-4 polypeptides, and pharmaceutical compositions comprising same.")

Metformin, a biguanide, is an antihyperglycemic agent which improves glucose tolerance in patients with type II diabetes by lowering both basal and post-prandial plasma glucose. Its pharmacologic mechanisms of action are different from other classes of oral antihyperglycemic agents. Metformin decreases hepatic glucose production, decreases intestinal absorption of glucose, and improves insulin sensitivity by increasing peripheral glucose uptake and utilization. However, metformin is reported to be substantially excreted by the kidney, and the risk of metformin accumulation and lactic acidosis increases with the degree of impairment of renal function. For example, in patients with known or suspected impaired renal function such as those with advanced age, metformin administration requires close dose monitoring and titration to prevent lactic acidosis, a potentially fatal metabolic complication. Patients with concomitant cardiovascular or liver disease, sepsis, and hypoxia have also increased the risk of lactic acidosis. Thus, metformin remains an unavailable and/or risky treatment for certain patient groups due to its side effects.

Until very recently, obesity treatments include two FDA-approved drugs. Orlistat (Xenical®) reduces intestinal fat absorption by inhibiting pancreatic lipase. Sibutramine (Meridia®), taken off the market in Europe and the USA, decreases appetite by inhibiting deactivation of the neurotransmitters norepinephrine, serotonin, and dopamine. Undesirable side-effects, including effects on blood pressure, have been reported with these drugs. (See, e.g., "Prescription Medications for the Treatment of Obesity," NIH Publication No. 07-4191, December 2007). Surgical treatments, including gastric bypass surgery and gastric banding, are available, but only in extreme cases. These procedures can be dangerous, and furthermore may not be appropriate options for patients with more modest weight loss goals.

SUMMARY OF THE INVENTION

Provided herein are compositions having at least one biguanide or related heterocyclic compound, including metformin, and methods of treatment using the compositions.

In some embodiments, the compositions herein are adapted to minimize the systemic bioavailability of the compound, e.g., reduce average systemic bioavailability of the biguanide compared to a composition having an equivalent amount of the compound formulated for immediate release. In some embodiments, the compositions described herein can be adapted for release to the upper or small intestine, to the lower or large intestine, or both. Administration of the compositions into the intestine is via any known method including oral. In some embodiments, the compositions described herein comprise a biguanide or related heterocyclic compound adapted to release a therapeutically effective amount of the biguanide or related heterocyclic compound beyond the stomach.

In certain embodiments, the biguanide or related heterocyclic compound is selected from a compound of structural Formula I,

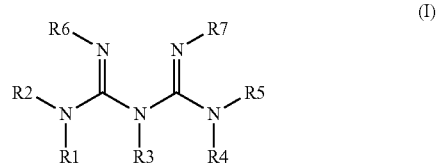

(I)

wherein:

R1, R2, R3, R4, R5, R6, and R7 are independently selected from:

H, OH,

O—Rx, wherein Rx is alkyl, cycloalkyl, alkylcycloalkyl, acyl, ester, thioester;

optionally substituted alkyl; cycloalkyl; alkylcycloalkyl; heterocycloalkyl; alkylheterocycloalkyl; optionally substituted alkenyl; optionally substituted alkynyl;

optionally substituted aryl; optionally substituted alkylary; optionally substituted heteroaryl; optionally substituted alkylheteroaryl; and or R6 and R7 may join to form a bond, together forming a ring including the nitrogen atoms to which they are attached;

or R1 and R2 may together form a 3 to 8 membered heterocyclic ring, including the nitrogen atoms to which they are attached;

or R4 and R5 may together form a ring selected from the group aziridine, pyrrolyl, imidazolyl, pyrazolyl, indolyl, indolinyl, pyrrolidinyl, piperazinyl and piperidyl, including the nitrogen atoms to which they are attached.

In some embodiments,

O—Rx is selected from: O—C1 to C8 straight chain or branched chain alkyl; O—C3 to C7 cycloalkyl; O—C4 to C8 alkylcycloalkyl; O-acyl; O-esters; and O-thioesters.

In other embodiments,

R2, R3, R4, R5, R6 and R7 are independently selected from H, methyl, ethyl, propyl or isopropyl; and R1 is selected, from:

H,

C1 to C12 straight chain or branched chain alkyl optionally hetero substituted with oxygen, silicon, sulphur or optionally substituted with OH, O-alkyl, SH, S-alkyl, NH2, NH-alkyl, C1 to C12 straight chain or branched chain alkenyl optionally hetero substituted with oxygen, silicon, sulphur or optionally substituted with OH, O-alkyl, SH, S-alkyl, NH2, NH-alkyl, C1 to C12 straight chain or branched chain alkynyl optionally hetero substituted with oxygen, silicon, sulphur or optionally substituted with OH, O-alkyl, SH, S-alkyl, NH2, NH-alkyl, C3 to C7 cycloalkyl, C2 to C6 heterocycloalkyl, where the heterocycle comprises one or two hetero atoms selected from O, S, or N, C4 to C12 alkylcycloalkyl, C3 to C11 alkylheterocycloalkyl, where the heterocycle comprises one or two hetero atoms selected from O, S, or N and wherein N is present in the heterocyclic ring, the nitrogen atom may be in the form of an amide, carbamate or urea, phenyl, substituted phenyl, naphthyl, substituted naphthyl, alkylphenyl, alkylsubstituted phenyl, alkylnaphthyl, alkylsubstituted naphthyl, pyridyl, furanyl, thiophenyl, pyrrollyl, oxazolyl, isoxazolyl, thiazolyl, diazolyl, pyrazolyl, triazolyl all of which are optionally substituted.

In certain embodiments, the biguanide or related heterocyclic compound is selected from a compound of structural Formula IA,

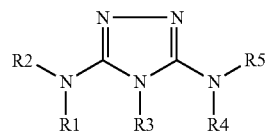

(IA)

wherein:

R1, R2, R3, R4, and R5 are independently selected from:

H, OH,

O—Rx, wherein Rx is alkyl, cycloalkyl, alkylcycloalkyl, acyl, ester, thioester;

optionally substituted alkyl; cycloalkyl; alkylcycloalkyl; heterocycloalkyl; alkylheterocycloalkyl; optionally substituted alkenyl; optionally substituted alkynyl;

optionally substituted aryl; optionally substituted alkylary; optionally substituted heteroaryl; optionally substituted alkylheteroaryl; and or R1 and R2 may together form a 3 to 8 membered heterocyclic ring, including the nitrogen atoms to which they are attached;

or R4 and R5 may together form a ring selected from the group aziridine, pyrrolyl, imidazolyl, pyrazolyl, indolyl, indolinyl, pyrrolidinyl, piperazinyl and piperidyl, including the nitrogen atoms to which they are attached.

In some embodiments,

O—Rx is selected from: O—C1 to C8 straight chain or branched chain alkyl; O—C3 to C7 cycloalkyl; O—C4 to C8 alkylcycloalkyl; O-acyl; O-esters; and O-thioesters.

In other embodiments,

R2, R3, R4 and R5 are independently selected from H, methyl, ethyl, propyl or isopropyl; and R1 is selected from:

H,

C1 to C12 straight chain or branched chain alkyl optionally hetero substituted with oxygen, silicon, sulphur or optionally substituted with OH, O-alkyl, SH, S-alkyl, NH2, NH-alkyl, C1 to C12 straight chain or branched chain alkenyl optionally hetero substituted with oxygen, silicon, sulphur or optionally substituted with OH, O-alkyl, SH, S-alkyl, NH2, NH-alkyl, C1 to C12 straight chain or branched chain alkynyl optionally hetero substituted with oxygen, silicon, sulphur or optionally substituted with OH, O-alkyl, SH, S-alkyl, NH2, NH-alkyl, C3 to C7 cycloalkyl, C2 to C6 heterocycloalkyl, where the heterocycle comprises one or two hetero atoms selected from O, S, or N, C4 to C12 alkylcycloalkyl, C3 to C11 alkylheterocycloalkyl, where the heterocycle comprises one or two hetero atoms selected from O, S, or N and wherein N is present in the heterocyclic ring, the nitrogen atom may be in the form of an amide, carbamate or urea, phenyl, substituted phenyl, naphthyl, substituted naphthyl, alkylphenyl, alkylsubstituted phenyl, alkylnaphthyl, alkylsubstituted naphthyl, pyridyl, furarnyl, thiophenyl, pyrrollyl, oxazolyl, isoxazolyl, thiazolyl, diazolyl, pyrazolyl, triazolyl all of which are optionally substituted.

In other embodiments, the biguanide or related heterocyclic compound is selected from a compound of structural Formula II,

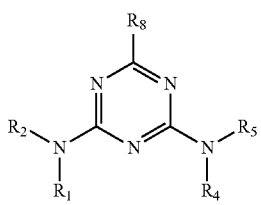

(II)

wherein:
R1, R2, R4, and R5, are independently selected from:
H, OH,
O—Rx, wherein Rx is alkyl, cycloalkyl, alkylcycloalkyl, acyl, ester, thioester;
optionally substituted alkyl; cycloalkyl; alkylcycloalkyl; heterocycloalkyl; alkylheterocycloalkyl; optionally substituted alkenyl; optionally substituted alkynyl;
optionally substituted aryl; optionally substituted alkylaryl; optionally substituted heteroaryl; optionally substituted alkylheteroaryl; and
or R1 and R2 may together form a 3 to 8 membered heterocyclic ring, including the nitrogen atoms to which they are attached;
or R4 and R5 may together form a ring selected from the group aziridine, pyrrolyl, imidazolyl, pyrazolyl, indolyl, indolinyl, pyrrolidinyl, piperazinyl and piperidyl, including the nitrogen atoms to which they are attached;
R8 is selected from:
H; optionally substituted alkynyl; cycloaklyl; alkylcycloalkyl; heterocycloalkyl; alkylheterocycloalkyl; optionally substituted aryl; optionally substituted alkylaryl (e.g., alkylphenyl, alkylsubstituted phenyl, alkylnaphthyl, alkylsubstituted naphthyl); optionally substituted heteroaryl; optionally substituted alkylheteroaryl; and —NRaRb
wherein Ra and Rb are independently selected from:
H; optionally substituted alkyl; optionally substituted alkenyl; optionally substituted alkynyl; cycloalkyl; alkylcycloalkyl; heterocyclalkyl; alkylheterocycloalkyl; optionally substituted aryl, optionally substituted alkylary, optionally substituted heteroaryl, and optionally substituted alkylheteroaryl.
In some embodiments,
O—Rx is selected from: O—C1 to C8 straight chain or branched chain alkyl; O—C3 to C7 cycloalkyl; O—C4 to C8 alkylcycloalkyl; O-acyl; O-esters; and O-thioesters.
In other embodiments,
R2, R3, and R4 are independently selected from H, methyl, ethyl, propyl or isopropyl;
R5 is selected from H, CH3, lower alkyl, NH2, NHCH3, N(CH3)2, NH-alkyl, N(alkyl)2; and
R1 is selected from:
H,
C1 to C12 straight chain or branched chain alkyl optionally hetero substituted with oxygen, silicon, sulphur or optionally substituted with OH, O-alkyl, SH, S-alkyl, NH2, NH-alkyl,
C1 to C12 straight chain or branched chain alkenyl optionally hetero substituted with oxygen, silicon, sulphur or optionally substituted with OH, O-alkyl, SH, S-alkyl, NH2, NH-alkyl,
C1 to C12 straight chain or branched chain alkynyl optionally hetero substituted with oxygen, silicon, sulphur or optionally substituted with OH, O-alkyl, SH, S-alkyl, NH2, NH-alkyl,
C3 to C7 cycloalkyl, C2 to C6 heterocycloalkyl, where the heterocycle comprises one or two hetero atoms selected from O, S, or N,
C4 to C12 alkylcycloalkyl,
C3 to C11 alkylheterocycloalkyl, where the heterocycle comprises one or two hetero atoms selected from O, S, or N and wherein N is present in the heterocyclic ring, the nitrogen atom may be in the form of an amide, carbamate or urea,
phenyl, substituted phenyl, naphthyl, substituted naphthyl,
alkylphenyl, alkylsubstituted phenyl, alkylnaphthyl, alkylsubstituted naphthyl,
pyridyl, furanyl, thiophenyl, pyrrollyl, oxazolyl, isoxazolyl, thiazolyl, diazolyl, pyrazolyl, triazolyl all of which are optionally substituted.
In some embodiments, the biguanide or related heterocyclic compound is selected from a compound of structural Formula III,

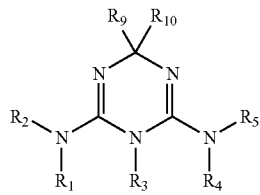

(III)

wherein:
R1, R2, R3, R4, R5, R9, and R10, are independently selected from:
H, OH,
O—Rx, wherein Rx is alkyl, cycloalkyl, alkylcycloalkyl, acyl, ester, thioester;
optionally substituted alkyl; cycloalkyl; alkylcycloalkyl; heterocycloalkyl; alkylheterocycloalkyl; optionally substituted alkenyl; optionally substituted alkynyl;
optionally substituted aryl; optionally substituted alkylaryl; optionally substituted heteroaryl; optionally substituted alkylheteroaryl; and
or R1 and R2 may together form a 3 to 8 membered heterocyclic ring, including the nitrogen atoms to which they are attached;
or R4 and R5 may together form a ring selected from the group aziridine, pyrrolyl, imidazolyl, pyrazolyl, indolyl, indolinyl, pyrrolidinyl, piperazinyl and piperidyl, including the nitrogen atoms to which they are attached.
In some embodiments,
O—Rx is selected from: O—C1 to C8 straight chain or branched chain alkyl; O—C3 to C7 cycloalkyl; O—C4 to (C8 alkylcycloalkyl; O-acyl; O-esters; and O-thioesters.
In some embodiments,
R2, R3, R4, R5, R6 and R7 are independently selected from H, methyl, ethyl, propyl or isopropyl; and R1 is selected from:
H,
C1 to C12 straight chain or branched chain alkyl optionally hetero substituted with oxygen, silicon, sulphur or optionally substituted with OH, O-alkyl, SH, S-alkyl, NH2, NH-alkyl,
C1 to C12 straight chain or branched chain alkenyl optionally hetero substituted with oxygen, silicon, sulphur or optionally substituted with OH, O-alkyl, SH, S-alkyl, NH2, NH-alkyl, C1 to C12 straight chain or branched chain alkynyl optionally hetero substituted with oxygen, silicon, sulphur or optionally substituted with OH, O-alkyl, SH, S-alkyl, NH2, NH-alkyl, C3 to C7 cycloalkyl, C2 to C6 heterocycloalkyl, where the heterocycle comprises one or two hetero atoms selected from O, S, or N, C4 to C12 alkylcycloalkyl, C3 to C11 alkylheterocycloalkyl, where the heterocycle comprises one or two hetero atoms selected from O, S, or N and wherein N is present in the heterocyclic ring, the nitrogen atom may be in the form of an amide, carbamate or urea, aryl, phenyl, substituted phenyl, naphthyl, substituted naphthyl, alkylaryl, alkylphenyl, alkylsubstituted phenyl, alkylnaphthyl, alkylsubstituted naphthyl, heteroaryl, pyridyl, furanyl, thiophenyl, pyrrollyl, oxazolyl, isoxazolyl, thiazolyl, diazolyl, pyrazolyl, triazolyl all of which are optionally substituted, alkylheteroaryl, pyridyl, furanyl, thiophenyl, pyrrollyl, oxazolyl, isoxazolyl, diazolyl, pyrazolyl, triazolyl all of which are optionally substituted.

In some embodiment, the biguanide or related heterocyclic compound is selected from a compound of structural Formula IV,

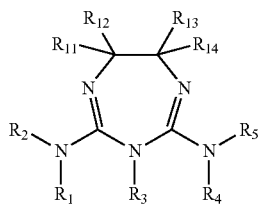

IV wherein:

wherein R3, R4, R5, R6, R7, R8 and R9 are independently selected from H, methyl, ethyl, propyl or isopropyl;

and wherein R1 and R2, and are independently selected from:

H; optionally substituted alkyl; cycloalkyl; alkylcycloalkyl; heterocycloalkyl; alkylheterocycloalkyl; optionally substituted alkenyl; optionally substituted alkynyl;

optionally substituted aryl; optionally substituted alkylaryl; optionally substituted heteroaryl; optionally substituted alkylheteroaryl; and or R1 and R2 may together form a 3 to 8 membered heterocyclic ring, including the nitrogen atoms to which they are attached.

In one embodiment,

O—Rx is selected from: O—C1 to C8 straight chain or branched chain alkyl; O—C3 to C7 cycloalkyl; O—C4 to C8 alkylcycloalkyl; O-acyl; O-esters; and O-thioesters.

In another embodiment,

R2, R3, R4, R5, R6, R7, R8 and R9 are independently selected from H or methyl; and R1 is selected from:

H,

C1 to C12 straight chain or branched chain alkyl optionally hetero substituted with oxygen, silicon, sulphur or optionally substituted with OH, O-alkyl, SH, S-alkyl, NH2, NH-alkyl, C1 to C12 straight chain or branched chain alkenyl optionally hetero substituted with oxygen, silicon, sulphur or optionally substituted with OH, O-alkyl, SH, S-alkyl, NH2, NH-alkyl, C1 to C12 straight chain or branched chain alkynyl optionally hetero substituted with oxygen, silicon, sulphur or optionally substituted with OH, O-alkyl, SH, S-alkyl, NH2, NH-alkyl, C3 to C7 cycloalkyl, C2 to C6 heterocycloalkyl, where the heterocycle comprises one or two hetero atoms selected from O, S, or N, C4 to C12 alkylcycloalkyl, C3 to C11 alkylheterocycloalkyl, where the heterocycle comprises one or two hetero atoms selected from O, S, or N and wherein N is present in the heterocyclic ring, the nitrogen atom may be in the form of an amide, carbamate or urea, phenyl, substituted phenyl, naphthyl, substituted naphthyl, alkylphenyl, alkylsubstituted phenyl, alkylnaphthyl, alkylsubstituted naphthyl, pyridyl, furanyl, thiophenyl, pyrrollyl, oxazolyl, isoxazolyl, thiazolyl, diazolyl, pyrazolyl, triazolyl all of which are optionally substituted.

In some embodiments, the biguanide or related heterocyclic compound is metformin or a salt thereof. In another embodiment, the biguanide or related heterocyclic compound is metformin hydrochloride.

In the compositions and methods disclosed herein, the biguanide or related heterocyclic compound may comprise an asymmetric center or centers and forms a composition of a racemic mixture, a diastereoisomeric mixture, a single enantiomer, an enantiomeric diastereomer, a meso compound, a pure epimer, or a mixture of epimers thereof, etc. In other embodiments, the biguanide or related heterocyclic compound comprises one or more double bonds, wherein the compound is a cis/trans, E/Z mixture or an E or Z geometric isomer thereof. The biguanide or related heterocyclic compound may be a salt selected from hydrochloride, hydrobromide, acetate, propionate, butyrate, sulfate, hydrogen sulfate, sulfite, carbonate, hydrogen carbonate, phosphate, phosphinate, oxalate, hemi-oxalate, malonate, hemi-malonate, fumarate, hemi-fumarate, maleate, hemi-maleate, citrate, hemi-citrate, tartrate, hemi-tartrate, aspartate and glutamate.

In the methods disclosed herein, the biguanide or related heterocyclic compound may be formulated as a composition comprising the components A, B, and C, wherein:

A is the protonated form of a natural or unnatural amino acid;

B is the dianion of an acid; and

C is the protonated form of any the biguanide or related heterocyclic compound.

In some embodiments,

A is the protonated form of a natural amino acid selected from alanine, aspartic acid, asparagine, arginine, glycine, glutamine, glutamic acid lysine, phenylalanine, tyrosine, serine, threonine, tryptophan, leucine, isoleucine, histidine, methionine, proline, cysteine, and cystine; and B is the dianion of an acid selected from oxalic, malonic, citric, maleic, fumaric, tartaric, aspartic, and glutamic acid.

C is the protonated form of the biguanide or related heterocyclic compound.

In other embodiments, the therapeutically effective amount of biguanide or related heterocyclic compound, e.g., metformin or salt thereof, is about 1 mg to about 2000 mg. In yet other embodiments, the therapeutically effective amount of metformin or salt thereof is about 10 mg to about 1500 mg. In further embodiments, the therapeutically effective amount of biguanide or related heterocyclic compound, e.g., metformin or salt thereof, is about 50 mg to about 1000 mg. In yet further embodiments, the therapeutically effective amount of biguanide or related heterocyclic compound, e.g., metformin or salt thereof, is about 100 mg to about 500 mg.

In preferred embodiments, the compositions described herein are adapted to reduce or minimize systemic bioavailability of the compound, e.g., minimize the circulating plasma concentration of the biguanide compound in the patient and/or reduce the average systemic bioavailability of the compound, e.g., when compared to a immediate release composition having an equivalent amount of the compound. In some embodiments, the minimized circulating plasma concentrations is below about 5 µg/mL, 4 µg/mL, 3 µg/mL, 2 µg/mL, 1 µg/mL, 0.5 µg/mL or 0.24 µg/mL in subjects with normal or impaired renal function. In other embodiments, an adapted compound composition has a relative bioavailability of 70%, 60%, 50%, 40%, 30%, 20% or 10% compared to an immediate release composition having the same amount of the compound.

In some embodiments, the compositions herein are adapted to release a therapeutically effective amount of a biguanide or related heterocyclic compound to one or more regions of the intestine.

In some embodiments, the compositions are adapted to release in the duodenum, jejunum, ileum, caecum, colon and/or rectum. In other embodiments, the compositions are adapted to release in the jejunum, ileum, caecum, colon and/or rectum. In some embodiments, the composition is formulated for release in the lower intestine. In further embodiments, the composition is formulated for release in the upper intestine. In still further embodiments, the composition is formulated for release in the upper intestine and lower intestine.

In one embodiment, a composition releases a biguanide or related heterocyclic compound at an onset of about 75 minutes, about 105 to about 135 minutes, about 165 to about 195 minutes or about 225 to about 255 minutes, or a combination of times thereof following oral administration to a subject.

In other embodiments, a composition releases a biguanide or related heterocyclic compound at an onset of about pH 5.0, about pH 5.5, about pH 6.0, about pH 6.5, about pH 7.0, or combination thereof following oral administration to a subject.

Also provided herein are compositions comprising biguanide or related heterocyclic compounds that further comprise one or more chemosensory receptor ligands is selected from a sweet receptor ligand, an umami receptor ligand, a fat receptor ligand, a bile acid receptor ligand, a bitter receptor ligand, or any combination thereof. In some embodiments, the composition further comprises a sweet receptor ligand. In other embodiments, the composition further comprises an umami receptor ligand. In other embodiments, the composition further comprises a sweet receptor ligand and an umami receptor ligand.

Sweet receptor ligands include glucose, sucralose, aspartame, Stevioside, Rebaudioside, Neotame, acesulfame-K, and saccharin. Umami receptor ligands include glutamate salts, glutamines, acetyl glycines, or aspartame. Fat receptor ligands include linoleic acids, oleic acids, palmitates, oleoylethanolamides, mixed fatty acid emulsion, omega-3 fatty acids and N-acylphosphatidylethanolamine (NAPE). Sour receptor ligands include citric acid and hydroxycitric acid. Bile acids include deoxycholic acids, taurocholic acids and chenodeoxycholic acids. In certain embodiments, the chemosensory receptor ligand is nonmetabolized. In certain embodiments, the chemosensory receptor ligand is an agonist. In certain embodiments, the chemosensory receptor ligand is an enhancer.

Accordingly, also provided herein are compositions comprising biguanide or related heterocyclic compounds that further comprise a chemosensory receptor enhancer selected from the group consisting of a sweet receptor enhancer, a bitter receptor enhancer, an umami receptor enhancer, a fat receptor enhancer, a sour receptor enhancer and a bile acid receptor enhancer. In certain embodiments, the chemosensory receptor enhancer is an umami receptor enhancer that enhances the effect of food on umami receptors in the intestine.

The compositions described herein can be formulated with an enteric coating. In another aspect, the compositions described herein can be formulated with a modified release system. In yet another aspect, the compositions described herein can be formulated with a timed release system. In a further aspect, the compositions described herein can be formulated with a modified release and enteric coating. In yet a further aspect, the compositions described herein can be formulated with a timed release and enteric coating.

Provided herein is a method of treating certain conditions in a subject comprising administering a composition comprising a biguanide or related heterocyclic compound described herein to the subject.

In one aspect, the method comprises administering at least one biguanide or related heterocyclic compound selected from any of the compounds described herein to the subject and wherein the composition is adapted to minimize the systemic bioavailability of the compound and/or release a therapeutically effective amount of a biguanide or related heterocyclic compound to one or more regions of the intestines.

In preferred embodiments, said administration results in a reduced or minimized systemic bioavailability of the compound, e.g., a minimized circulating plasma concentration of the biguanide compound in the patient and/or reduced average systemic bioavailability of the compound, e.g., when compared to a immediate release composition having an equivalent amount of the compound. In some embodiments, the minimized circulating plasma concentration is below about 5 µg/mL, 4 µg/mL, 3 µg/mL, 2 µg/mL, 1 µg/mL, 0.5 µg/mL or 0.25 µg/mL in subjects with normal or impaired renal function. In other embodiments, the compound has 60%, 50%, 40%, 30%, or 20% less relative bioavailability compared to an immediate release composition having the same amount of the compound.

Provided herein is a method of treating certain conditions by administering a composition having at least one biguanide or related heterocyclic compound to the lower intestine of a subject. In another embodiment, the composition comprising at least one biguanide or related heterocyclic compound is administered to the upper intestine of a subject. In yet another embodiment, the composition comprising at least one biguanide or related heterocyclic compound is administered to the upper intestine and lower intestine of a subject. In certain instances, the biguanide or related heterocyclic compound in the upper intestine and lower intestine is the same biguanide or related heterocyclic compound. In certain instances, a biguanide or related heterocyclic compound in the upper intestine and lower intestine are different.

Provided herein is a method of treating certain conditions by administering a composition having at least one biguanide or related heterocyclic compound to the duodenum, jejunum, ileum, caecum, colon, and/or rectum. In other embodiments, the composition comprising at least one biguanide or related heterocyclic compound is administered to the duodenum of a subject. In another embodiment, the composition comprising at least one biguanide or related heterocyclic compound is administered to the jejunum of a subject. In another embodiment, the composition comprising at least one biguanide or related heterocyclic compound is administered to the ileum of a subject. In another embodiment, the composition comprising at least one biguanide or related heterocyclic compound is administered to the caecum of a subject. In another embodiment, the composition comprising at least one biguanide or related heterocyclic compound is administered to the colon of a subject. In another embodiment, the composition comprising at least one biguanide or related heterocyclic compound is administered to the rectum of a subject. In another embodiment, the composition comprising at least one biguanide or related heterocyclic compound is administered to the duodenum, jejunum, ileum, caecum, colon and/or rectum of a subject.

Provided herein is a method of treating certain conditions by administering one or more biguanide or related heterocyclic compound compositions that release at an onset about 75 minutes, 105 to about 135 minutes, about 165 to about 195 minutes, about 225 to about 255 minutes or a combination of times thereof following oral administration to a subject.

Provided herein is a method of treating certain conditions by administering one or more biguanide or related heterocyclic compound compositions that have an onset of about 120 minutes, about 180 minutes, about 240 minutes or a combination of times thereof following oral administration to a subject. In one embodiment, the composition releases at an onset of about 120 minutes following administration to a subject. In one embodiment, the composition releases at an onset of about 180 minutes following administration to a subject. In one embodiment, the composition releases at an onset of about 240 minutes following administration to a subject. In one embodiment, the composition releases at an onset of about 120 minutes, about 180 minutes and about 240 minutes following oral administration to a subject In certain embodiments, the biguanide or related heterocyclic compound composition(s) have an onset of release at about pH 5.5, about pH 6.0, about pH 6.5, and/or about pH 7.0.

In certain embodiments, the biguanide or related heterocyclic compound compositions release at an onset of two different pH ranges, wherein said two pH ranges are selected from about pH 5.0 to about pH 6.0, about pH 6.0 to about pH 7.0 and about pH 7.0 to about pH 8.0.

Provided herein are methods of modulating circulating concentrations of one or more hormones, including but not limited to GLP-1, GLP-2, GIP, oxyntomodulin, PYY, CCK, glycentin, insulin, glucagon, ghrelin, amylin, insulin, C-peptide and uroguanylin, by administering a composition comprising at least one biguanide or related heterocyclic compound described herein to a subject. Provided herein are methods of modulating the hormonal profile of lower intestine by administering a composition having at least one biguanide or related heterocyclic compound to the lower intestine of a subject. In one embodiment, the hormonal profile is that of GLP-1, oxyntomodulin, and PYY.

Provided herein are methods of modulating the hormonal profile of upper intestine by administering a composition having at least one biguanide or related heterocyclic compound to the upper intestine of a subject. In one embodiment, the hormonal profile is that of GLP-1, GLP-2, oxyntomodulin, PYY, GIP, C-peptide, glucagon, insulin, CCK, or any combination thereof.

Further provided herein are methods to sensitize lower intestinal chemosensory receptors by stimulating bitter receptors in the upper intestine with a biguanide or related heterocyclic compound.

Provided herein are methods of treating certain conditions with the biguanides or related heterocyclic compound compositions described herein. These conditions include metabolic syndrome, diabetes type I, diabetes type II, obesity, binge eating, undesired food cravings, food addiction, a desire to reduce food intake or to lose weight or maintain weight loss, desire to maintain healthy weight, desire to maintain normal blood glucose metabolism, anorexia, pre-diabetes, glucose intolerance, gestational diabetes mellitus (GDM), impaired fasting glycemia (IFG), post-prandial hyperglycemia, accelerated gastric emptying, dumping syndrome, delayed gastric emptying, dyslipidemia, post-prandial dyslipidemia, hyperlipidemia, hypertriglyceridemia, post hypertriglyceridemia, insulin resistance, bone loss disorders, osteopenia, osteoporosis, muscle wasting disease, muscle degenerative disorders, polycystic ovary syndrome (PCOS), non-alcoholic fatty liver disease (NAFL), non-alcoholic steatohepatitis (NASH), immune disorders of the gut, (e.g., celiac disease), bowel irregularity, irritable bowel syndrome (IBS), inflammatory bowel disease (IBD), including, e.g., ulcerative colitis, Crohn's disease, short bowel syndrome and peripheral neuropathy, e.g., diabetic neuropathy. In some embodiments, the condition is obesity. In certain embodiments, the condition is diabetes. In further embodiments, the subject has undergone bariatric surgery. In yet other embodiments, methods provided herein further include administering a drug for diabetes or obesity.

In certain embodiments, these conditions include sadness, stress, grief, anxiety, anxiety disorder (e.g., generalized anxiety disorder, obsessive-compulsive disorder, panic disorder, post-traumatic stress disorder or social anxiety disorder or a mood disorder (e.g., depression, bipolar disorder, dysthymic disorder and cyclothymic disorder). In certain embodiments, the compositions described herein may be used for inducing feelings of happiness, well-being or contentment.

Additionally, the compositions described herein may be used for the dietary management of the conditions listed above.

Also provided herein are methods for treating a disease, disorder or defect in energy homeostasis in a subject comprising administering a composition described herein. In one aspect, the composition is adapted to release a therapeutically effective amount of a biguanide or related heterocyclic compound to one or more regions of the intestine.

Also provided herein are methods for treating overweight in a subject comprising administering a composition described herein. In one aspect, the composition is adapted to release a therapeutically effective amount of a biguanide or related heterocyclic compound to one or more regions of the intestine.

Also provided herein are methods for treating obesity in a subject comprising administering a composition described herein. In one aspect, the composition is adapted to release a therapeutically effective amount of a biguanide or related heterocyclic compound to one or more regions of the intestine.

Also provided herein are methods for reducing food intake in a subject comprising administering a composition described herein. In one aspect, the composition is adapted to release a therapeutically effective amount of a biguanide or related heterocyclic compound to one or more regions of the intestine.

Also provided herein are methods for treating type II diabetes in a subject comprising administering a composition described herein. In one aspect, the composition is adapted to release a therapeutically effective amount of a biguanide or related heterocyclic compound to one or more regions of the intestine.

Also provided herein are methods for maintaining healthy body weight in a subject comprising administering a composition described herein. In one aspect, the composition is adapted to release a therapeutically effective amount of a biguanide or related heterocyclic compound to one or more regions of the intestine.

Also provided herein are methods for treating pre-diabetes in a subject comprising administering a composition described herein. In one aspect, the composition is adapted to release a therapeutically effective amount of a biguanide or related heterocyclic compound to one or more regions of the intestine.

Also provided herein are methods for increasing GLP-1 concentration in a subject comprising administering a composition described herein. In one aspect, the composition is adapted to release a therapeutically effective amount of a biguanide or related heterocyclic compound to one or more regions of the intestine.

Also provided, herein are methods for increasing PYY concentration in a subject comprising administering a composition described herein. In one aspect, the composition is adapted to release a therapeutically effective amount of a biguanide or related heterocyclic compound to one or more regions of the intestine.

In some embodiments of the methods provided herein, prior to administration of the composition, the subject is prescreened for endogenous chemosensory receptor levels and types for use in adjusting the amount of the composition for administration.

The methods disclosed herein may also further comprise administration of a DPP-IV inhibitor, a chemosensory receptor ligand (e.g., a sweet receptor ligand, bitter receptor ligand, umami receptor ligand, sour receptor ligand, fat receptor ligand or bile acid receptor ligand, or combination thereof, a chemosensory receptor antagonist (e.g., lactisole), a chemosensory receptor enhancer), an anti-obesity or anti-diabetes agent.

Also provided herein are pharmaceutical dosage forms comprising (a) a pH 6.5 enterically coated immediate release component comprising metformin hydrochloride and a pharmaceutically acceptable excipient; and (b) a pH 6.5 enterically coated extended release component comprising metformin hydrochloride and a pharmaceutically acceptable excipient; and wherein the combined amount of metformin from both components is less than 400 mg and wherein the metformin has sub-therapeutic plasma AUC and sub-therapeutic plasma Cmax.

In some embodiments, the proportion of metformin hydrochloride in the immediate release component to the metformin hydrochloride in the delayed release component is about 20/80, 30/70, 35/65, 40/60, 45/55 or 50/50. In other embodiments, the dosage form exhibits a dissolution release profile of 80-100% amount of metformin hydrochloride after 75 minutes after oral administration.

In some embodiments, the plasma AUC and plasma Cmax resulting from administration of the dosage form is 50% or less than the plasma AUC and Cmax resulting from administration of a single dose of GLUMETZA 500 mg.

In some embodiments, the dosage form further comprises a DPP-IV inhibitor in (a), (b) or both. In other embodiments, the dosage form further comprises an antidiabetic or anti-obesity agent.

In some embodiments, the dosage form further comprises (c) an immediate release component comprising metformin hydrochloride. In some instances, the (c) immediate release component has a pH 5.0 enteric coating. In some instances, the combined amount of metformin from components (a)-(c) is less than 600 mg.

In some embodiments, the excipient in the extended release component is selected from the group consisting of ethylcellulose, hydroxypropylmethylcellulose, hydroxypropylcellulose, polyvinylpyrrolidone, xanthan gum, sodium alginate, polysorbate-80 and mixtures thereof.

In some embodiments, the combined amount of metformin hydrochloride is about 250 mg.

In some embodiments, the dosage form is a bi-layer tablet. In other embodiments, the dosage form is a capsule with the two components as encapsulated mini-tablets.

Also provided herein are pharmaceutical dosage forms comprising (a) a pH 6.5 enterically coated immediate release component comprising metformin hydrochloride and a pharmaceutically acceptable excipient; and (b) a pH 6.5 enterically coated extended release component comprising metformin hydrochloride and a pharmaceutically acceptable excipient; and wherein the metformin hydrochloride has reduced average systemic bioavailability.

In some embodiments, the average systemic bioavailability is less than the average systemic bioavailability of an immediate release metformin formulation having an equivalent amount of metformin. In other embodiments, the average systemic bioavailability is less than 15%.

In some embodiments, the combined amount of metformin hydrochloride is less than 400 mg.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE FIGURES

FIG. 4C shows the plasma concentration of total GLP-1 (x-axis; GLP-1T pmol/L) as a function of time (y-axis; min) in subjects at baseline (□,○) or after ingestion of either Metformin (●) or Re-Metformin (■) and after a meal at t=0 min. For FIGS. 4A-4C, percent increase in Abs AUC is compared to baseline values.

DETAILED DESCRIPTION OF THE INVENTION

Figure 1:
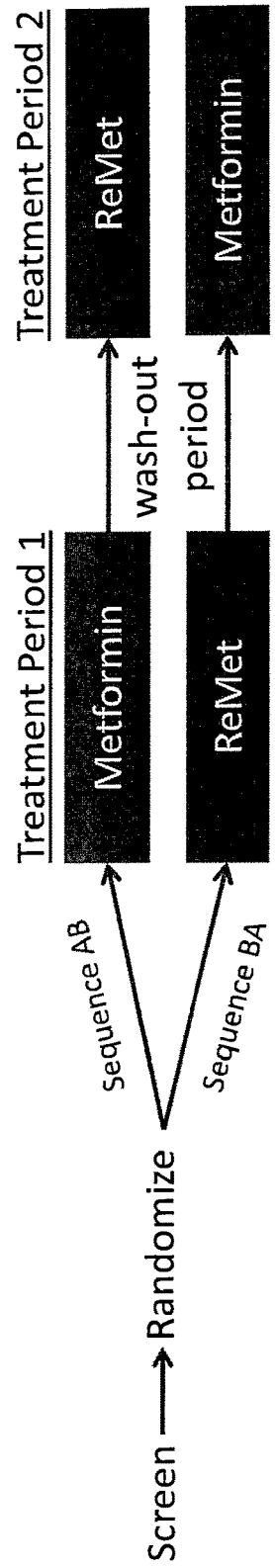
FIG. 1 shows the design of the study described in Example 5.

The present invention relates to methods and compositions for treating certain conditions, for example, metabolic conditions including obesity and diabetes, using a biguanide or related heterocyclic compound or combination of biguanide or related heterocyclic compounds. Biguanide or related heterocyclic compound(s) modulate the synthesis, secretion and/or storage of hormones, e.g., GLP-1, GLP-2, oxyntomodulin, PYY, GIP, insulin, C-peptide, glycentin, glucagon, amylin, ghrelin, uroguanylin and/or CCK that are key regulators of energy and metabolic processes such as glucose metabolism.

The present embodiments described herein additionally contemplate targeting administration of biguanide or related heterocyclic compounds to specific sites throughout the gut. Enteroendocrine cells, e.g., L cells, K cells, and I cells, that each secrete a different set of metabolic hormones in response to chemosensory stimulation, occur throughout the length of the intestine. The concentrations and proportions of these enteroendocrine cell types are different in the various intestinal segments, and, as noted above, each cell type has a different metabolic hormone expression profile. Targeted administration of the compositions of the invention to specific intestinal segments, for example, through the use of formulations designed for release within one or more desired segments of the intestine, provides an additional level of control over the effect of such compositions, e.g., in the modulation of hormones involved in metabolism.

The present embodiments described herein thus include a novel approach to treating certain conditions by, for example, modulating the secretion of metabolic hormones through enteroendocrine chemosensory receptor activation using biguanide or related heterocyclic compounds. The embodiments further include the capability to select combination therapies tailored to the specific needs of individuals having varying hormone profiles.

A biguanide or related heterocyclic compound may be used in combination with one or more chemosensory receptor ligands to modulate hormone profiles in an individual. Exemplary chemosensory receptor ligands and their use in modulating hormone profiles is described, e.g., in U.S. Application Publication Nos.: 20100267643, 20110065660, and 20120094942; and PCT Application Publication Nos. WO2010123930, WO2011133180, WO2012054523, WO2012054526, WO2012054527, WO2012054528, and WO2012054530, each of which is incorporated herein in its entirety by reference.

The embodiments described herein include compositions and methods for modulating the concentrations of circulating enteroendocrine cell hormones, including, but not limited to, GLP-1, GLP-2, GIP, oxyntomodulin, PYY, CCK, glycentin, insulin, glucagon, C-peptide, ghrelin, amylin, uroguanylin, etc., such compositions and methods comprising administering at least one biguanide or related heterocyclic compound to a subject to treat certain conditions. Hormone modulation can be achieved by administering a composition comprising a biguanide or related heterocyclic compound acting on a bitter receptor.

In particular embodiments, a combination of a biguanide or related heterocyclic compound with one or more agonists of the sweet, umami, bitter, free fatty acid, and bile acid receptors will simulate the synchronous release of important hormones and neural signals from the enteroendocrine cells and thus facilitate the assimilation and disposition of meal nutrients. In additional embodiments, a combination of a biguanide or related heterocyclic compound with one or more agonists of the sweet, umami, bitter, free fatty acid, and bile acid receptors suppresses ghrelin synthesis, activity or action, or its post-translational modification (Ghrelin Octonoyl Acyl Transferase activity or GOAT) and/or ghrelin secretion or release.

Biguanides and Related Heterocyclic Compounds

The compositions and methods disclosed herein relate to biguanides and related heterocyclic compounds. By way of background, metformin is one of the simplest structural variants of a class of compounds known as the biguanides. From a structural perspective metformin resembles a pharmacophore or fragment of a larger biologically active chemical structure. The parent biguanide structure, as well the structure of metformin phenformin, buformin, proguanil, imeglimin and its enantiomer are shown below.

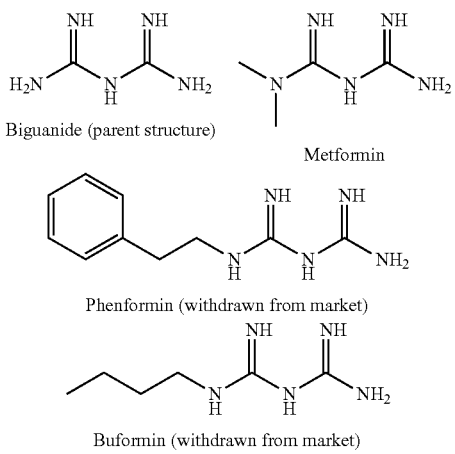

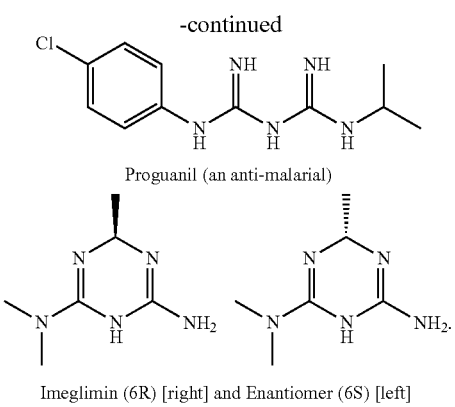

Proguanil (an anti-malarial)

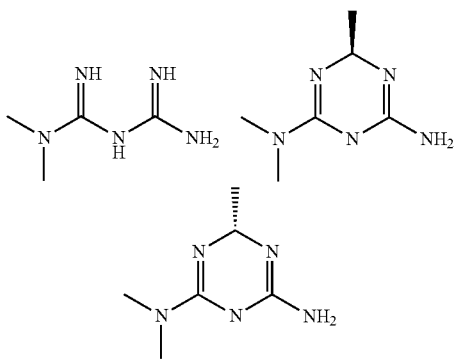

Imeglimin (6R) [right] and Enantiomer (6S) [left]

Without intending to be limited by theory, while the geometry of metformin and related open chain biguanides in the context of their interactions with biological targets are not well understood, the geometries are expected to be limited to the cisoid and transoid forms shown below.

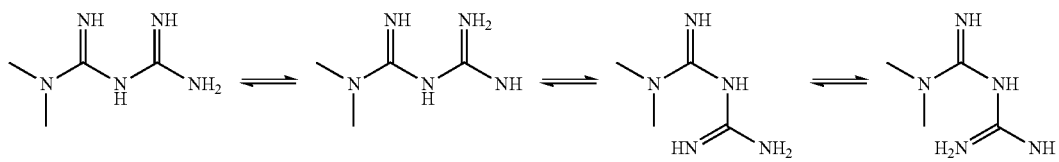

Again, not intending to be limited by theory, these two forms represent the low energy forms of the structure with an inherent energy barrier to the key bond rotation that allows the cisoid form to interconvert with the transoid form. An X-ray crystal study of metformin dinitrate shows the "cisoid" structure to be the favored conformer in the solid phase. Fridrichová M, Císařová I, Němec I. 1,1-Dimethyl-biguanidium(2+) dinitrate. Acta Crystallogr Sect E Struct Rep Online. 2012 Jan. 1; 68(Pt 1):o18-9. Epub 2011 Dec. 3. A related set of structures, the dihydrotriazines, exemplified by the compound known as Imeglimin (currently in late stage clinical evaluation by Poxel Pharmaceuticals) have the "cisoid" conformation fixed within their structures as shown below:

In an aspect of the disclosure, biguanides and related heterocyclic compounds are provided, including those comprising elements which rigidify or fix the "cisoid" biguanide conformation, as illustrated below with the metformin variant of each of the exemplary structural types. More particularly, the relationship between Metformin series [representative of Formula (I) herein], the triazole series [representative of Formula (IA) herein], the triazine series [representative of Formula (II) herein], the dihydrotriazine series [representative of Formula (III) herein], and the 7-ring series [representative of Formula (IV) herein] is illustrated.

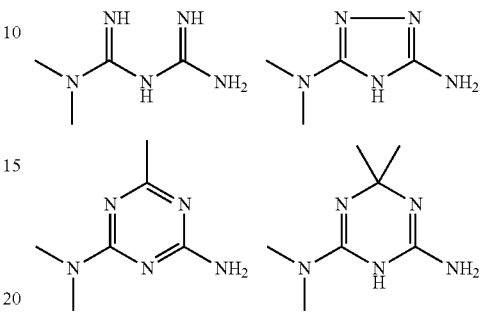

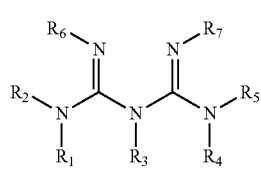

In one embodiment, compounds of Formula I may be used in connection with the compositions and methods of the disclosure.

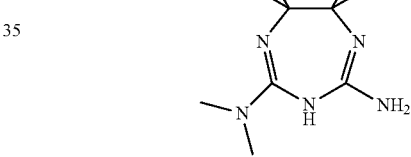

I

Wherein:

$R_1$, $R_2$, $R_3$, $R_4$, $R_5$, $R_6$, and $R_7$ are independently selected from:

H, OH,

O—Rx, wherein Rx is alkyl, cycloalkyl, alkylcycloalkyl, acyl, ester, thioester;

optionally substituted alkyl (e.g., a $C_1$ to $C_{12}$ straight chain or branched chain alkyl optionally substituted with oxygen, silicon, sulphur or optionally substituted with OH, O-alkyl, SH, S-alkyl, $NH_2$, NH-alkyl); cycloalkyl (e.g., $C_3$ to $C_7$ cycloalkyl); alkylcycloalkyl (e.g., $C_4$ to $C_{12}$ alkylcycloalkyl); heterocycloalkyl (e.g., where the heterocycle comprises one or two hetero atoms selected from O, S, or N, including a $C_2$ to $C_6$ heterocycloalkyl); alkylheterocycloalkyl (e.g., where the heterocycle comprises one or two hetero atoms selected from O, S, or N, including a $C_3$ to $C_{11}$ alkylheterocycloalkyl, and including wherein when N is present in the heterocyclic ring, the nitrogen atom may be in the form of an amide, carbamate or urea); optionally substituted alkenyl (e.g., $C_1$ to $C_{12}$ straight chain or branched chain alkenyl optionally substituted with oxygen, silicon, sulphur or optionally substituted with OH, O-alkyl, SH, S-alkyl, $NH_2$, NH-alkyl); optionally substituted alkynyl (e.g., $C_1$ to $C_{12}$ straight chain or branched chain alkynyl optionally substituted with oxygen, silicon, sulphur or optionally substituted with OH, O-alkyl, SH, S-alkyl, $NH_2$, NH-alkyl);

optionally substituted aryl (e.g., phenyl, substituted phenyl, naphthyl, substituted naphthyl); optionally substituted alkylaryl (e.g., alkylphenyl, alkylsubstituted phenyl, alkylnaphthyl, alkylsubstituted naphthyl); optionally substituted heteroaryl (e.g., pyridyl, furanyl, thiophenyl, pyrrollyl, oxazolyl, isoxazolyl, thiazolyl, diazolyl, pyrazolyl, triazolyl all of which are optionally substituted); optionally substituted alkylheteroaryl; and or $R_6$ and $R_7$ may join to form a bond, together forming a ring including the nitrogen atoms to which they are attached;

or $R_1$ and $R_2$ may together form a 3 to 8 membered heterocyclic ring, including the nitrogen atoms to which they are attached;

or $R_4$ and $R_5$ may together form a ring selected from the group aziridine, pyrrolyl, imidazolyl, pyrazolyl, indolyl, indolinyl, pyrrolidinyl, piperazinyl and piperidyl, including the nitrogen atoms to which they are attached In certain embodiments, O—Rx may be selected from: O—C1 to C8 straight chain or branched chain alkyl; O—C3 to C7 cycloalkyl; O—C4 to C8 alkylcycloalkyl; O-acyl; O-esters; and O-thioesters.

In other embodiments, optional substitutions may include, e.g., OH, O-alkyl, SH, S-alkyl, NH2, NH-alkyl. Further, an alkyl, alkenyl, alkynyl, etc. may be substituted with an oxygen, silicon, sulphur, etc. to form a heteroalkyl, heteroalkenyl, heteroalkynyl, etc.

In certain embodiments, each of: R3, R6, and R7, or R3, R4, R5, and R7, or R3, R4, R5, and R7, or R3, R4, R5, R6 and R7, or R2, R3, R4, R5, R6 and R7 are independently selected from:

H, methyl, ethyl, propyl or isopropyl;

and each of the remaining substitutent groups: $R_1$, $R_2$, $R_4$, and $R_5$, or $R_1$, $R_2$, and $R_6$, or $R_1$, $R_2$, and $R_6$, or $R_1$ and $R_2$, or $R_1$, respectively, are independently selected from:

H; optionally substituted alkyl (e.g., $C_1$ to $C_{12}$ straight chain or branched chain alkyl optionally hetero substituted with oxygen, silicon, sulphur or optionally substituted with OH, O-alkyl, SH, S-alkyl, $NH_2$, NH-alkyl); optionally substituted alkenyl (e.g., $C_1$ to $C_{12}$ straight chain or branched chain alkenyl optionally hetero substituted with oxygen, silicon, sulphur or optionally substituted with OH, O-alkyl, SH, S-alkyl, $NH_2$, NH-alkyl); optionally substituted alkynyl (e.g., $C_1$ to $C_{12}$ straight chain or branched chain alkynyl optionally hetero substituted with oxygen, silicon, sulphur or optionally substituted with OH, O-alkyl, SH, S-alkyl, $NH_2$, NH-alkyl); cycloalkyl (e.g., $C_3$ to $C_7$ cycloalkyl); alkylcycloalkyl (e.g., $C_4$ to $C_{12}$ alkylcycloalkyl); heterocycloalkyl (e.g., where the heterocycle comprises one or two hetero atoms selected from O, S, or N, including $C_2$ to $C_6$ heterocycloalkyl); alkylheterocycloalkyl (e.g., where the heterocycle comprises one or two hetero atoms selected from O, S, or N, including $C_3$ to $C_{11}$ alkylheterocycloalkyl, and including wherein when N is present in the heterocyclic ring, the nitrogen atom may be in the form of an amide, carbamate or urea); aryl (e.g., phenyl, substituted phenyl, naphthyl, substituted naphthyl); alkylaryl (e.g., alkylphenyl, alkylsubstituted phenyl, alkylnaphthyl, alkylsubstituted naphthyl); heteroaryl (e.g., pyridyl, furanyl, thiophenyl, pyrrollyl, oxazolyl, isoxazolyl, thiazolyl, diazolyl, pyrazolyl, triazolyl all of which are optionally substituted); alkylheteroaryl;

or $R_1$ and $R_2$ may together form a 3 to 8 membered heterocyclic ring, including the nitrogen atoms to which they are attached;

or $R_4$ and $R_5$ may together form a ring selected from the group aziridine, pyrrolyl, imidazolyl, pyrazolyl, indolyl, indolinyl, pyrrolidinyl, piperazinyl and piperidyl, including the nitrogen atoms to which they are attached.

Exemplary compounds and substituents of R1, R2, R3, R4, R5, R6, and R7 of Formula I are shown below. However, additional combinations of selections of substituents of R1, R2, R3, R4, R5, R6, and R7 are envisioned.

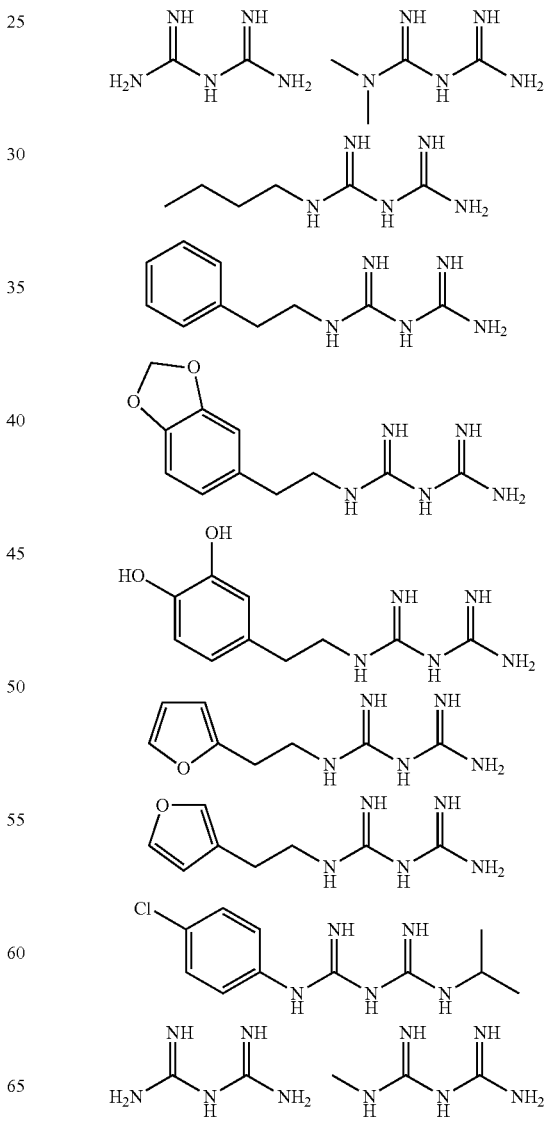

-continued
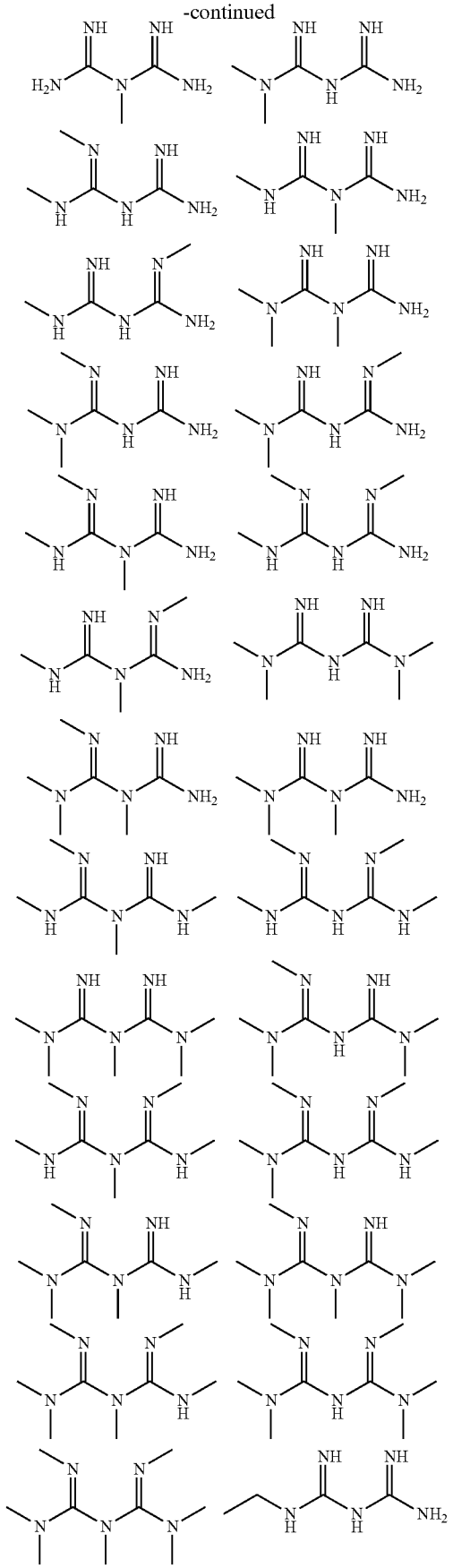
-continued
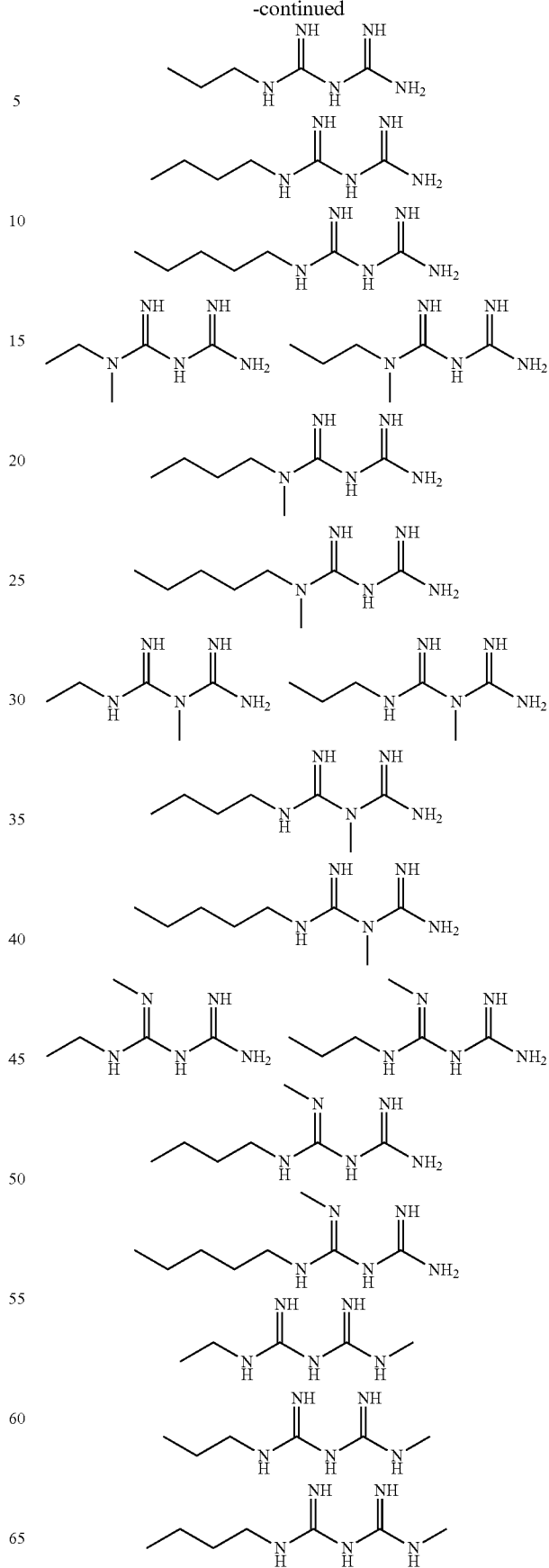

-continued
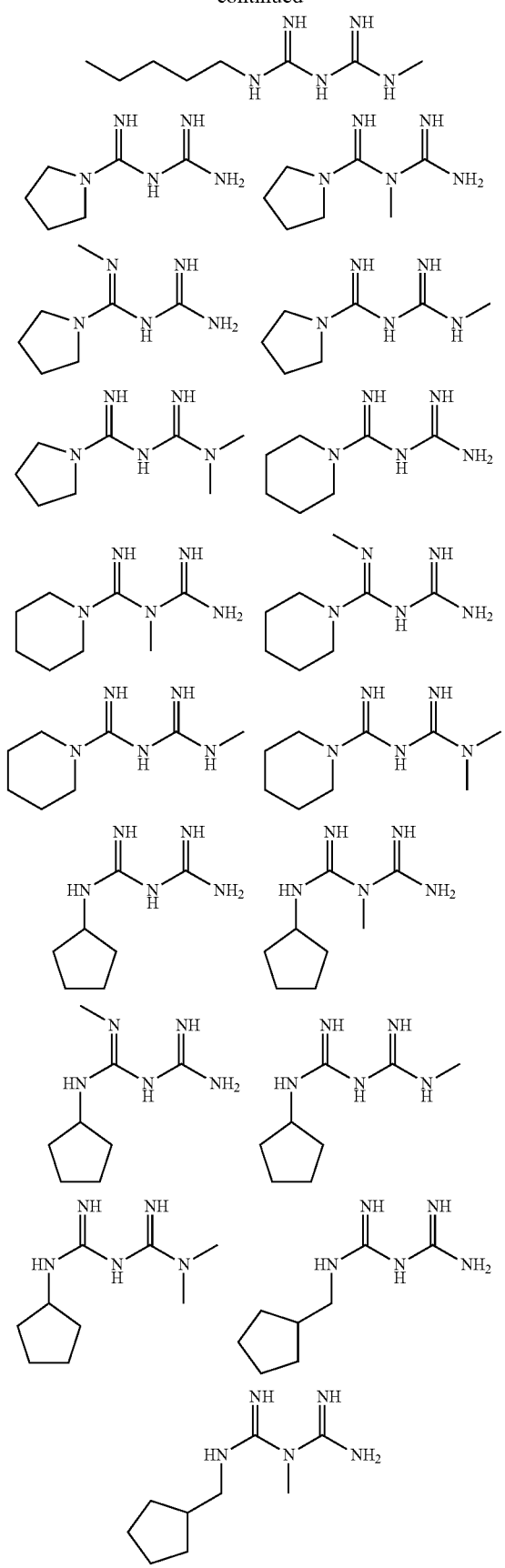
-continued
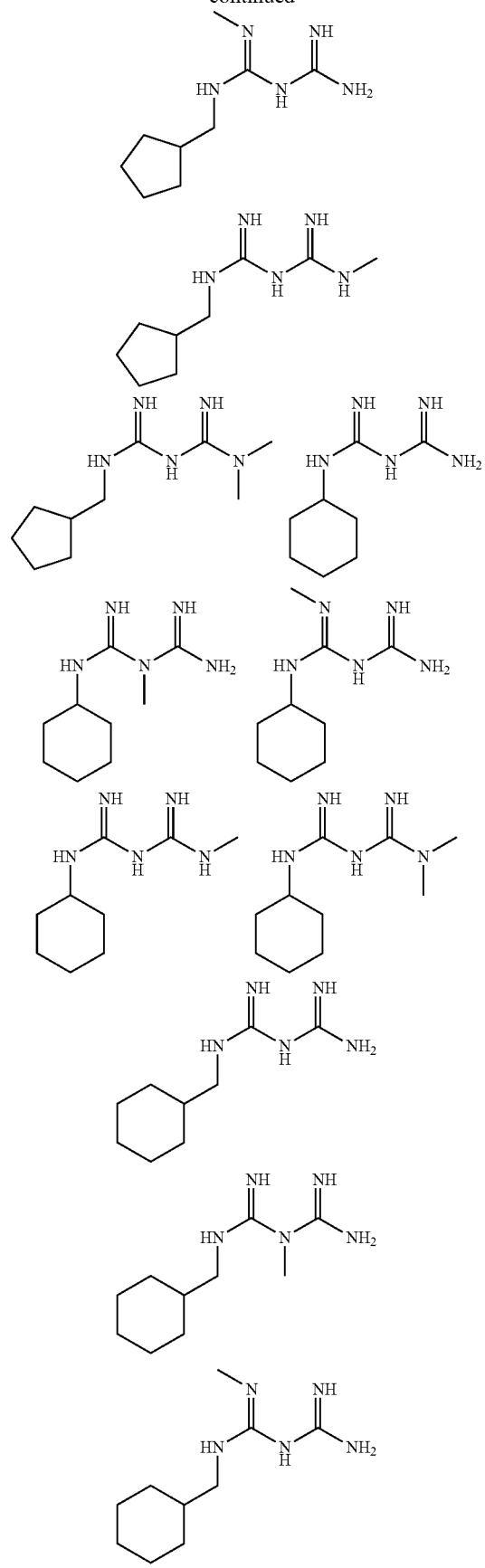

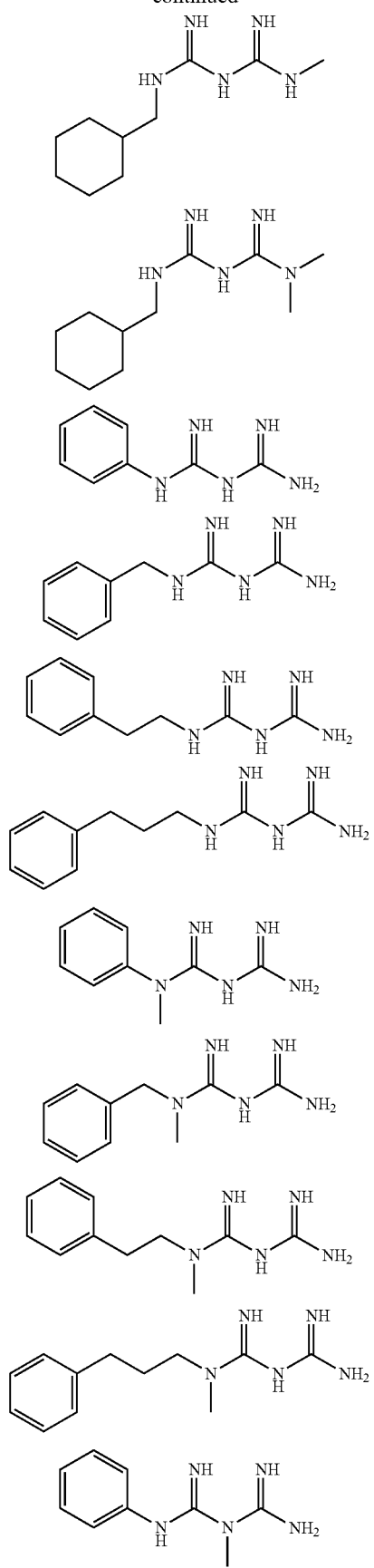
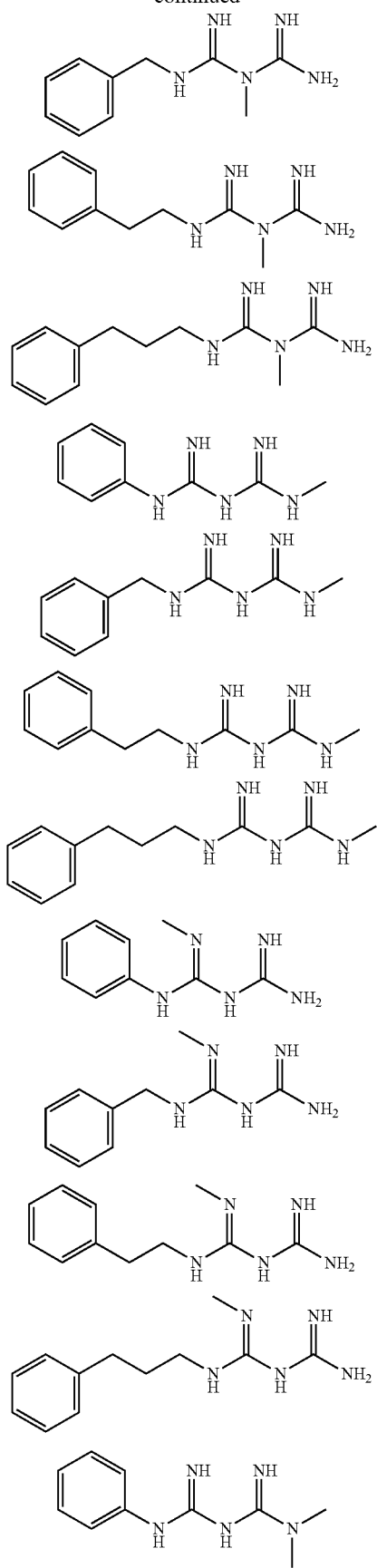

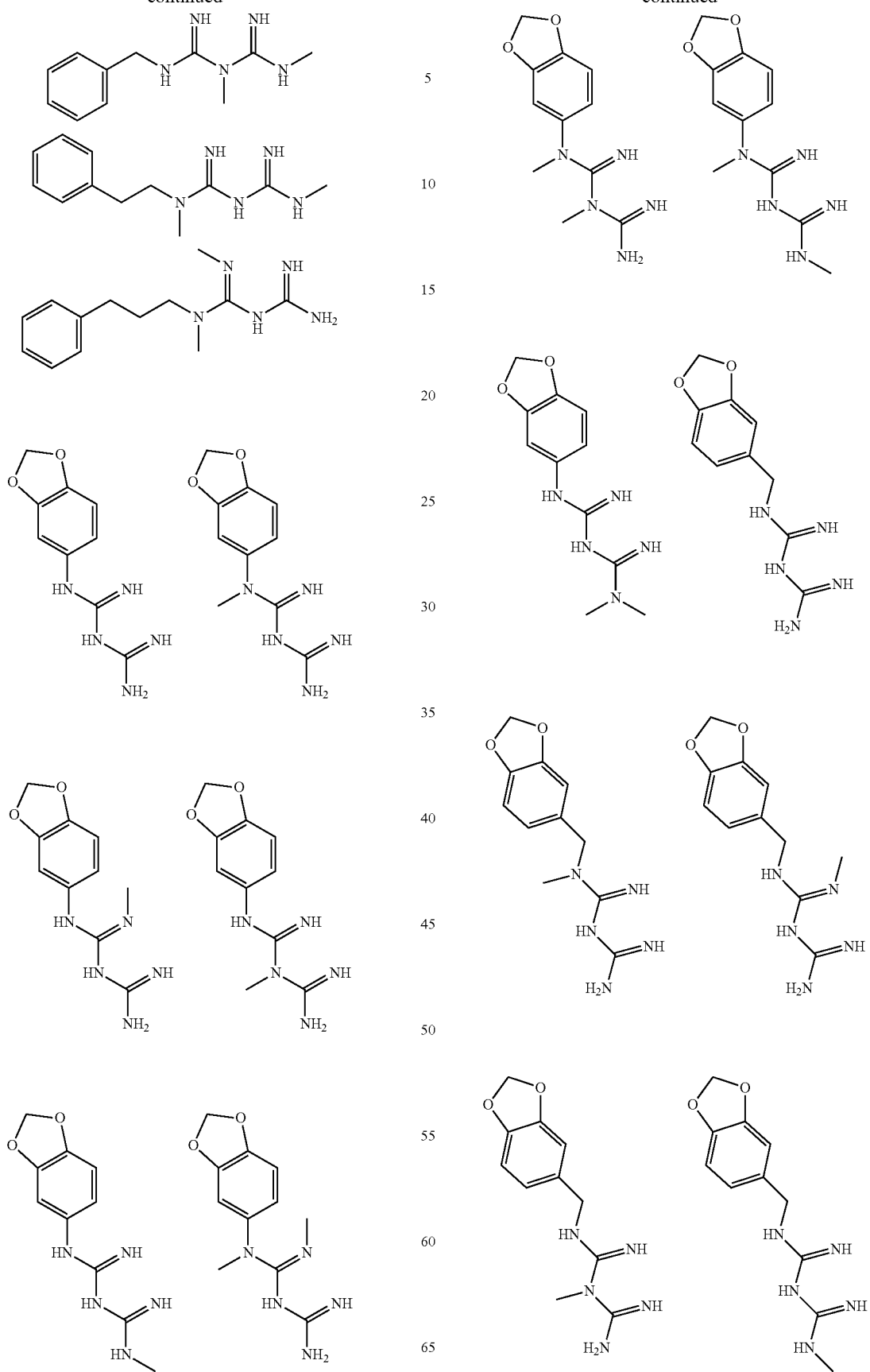

-continued
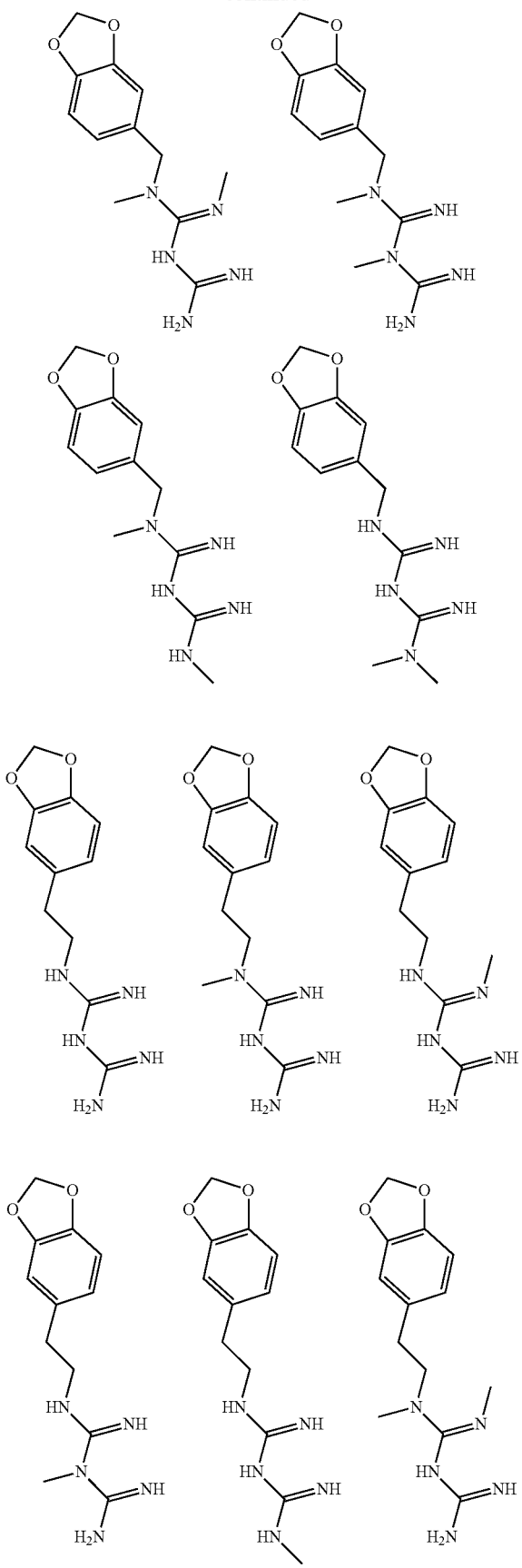
-continued
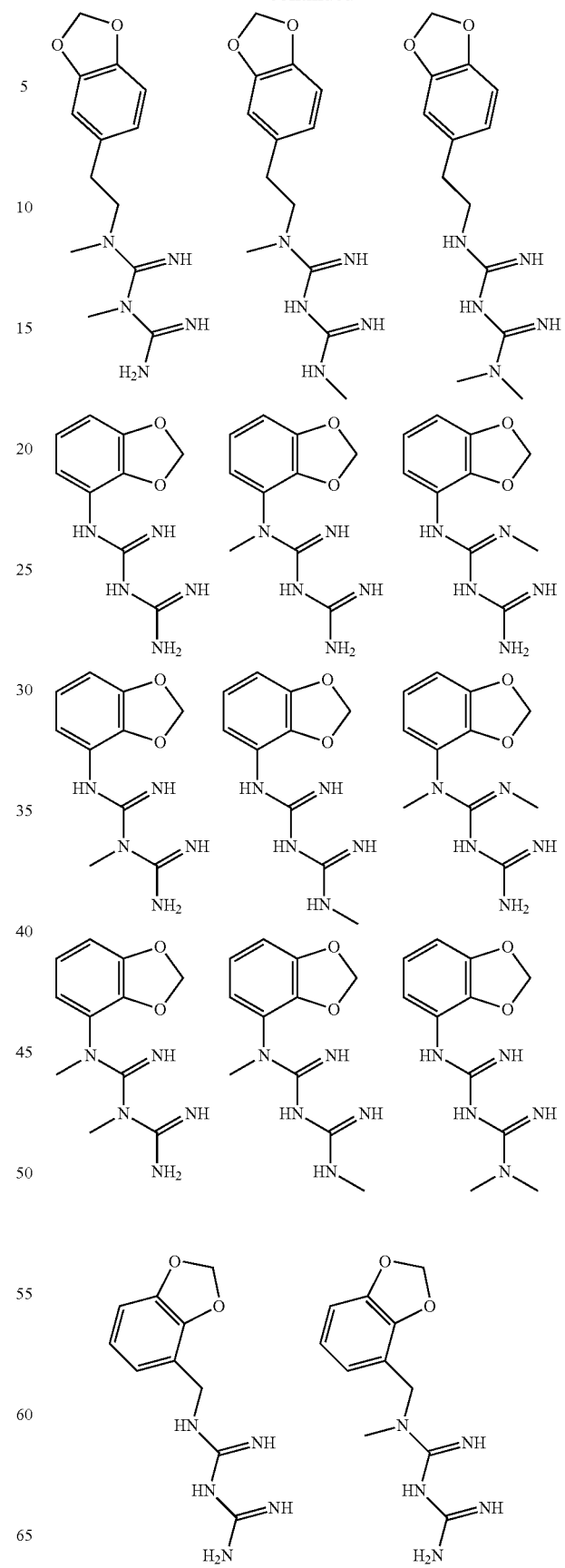

-continued
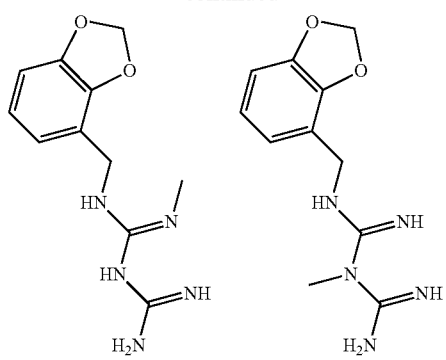
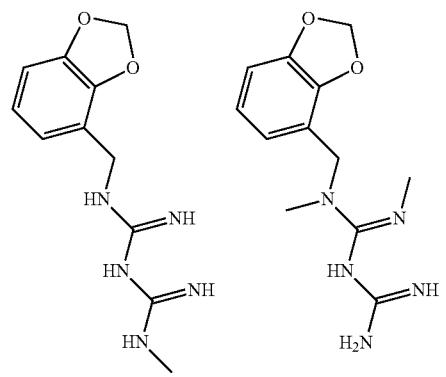
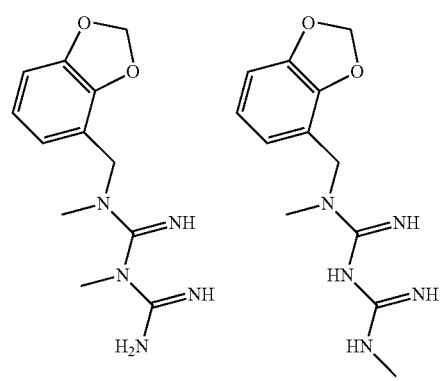
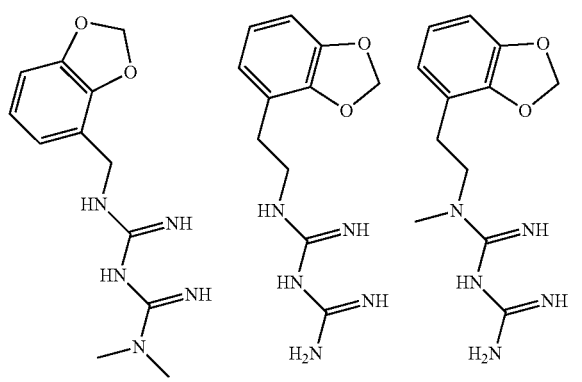
-continued
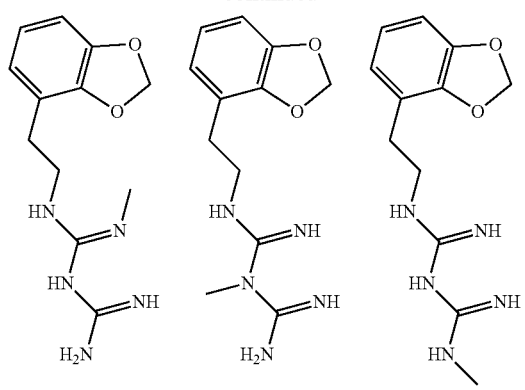
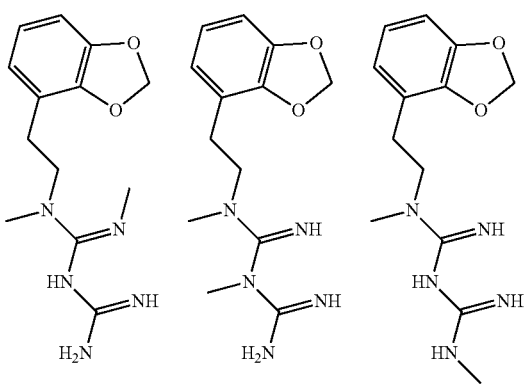
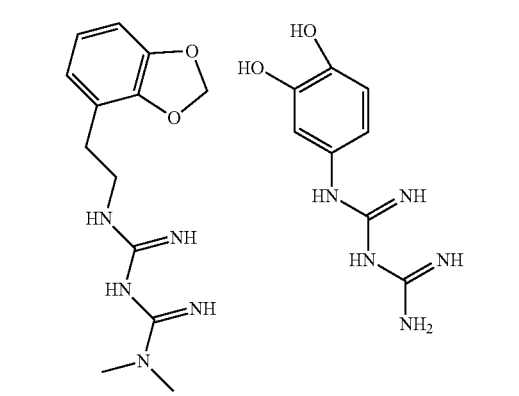
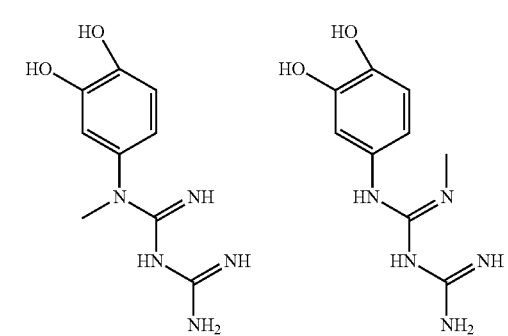

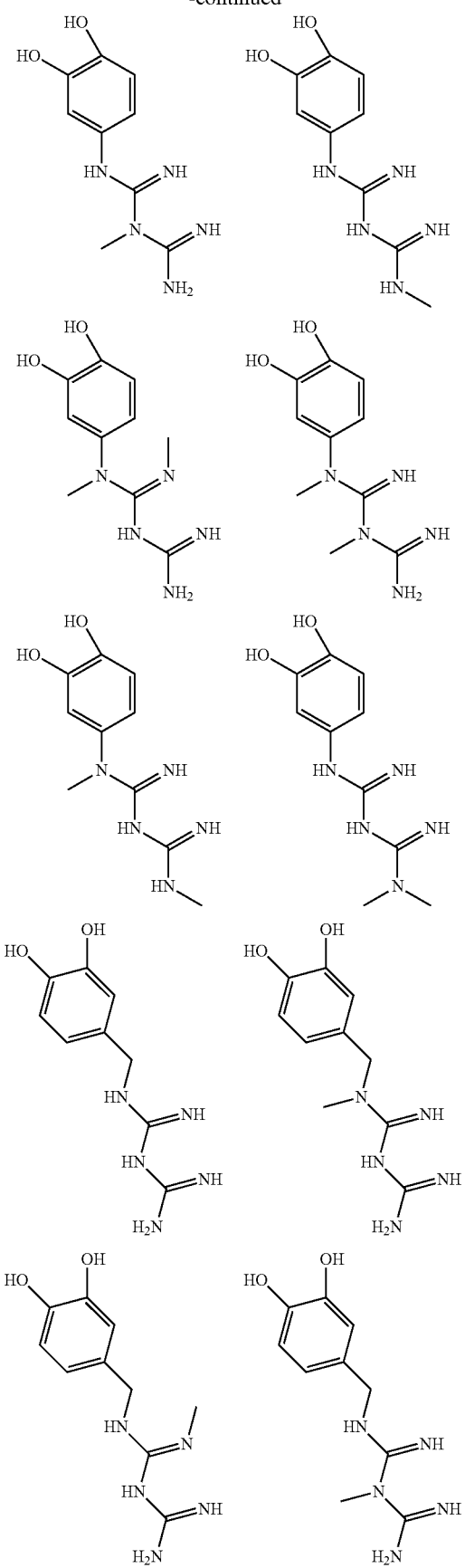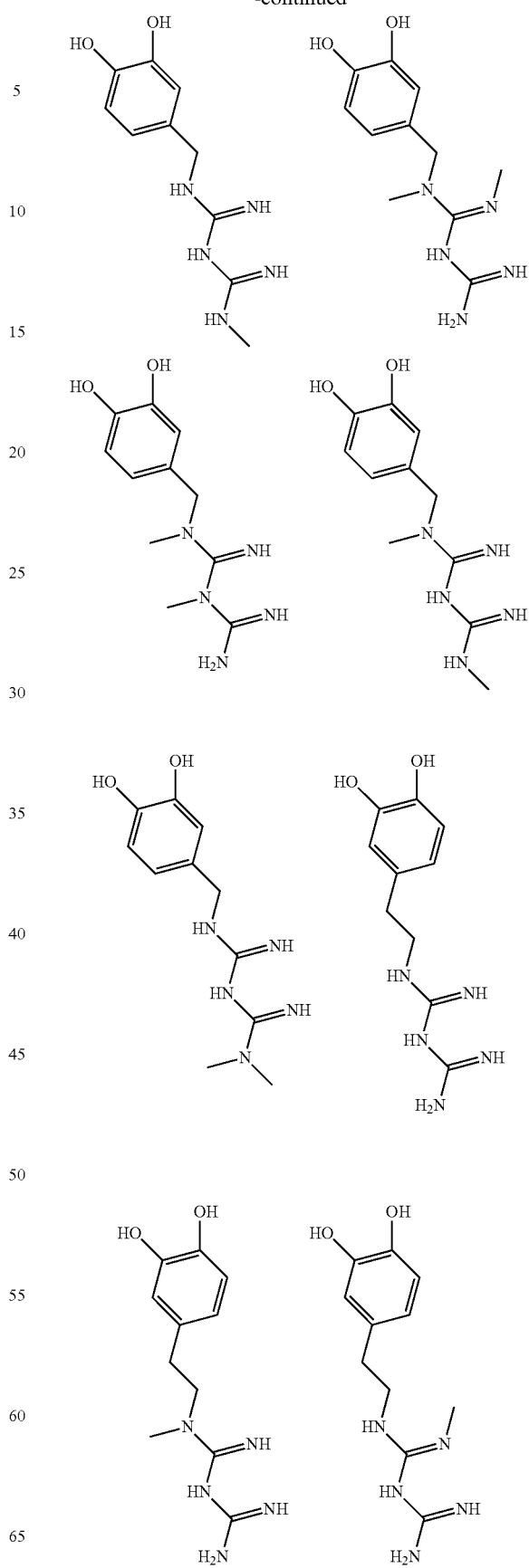

-continued
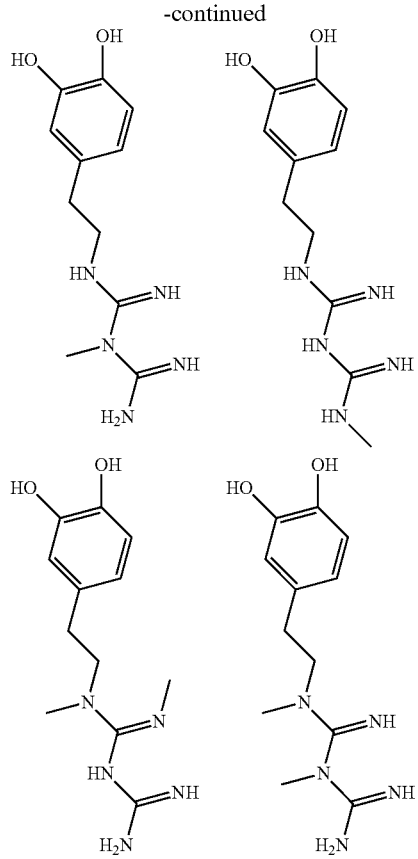
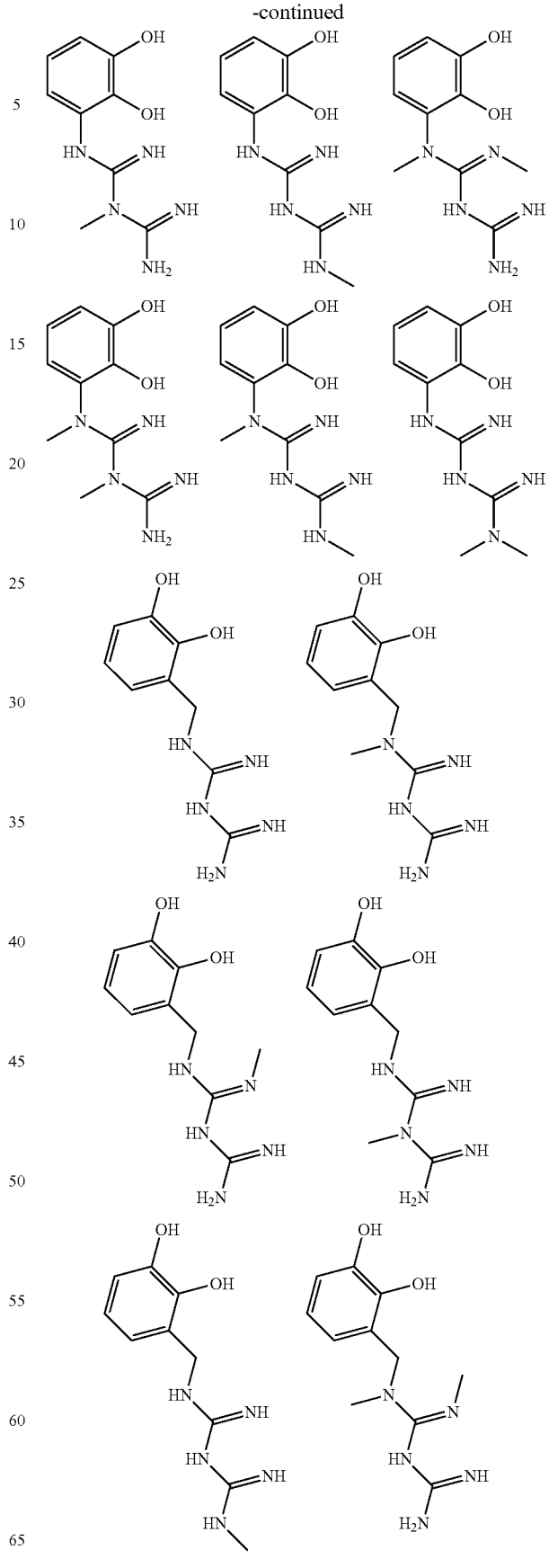

37
-continued
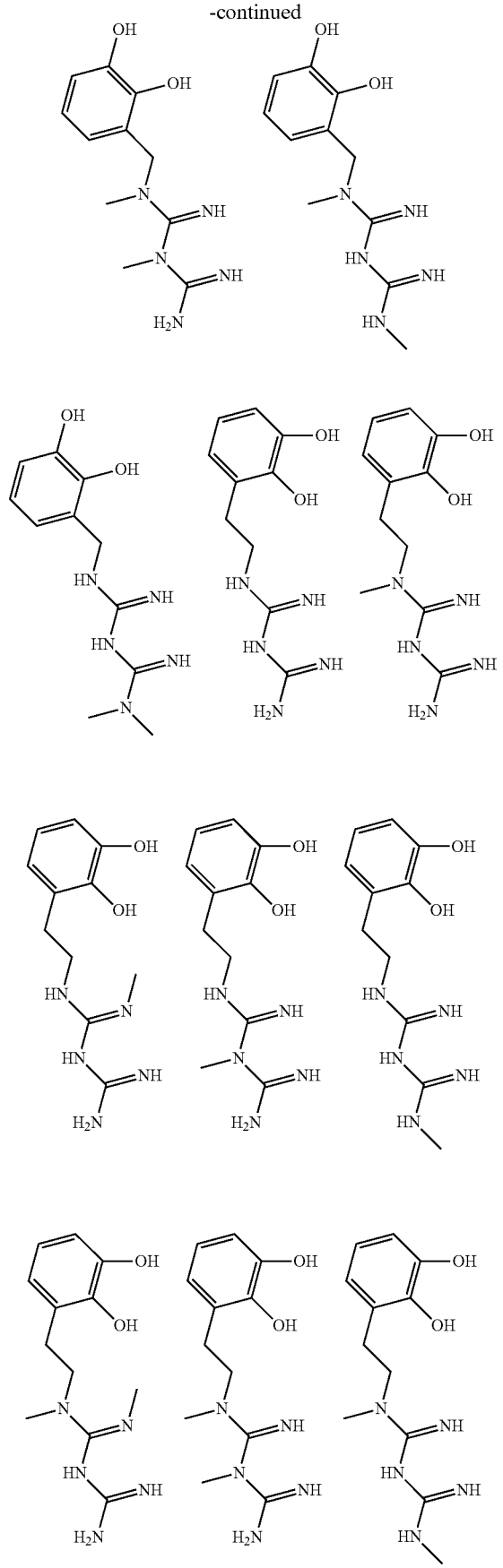
38
-continued
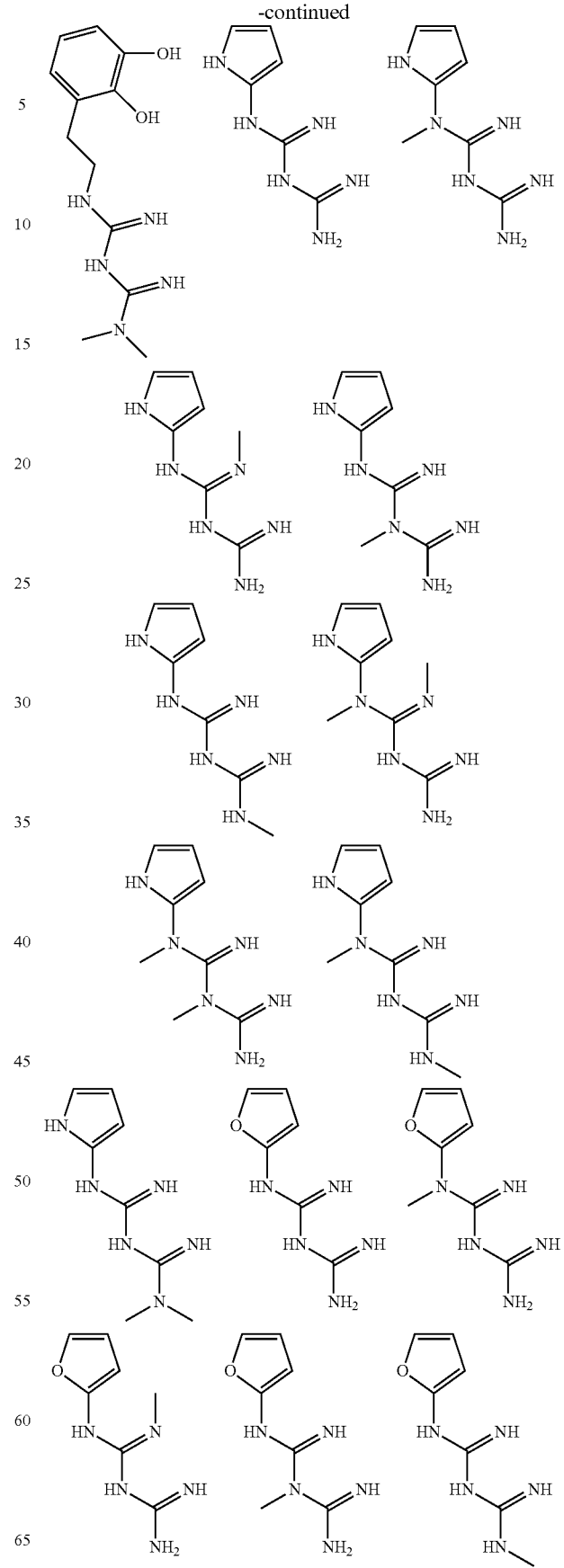

-continued
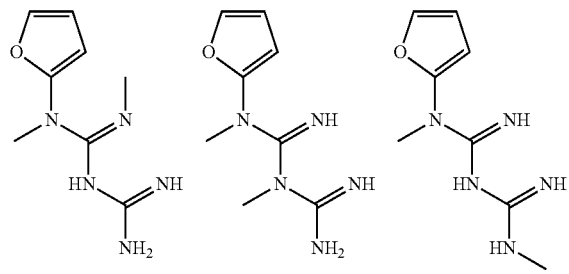
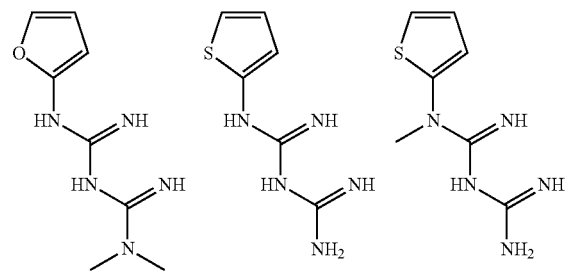
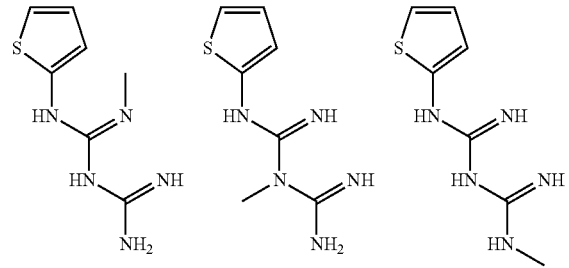
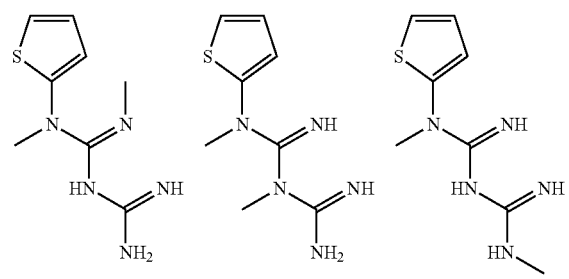
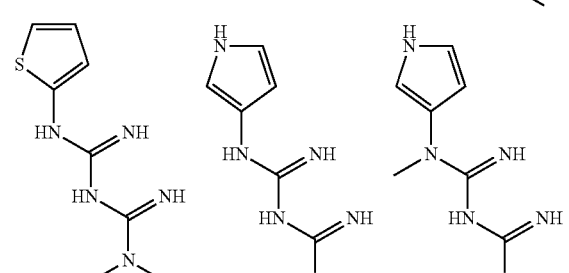
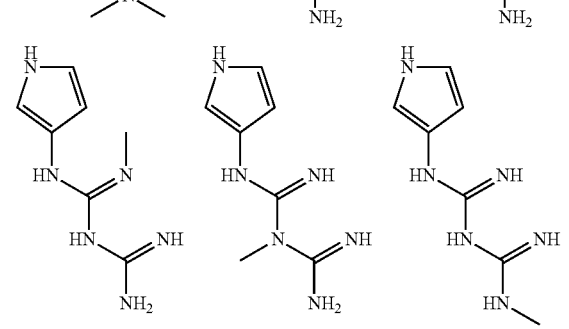
-continued
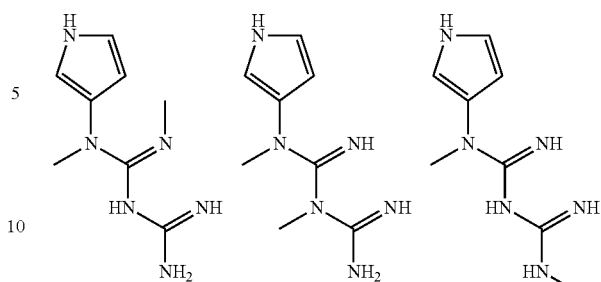
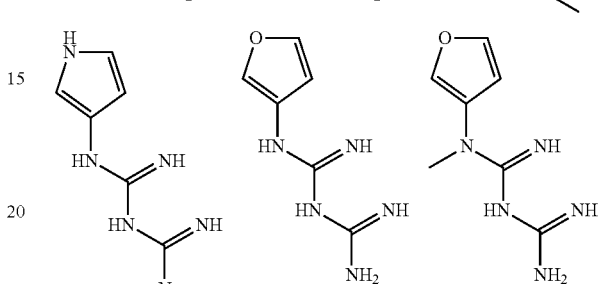
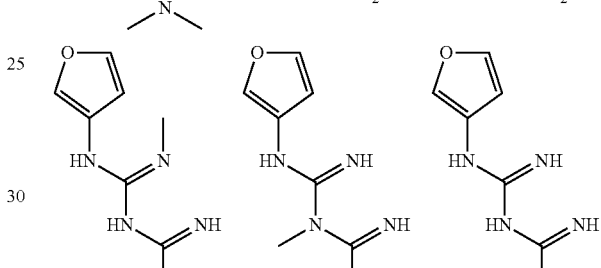
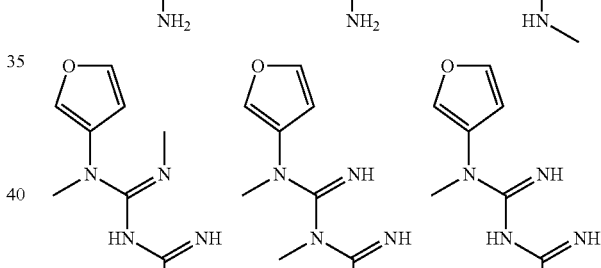
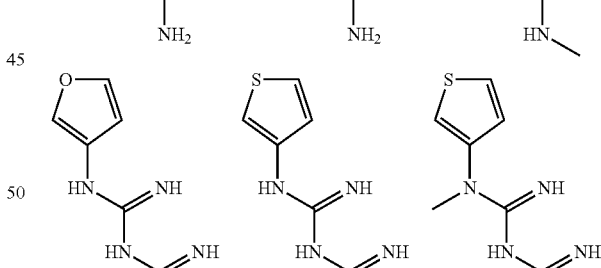
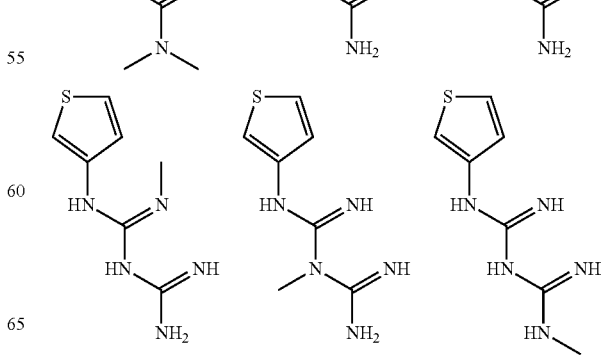

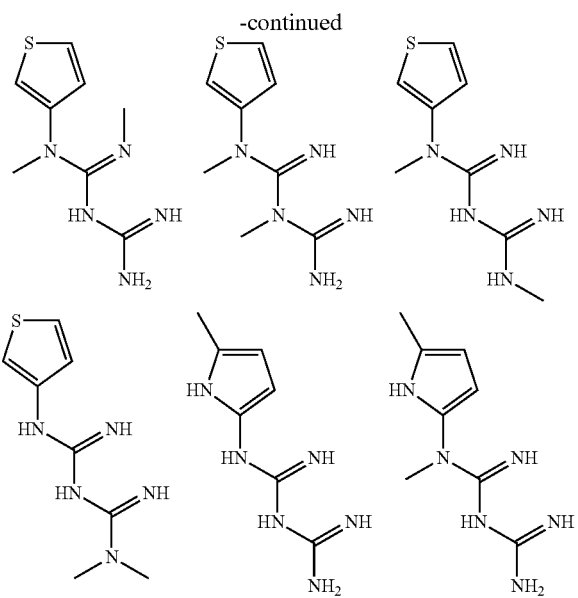
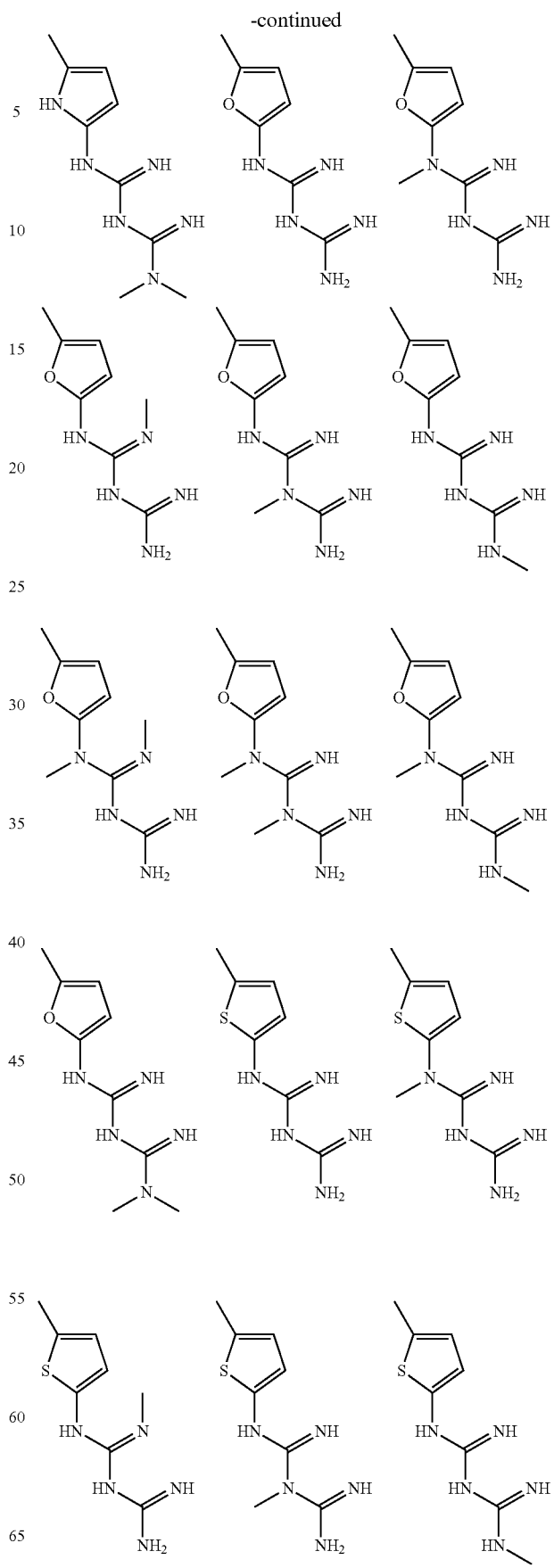

-continued
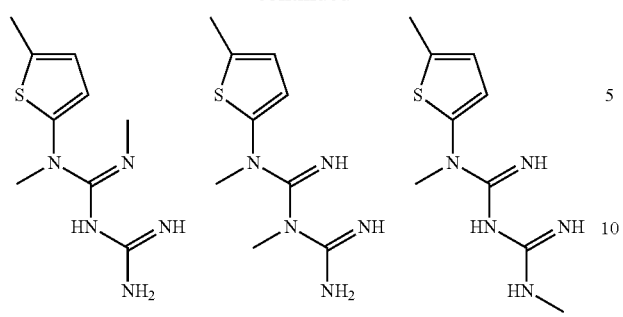
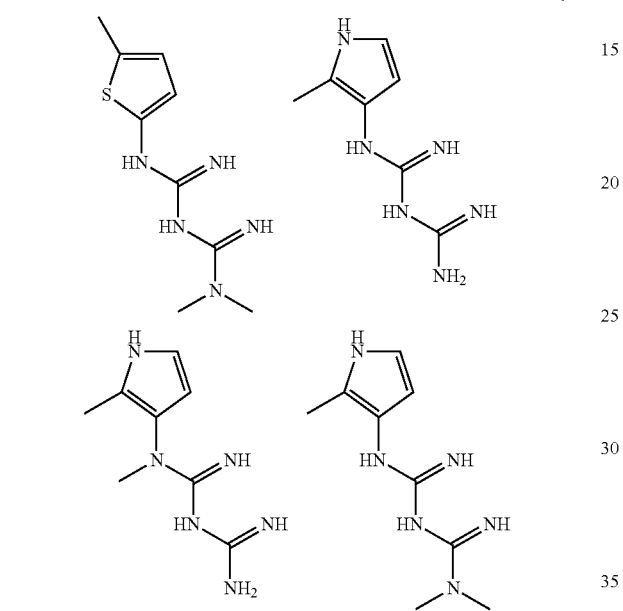
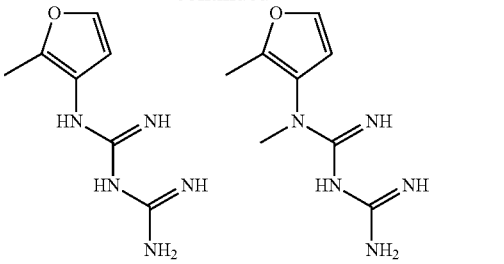
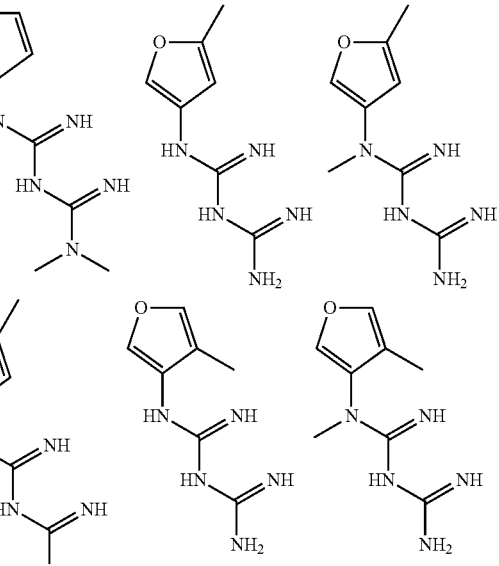
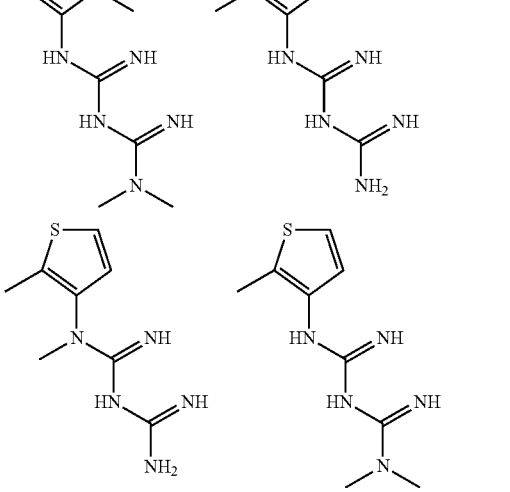
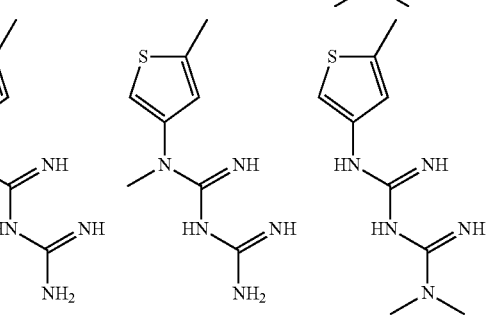

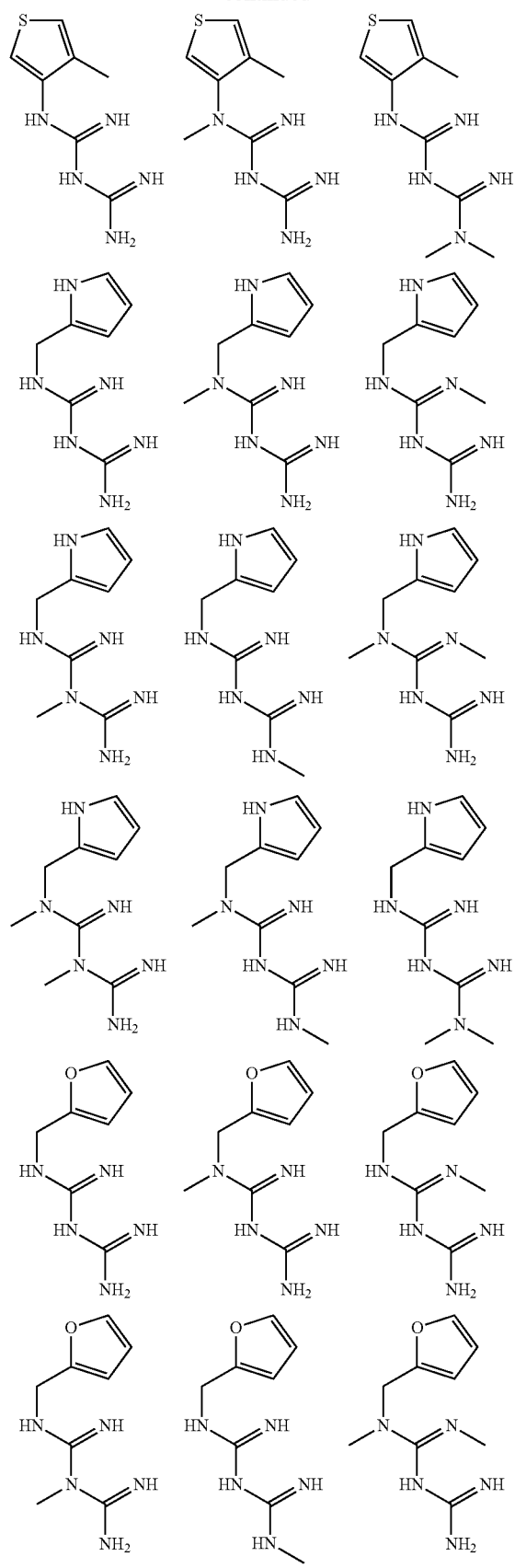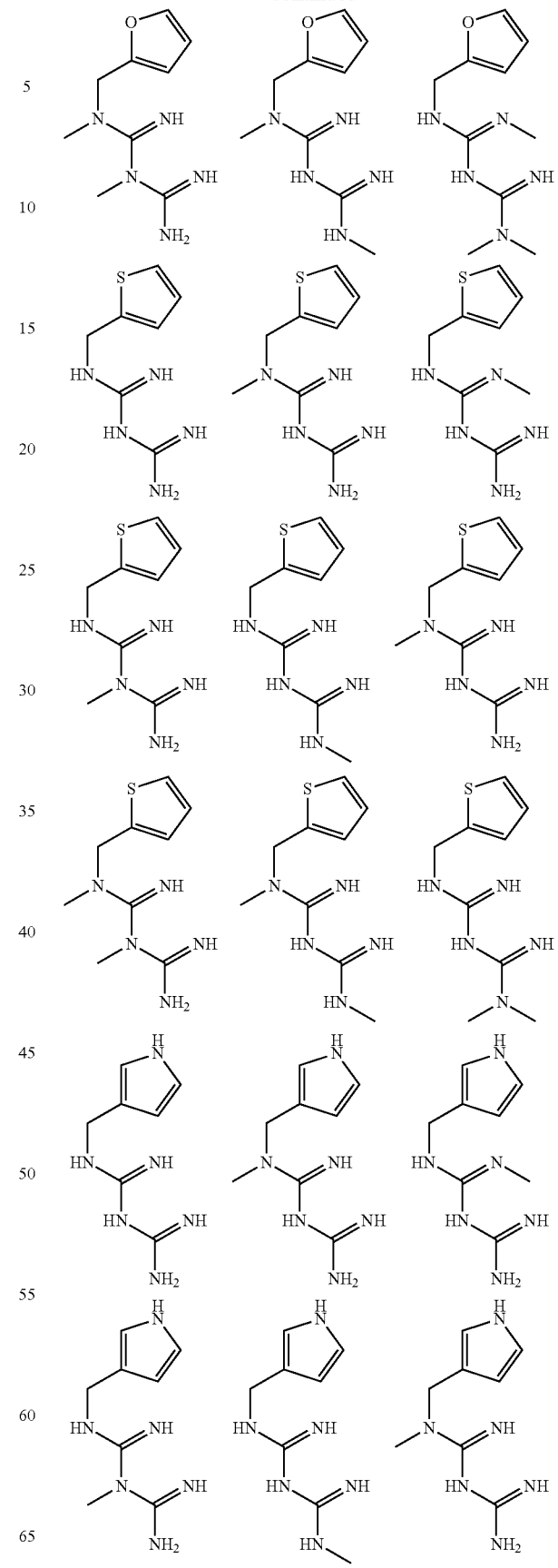

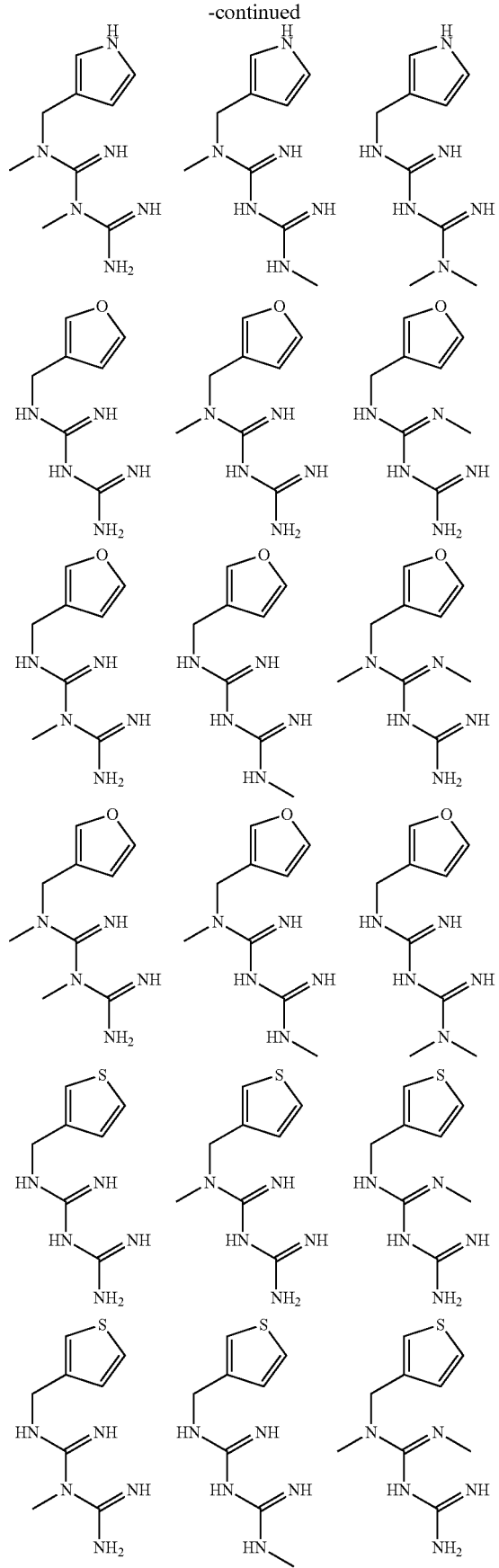
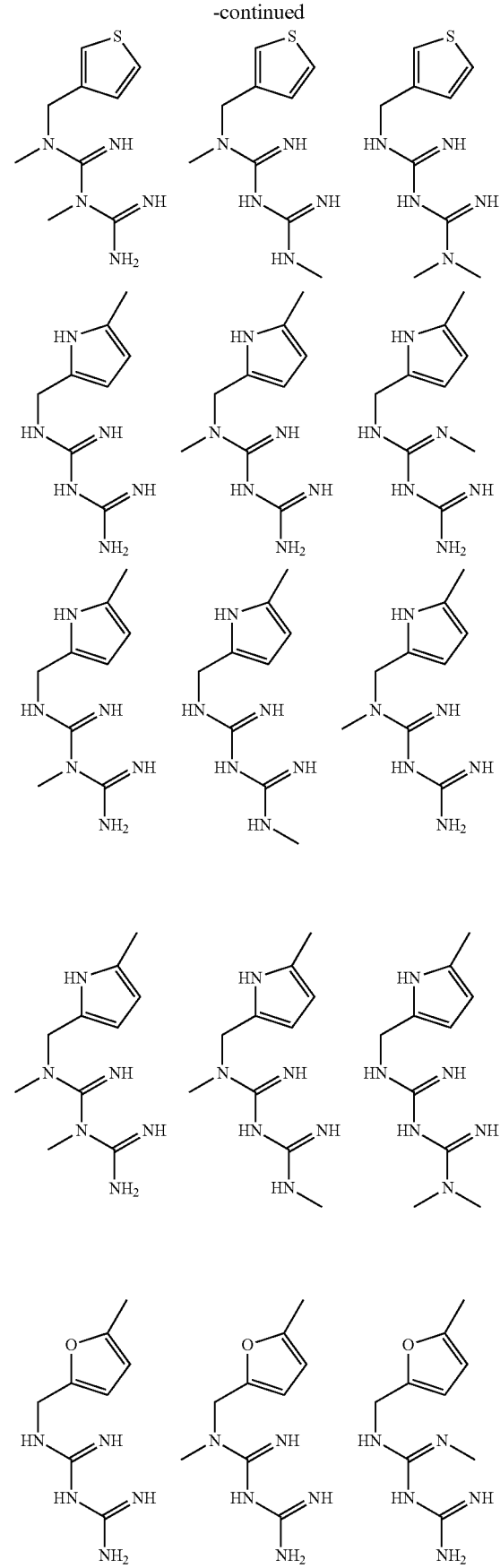

-continued
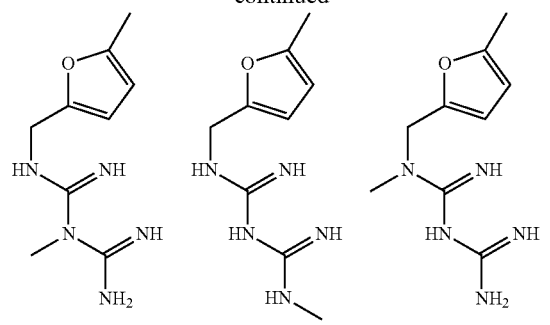
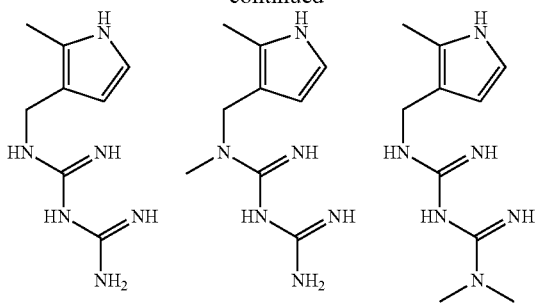
-continued
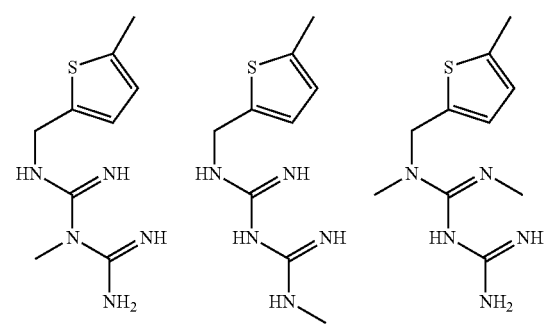
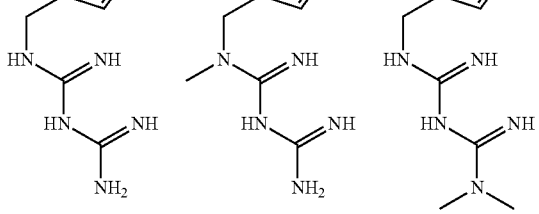
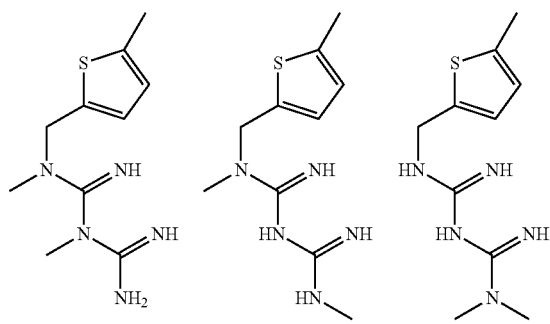
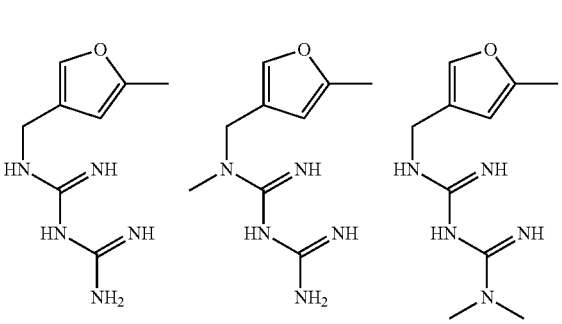

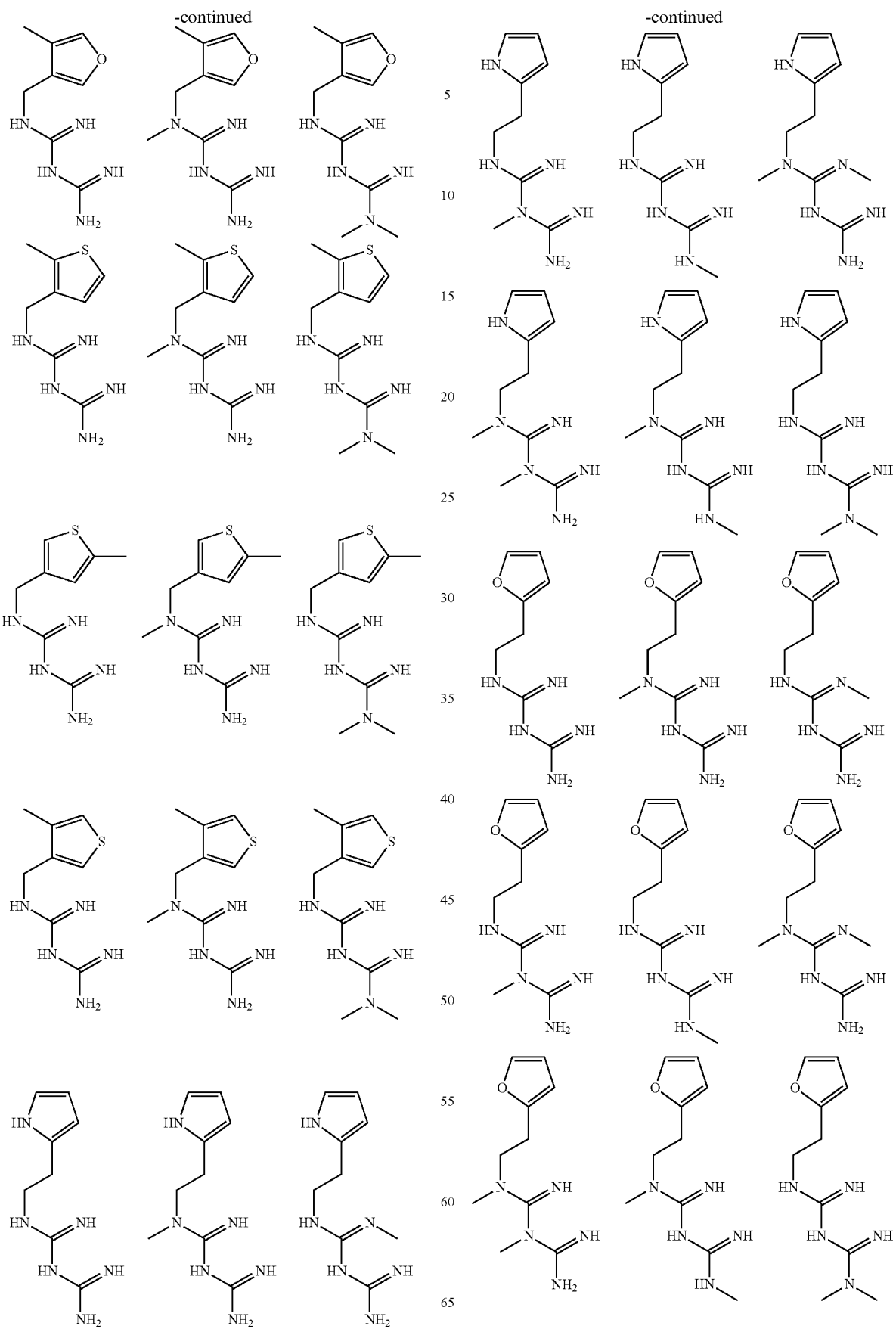

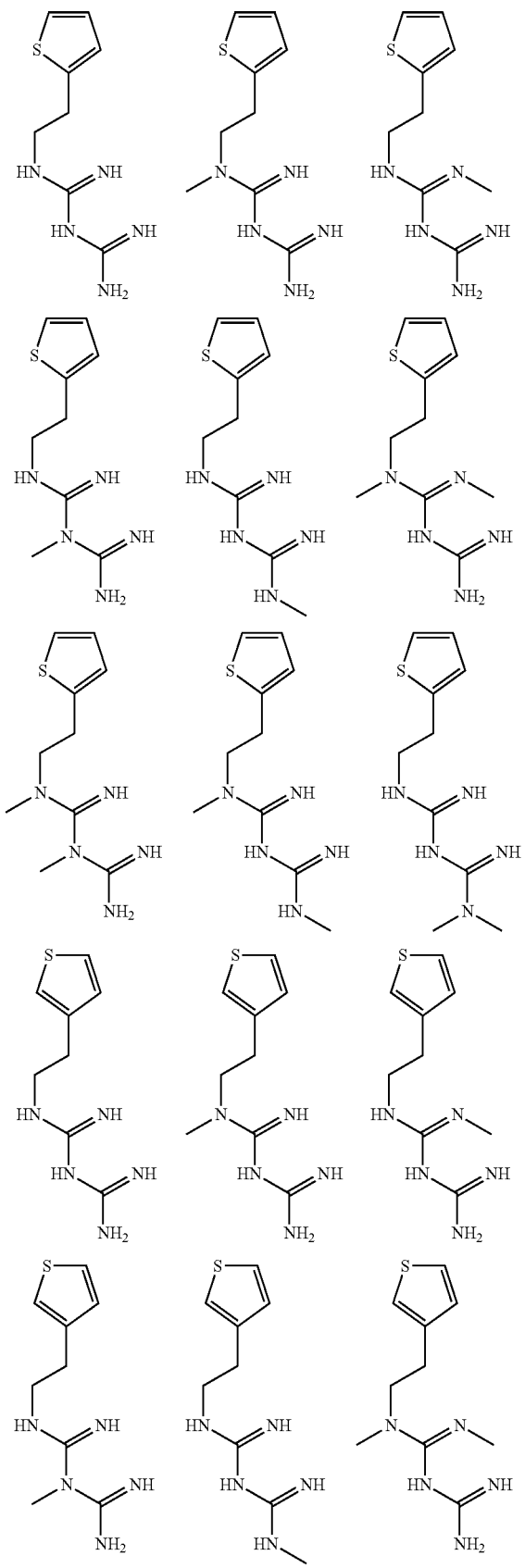
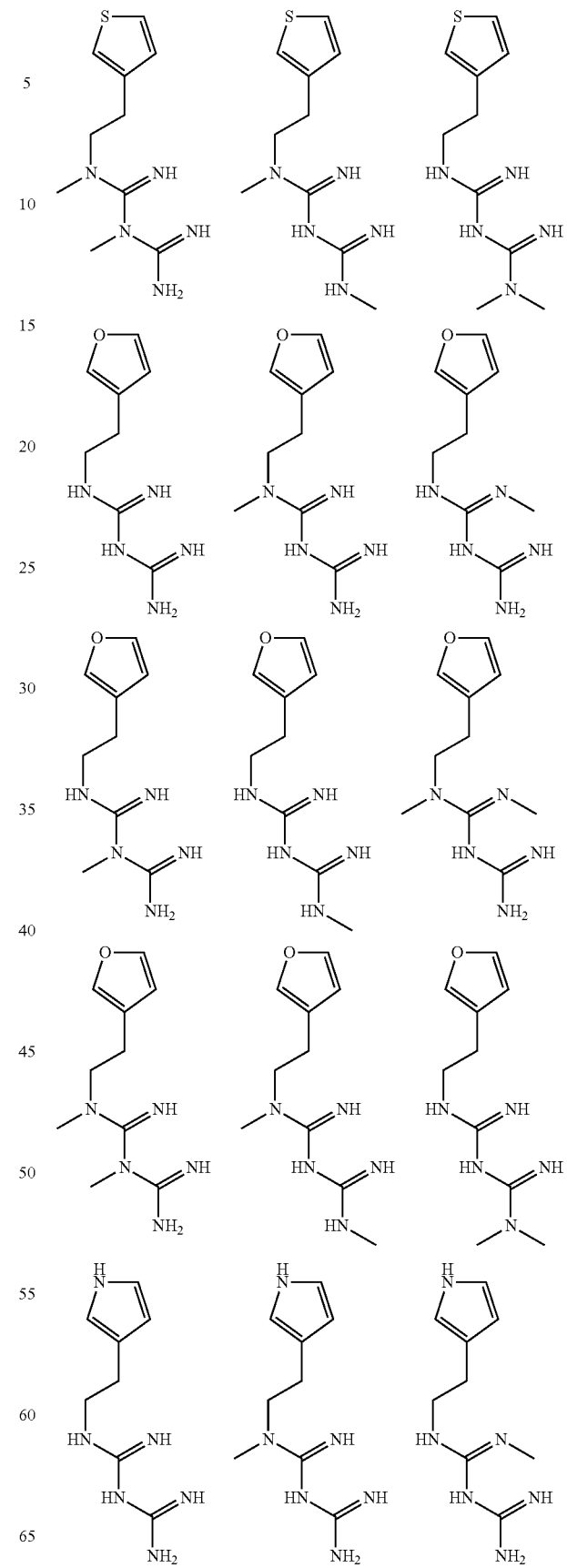

55 56
-continued -continued

57
-continued
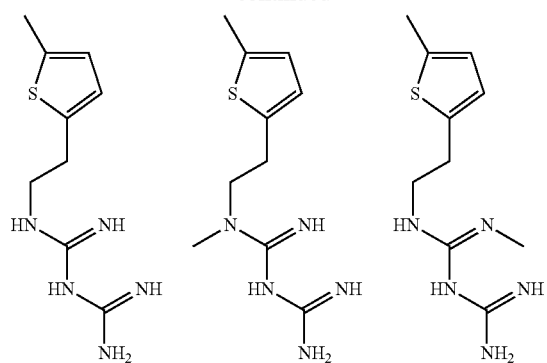
58
-continued
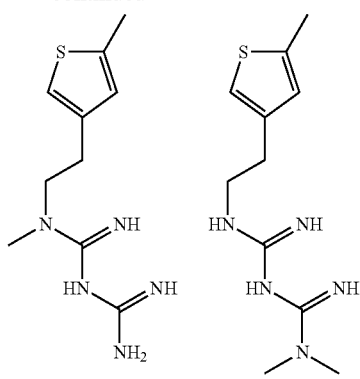
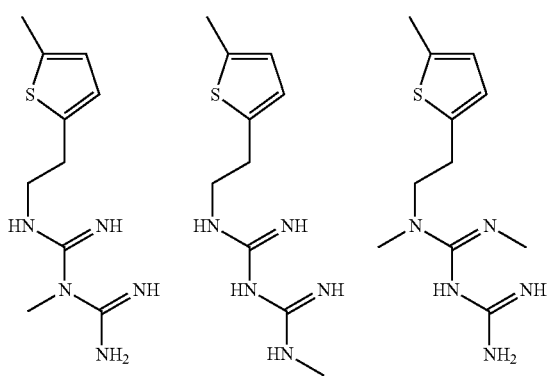
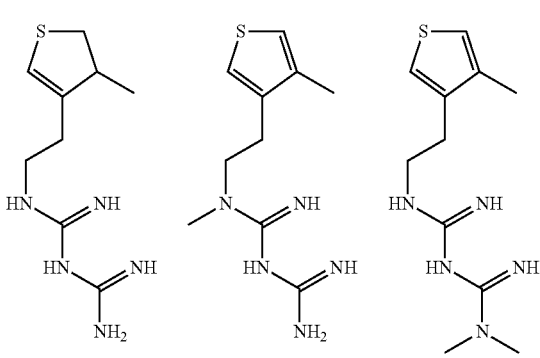
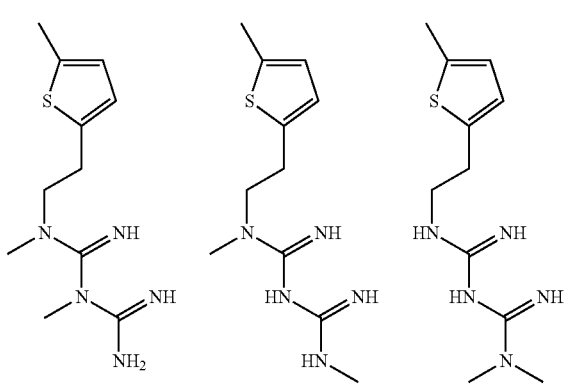
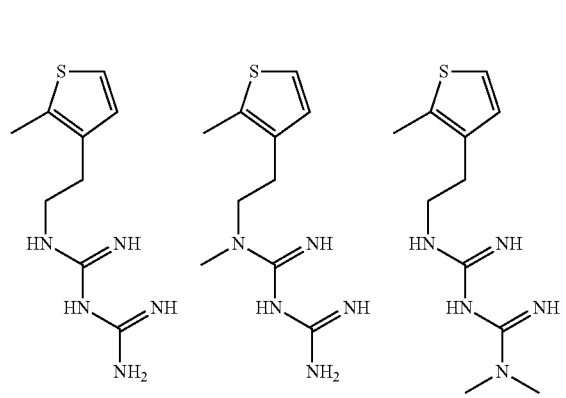
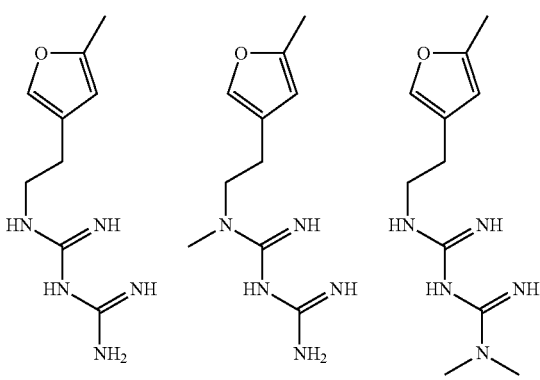

-continued

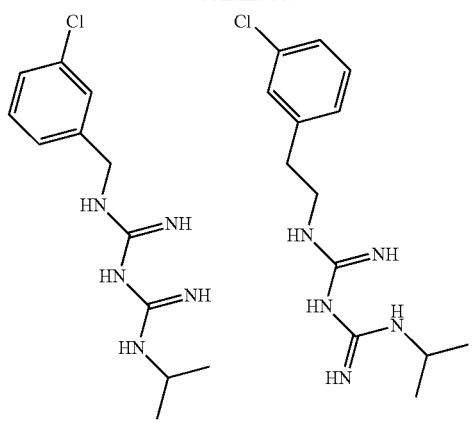
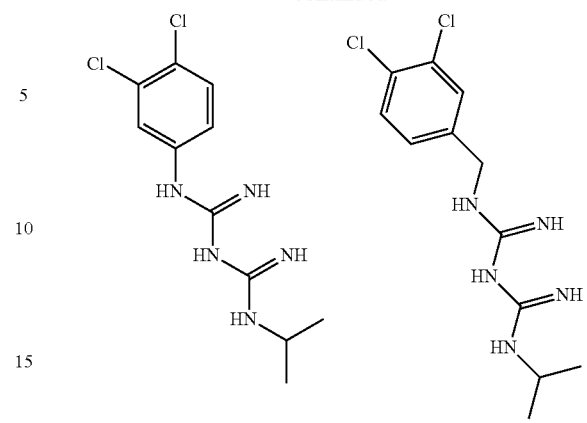
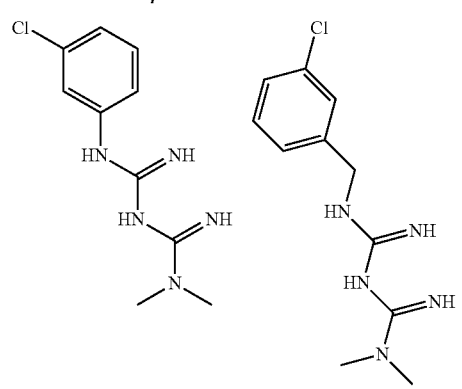
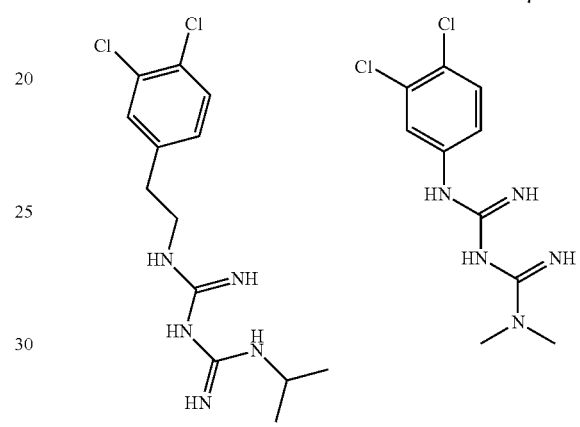
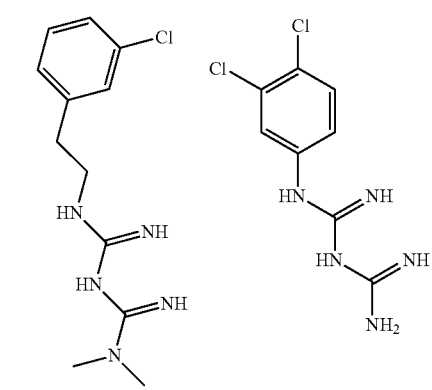
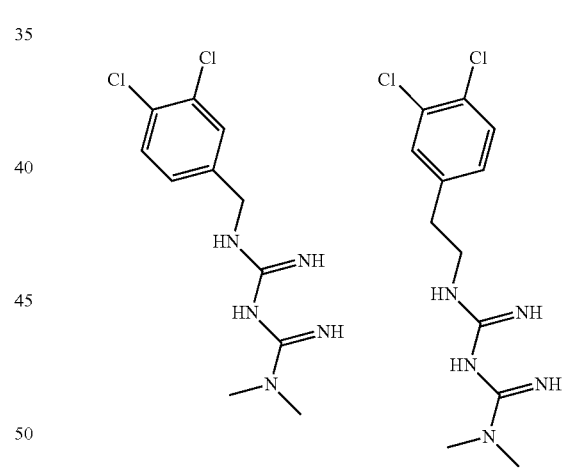
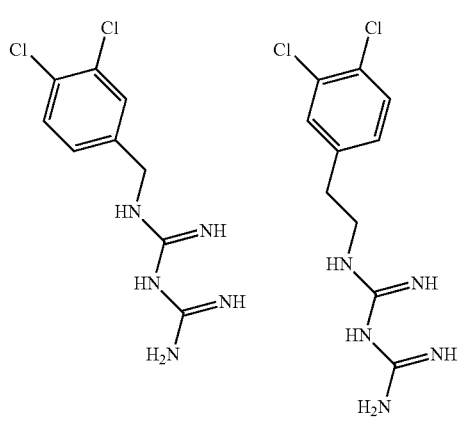
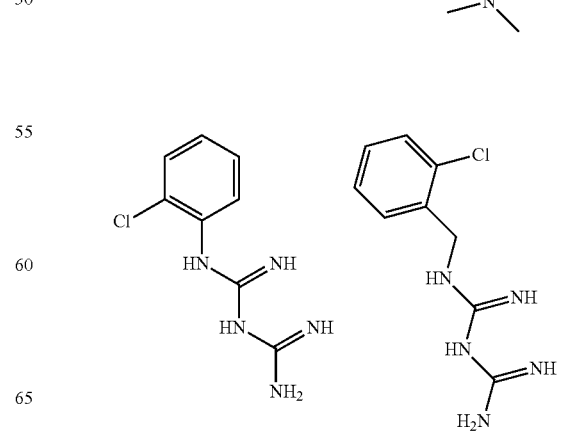

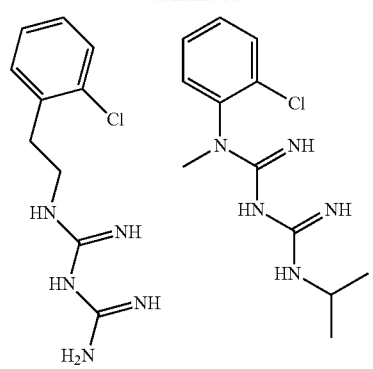
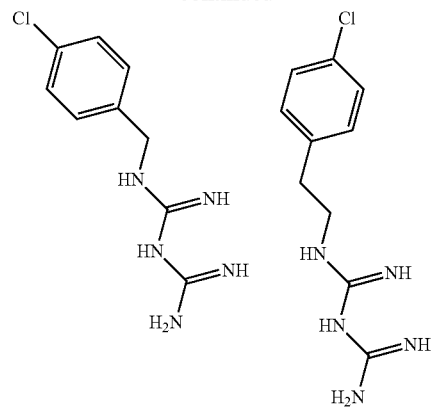
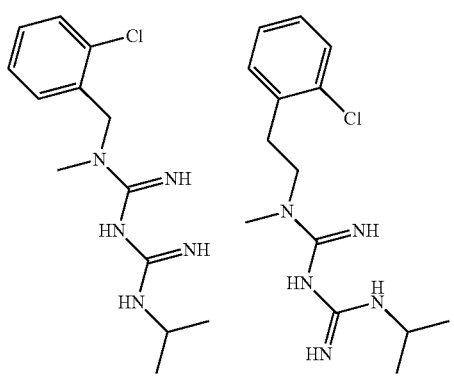
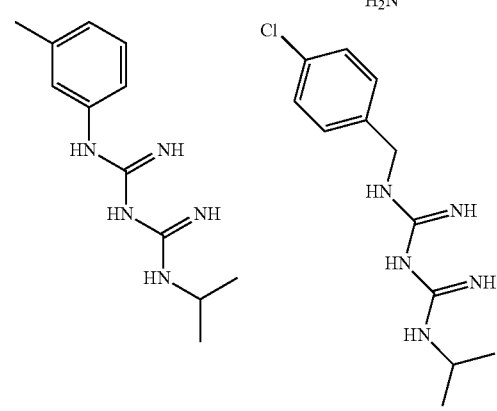
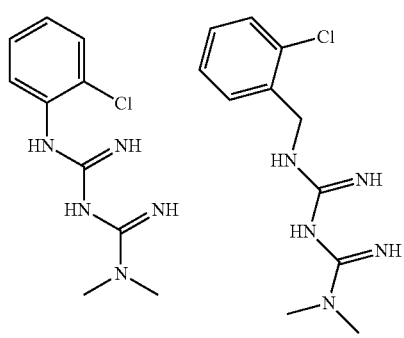
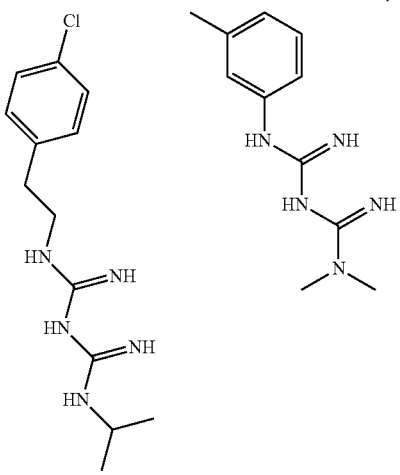
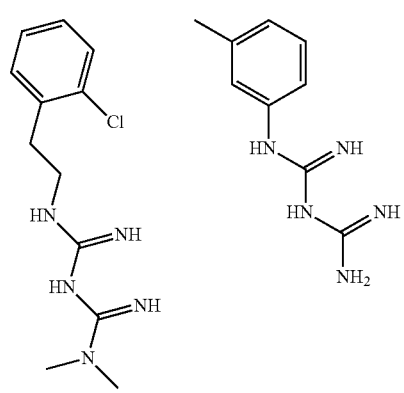
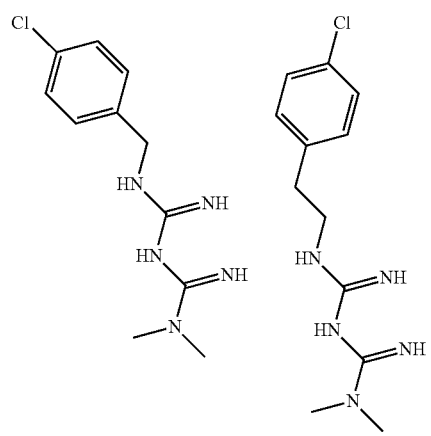 [SMILES: CN(C)C(=N)NC(=N)NCc1ccc(Cl)cc1 ; CN(C)C(=N)NC(=N)NCCc1ccc(Cl)cc1]

In other embodiments of compounds of Formula I, $R_6$ and $R_7$ are joined to form a bond, together forming a ring including the nitrogen atoms to which they are attached, thereby providing triazole compounds of Formula IA, which compounds may be used in connection with the compositions and methods of the disclosure. Substituent definitions, unless otherwise indicated, are the same as provided with reference to Formula I.

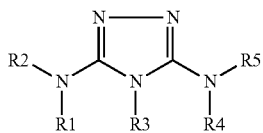

IA wherein:

$R_1$, $R_2$, $R_3$, $R_4$, and $R_5$, are independently selected from:
H, OH,
O—Rx, wherein Rx is alkyl, cycloalkyl, alkylcycloalkyl, acyl, ester, thioester;
optionally substituted alkyl (e.g., a $C_1$ to $C_{12}$ straight chain or branched chain alkyl optionally substituted with oxygen, silicon, sulphur or optionally substituted with OH, O-alkyl, SH, S-alkyl, $NH_2$, NH-alkyl); cycloalkyl (e.g., $C_3$ to $C_7$ cycloalkyl); alkylcycloalkyl (e.g., $C_4$ to $C_{12}$ alkylcycloalkyl); heterocycloalkyl (e.g., where the heterocycle comprises one or two hetero atoms selected from O, S, or N, including a $C_2$ to $C_6$ heterocycloalkyl); alkylheterocycloalkyl (e.g., where the heterocycle comprises one or two hetero atoms selected from O, S, or N, including a $C_3$ to $C_{11}$ alkylheterocycloalkyl, and including wherein when N is present in the heterocyclic ring, the nitrogen atom may be in the form of an amide, carbamate or urea); optionally substituted alkenyl (e.g., $C_1$ to $C_{12}$ straight chain or branched chain alkenyl optionally substituted with oxygen, silicon, sulphur or optionally substituted with OH, O-alkyl, SH, S-alkyl, $NH_2$, NH-alkyl); optionally substituted alkynyl (e.g., $C_1$ to $C_{12}$ straight chain or branched chain alkynyl optionally substituted with oxygen, silicon, sulphur or optionally substituted with OH, O-alkyl, SH, S-alkyl, $NH_2$, NH-alkyl);
optionally substituted aryl (e.g., phenyl, substituted phenyl, naphthyl, substituted naphthyl); optionally substituted alkylaryl (e.g., alkylphenyl, alkylsubstituted phenyl, alkylnaphthyl, alkylsubstituted naphthyl); optionally substituted heteroaryl (e.g., pyridyl, furanyl, thiophenyl, pyrrollyl, oxazolyl, isoxazolyl, thiazolyl, diazolyl, pyrazolyl, triazolyl all of which are optionally substituted); optionally substituted alkylheteroaryl; and
or $R_1$ and $R_2$ may together form a 3 to 8 membered heterocyclic ring, including the nitrogen atoms to which they are attached;
or $R_4$ and $R_5$ may together form a ring selected from the group aziridine, pyrrolyl, imidazolyl, pyrazolyl, indolyl, indolinyl, pyrrolidinyl, piperazinyl and piperidyl, including the nitrogen atoms to which they are attached.

In certain embodiments, O—Rx may be selected from:
O—$C_1$ to $C_8$ straight chain or branched chain alkyl; O—$C_3$ to $C_7$ cycloalkyl; O—$C_4$ to $C_8$ alkylcycloalkyl; O-acyl; O-esters; and O-thioesters.

In other embodiments, optional substitutions may include, e.g., OH, O-alkyl, SH, S-alkyl, $NH_2$, NH-alkyl. Further, an alkyl, alkenyl, alkynyl, etc. may be substituted with an oxygen, silicon, sulphur, etc. to form a heteroalkyl, heteroalkenyl, heteroalkynyl, etc.

In certain embodiments, each of: $R_3$, or $R_3$, and $R_4$, or $R_3$, $R_4$, and $R_5$, or $R_2$, $R_3$, $R_4$, and $R_5$ are independently selected from:
H, methyl, ethyl, propyl or isopropyl;
and each of the remaining substituent groups: $R_1$, $R_2$, $R_4$, and $R_5$, or $R_1$, $R_2$, and $R_5$, or $R_1$ and $R_2$, or $R_1$ and $R_2$, or $R_1$, respectively, are independently selected from:
H; optionally substituted alkyl (e.g., $C_1$ to $C_{12}$ straight chain or branched chain alkyl optionally hetero substituted with oxygen, silicon, sulphur or optionally substituted with OH, O-alkyl, SH, S-alkyl, $NH_2$, NH-alkyl); optionally substituted alkenyl (e.g., $C_1$ to $C_{12}$ straight chain or branched chain alkenyl optionally hetero substituted with oxygen, silicon, sulphur or optionally substituted with OH, O-alkyl, SH, S-alkyl, $NH_2$, NH-alkyl); optionally substituted alkynyl (e.g., $C_1$ to $C_{12}$ straight chain or branched chain alkynyl optionally hetero substituted with oxygen, silicon, sulphur or optionally substituted with OH, O-alkyl, SH, S-alkyl, $NH_2$, NH-alkyl); cycloalkyl (e.g., $C_3$ to $C_7$ cycloalkyl); alkylcycloalkyl (e.g., $C_4$ to $C_{12}$ alkylcycloalkyl); heterocycloalkyl (e.g., where the heterocycle comprises one or two hetero atoms selected from O, S, or N, including $C_2$ to $C_6$ heterocycloalkyl); alkylheterocycloalkyl (e.g., where the heterocycle comprises one or two hetero atoms selected from O, S, or N, including $C_3$ to $C_{11}$ alkylheterocycloalkyl, and including wherein when N is present in the heterocyclic ring, the nitrogen atom may be in the form of an amide, carbamate or urea); aryl (e.g., phenyl, substituted phenyl, naphthyl, substituted naphthyl); alkylaryl (e.g., alkylphenyl, alkylsubstituted phenyl, alkylnaphthyl, alkylsubstituted naphthyl); heteroaryl (e.g., pyridyl, furanyl, thiophenyl, pyrrollyl, oxazolyl, isoxazolyl, thiazolyl, diazolyl, pyrazolyl, triazolyl all of which are optionally substituted); alkylheteroaryl;
or $R_1$ and $R_2$ may together form a 3 to 8 membered heterocyclic ring, including the nitrogen atoms to which they are attached;
or $R_4$ and $R_5$ may together form a ring selected from the group aziridine, pyrrolyl, imidazolyl, pyrazolyl, indolyl, indolinyl, pyrrolidinyl, piperazinyl and piperidyl, including the nitrogen atoms to which they are attached.

Exemplary compounds and substituents of $R_1$, $R_2$, $R_3$, $R_4$, and $R_5$, of Formula IA are shown below. However, additional combinations of selections of substituents of $R_1$, $R_2$, $R_3$, $R_4$, and $R_5$ are envisioned.

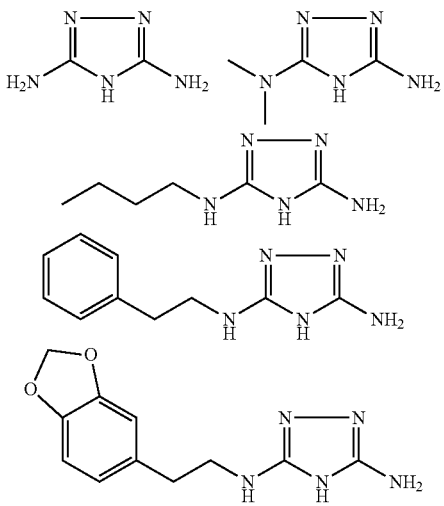

67
-continued
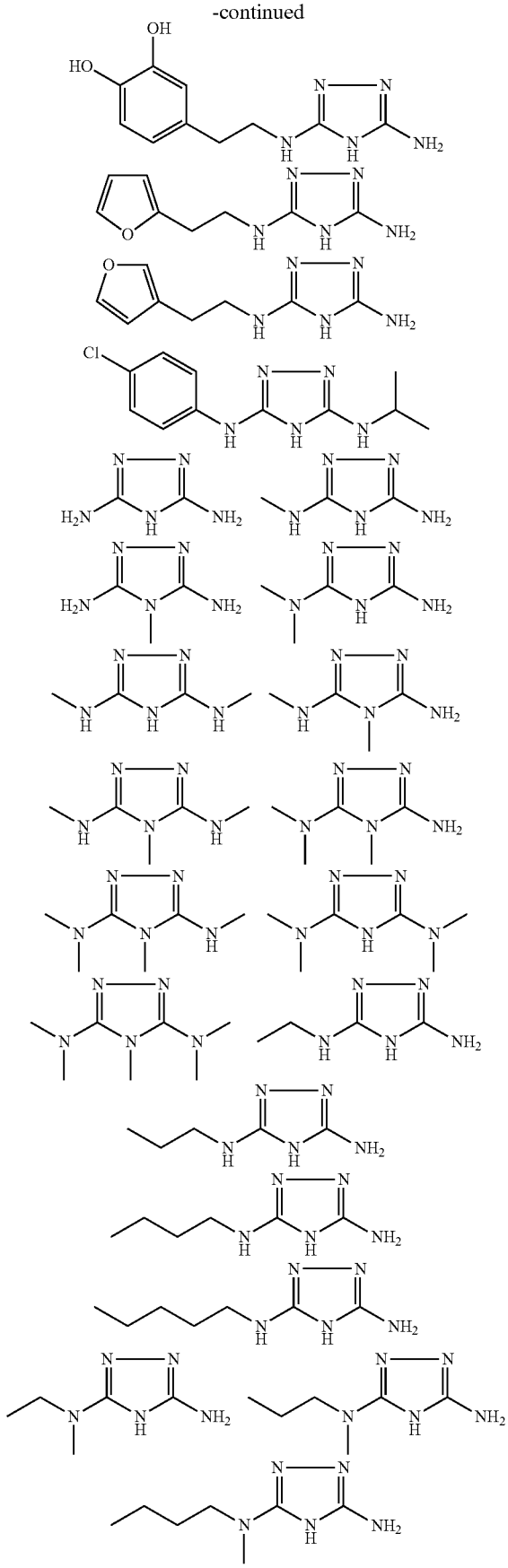
68
-continued
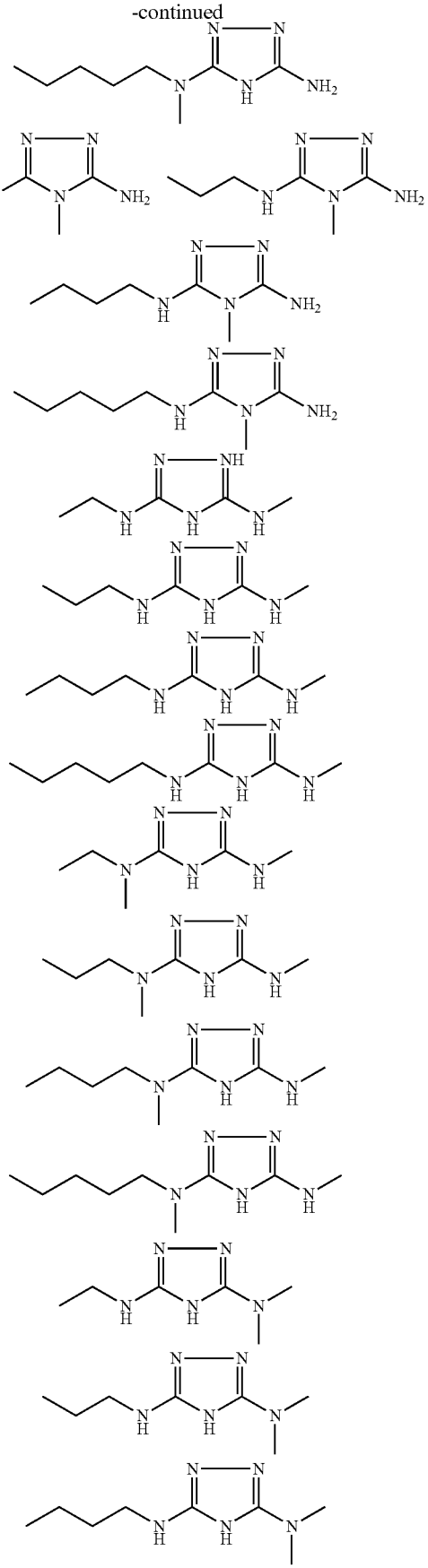

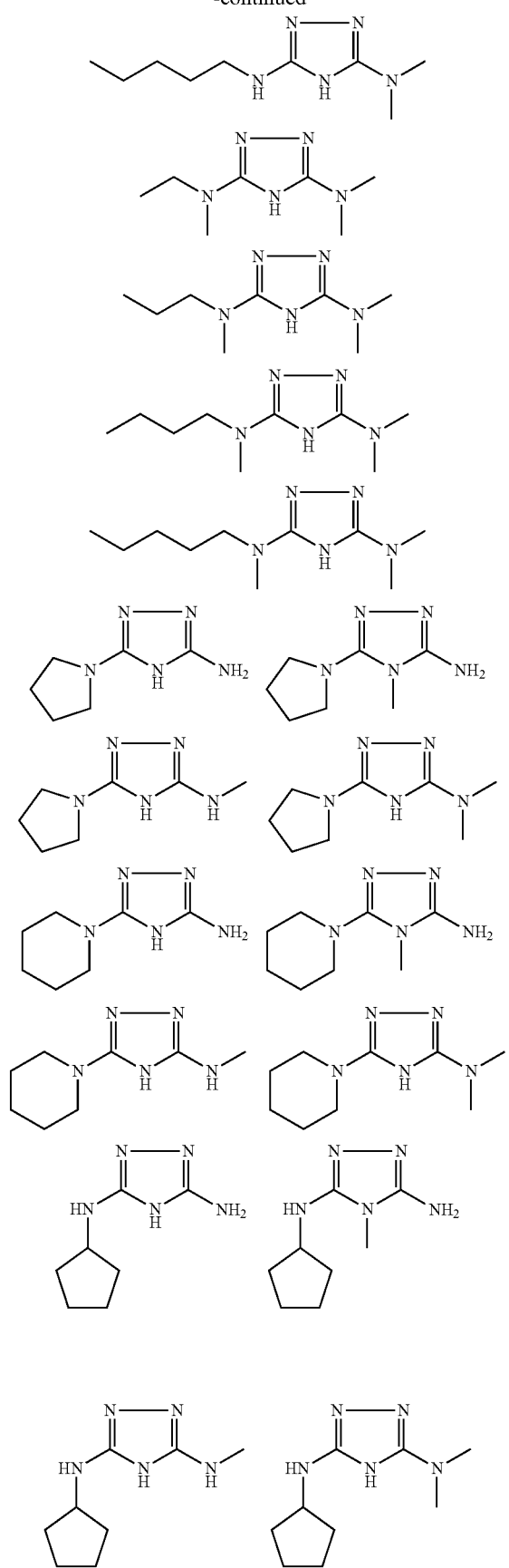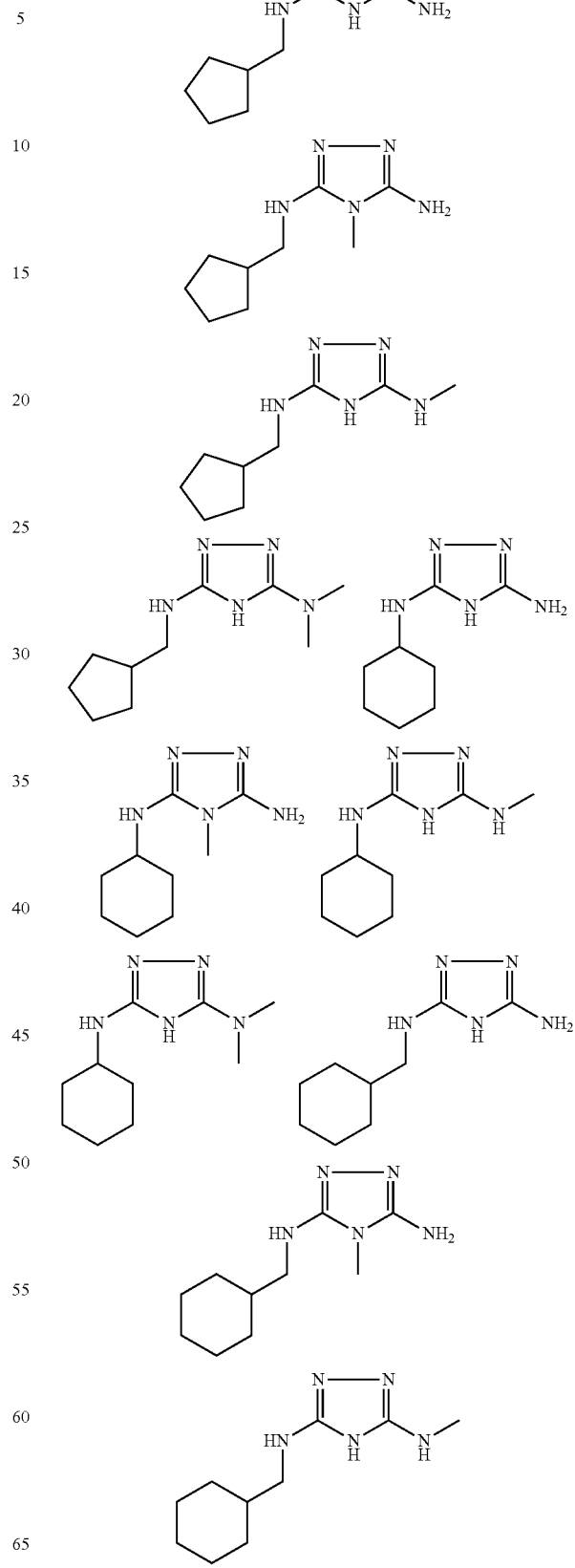

-continued
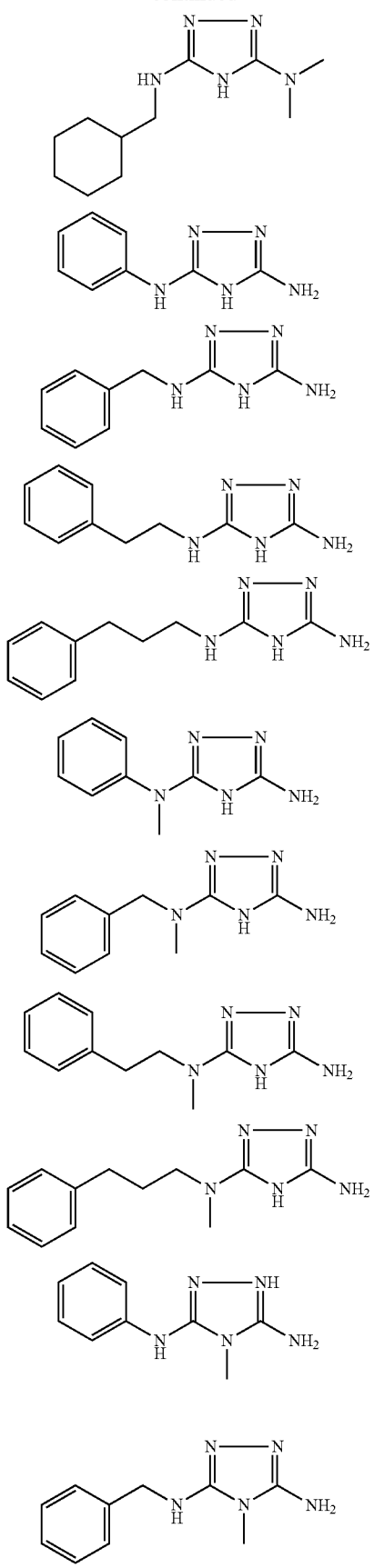
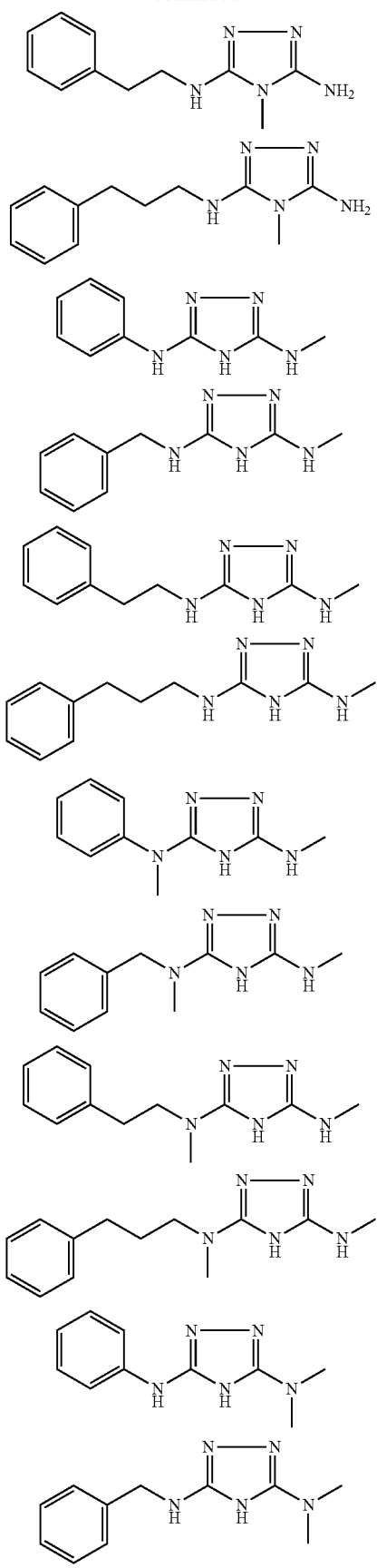

-continued
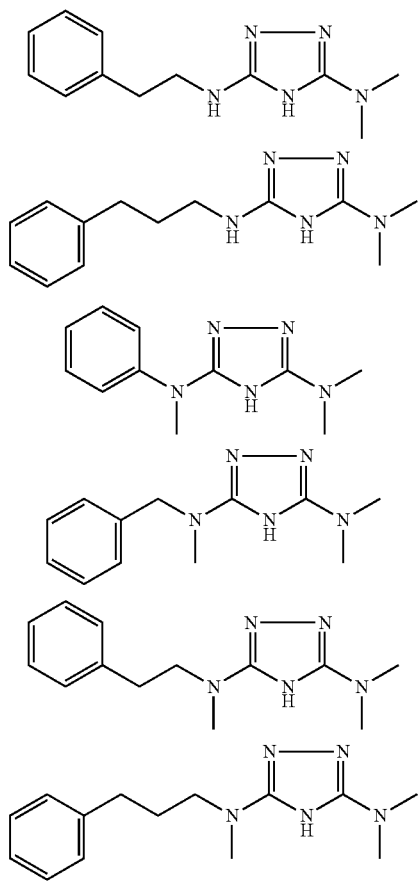
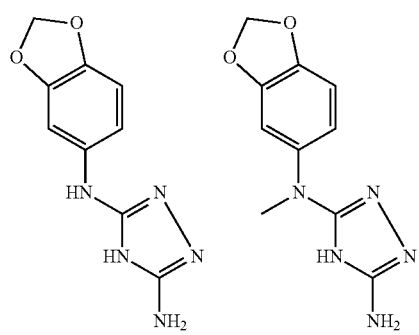
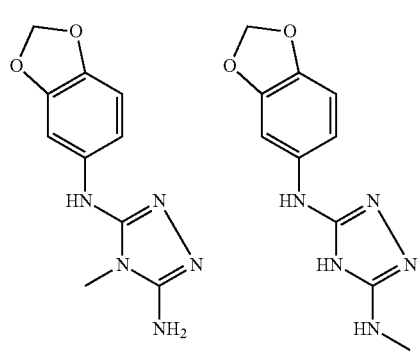
-continued
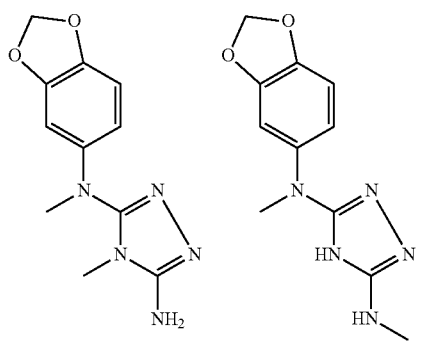
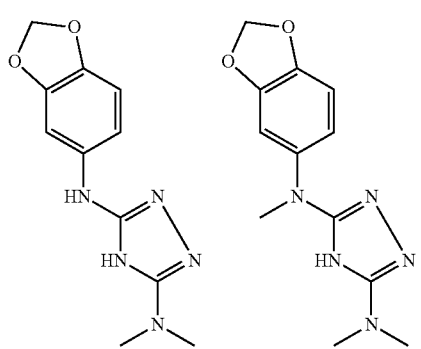
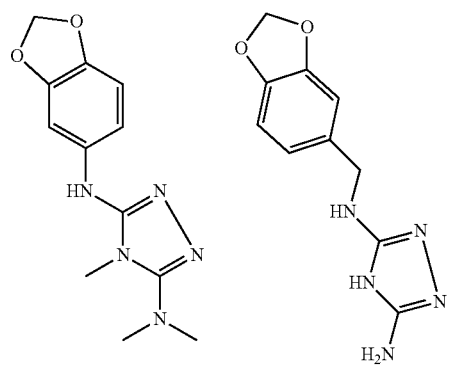
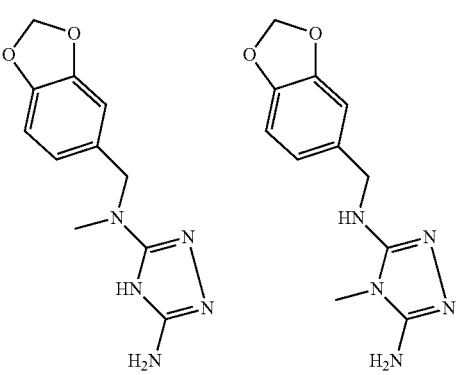

75
-continued
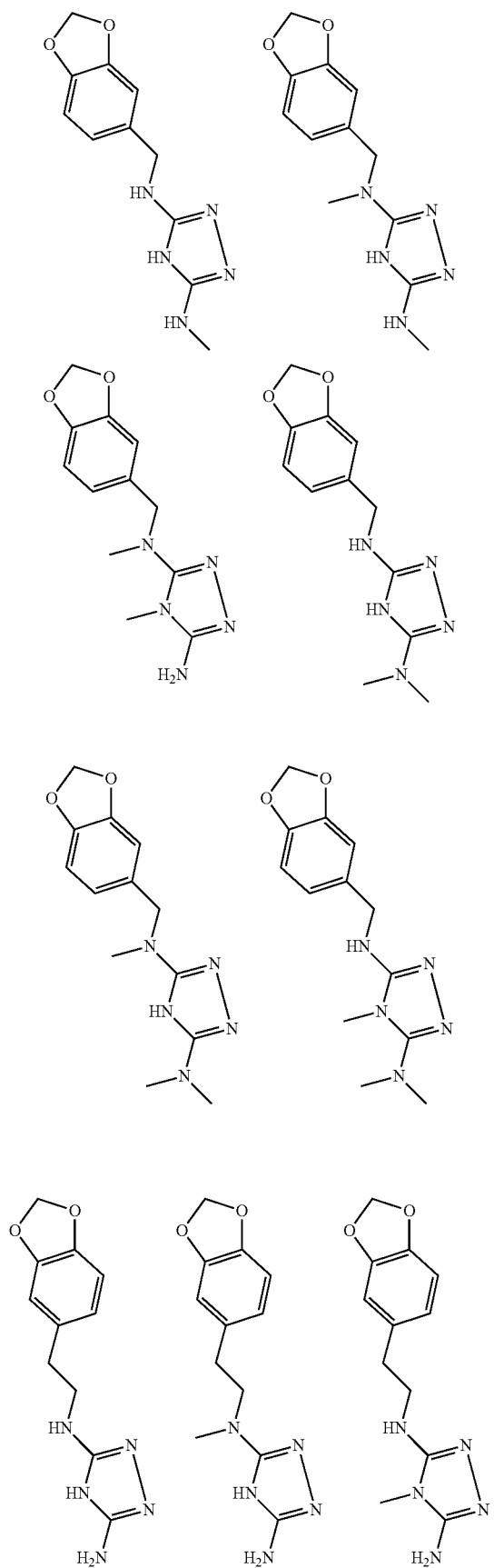
76
-continued
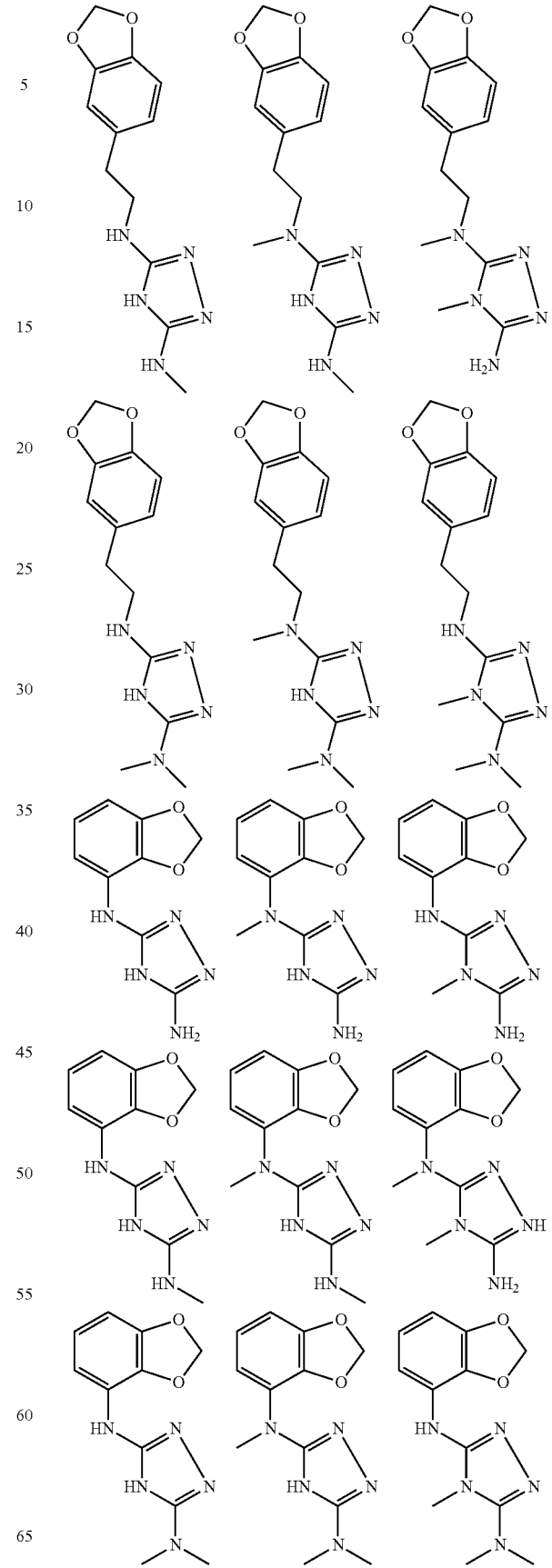

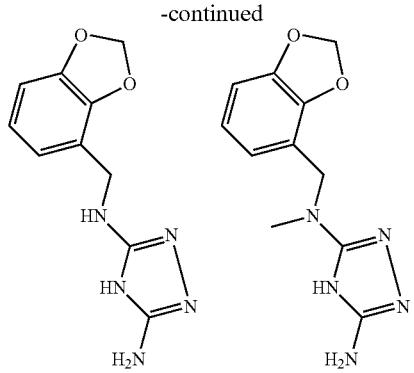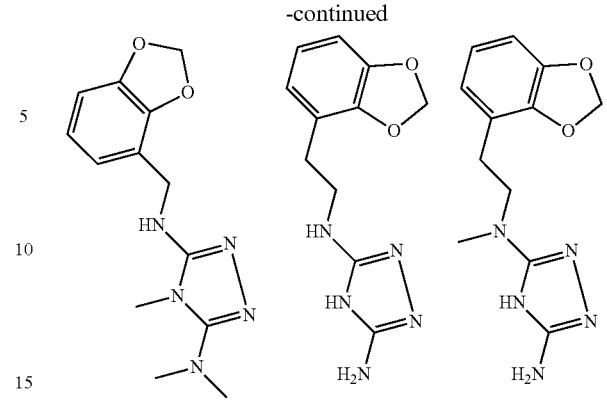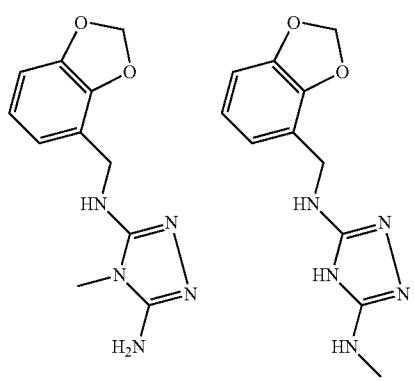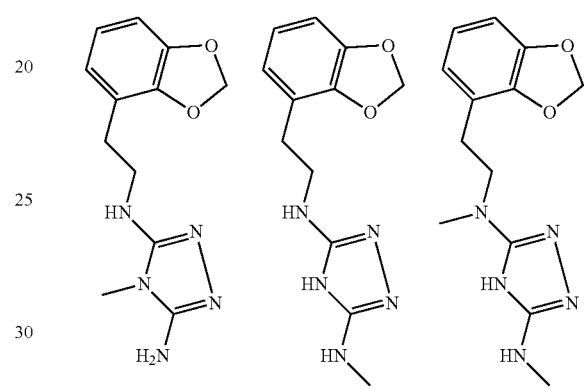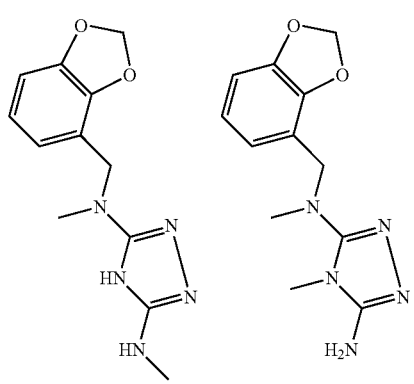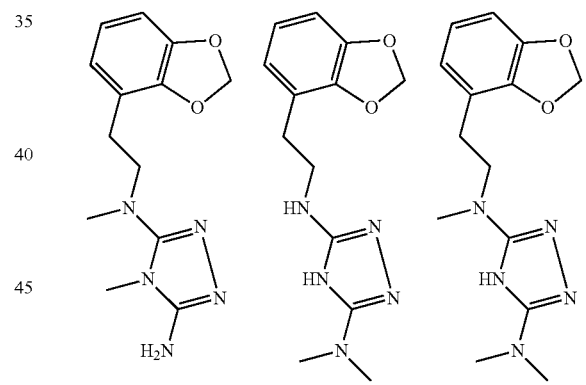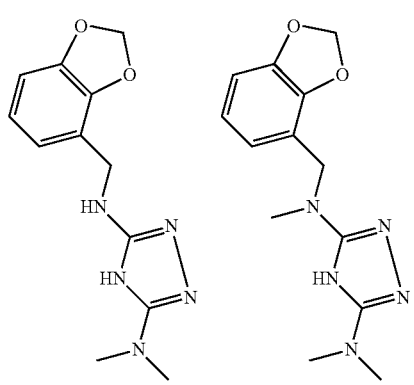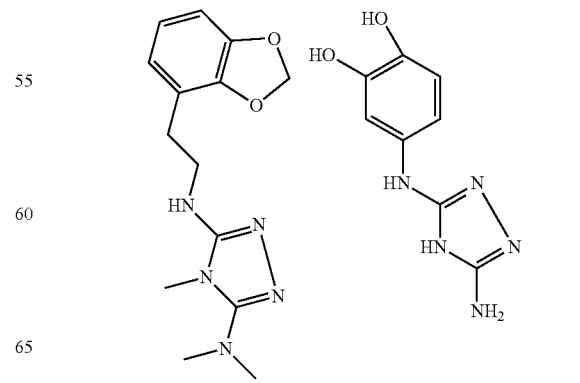

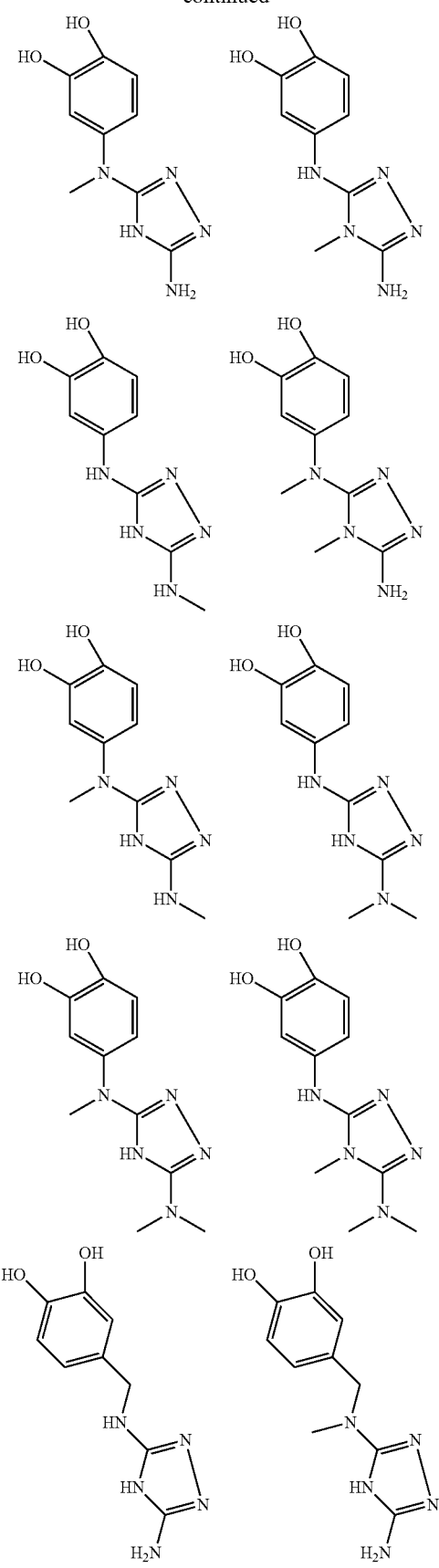
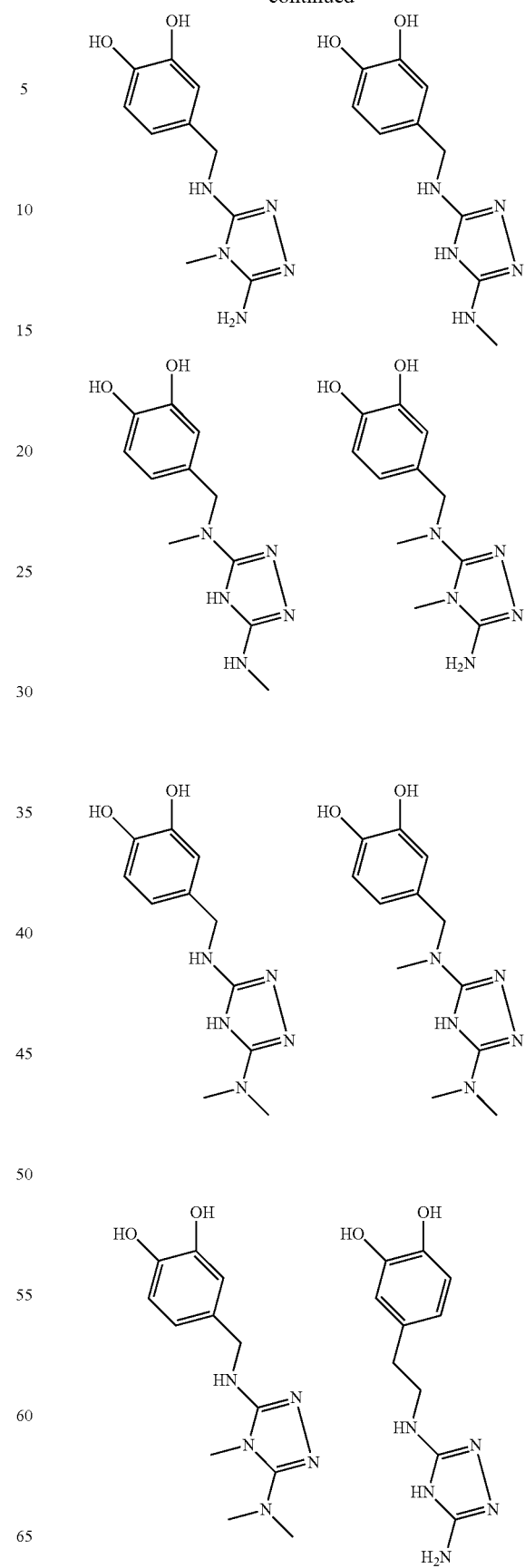

-continued
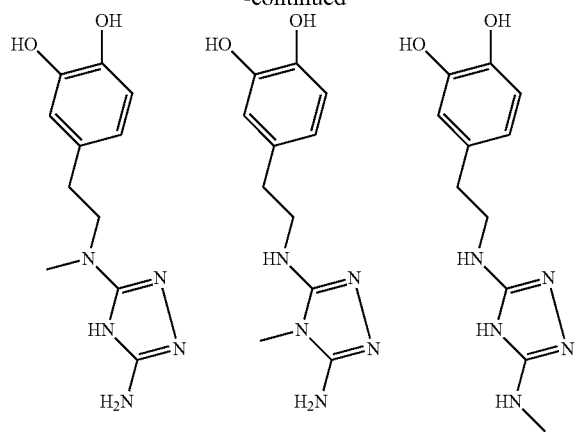
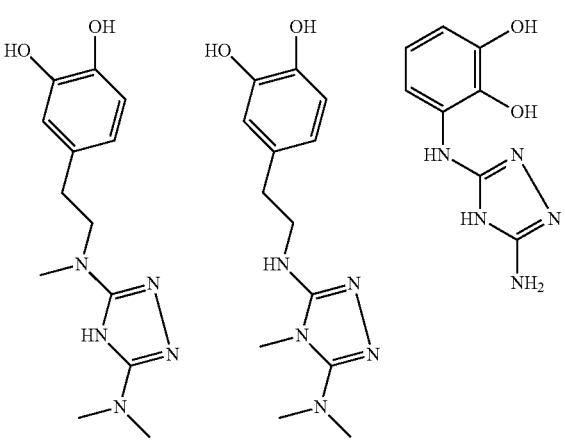
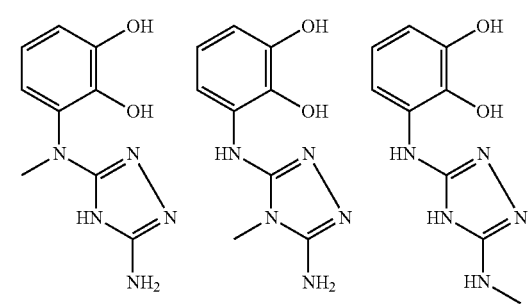
-continued
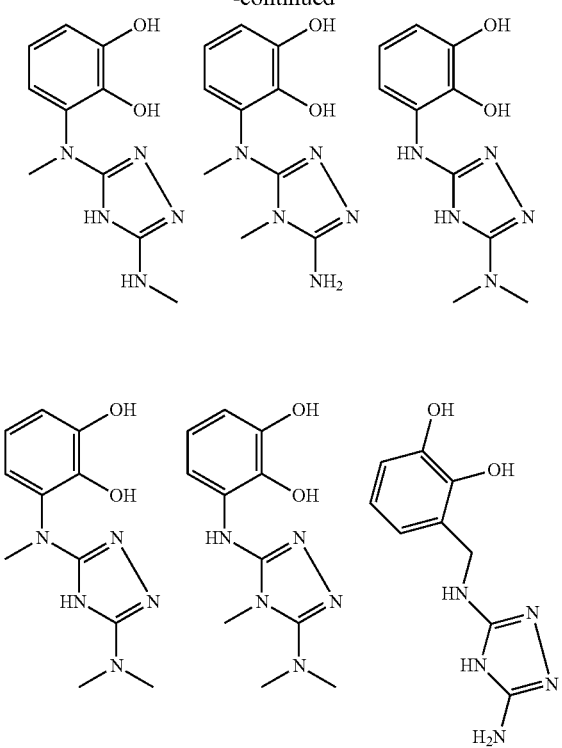
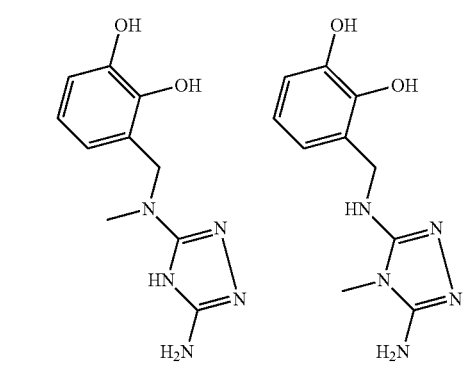
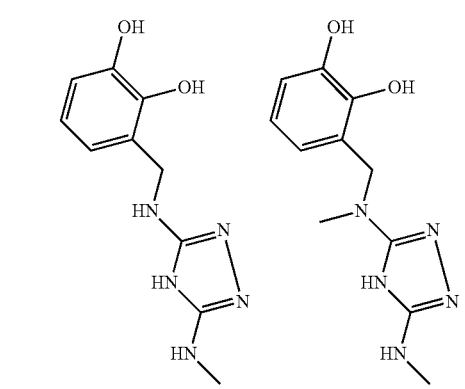

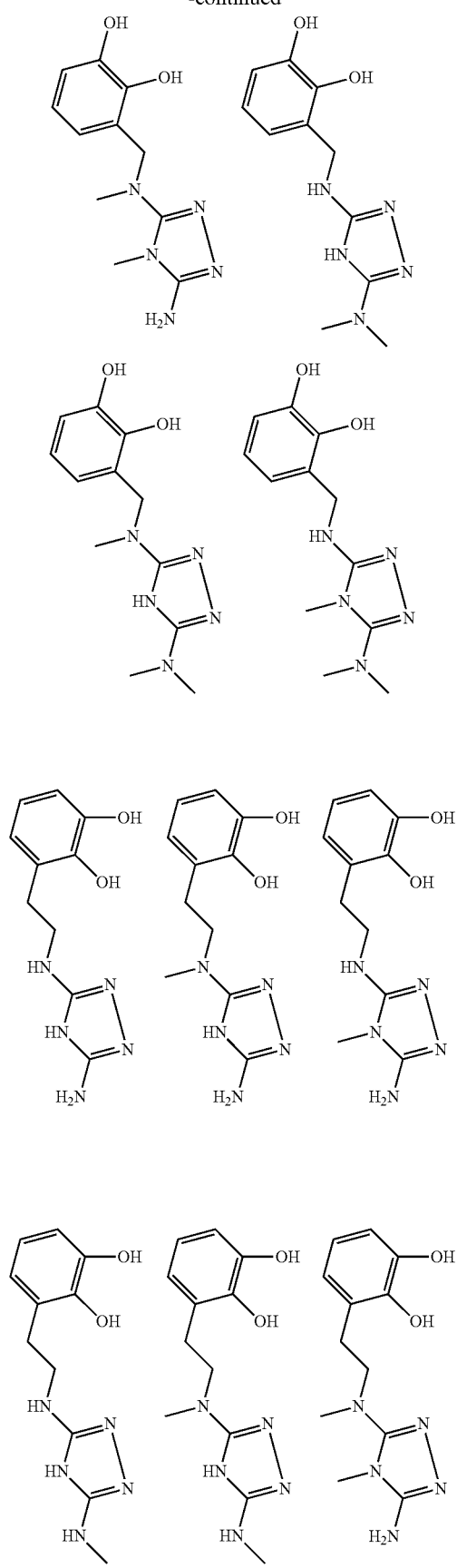
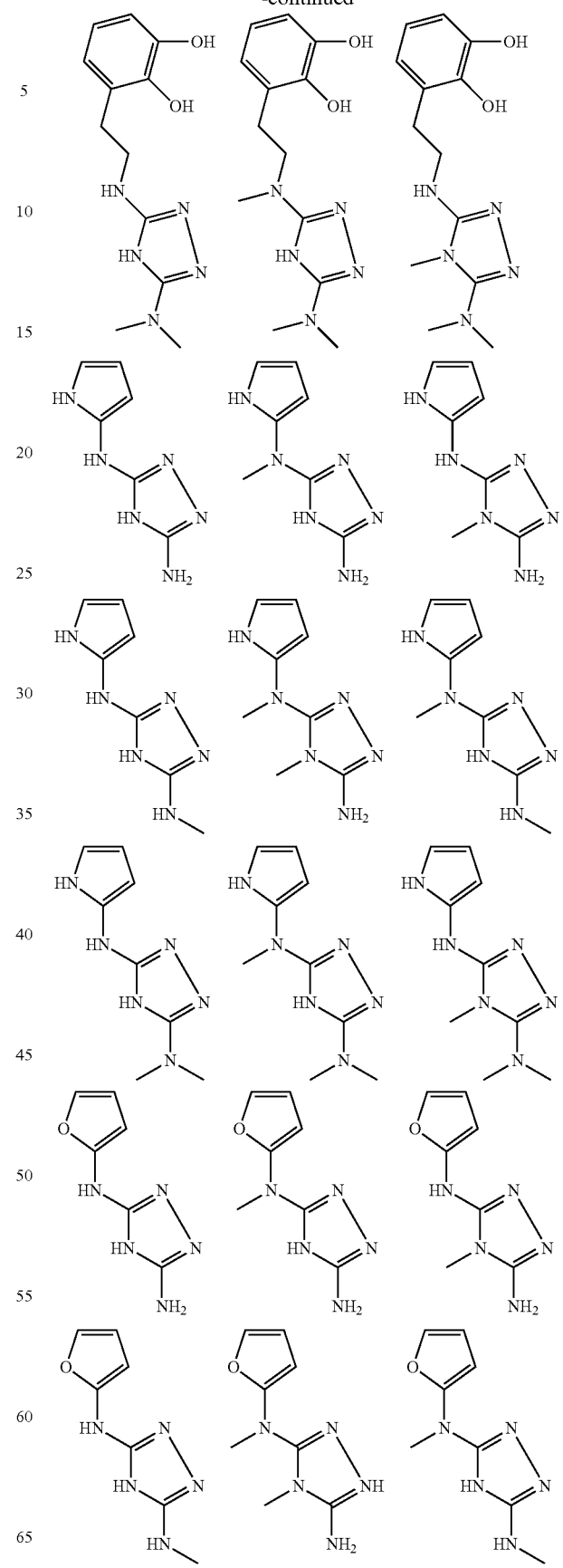

-continued
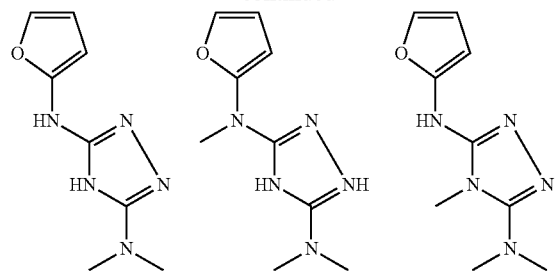
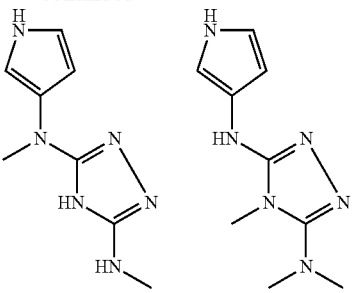
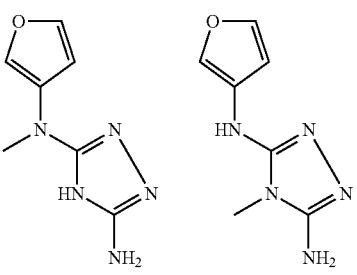
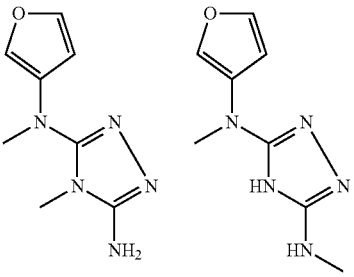
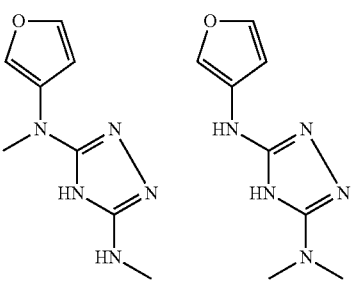
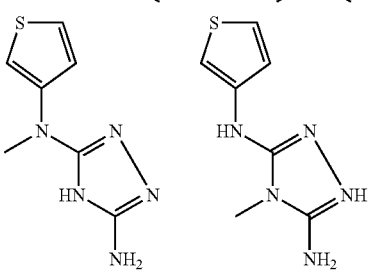
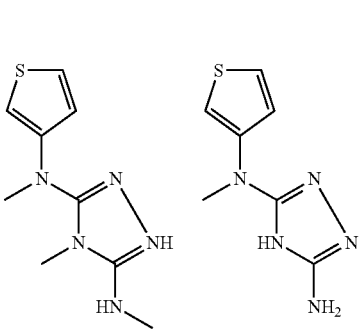

-continued

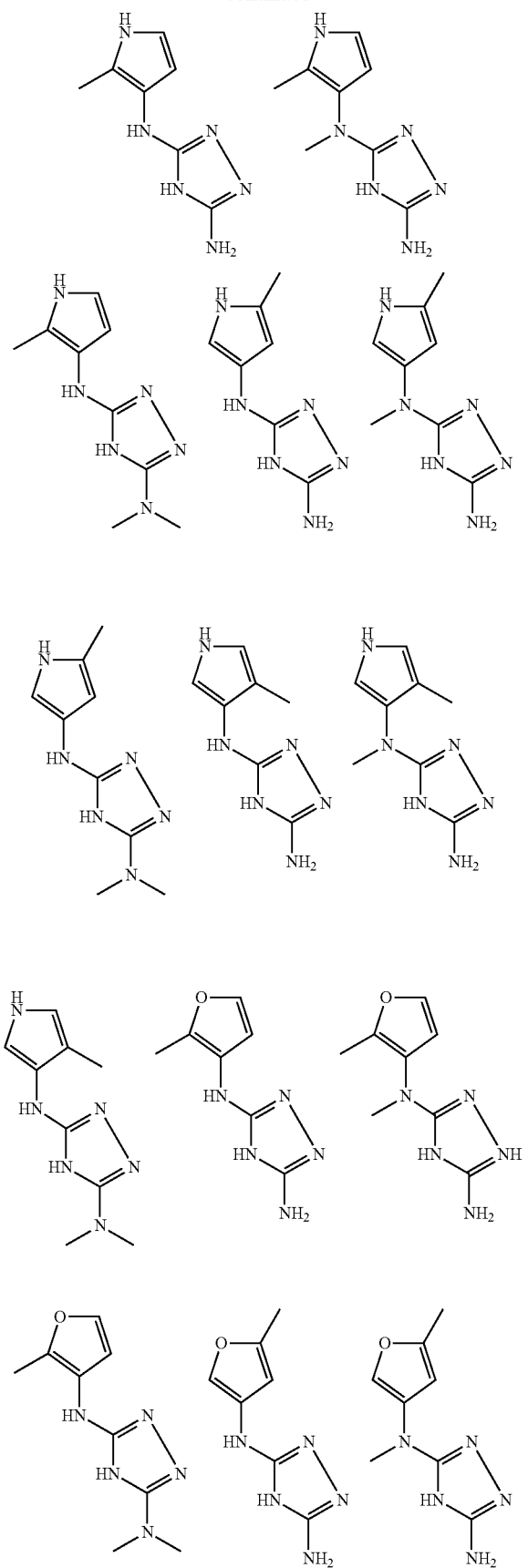
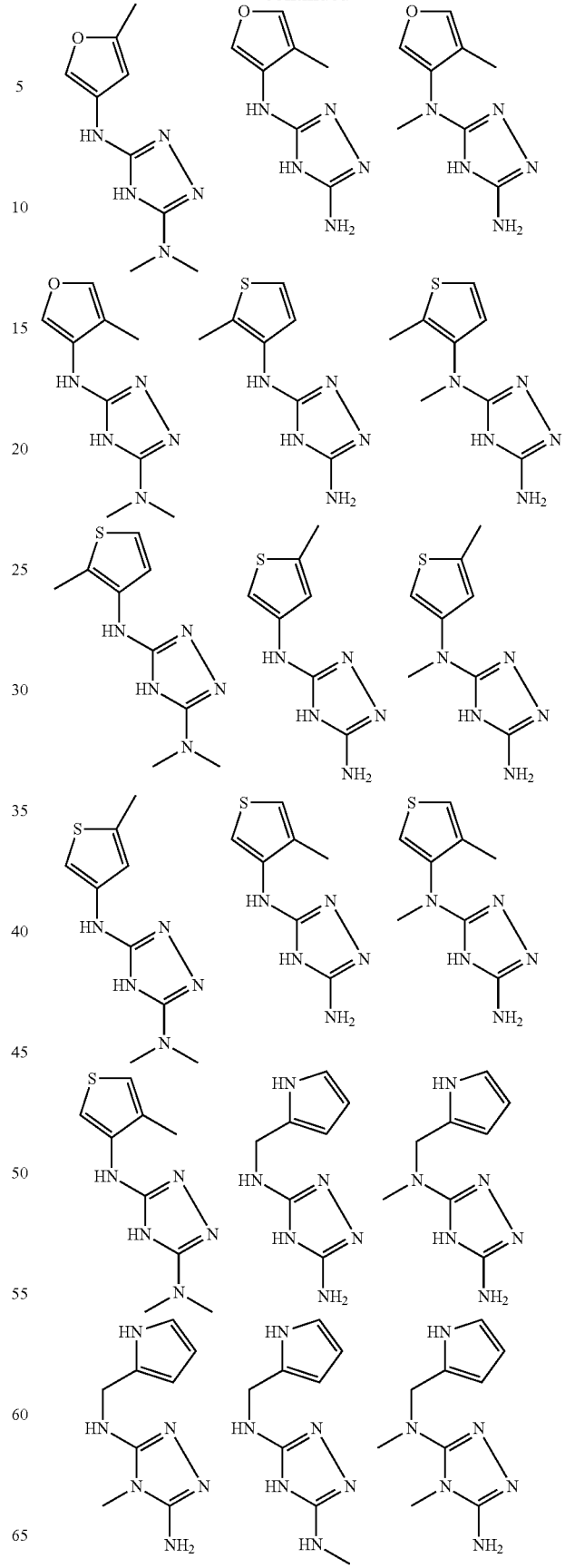

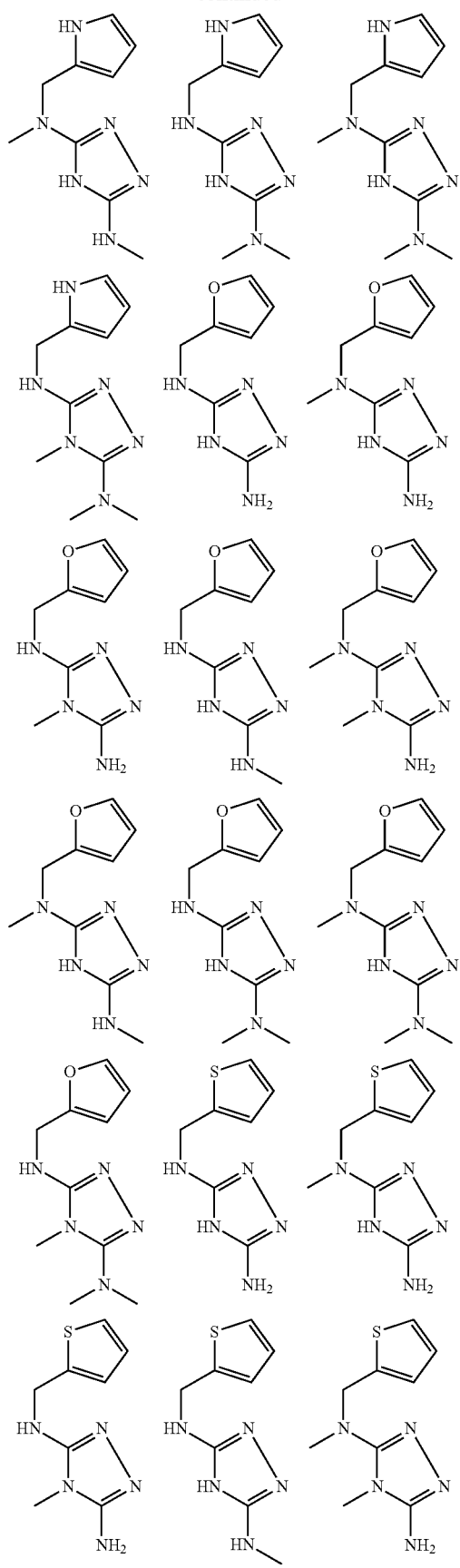
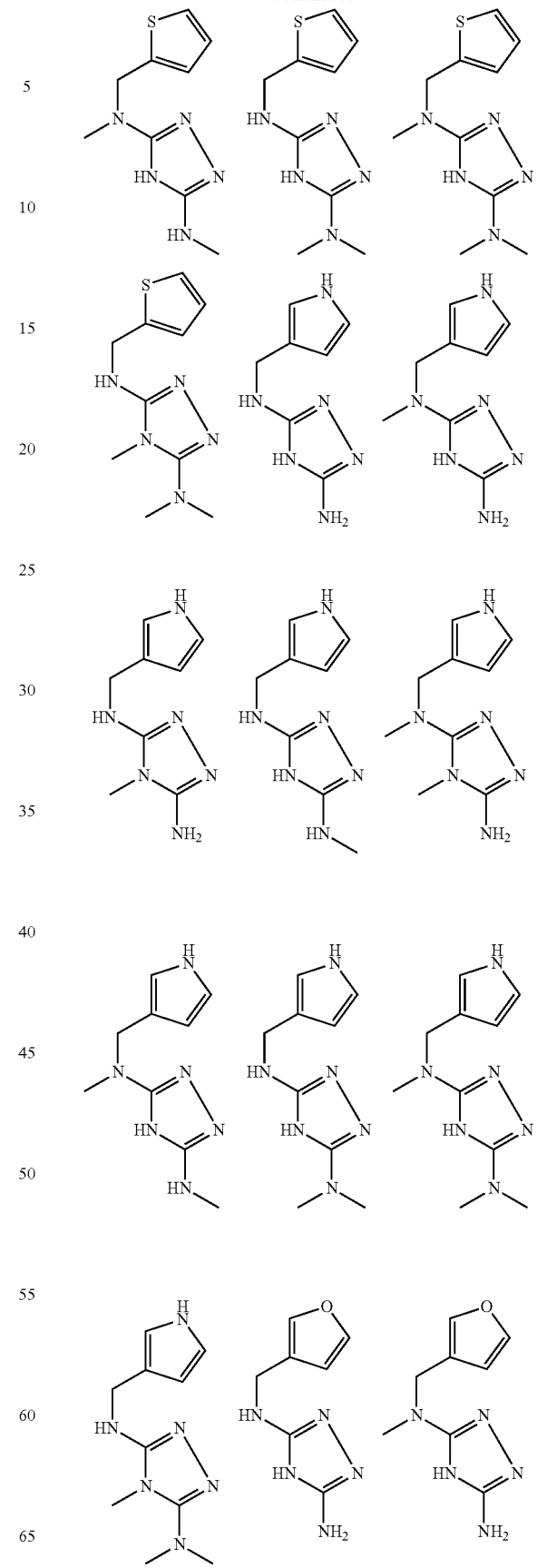

-continued
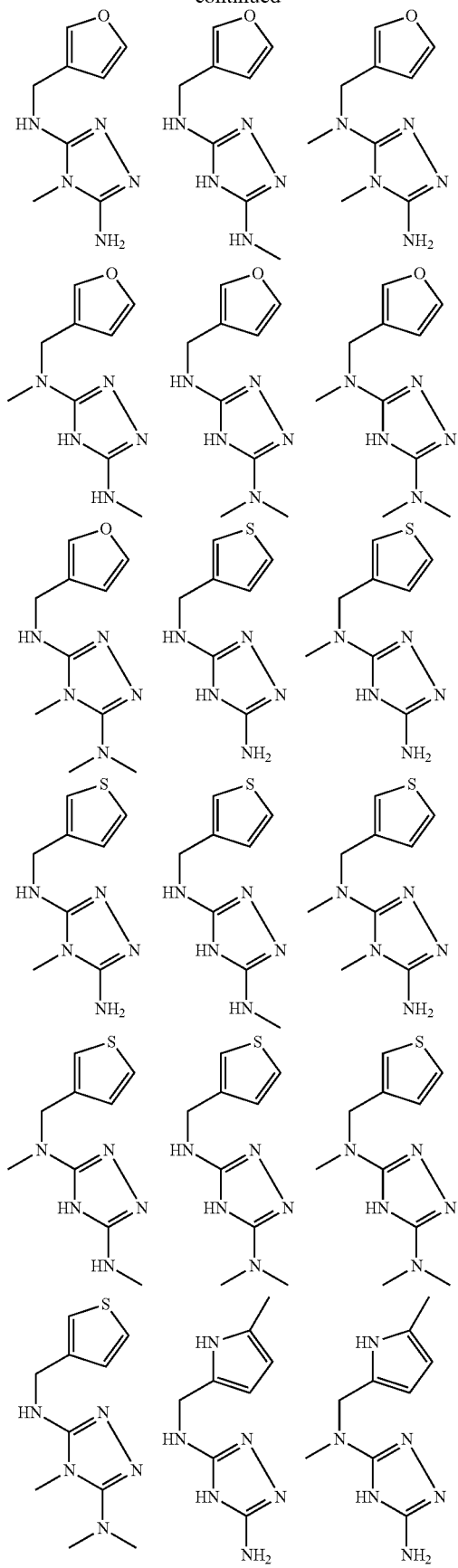
-continued
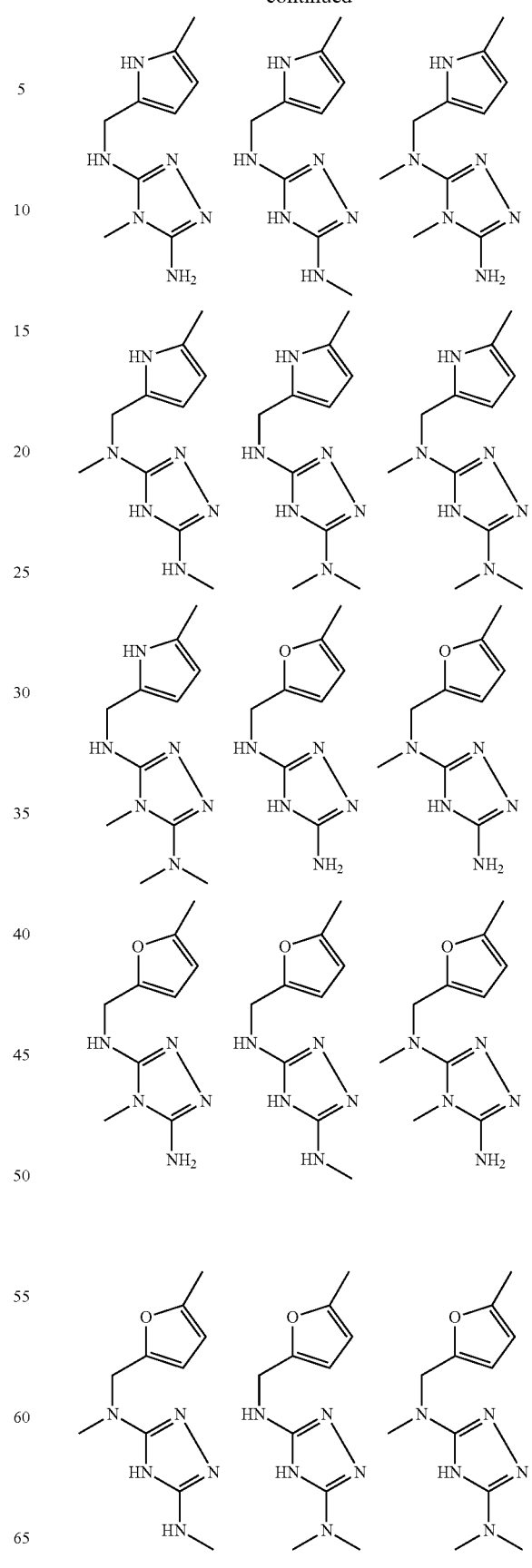

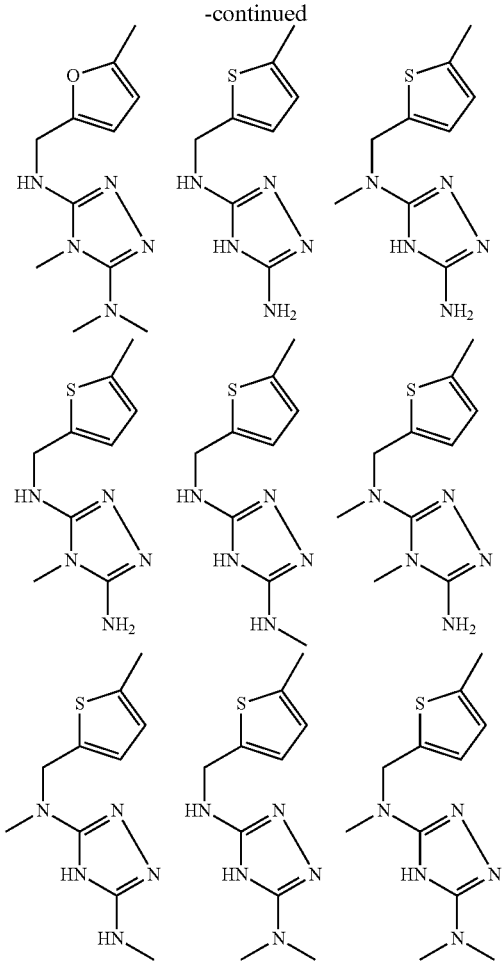
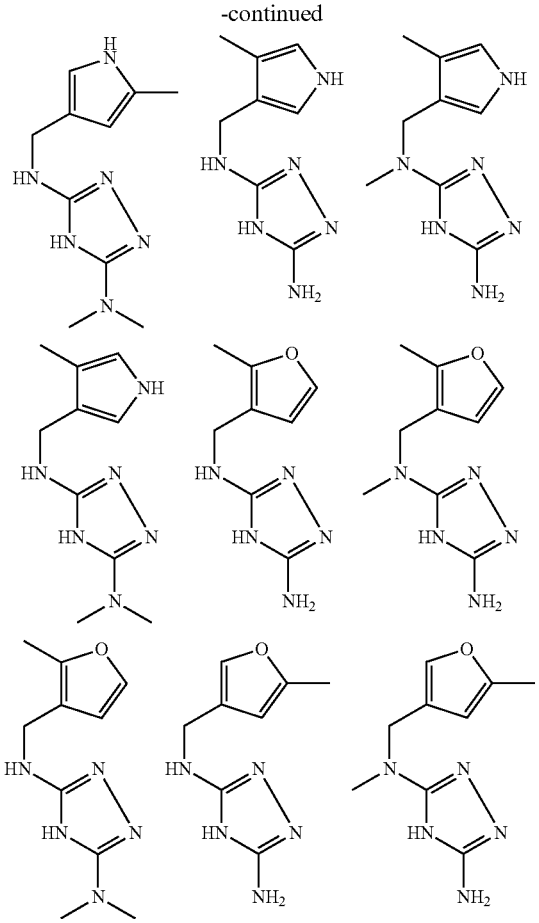
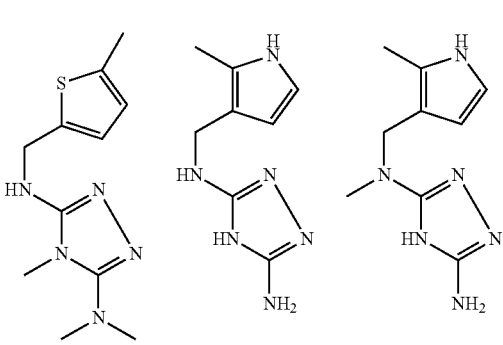
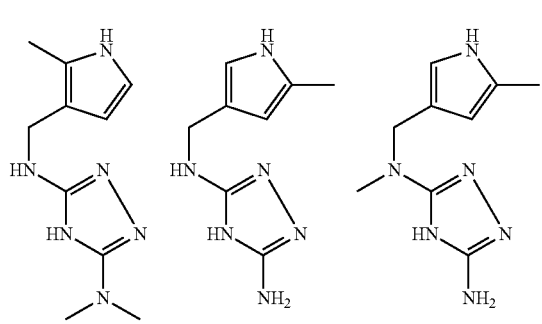
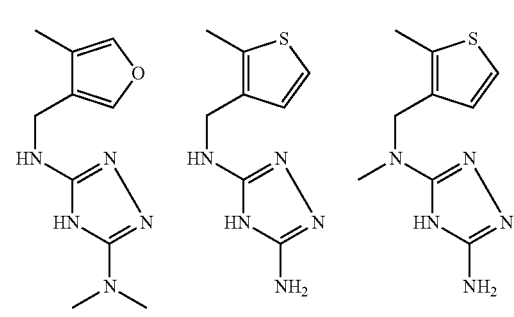

97
-continued
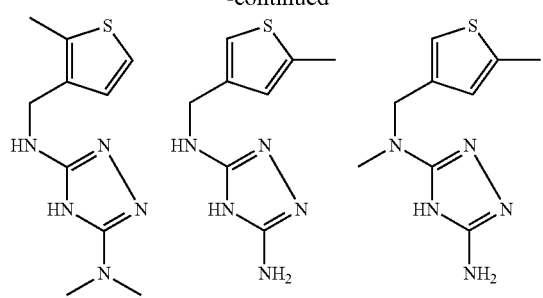
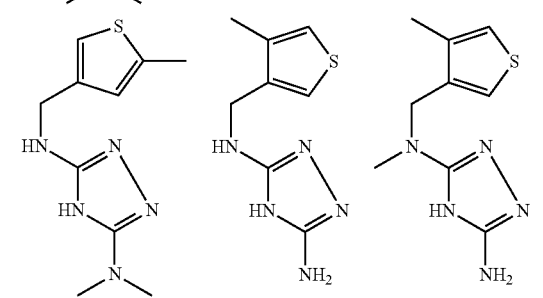
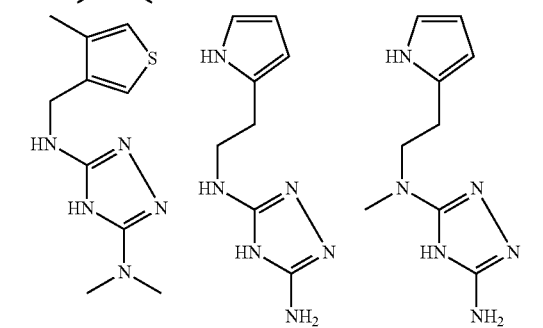
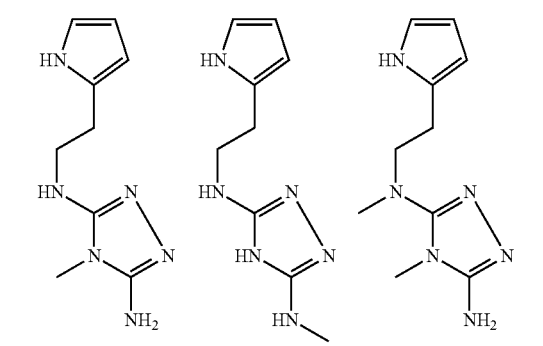
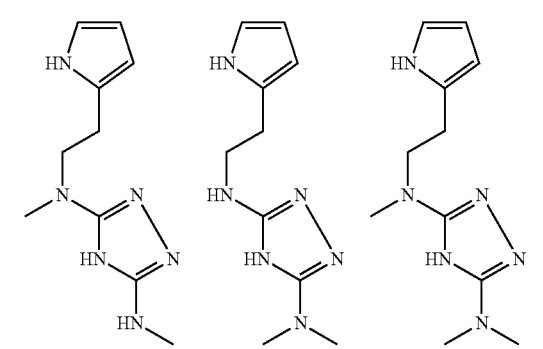
98
-continued
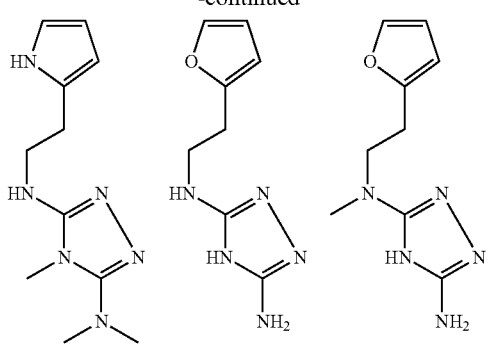
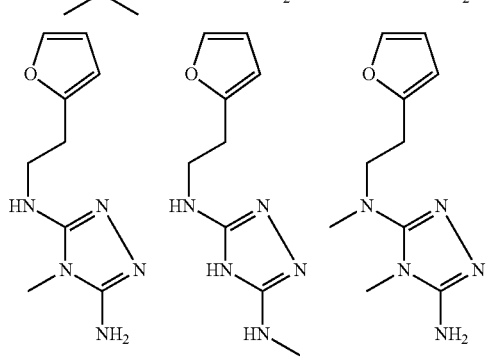
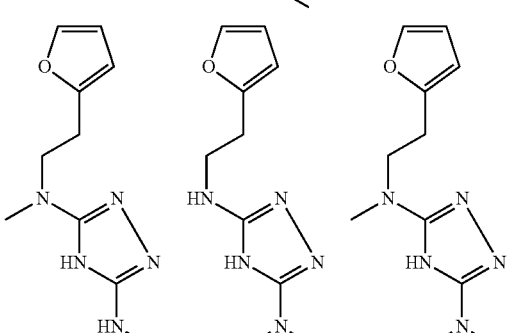
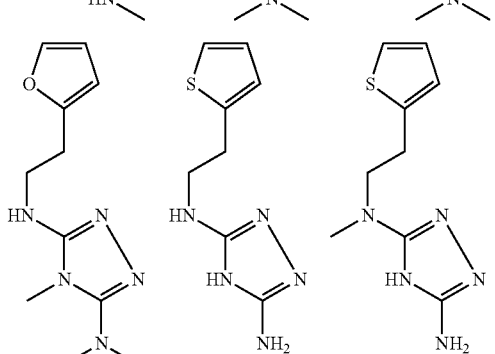
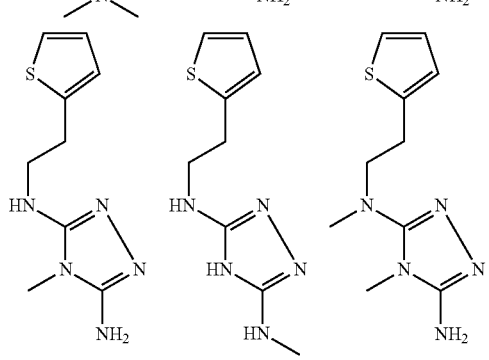

99
-continued
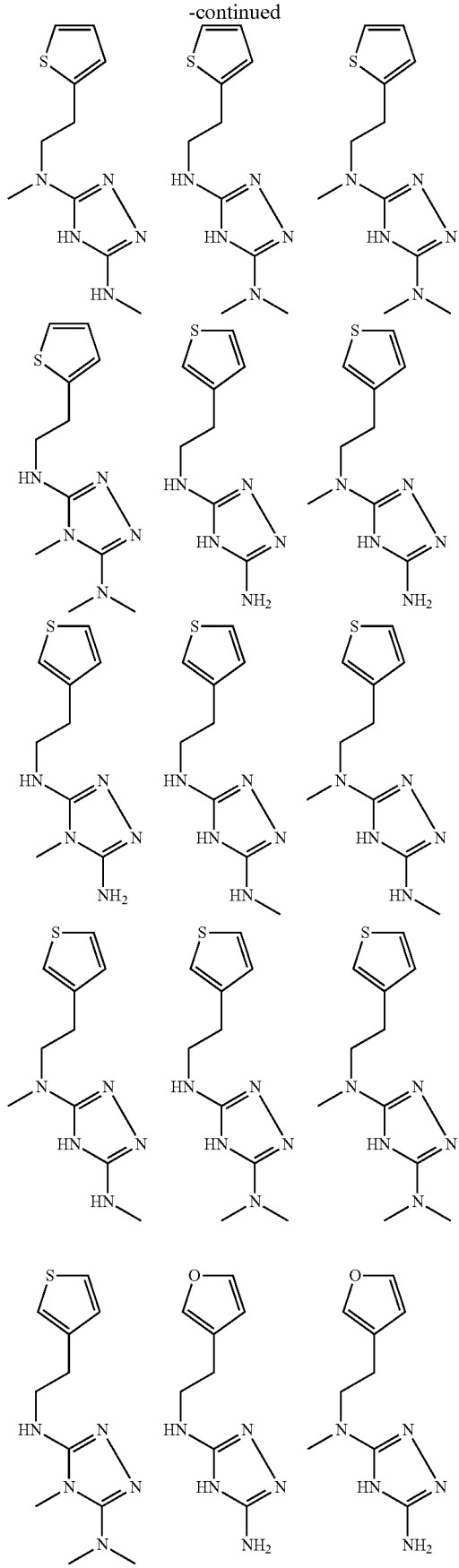
100
-continued
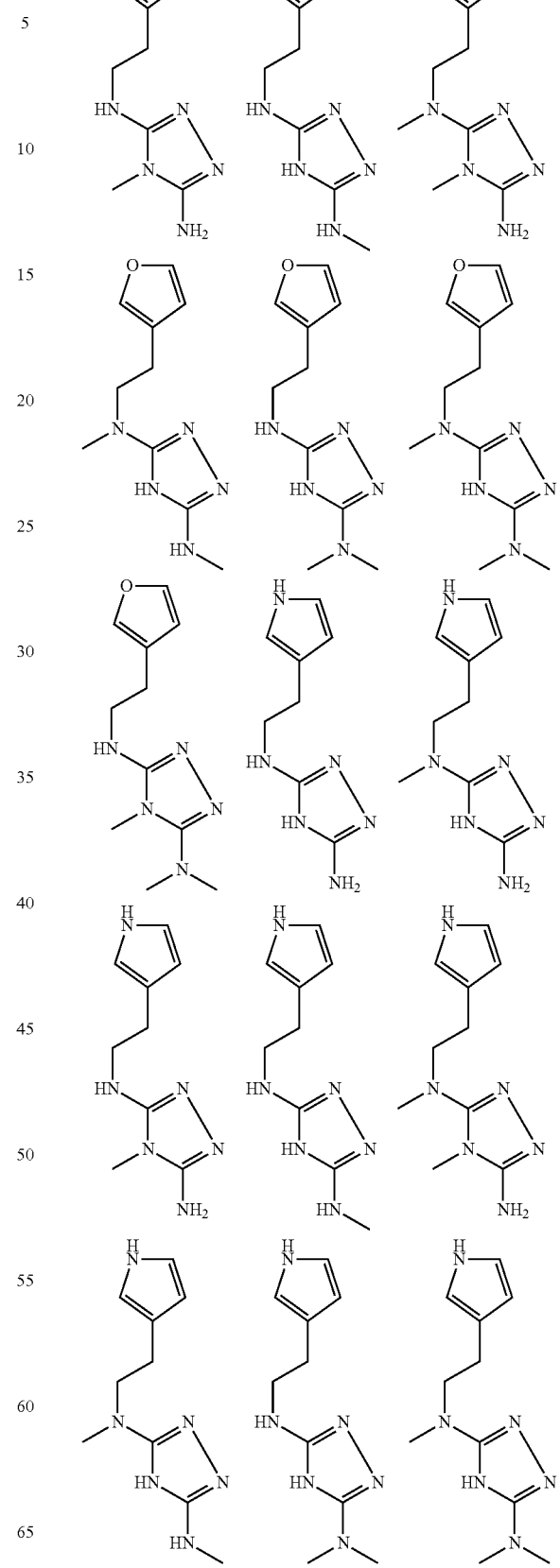

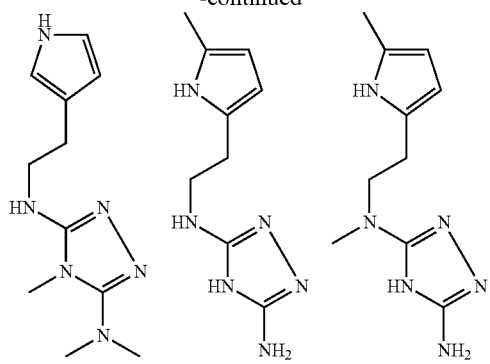
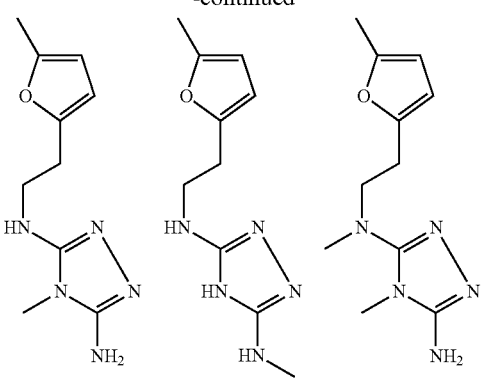

103
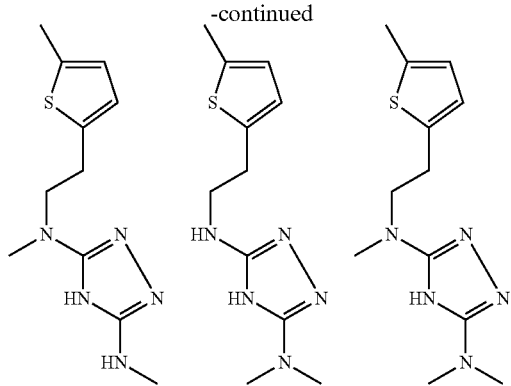
104
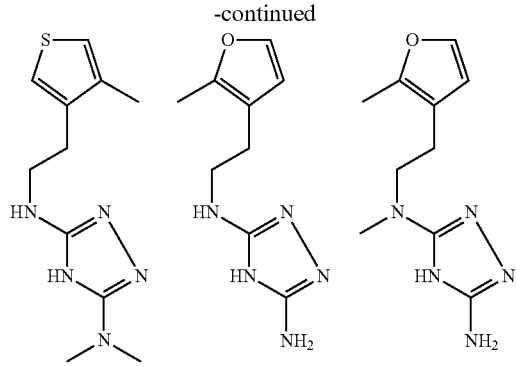
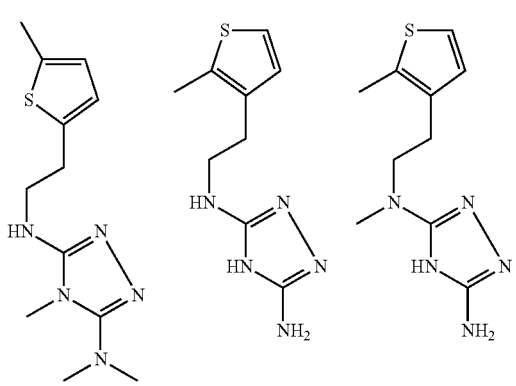
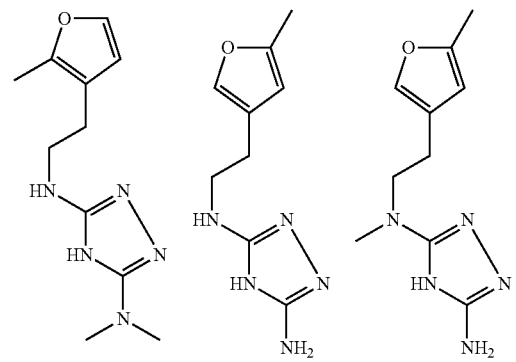
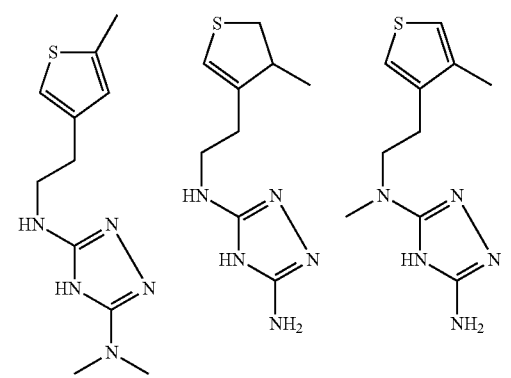
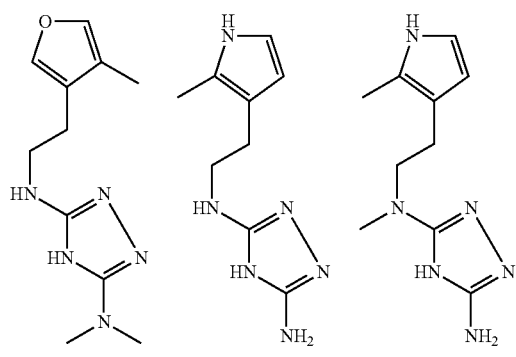

-continued
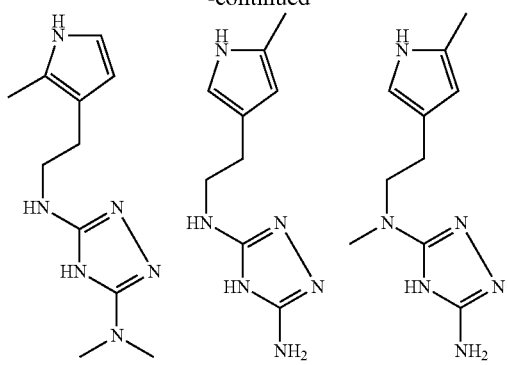
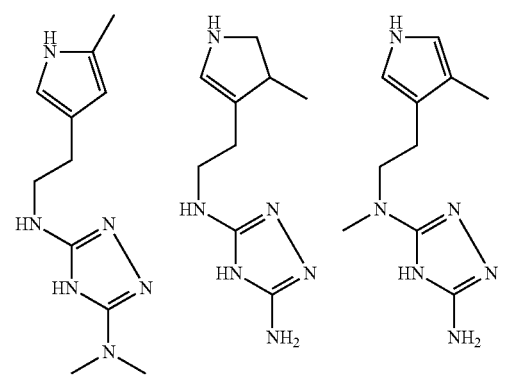
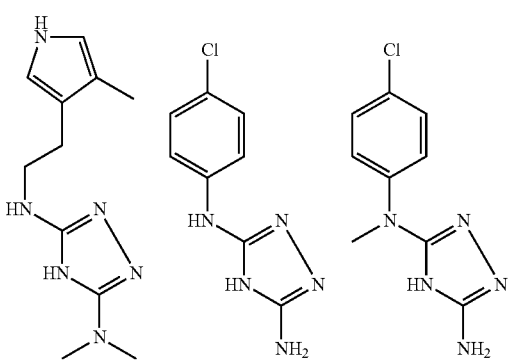
-continued
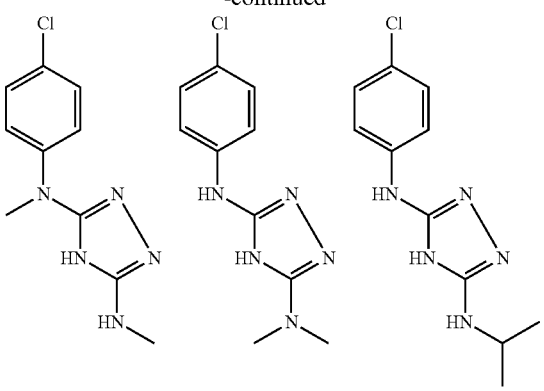
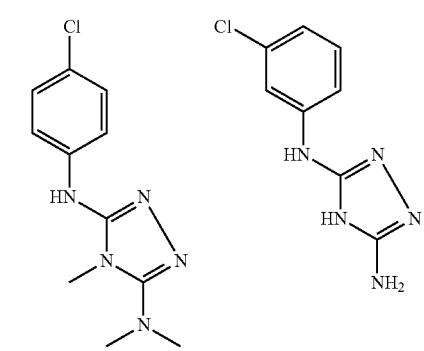
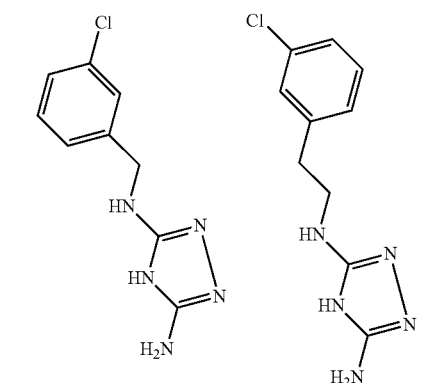
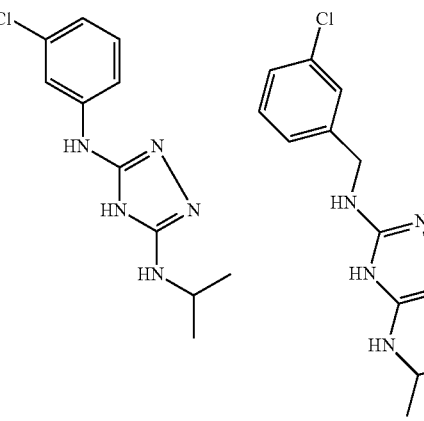

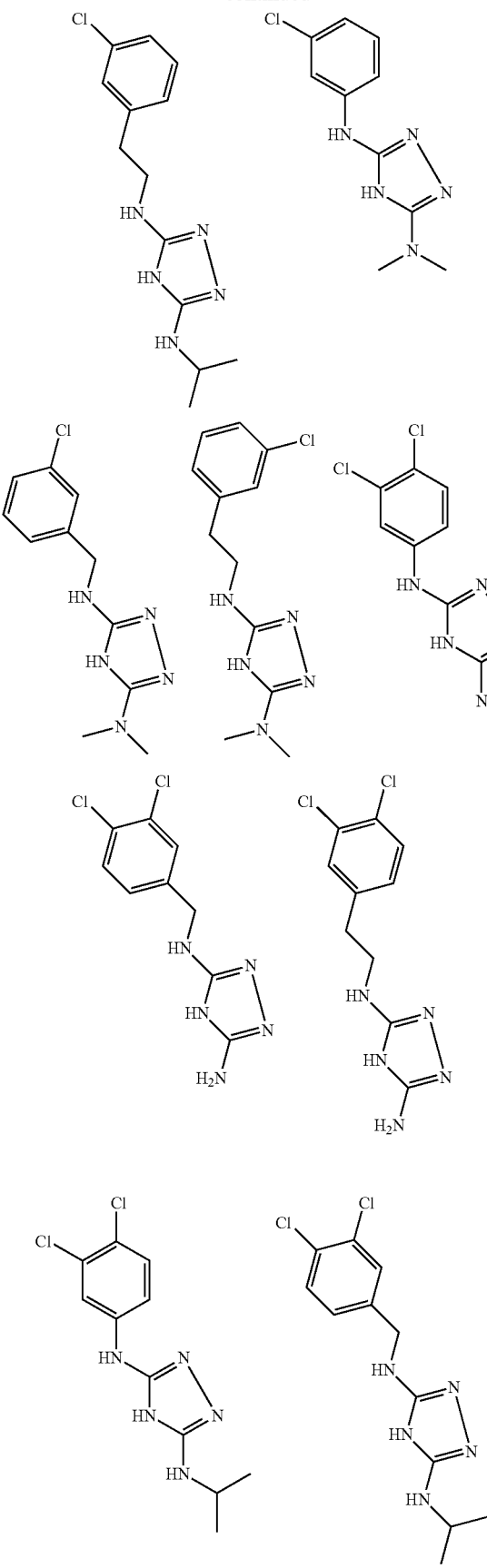
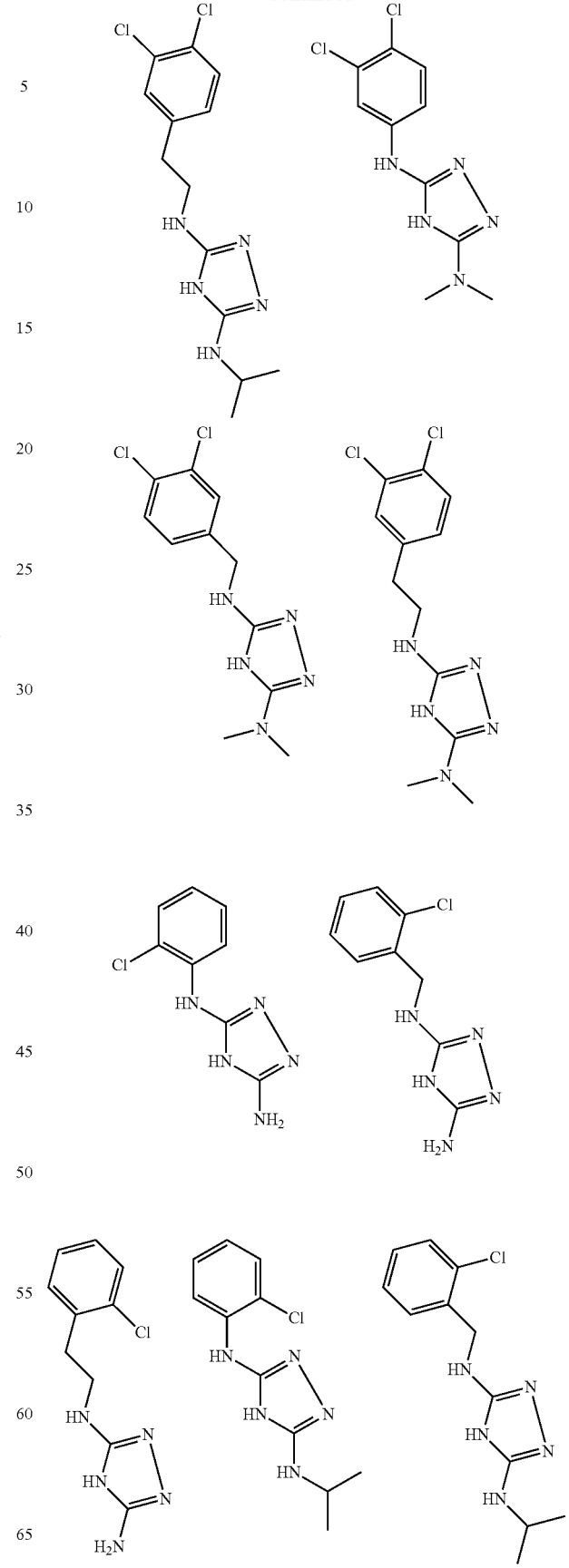

-continued

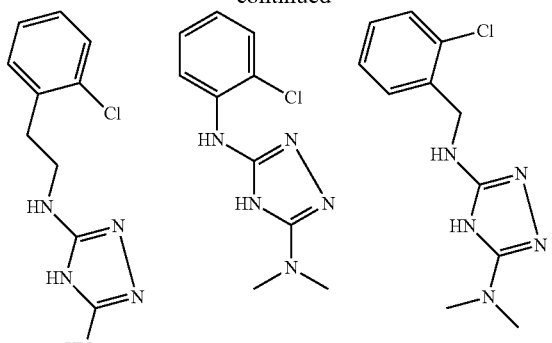

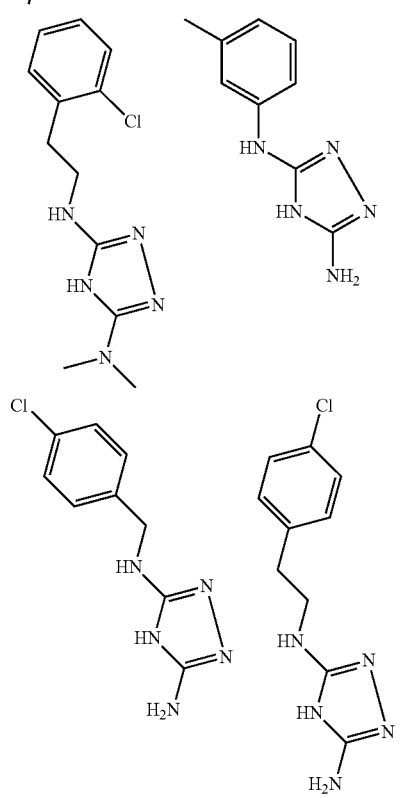

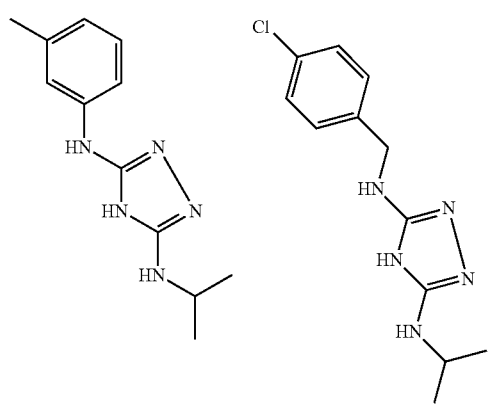

-continued

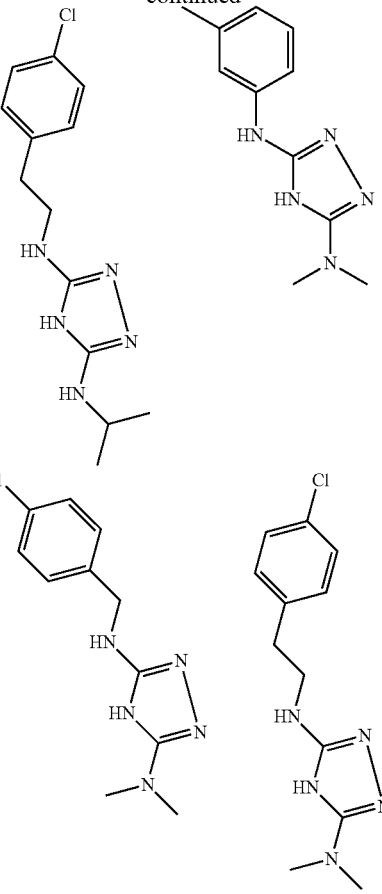

In other embodiments, triazine compounds of Formula II may be used in connection with the compositions and methods of the disclosure. Substituent definitions, unless otherwise indicated, are the same as provided with reference to Formula I.

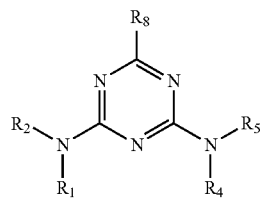

II wherein:
$R_1$, $R_2$, $R_4$, and $R_5$, are independently selected from:
H, OH,
O—Rx, wherein Rx is alkyl, cycloalkyl, alkylcycloalkyl, acyl, ester, thioester;
optionally substituted alkyl (e.g., a $C_1$ to $C_{12}$ straight chain or branched chain alkyl optionally substituted with oxygen, silicon, sulphur or optionally substituted with OH, O-alkyl, SH, S-alkyl, $NH_2$, NH-alkyl); cycloalkyl (e.g., $C_3$ to $C_7$ cycloalkyl); alkylcycloalkyl (e.g., $C_4$ to $C_{12}$ alkylcycloalkyl); heterocycloalkyl (e.g., where the heterocycle comprises one or two hetero atoms selected from O, S, or N, including a $C_2$ to $C_6$ heterocycloalkyl); alkylheterocycloalkyl (e.g., where the heterocycle comprises one or two hetero atoms selected from O, S, or N, including a $C_3$ to $C_{11}$ alkylheterocycloalkyl, and including wherein when N is present in the heterocyclic ring, the nitrogen atom may be in the form of an amide, carbamate or urea); optionally substituted alkenyl (e.g., $C_1$ to $C_{12}$ straight chain or branched chain alkenyl optionally substituted with oxygen, silicon, sulphur or optionally substituted with OH, O-alkyl, SH, S-alkyl, $NH_2$, NH-alkyl); optionally substituted alkynyl (e.g., $C_1$ to $C_{12}$ straight chain or branched chain alkynyl optionally substituted with oxygen, silicon, sulphur or optionally substituted with OH, O-alkyl, SH, S-alkyl, $NH_2$, NH-alkyl);

optionally substituted aryl (e.g., phenyl, substituted phenyl, naphthyl, substituted naphthyl); optionally substituted alkylaryl (e.g., alkylphenyl, alkylsubstituted phenyl, alkylnaphthyl, alkylsubstituted naphthyl); optionally substituted heteroaryl (e.g., pyridyl, furanyl, thiophenyl, pyrrollyl, oxazolyl, isoxazolyl, thiazolyl, diazolyl, pyrazolyl, triazolyl all of which are optionally substituted); optionally substituted alkylheteroaryl; and or $R_1$ and $R_2$ may together form a 3 to 8 membered heterocyclic ring, including the nitrogen atoms to which they are attached;

or $R_4$ and $R_5$ may together form a ring selected from the group aziridine, pyrrolyl, imidazolyl, pyrazolyl, indolyl, indolinyl, pyrrolidinyl, piperazinyl and piperidyl, including the nitrogen atoms to which they are attached;

$R_8$ is selected from:

H; optionally substituted alkynyl (e.g., $C_1$ to $C_{12}$ straight chain or branched chain alkynyl optionally hetero substituted with oxygen, silicon, sulphur or optionally substituted with OH, O-alkyl, SH, S-alkyl, $NH_2$, NH-alkyl); cycloaklyl (e.g., $C_3$ to $C_7$ cycloalkyl); alkylcycloalkyl (e.g., $C_4$ to $C_{12}$ alkylcycloalkyl); heterocycloalkyl (e.g., where the heterocycle comprises one or two hetero atoms selected from O, S, or N, including $C_2$ to $C_6$ heterocycloalkyl); alkylheterocycloalkyl (e.g., where the heterocycle comprises one or two hetero atoms selected from O, S, or N, including $C_3$ to $C_{11}$ alkylheterocycloalkyl and including wherein when N is present in the heterocyclic ring, the nitrogen atom may be in the form of an amide, carbamate or urea); optionally substituted aryl (e.g., phenyl, substituted phenyl, naphthyl, substituted naphthyl); optionally substituted alkylaryl (e.g., alkylphenyl, alkylsubstituted phenyl, alkylnaphthyl, alkylsubstituted naphthyl); optionally substituted heteroaryl (e.g., pyridyl, furanyl, thiophenyl, pyrrollyl, oxazolyl, isoxazolyl, thiazolyl, diazolyl, pyrazolyl, triazolyl all of which are optionally substituted); optionally substituted alkylheteroaryl; and —$NR_aR_b$ wherein $R_a$ and $R_b$ are independently selected from:

H; optionally substituted alkyl (e.g., $C_1$ to $C_{12}$ straight chain or branched chain alkyl optionally substituted with oxygen, silicon, sulphur or optionally substituted with OH, O-alkyl, SH, S-alkyl, $NH_2$, NH-alkyl); optionally substituted alkenyl ($C_1$ to $C_{12}$ straight chain or branched chain alkenyl optionally substituted with oxygen, silicon, sulphur or optionally substituted with OH, O-alkyl, SH, S-alkyl, $NH_2$, NH-alkyl); optionally substituted alkynyl ($C_1$ to $C_{12}$ straight chain or branched chain alkynyl optionally substituted with oxygen, silicon, sulphur or optionally substituted with OH, O-alkyl, SH, S-alkyl, $NH_2$, NH-alkyl); cycloalkyl (e.g., $C_3$ to $C_7$ cycloalkyl); alkylcycloalkyl (e.g., $C_4$ to $C_{12}$ alkylcycloalkyl); heterocyclalkyl (e.g., where the heterocycle comprises one or two hetero atoms selected from O, S, or N, including $C_2$ to $C_6$ heterocycloalkyl); alkylheterocycloalkyl (e.g., where the heterocycle comprises one or two hetero atoms selected from O, S, or N, including $C_3$ to $C_{11}$ alkylheterocycloalkyl, and including wherein when N is present in the heterocyclic ring, the nitrogen atom may be in the form of an amide, carbamate or urea); optionally substituted aryl (e.g., phenyl, substituted phenyl, naphthyl, substituted naphthyl), optionally substituted alkylary (e.g., alkylphenyl, alkylsubstituted phenyl, alkylnaphthyl, alkylsubstituted naphthyl), optionally substituted heteroaryl (e.g., pyridyl, furanyl, thiophenyl, pyrrollyl, oxazolyl, isoxazolyl, thiazolyl, diazolyl, pyrazolyl, triazolyl all of which are optionally substituted), and optionally substituted alkylheteroaryl.

In certain embodiments, O—Rx may be selected from: O—$C_1$ to $C_8$ straight chain or branched chain alkyl; O—$C_3$ to $C_7$ cycloalkyl; O—$C_4$ to $C_8$ alkylcycloalkyl; O-acyl; O-esters; and O-thioesters.

In other embodiments, optional substitutions may include, e.g., OH, O-alkyl, SH, S-alkyl, $NH_2$, NH-alkyl. Further, an alkyl, alkenyl, alkynyl, etc. may be substituted with an oxygen, silicon, sulphur, etc. to form a heteroalkyl, heteroalkenyl, heteroalkynyl, etc.

In certain embodiments, $R_8$ may be selected from H; lower alkyl, including $CH_3$; $NH_2$; NH-alkyl, N(alkyl)$_2$, including $NHCH_3$, $N(CH_3)_2$. In certain aspects, in combination with these particular selections of $R_8$ if desired, each of $R_1$, $R_2$, $R_4$, and $R_5$, or $R_2$, $R_4$ and $R_5$, or $R_4$ and $R_5$, or $R_5$ may be independent selected from:

H, methyl, ethyl, propyl or isopropyl;

and each of the remaining substitutent groups: $R_1$ or $R_1$ and $R_2$, or $R_1$, $R_2$, and $R_5$, respectively, are independently selected from:

H; optionally substituted alkyl (e.g., $C_1$ to $C_{12}$ straight chain or branched chain alkyl optionally hetero substituted with oxygen, silicon, sulphur or optionally substituted with OH, O-alkyl, SH, S-alkyl, $NH_2$, NH-alkyl); optionally substituted alkenyl (e.g., $C_1$ to $C_{12}$ straight chain or branched chain alkenyl optionally hetero substituted with oxygen, silicon, sulphur or optionally substituted with OH, O-alkyl, SH, S-alkyl, $NH_2$, NH-alkyl); optionally substituted alkynyl (e.g., $C_1$ to $C_{12}$ straight chain or branched chain alkynyl optionally hetero substituted with oxygen, silicon, sulphur or optionally substituted with OH, O-alkyl, SH, S-alkyl, $NH_2$, NH-alkyl); cycloalkyl (e.g., $C_3$ to $C_7$ cycloalkyl); alkylcycloalkyl (e.g., $C_4$ to $C_{12}$ alkylcycloalkyl); heterocycloalkyl (e.g., where the heterocycle comprises one or two hetero atoms selected from O, S, or N, including $C_2$ to $C_6$ heterocycloalkyl); alkylheterocycloalkyl (e.g., where the heterocycle comprises one or two hetero atoms selected from O, S, or N, including $C_3$ to $C_{11}$ alkylheterocycloalkyl, and including wherein when N is present in the heterocyclic ring, the nitrogen atom may be in the form of an amide, carbamate or urea); aryl (e.g., phenyl, substituted phenyl, naphthyl, substituted naphthyl); alkylaryl (e.g., alkylphenyl, alkylsubstituted phenyl, alkylnaphthyl, alkylsubstituted naphthyl); heteroaryl (e.g., pyridyl, furanyl, thiophenyl, pyrrollyl, oxazolyl, isoxazolyl, thiazolyl, diazolyl, pyrazolyl, triazolyl all of which are optionally substituted); alkylheteroaryl;

or $R_1$ and $R_2$ may together form a 3 to 8 membered heterocyclic ring, including the nitrogen atoms to which they are attached;

or $R_4$ and $R_5$ may together form a ring selected from the group aziridine, pyrrolyl, imidazolyl, pyrazolyl, indolyl, indolinyl, pyrrolidinyl, piperazinyl and piperidyl, including the nitrogen atoms to which they are attached.

Exemplary compounds and substituents of $R_1$, $R_2$, $R_4$, $R_5$, and $R_8$ of Formula II are shown below. However, additional combinations of selections of substituents of $R_1$, $R_2$, $R_4$, $R_5$, and $R_8$ are envisioned.
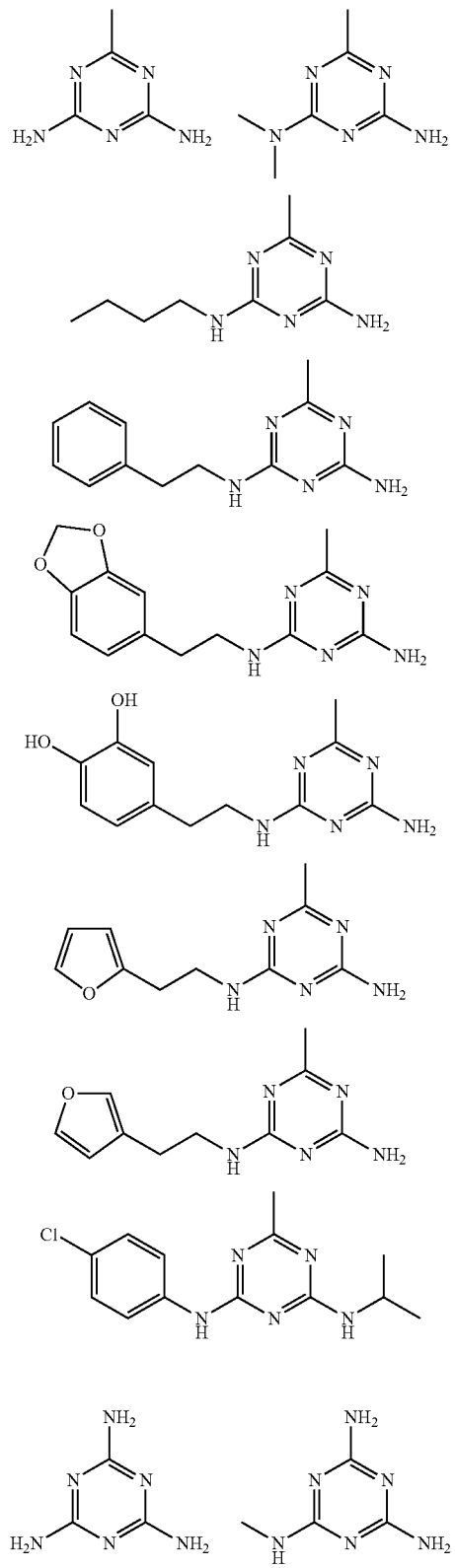
-continued
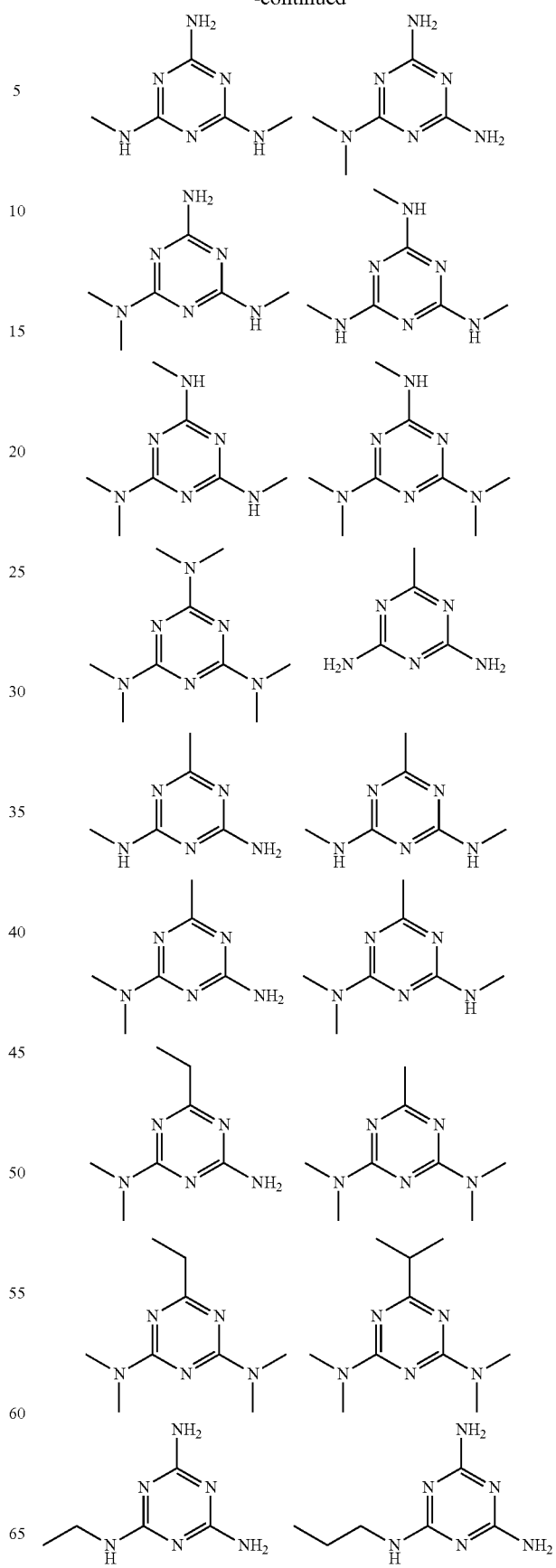

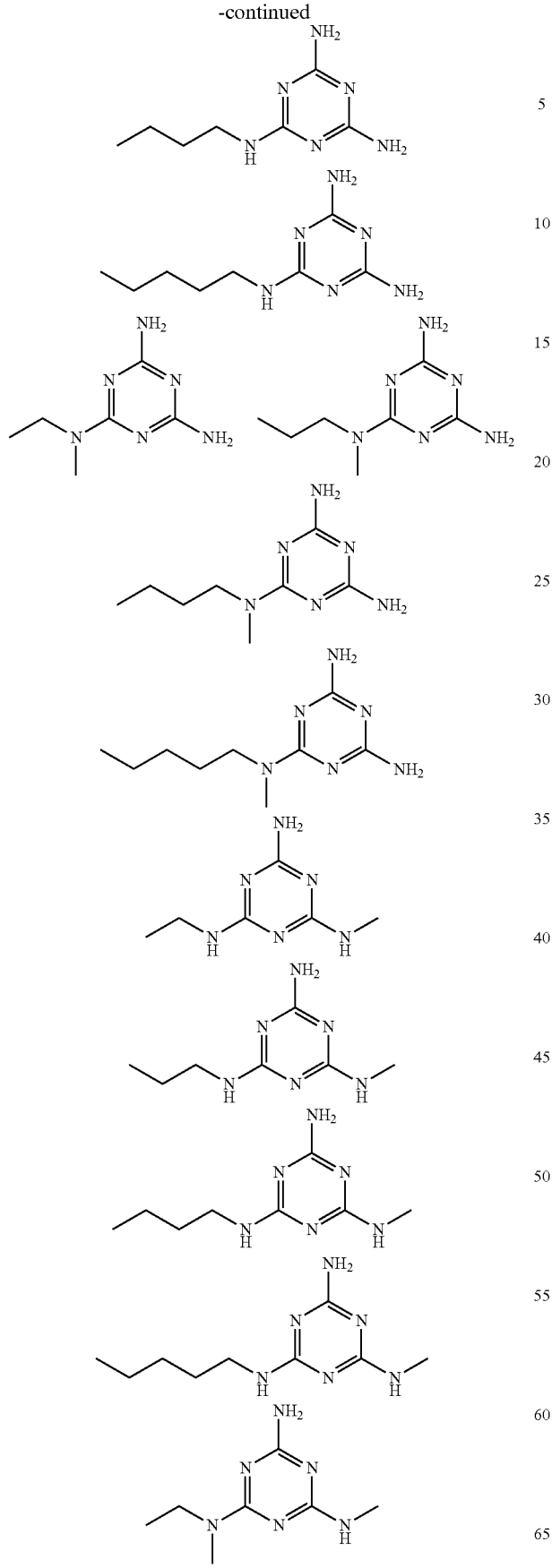
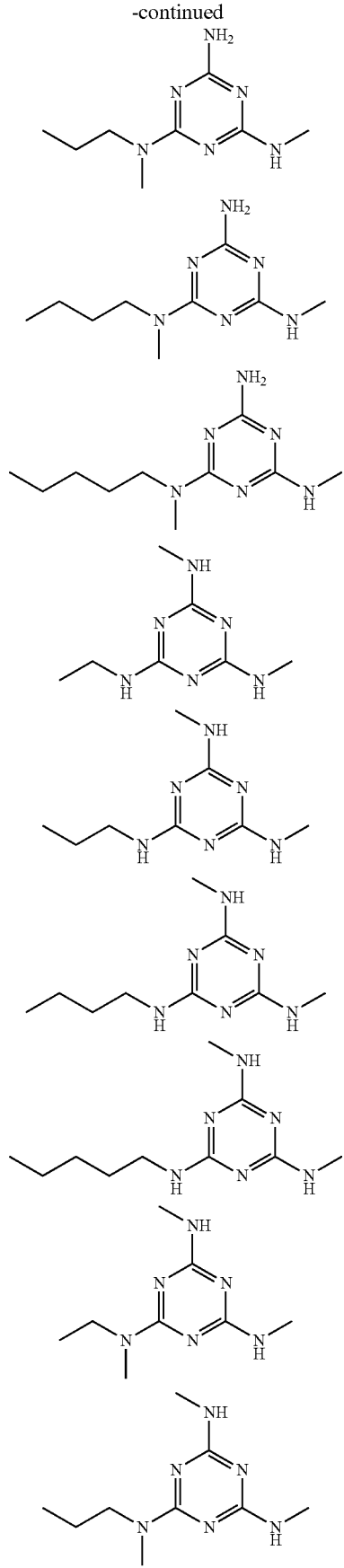

-continued
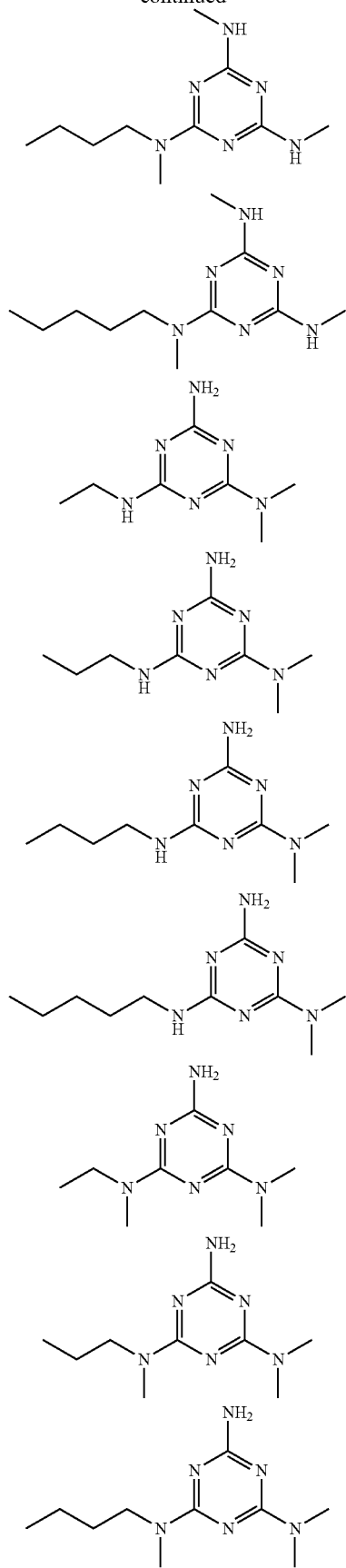
-continued
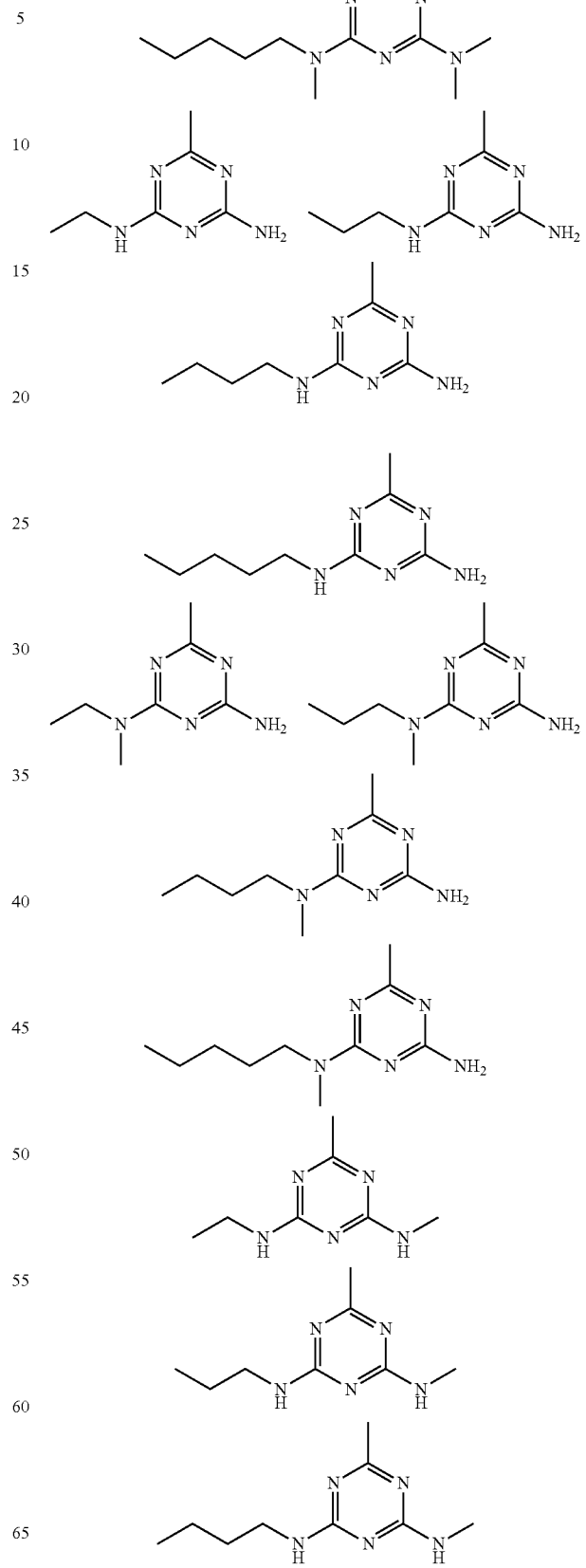

-continued
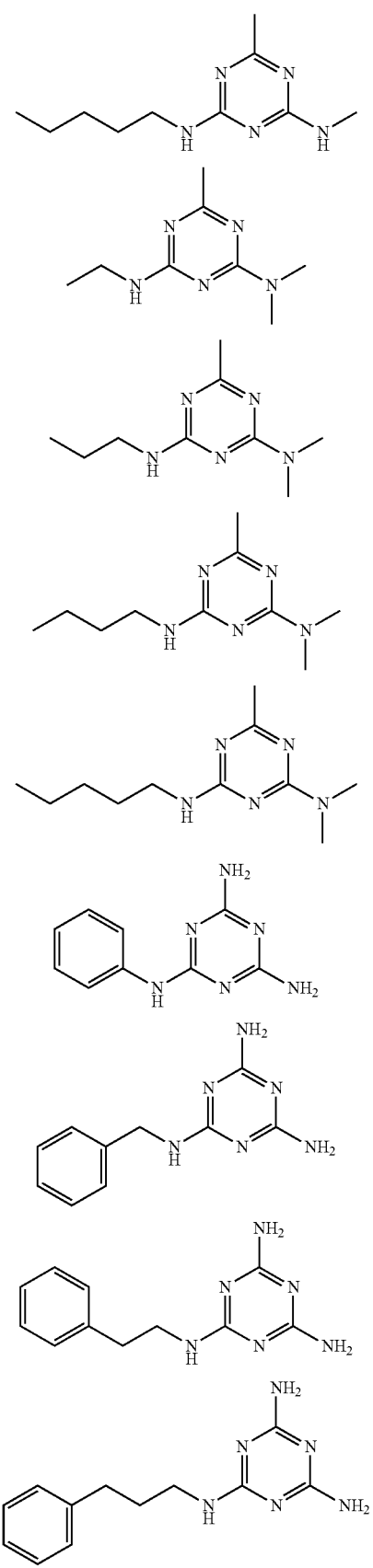
-continued
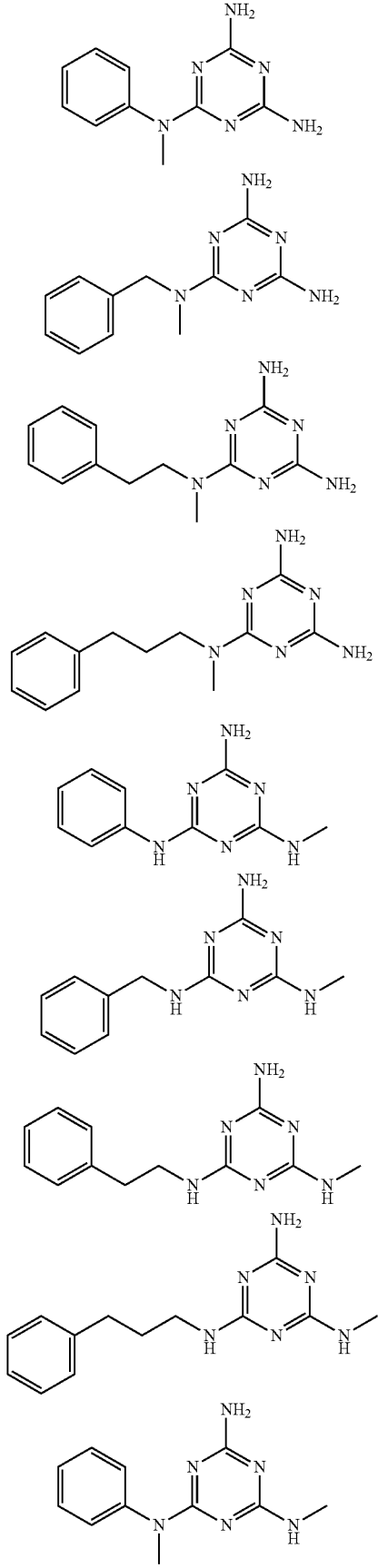

121
-continued
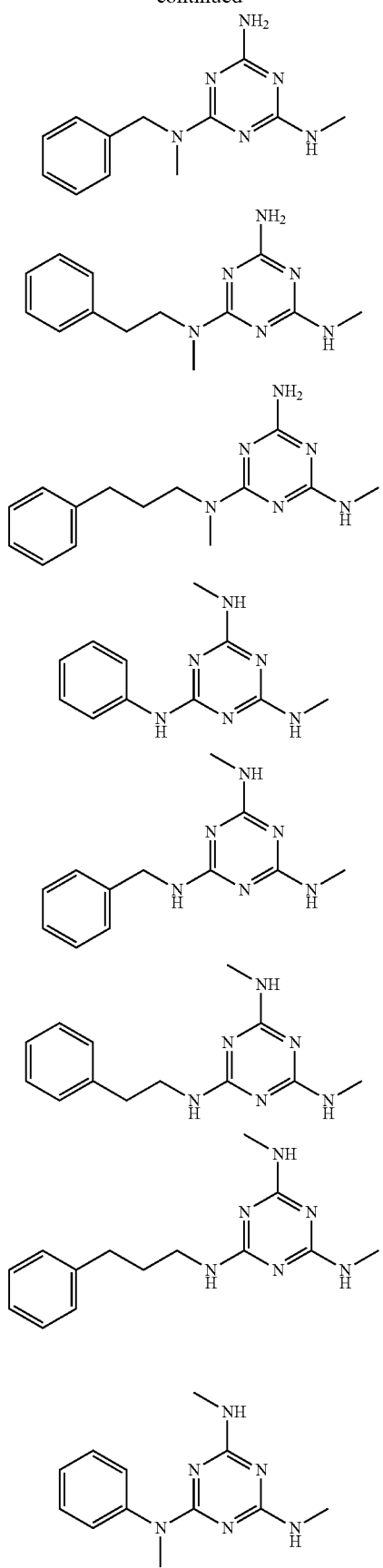
122
-continued
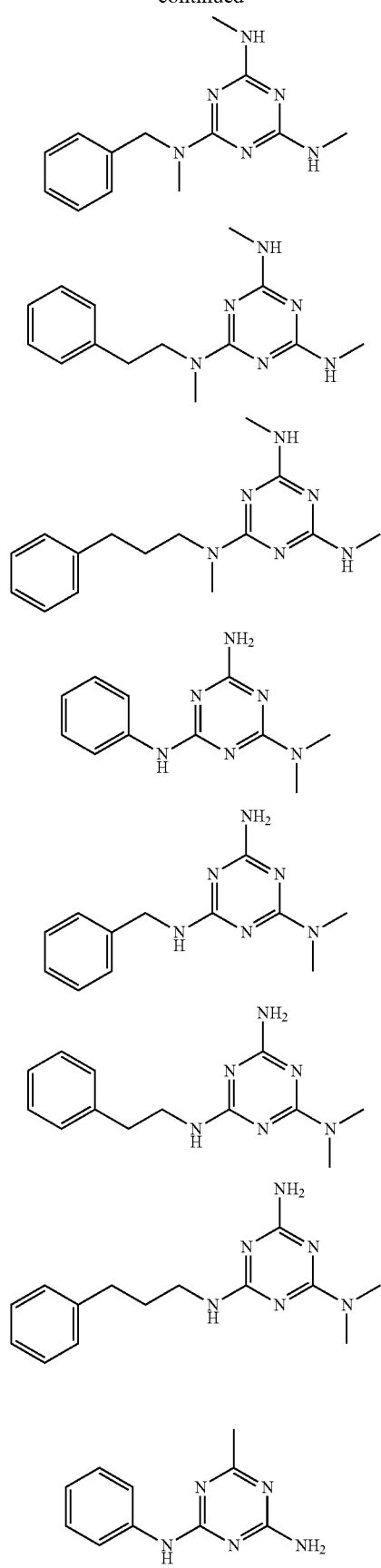

123
-continued
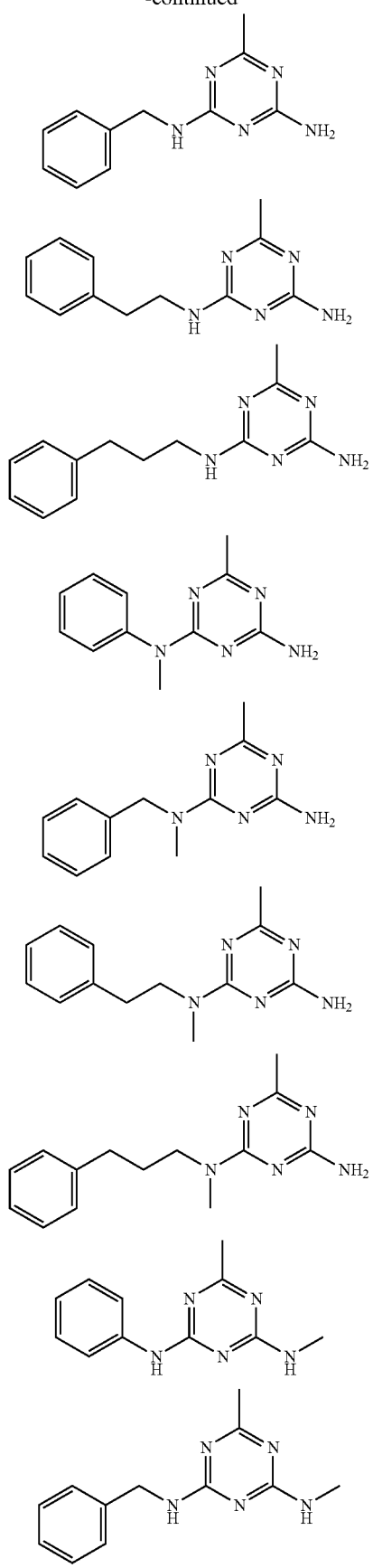
124
-continued
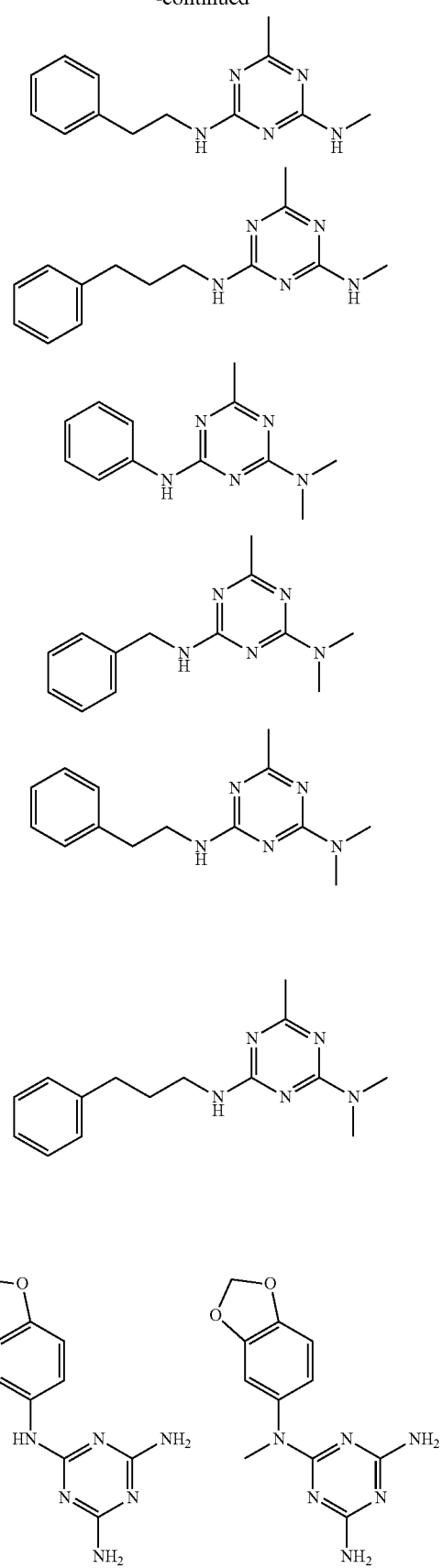

-continued
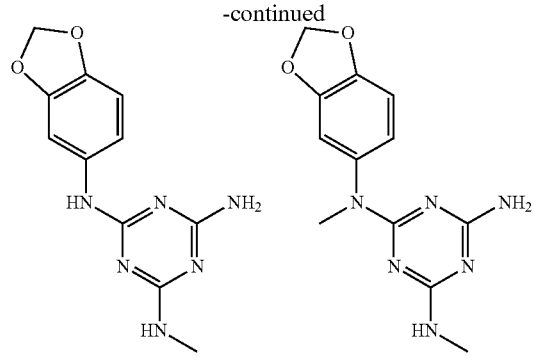
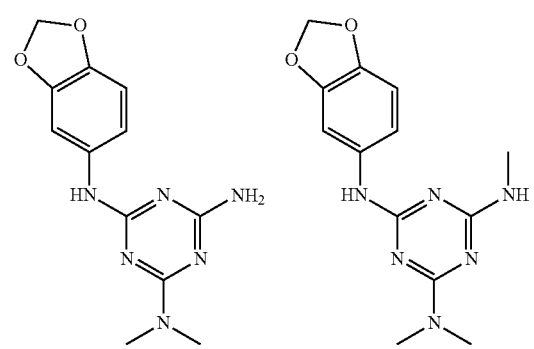
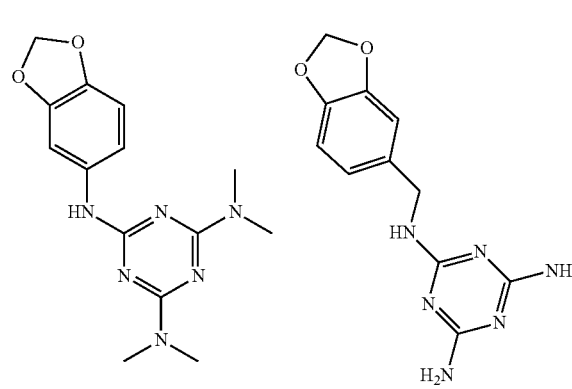
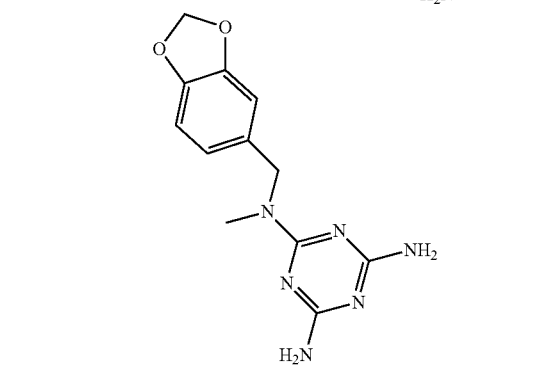
-continued
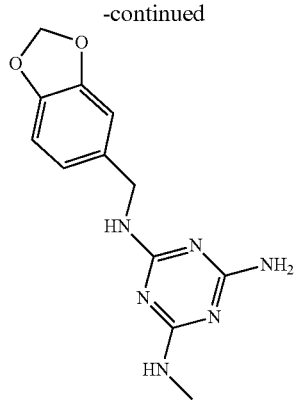
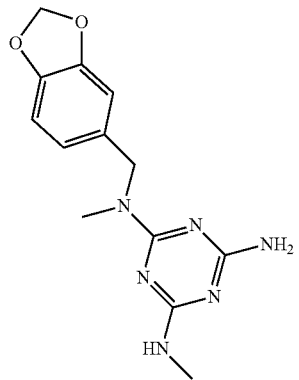
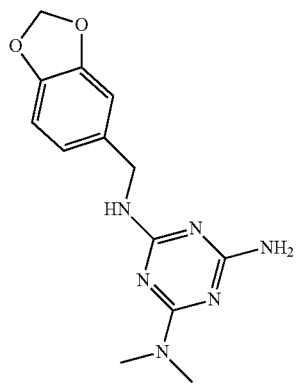
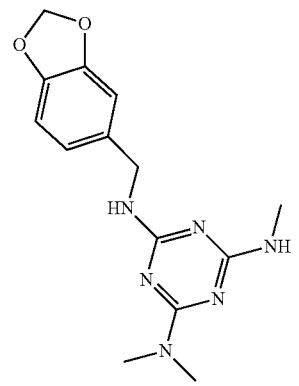

127
-continued
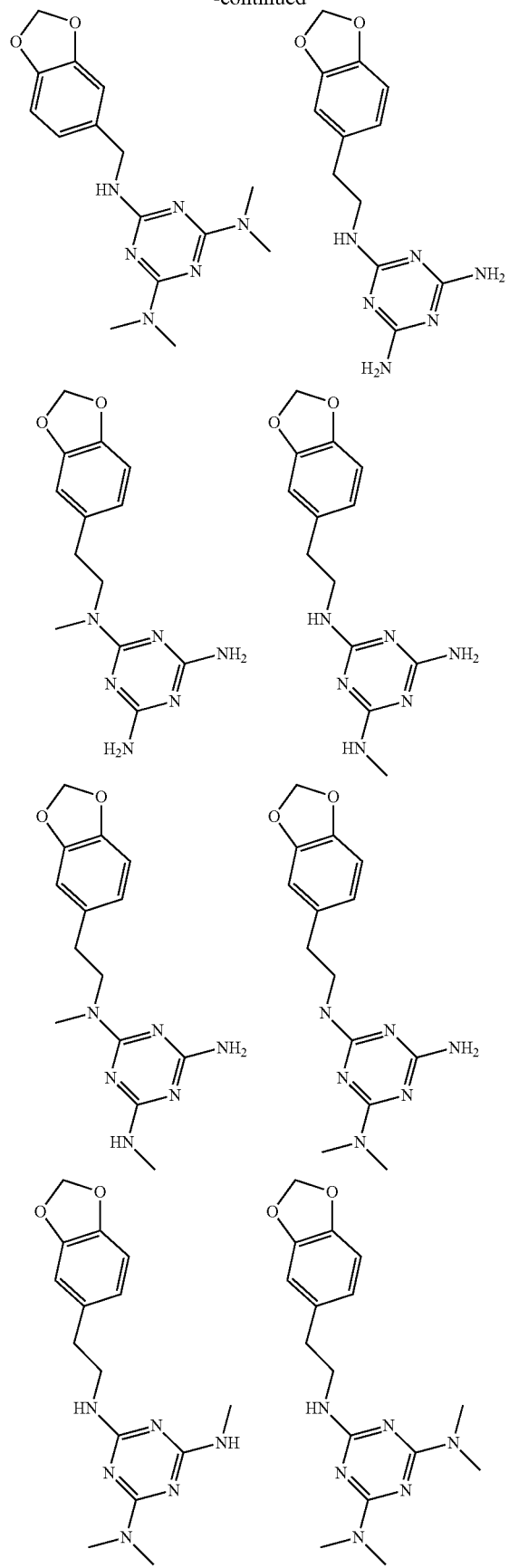
128
-continued
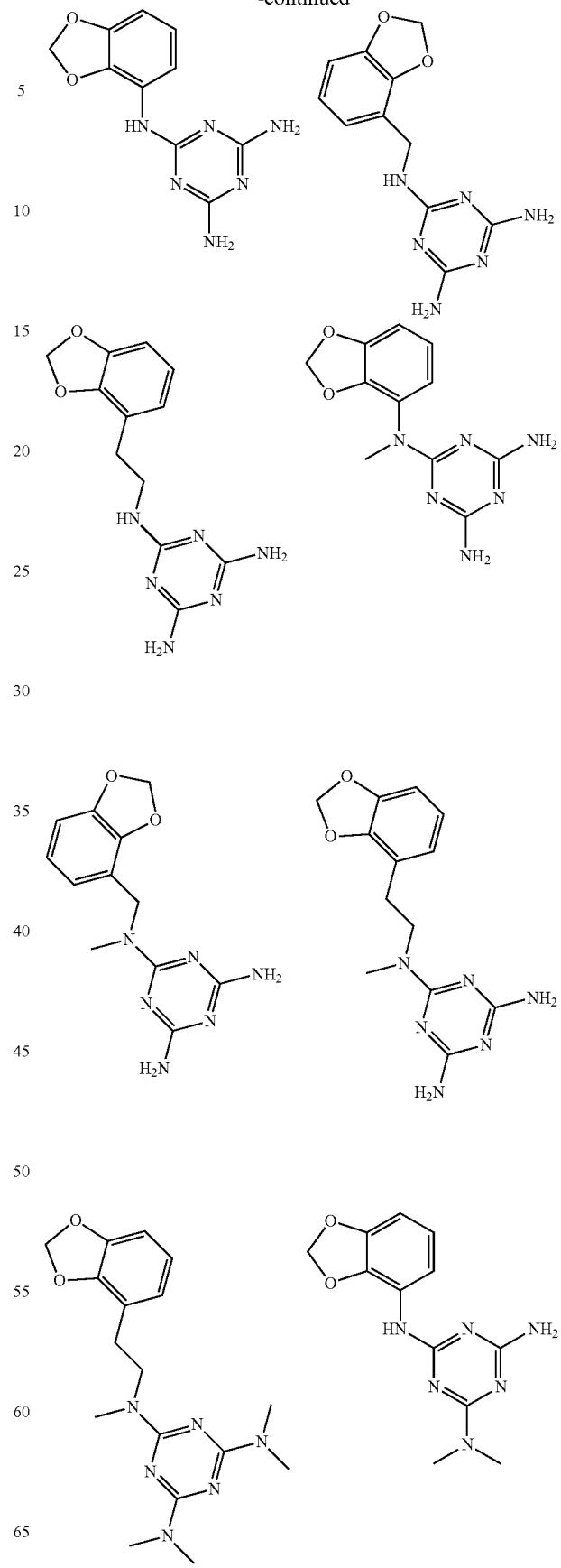

-continued
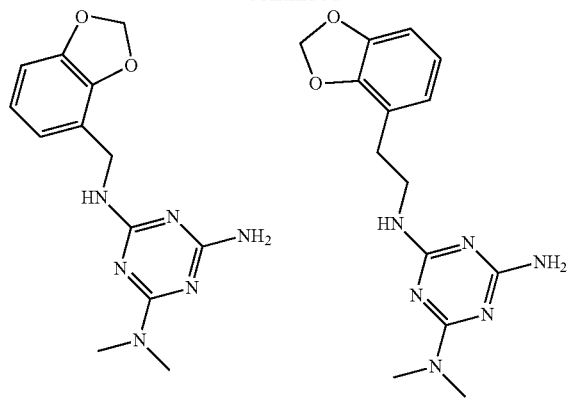
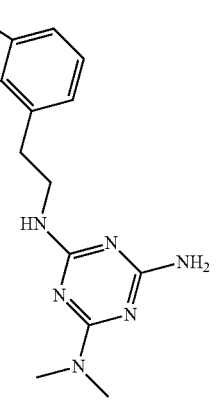
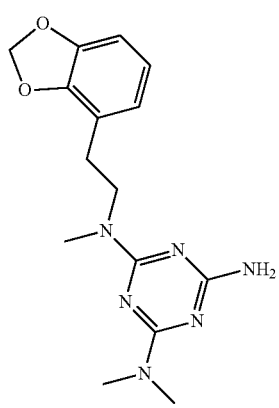
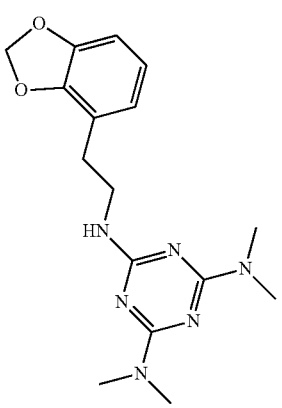
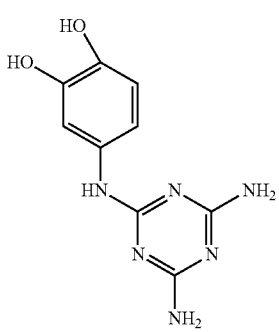
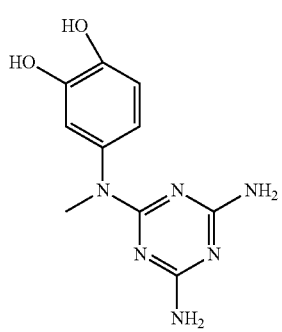
-continued
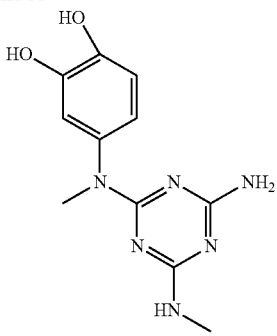
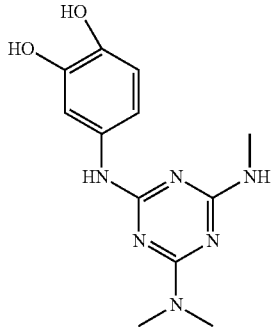
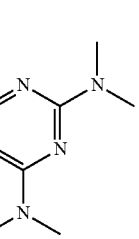
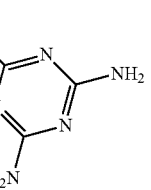

-continued
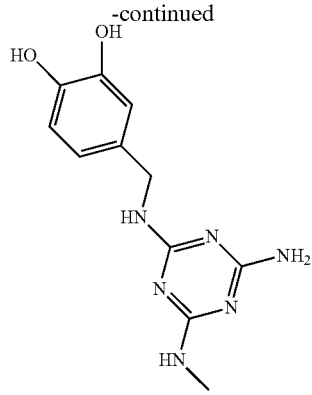
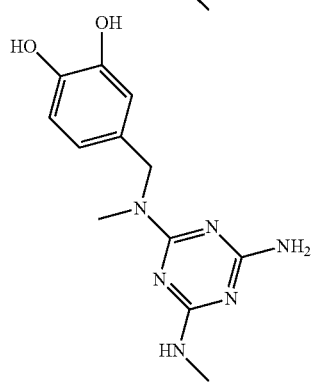
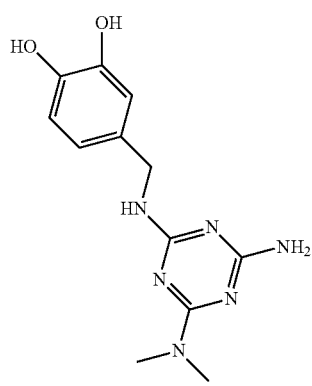
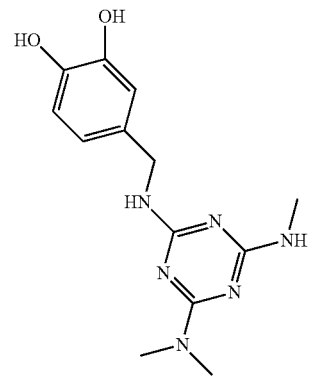
-continued
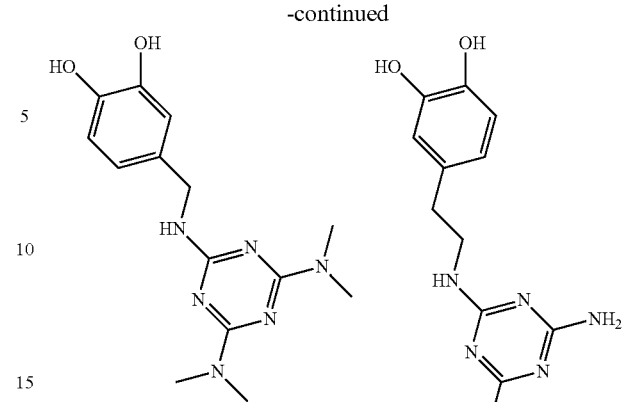
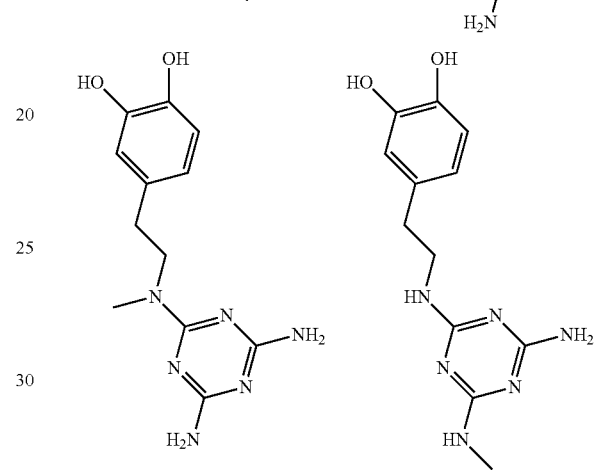
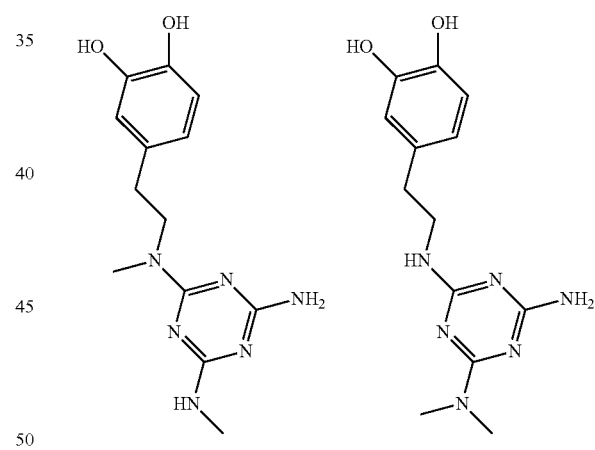
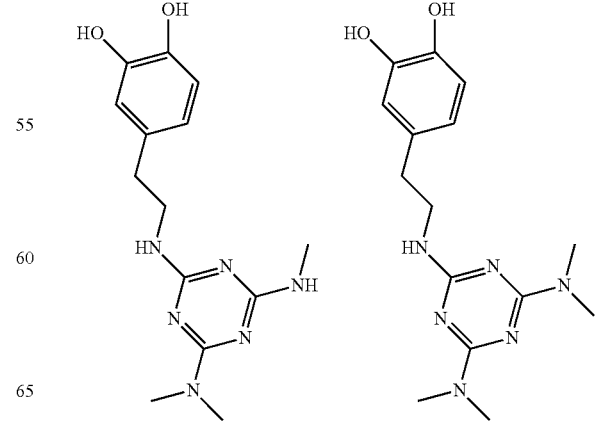

-continued
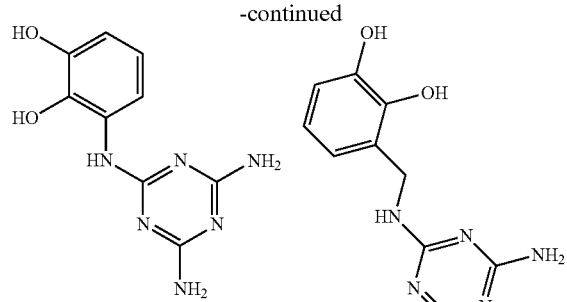
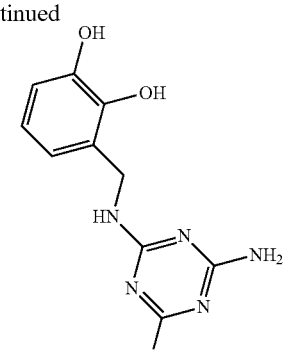
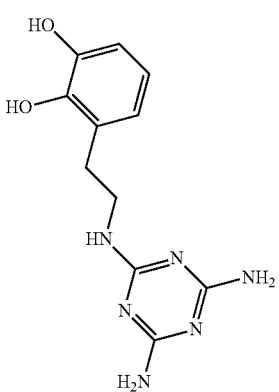
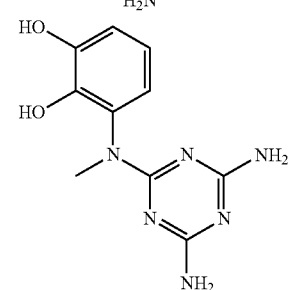
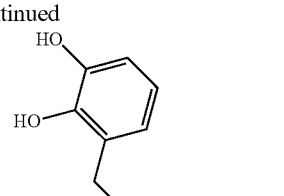
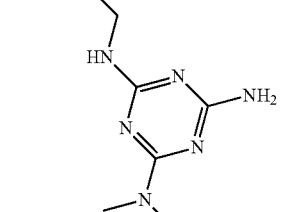
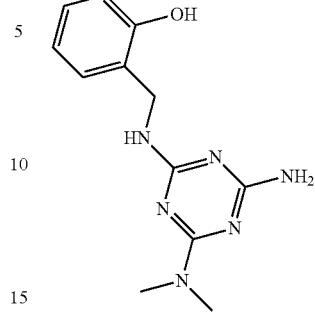
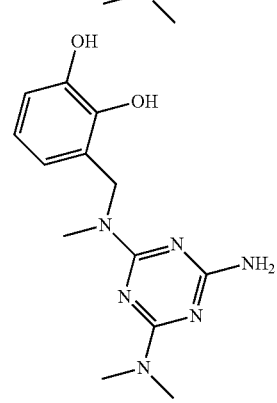
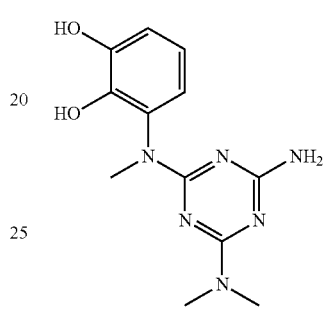
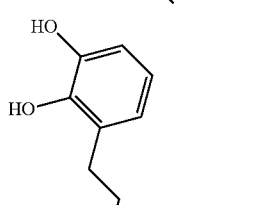
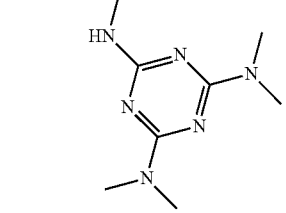
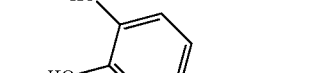
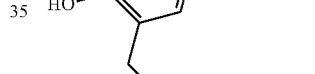
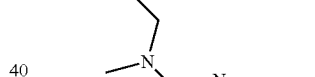
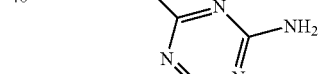
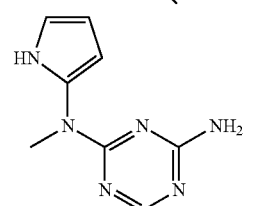
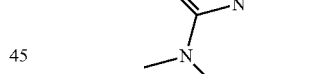
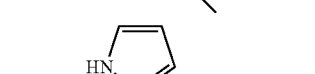
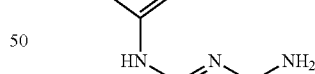
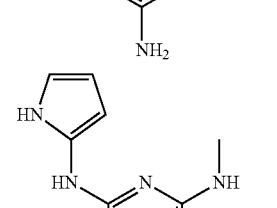
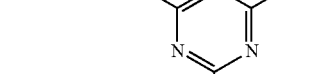

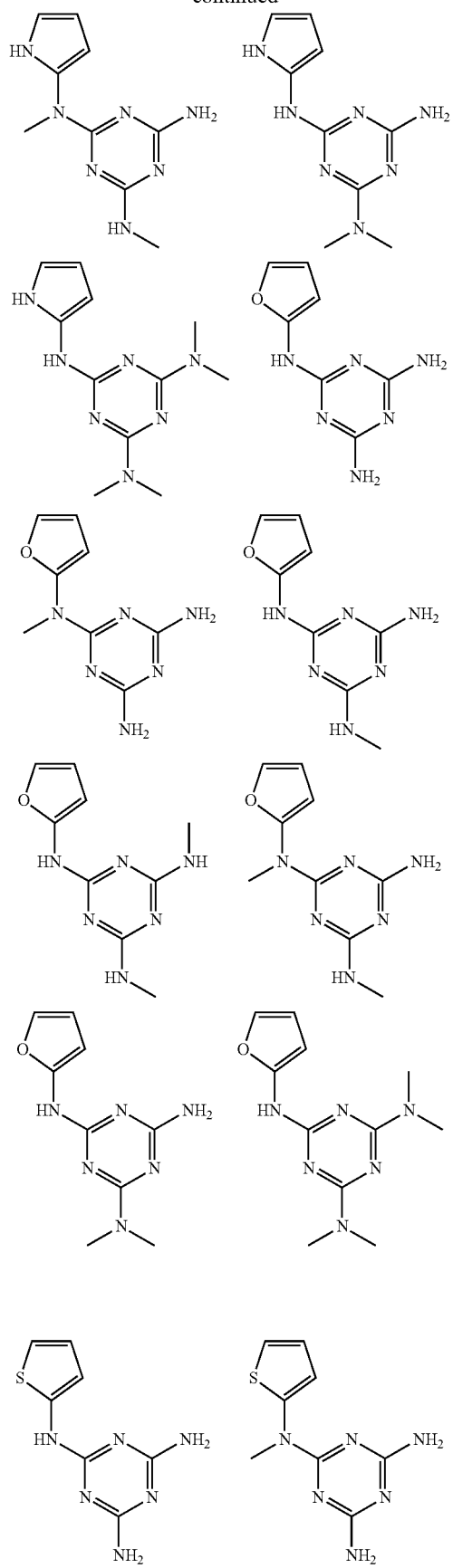
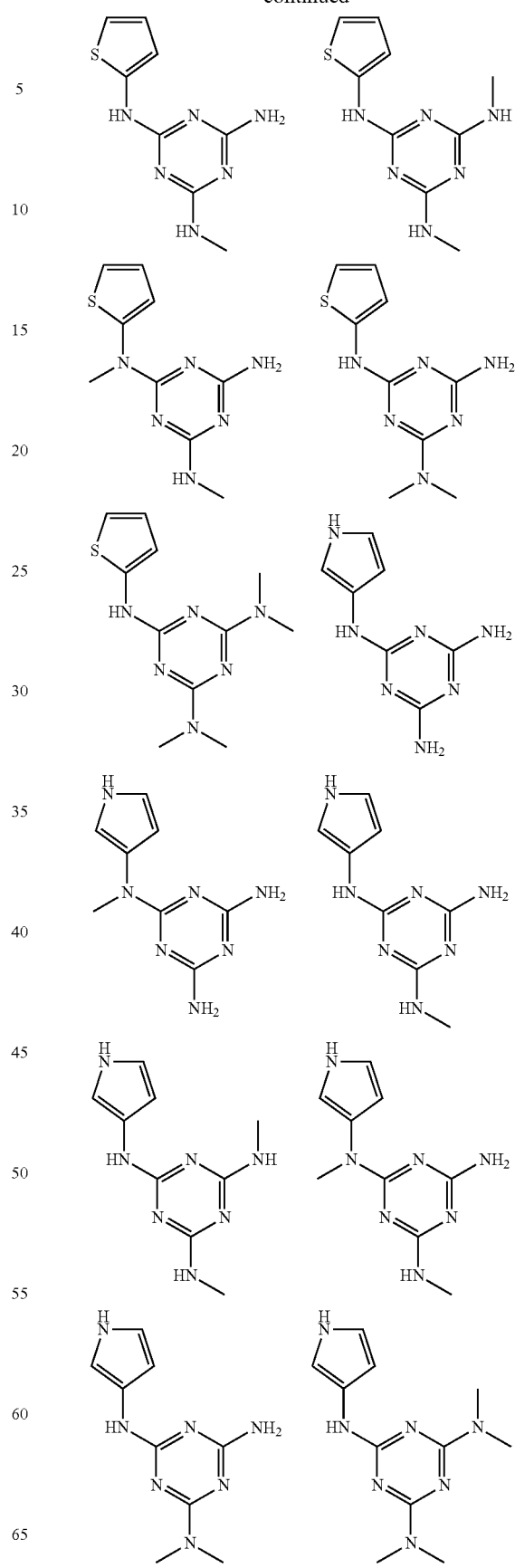

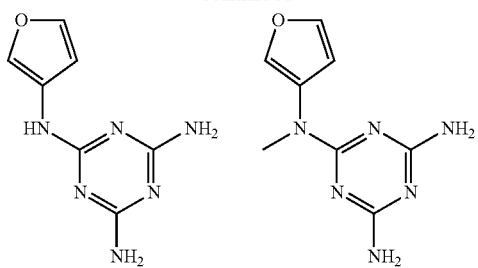
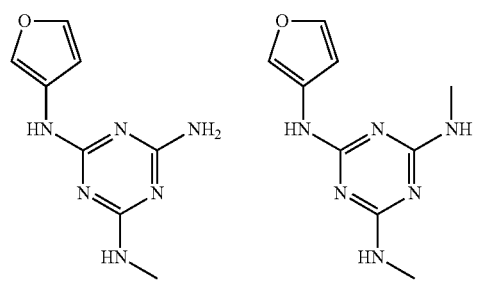
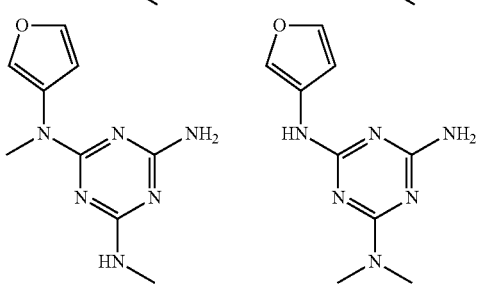
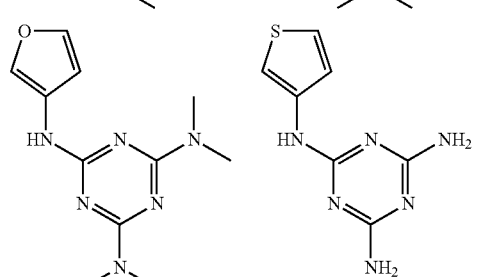
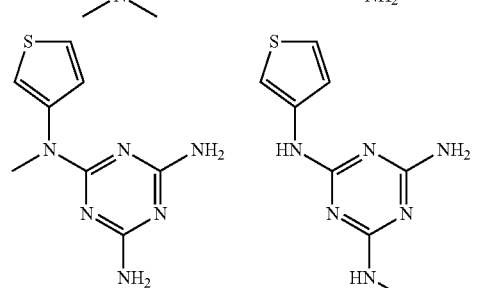
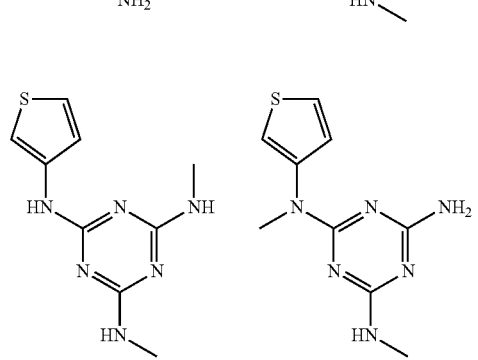
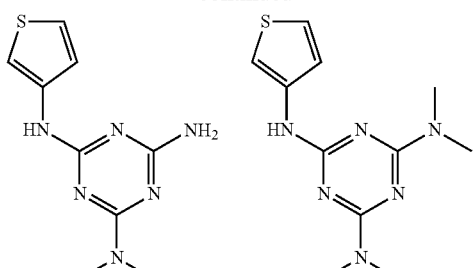
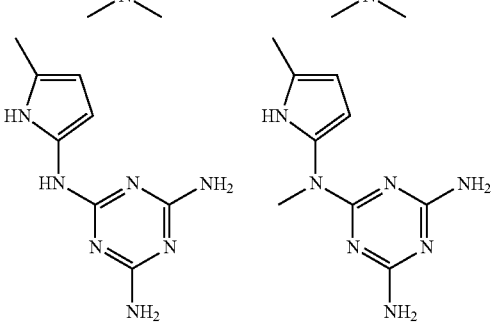
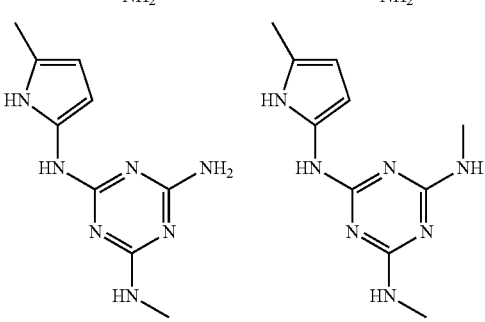
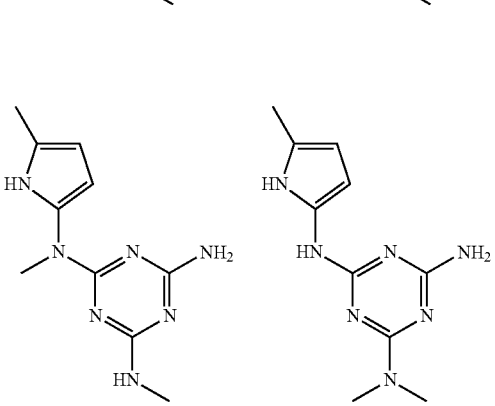
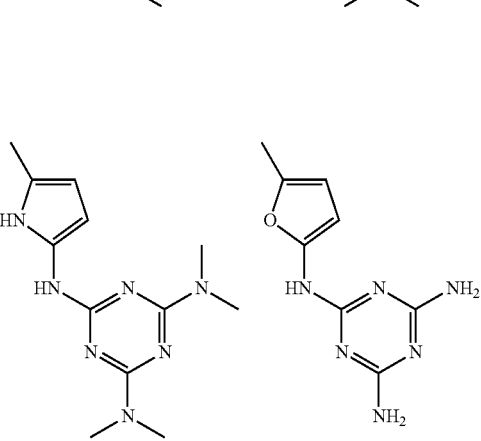

-continued
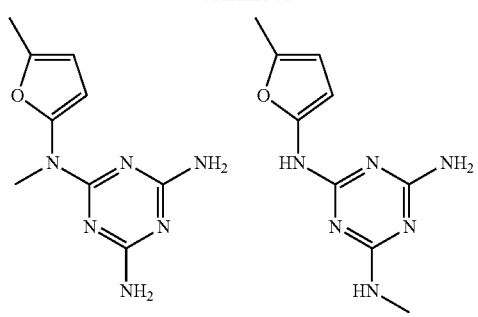
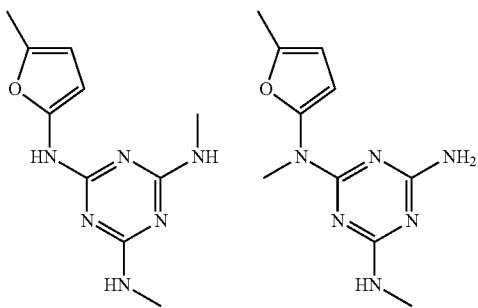
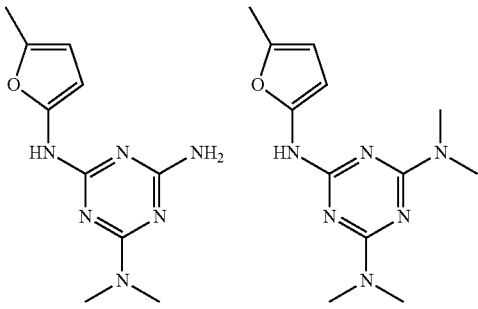
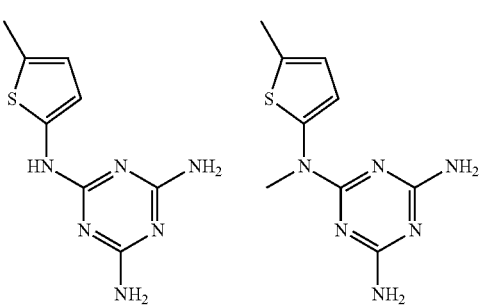
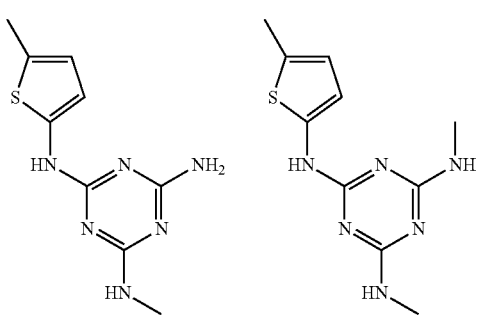
-continued
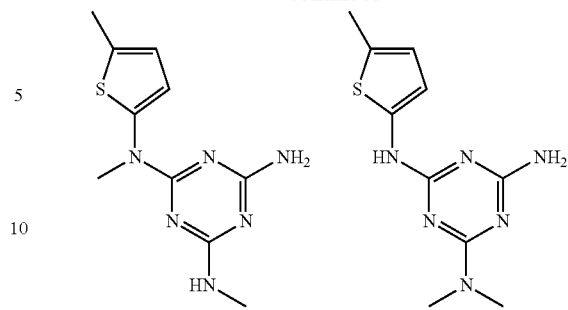
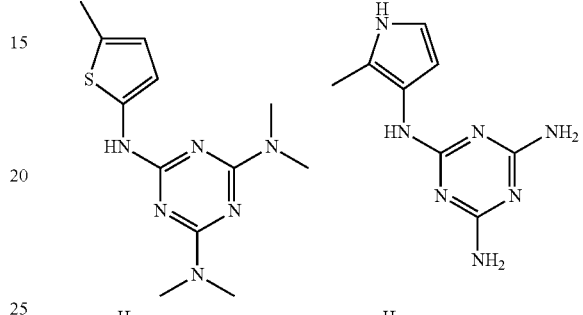
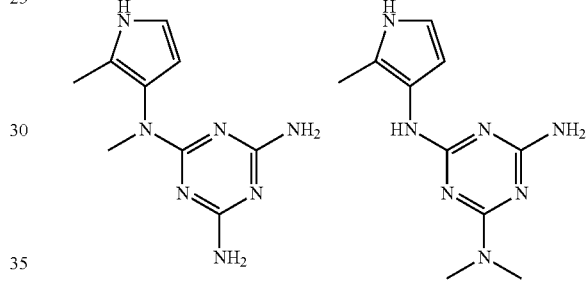
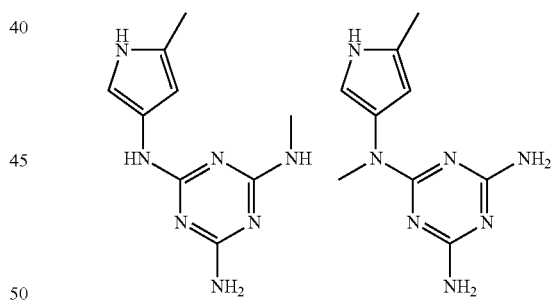
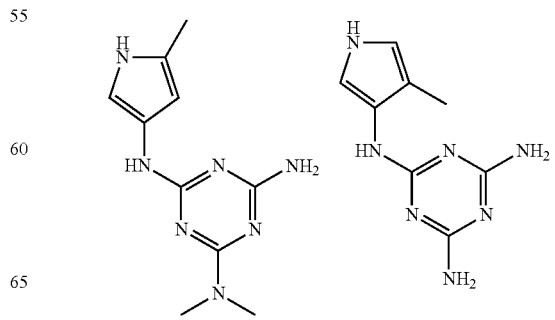

141
-continued
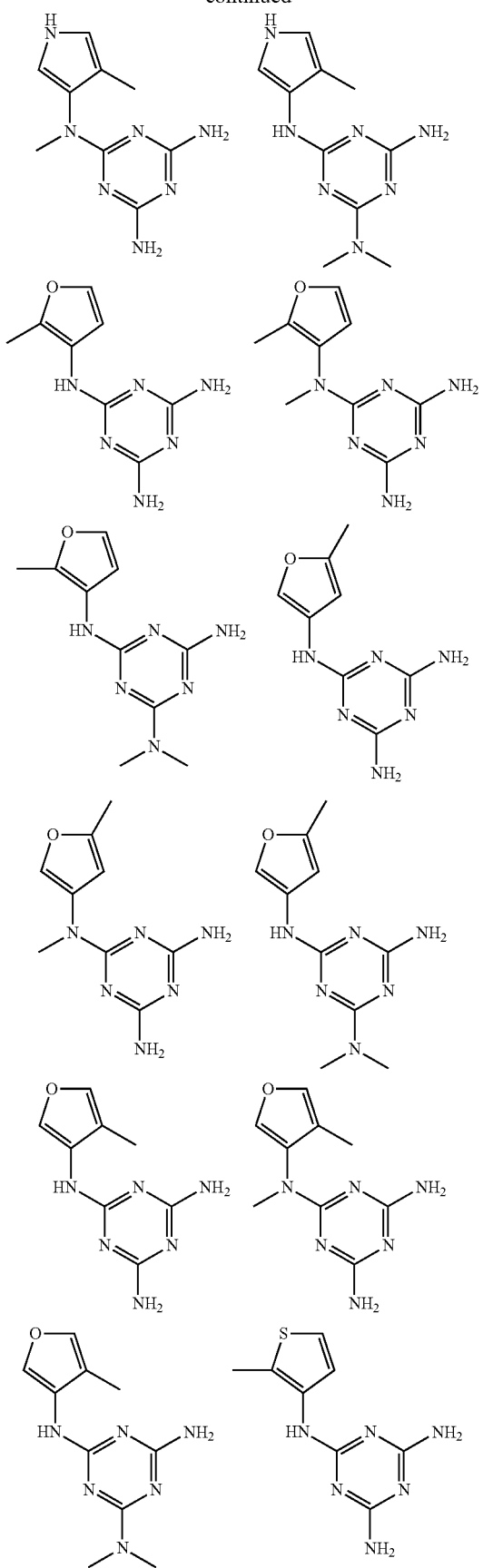
142
-continued
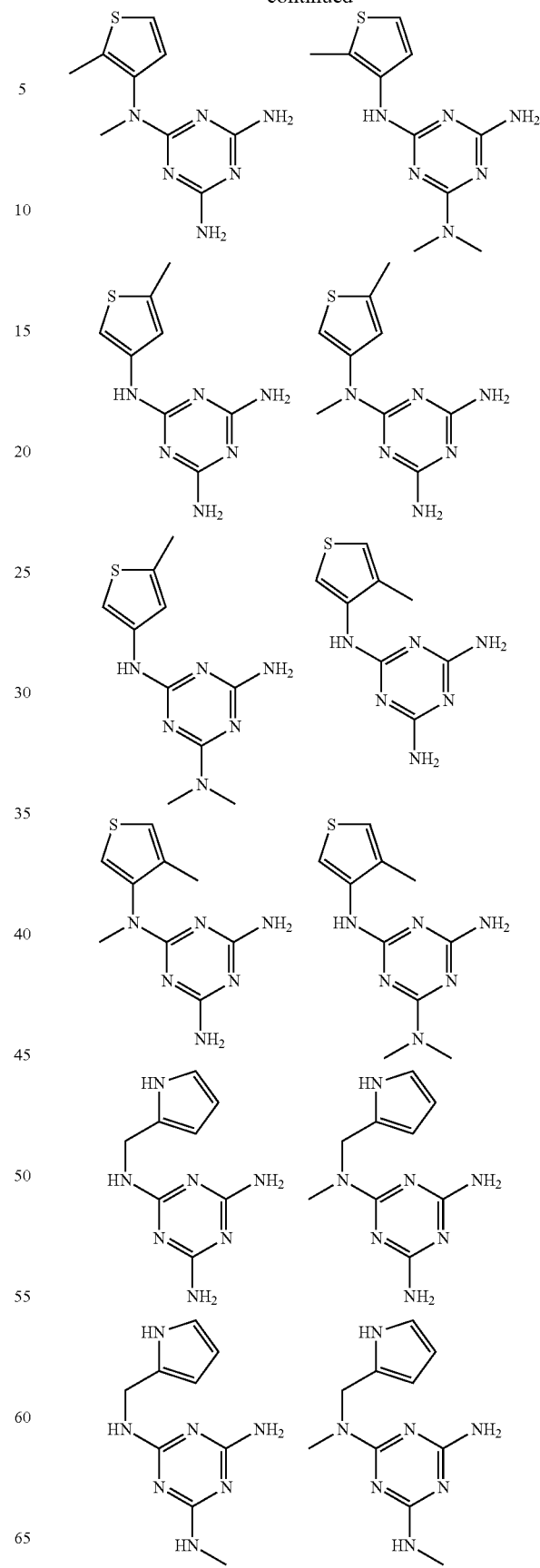

143
-continued
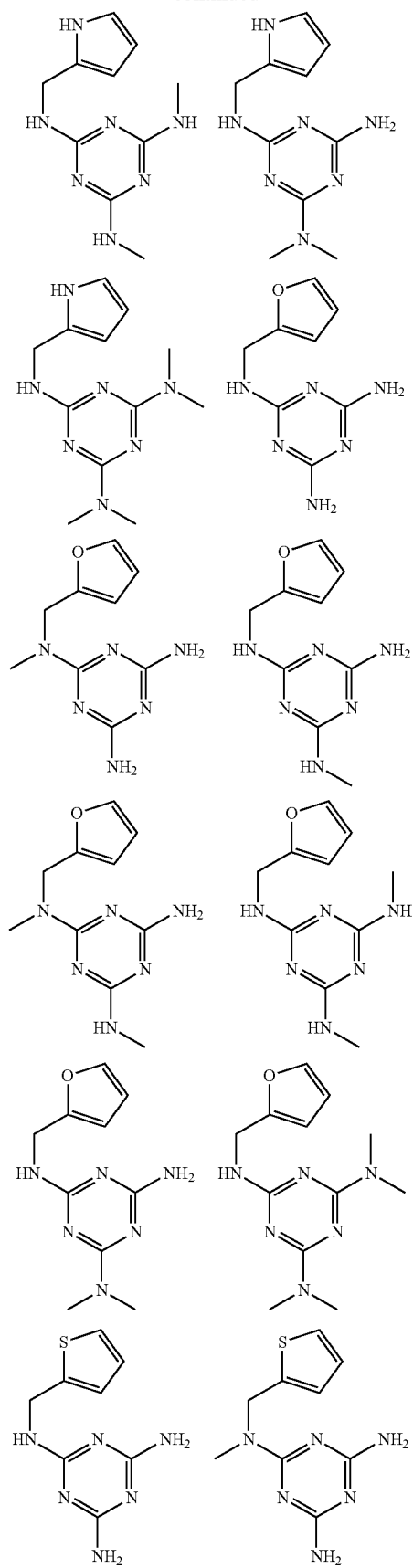
144
-continued
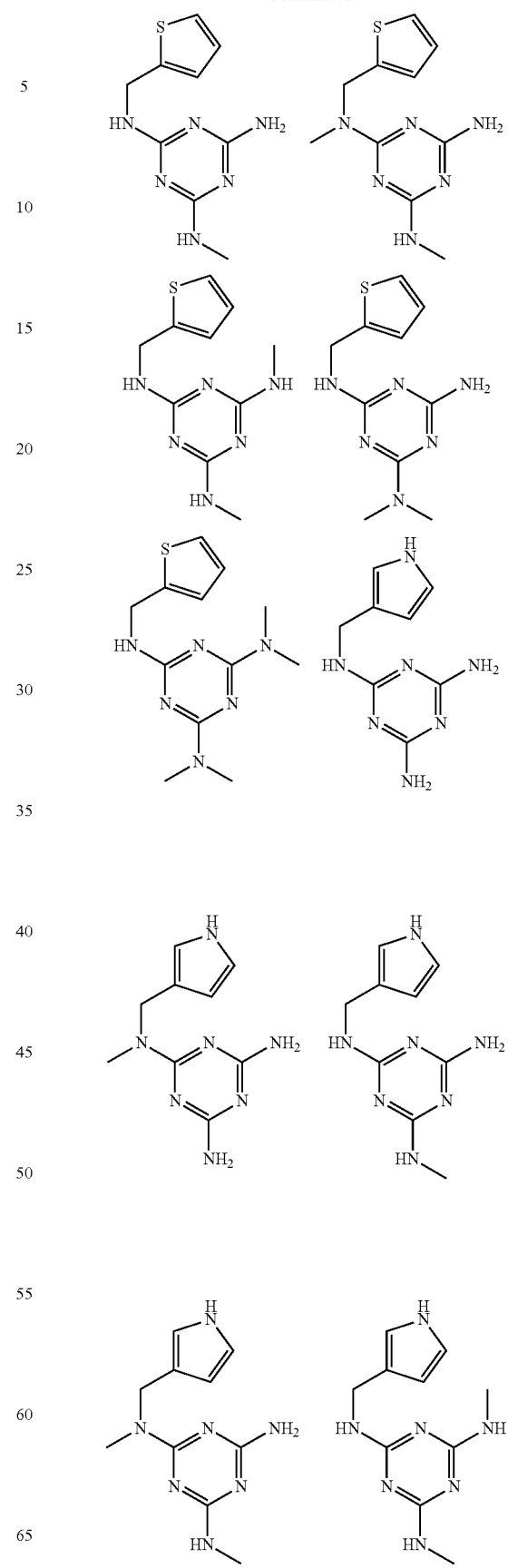

-continued
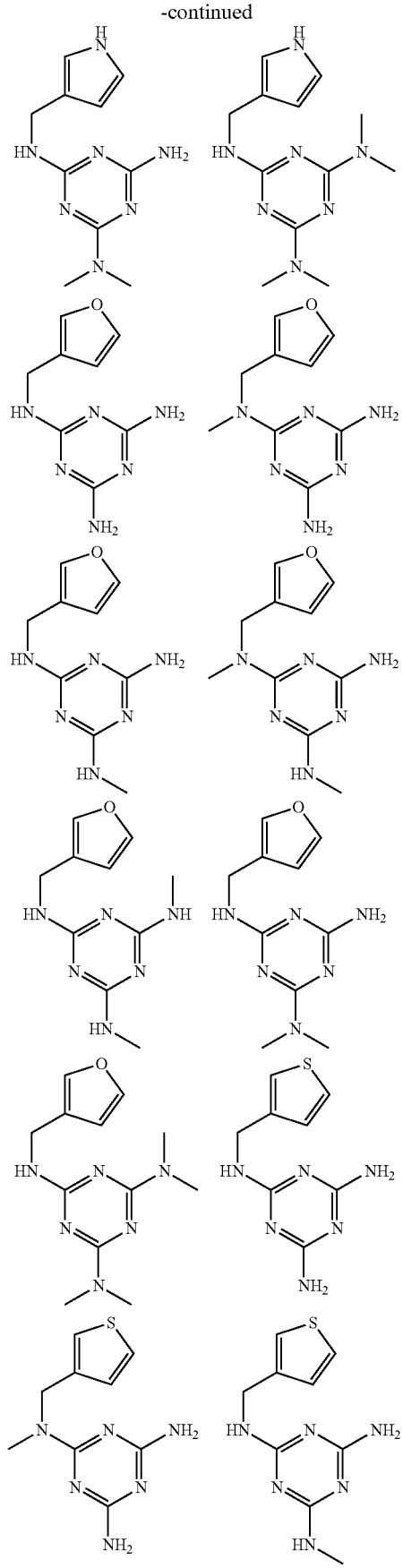
-continued
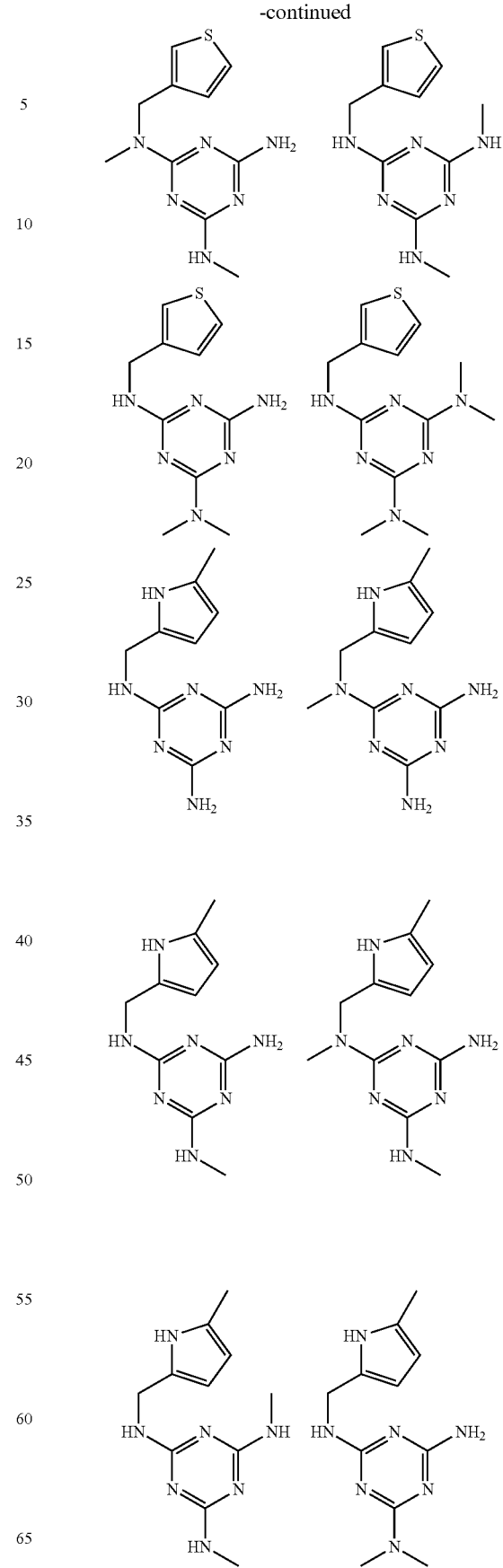

147
-continued
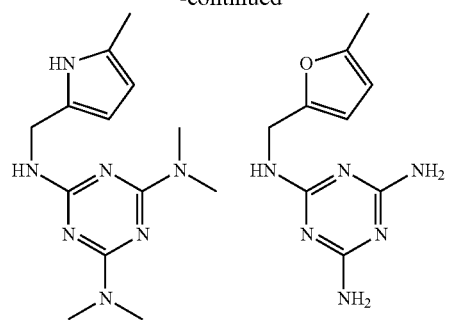
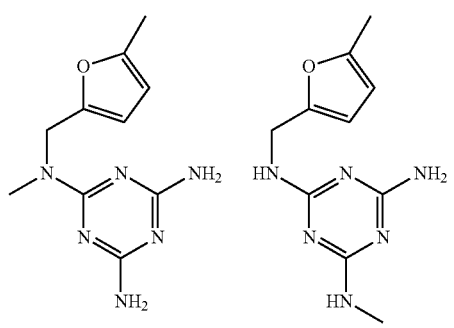
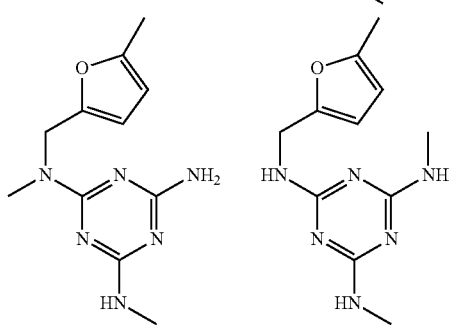
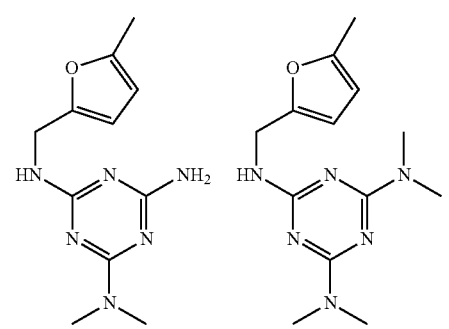
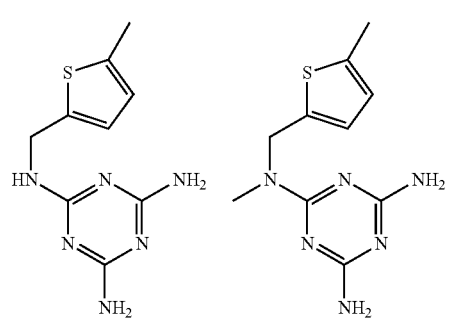
148
-continued
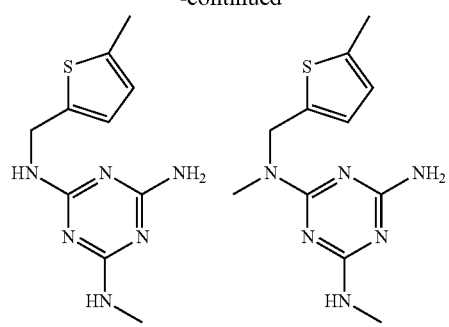
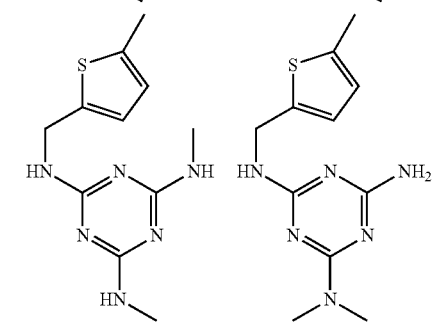
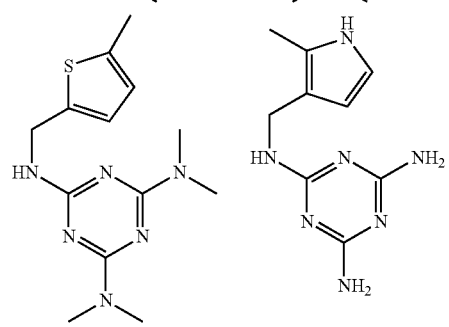
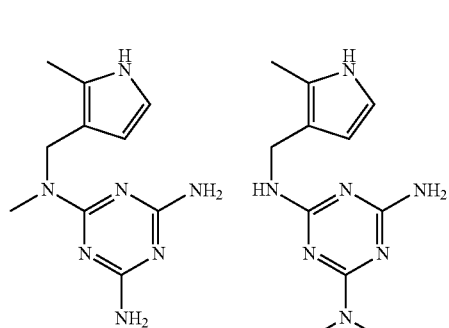
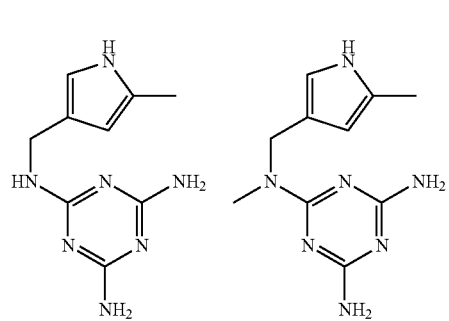

-continued
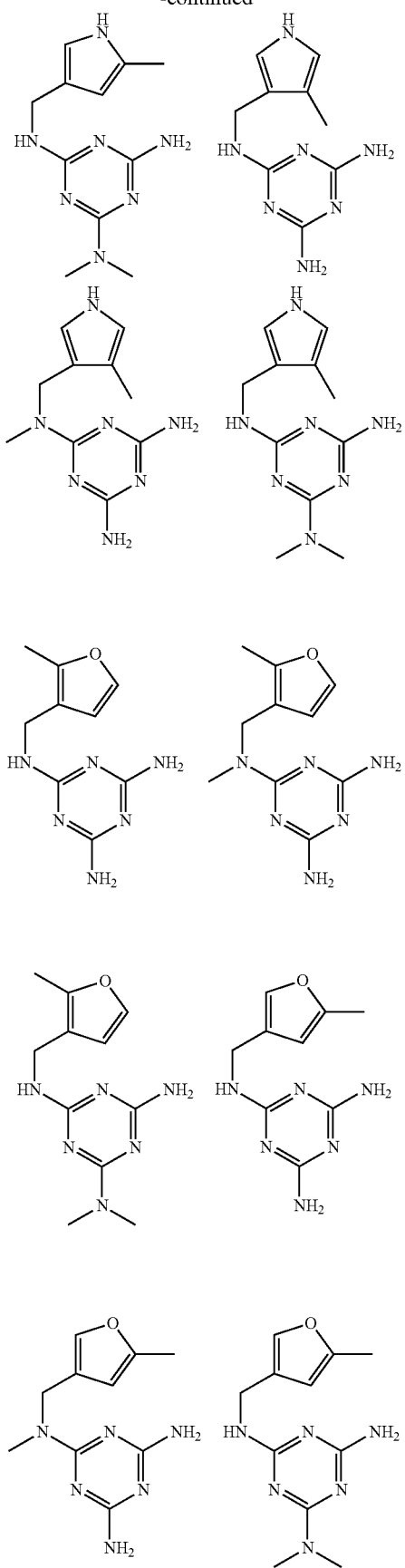
-continued
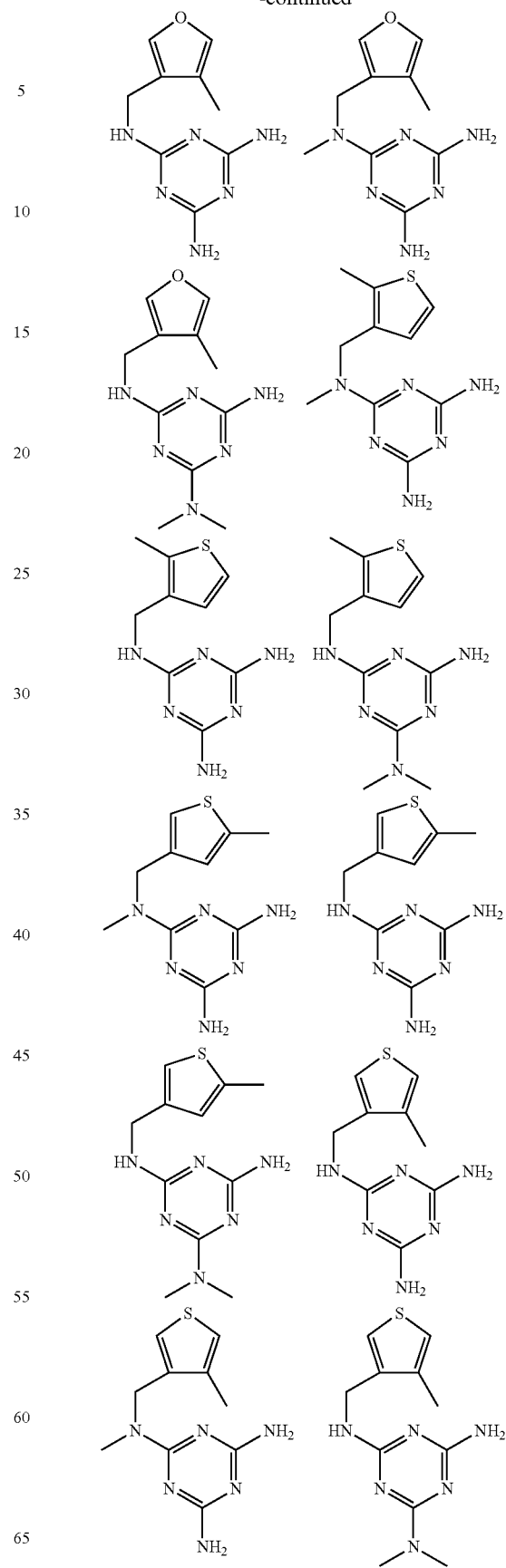

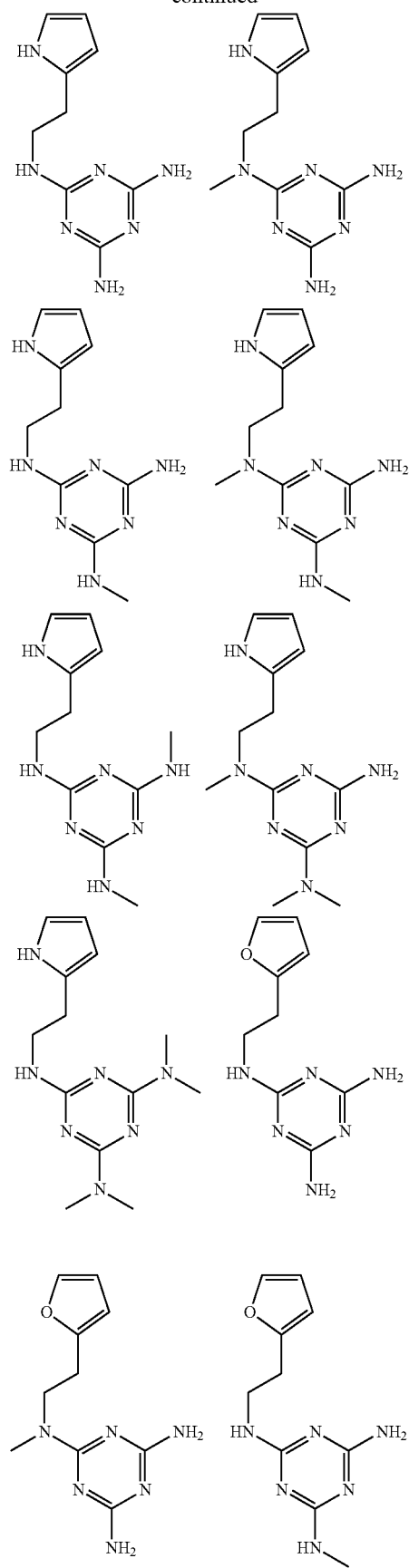
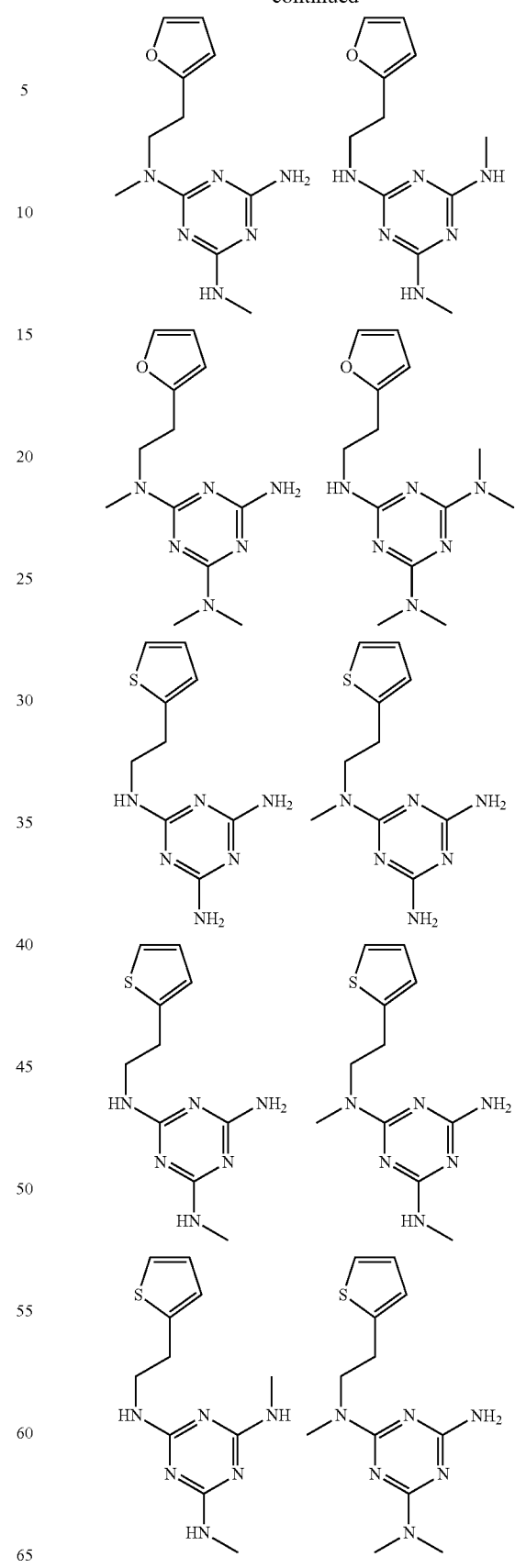

153
-continued
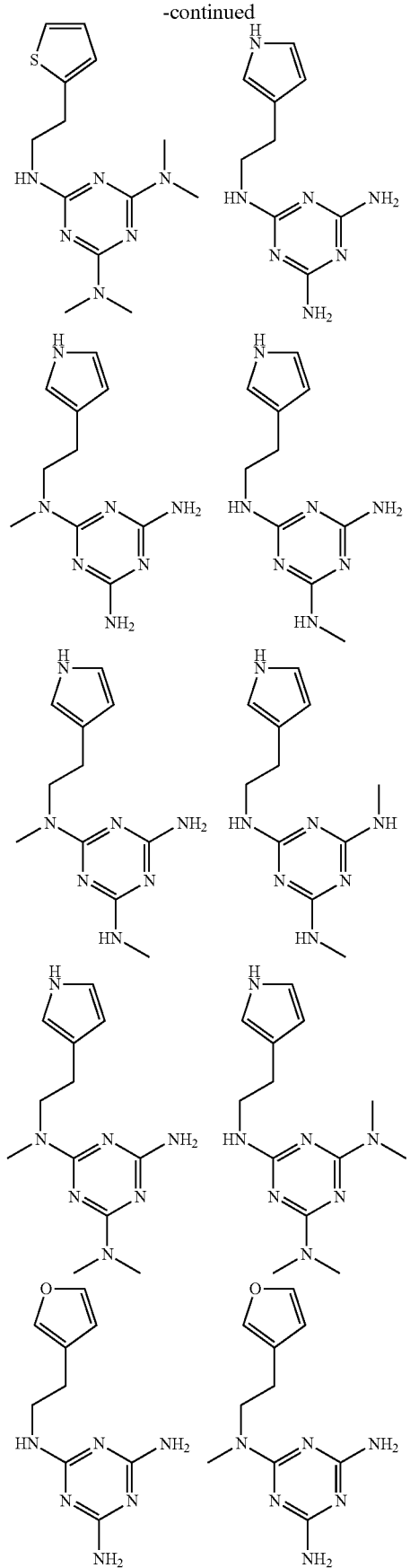
154
-continued
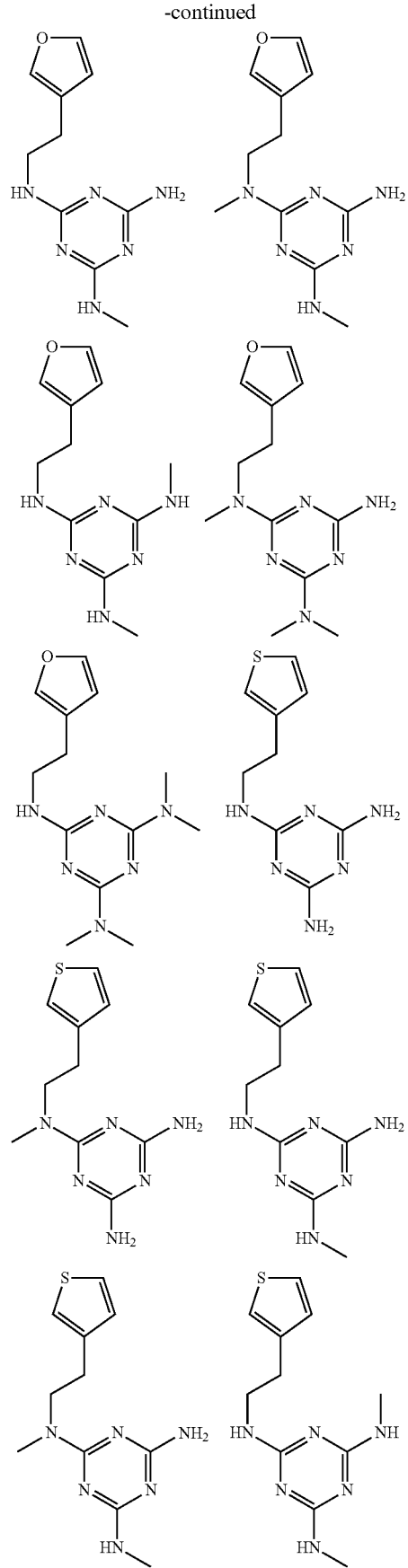

-continued
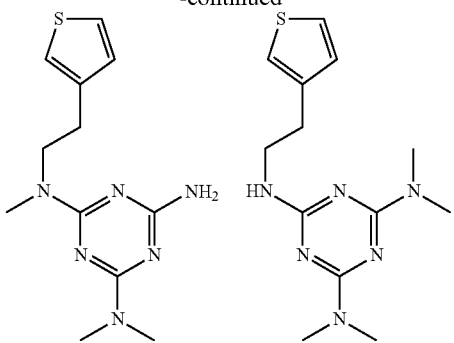
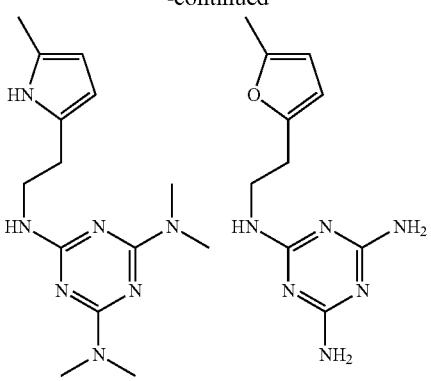
-continued
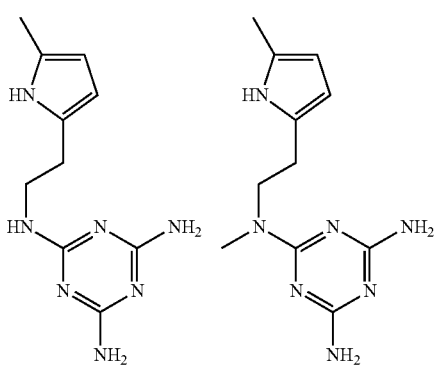
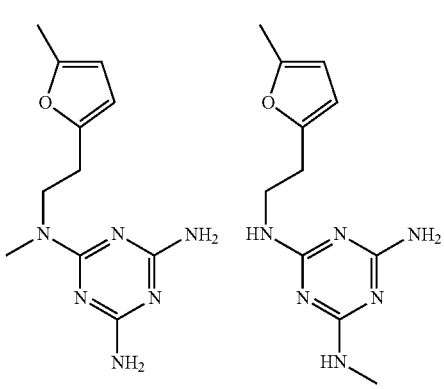
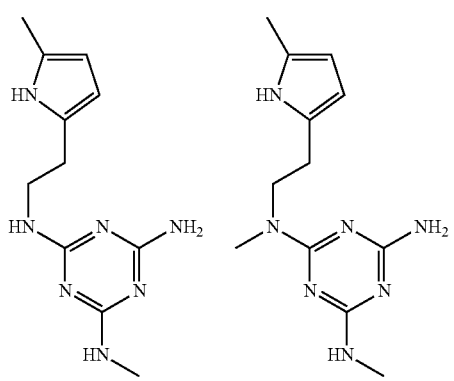
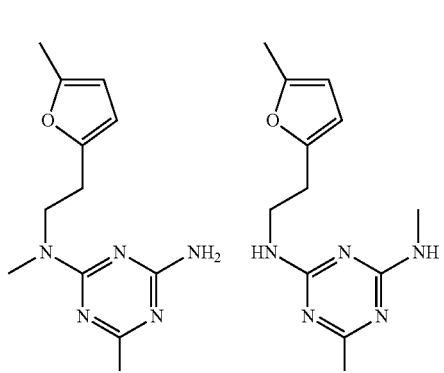
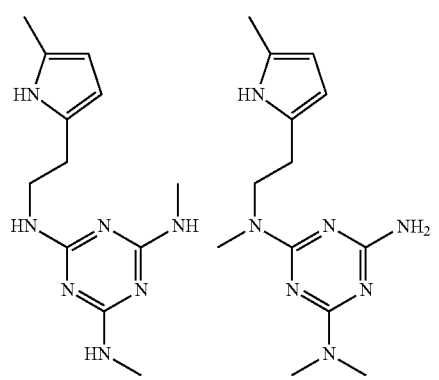
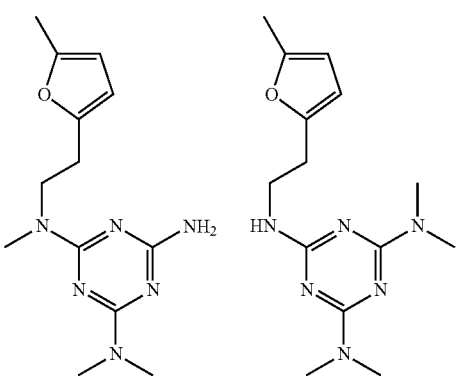

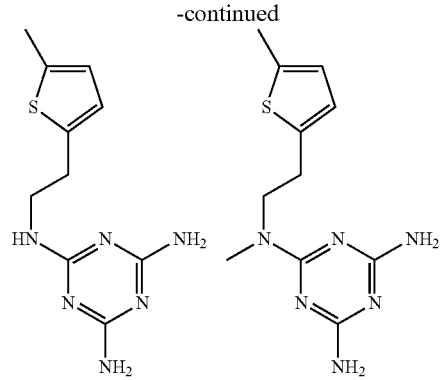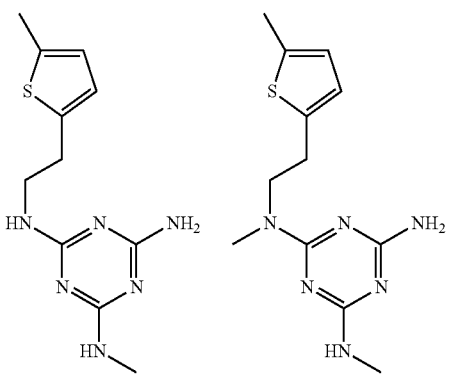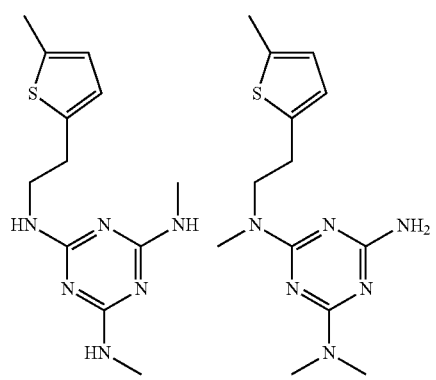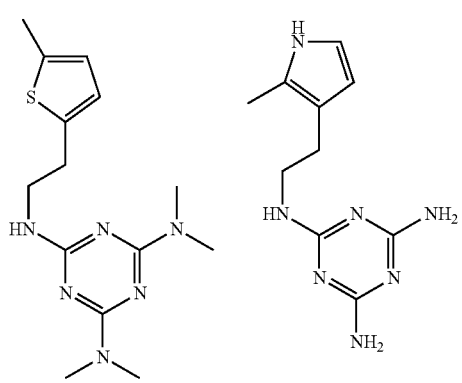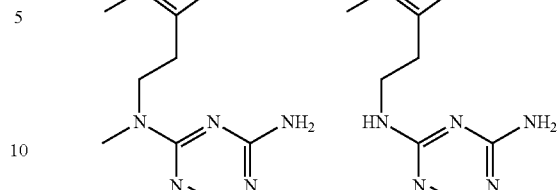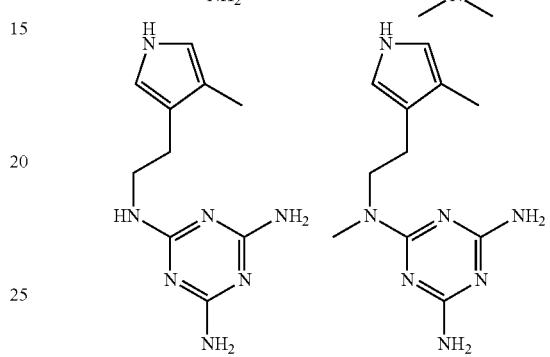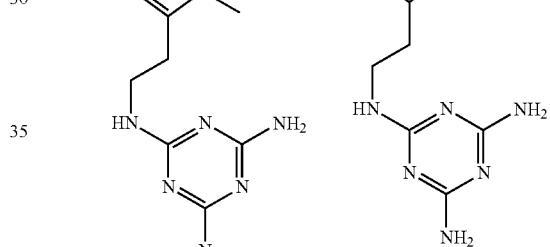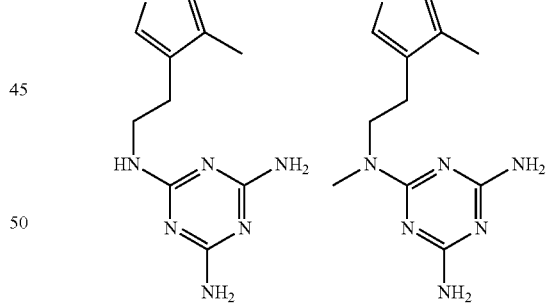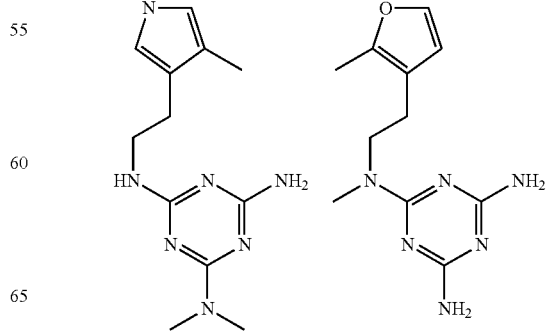

159
-continued
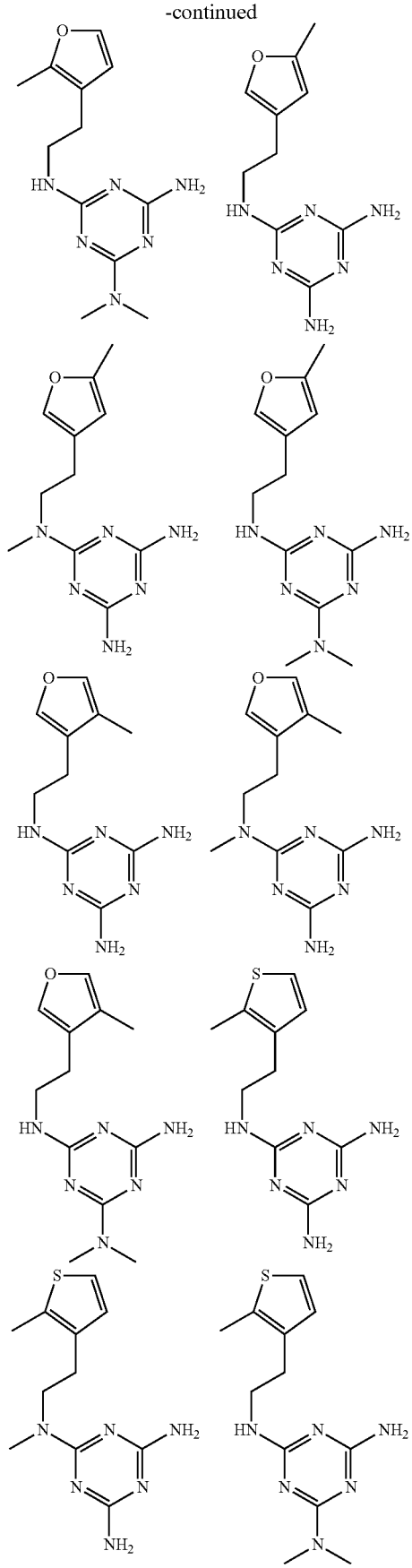
160
-continued
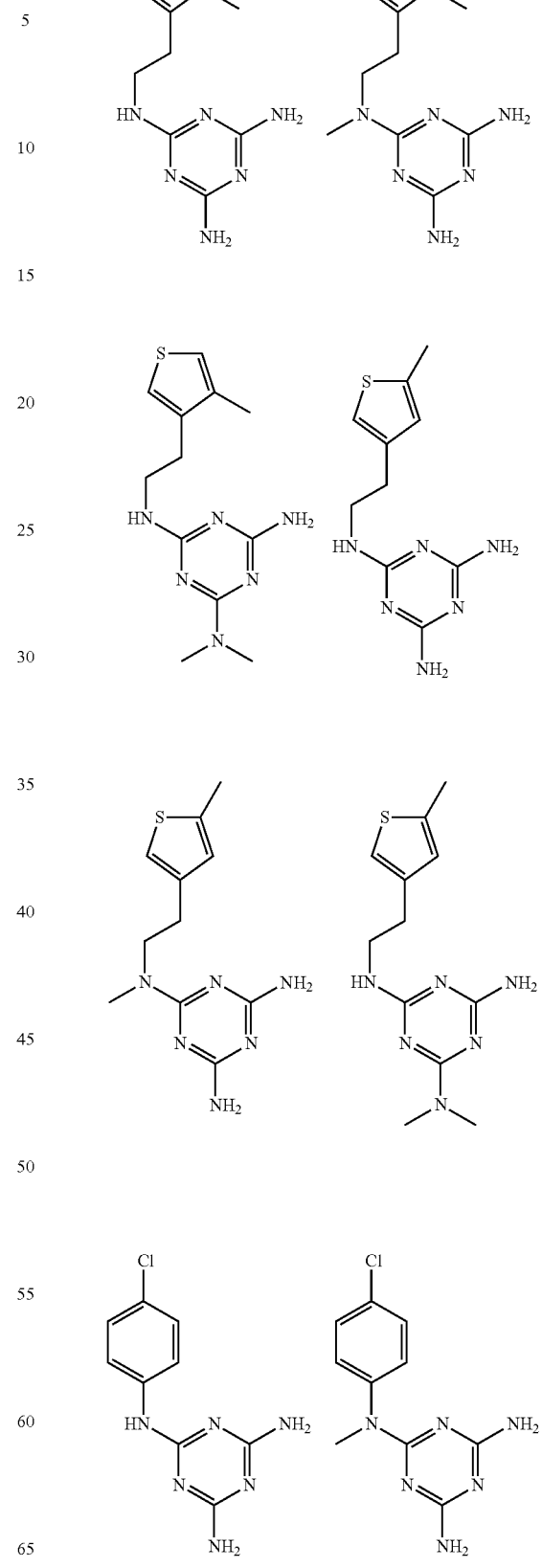

-continued
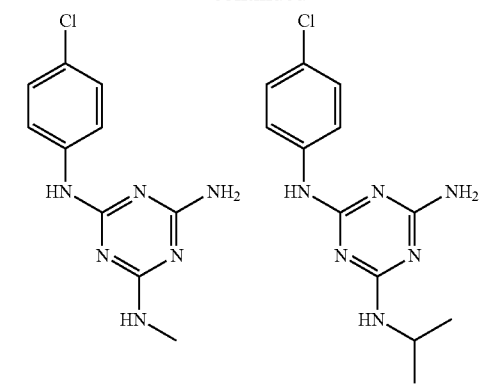
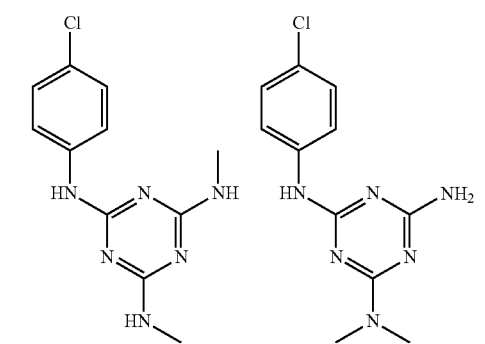
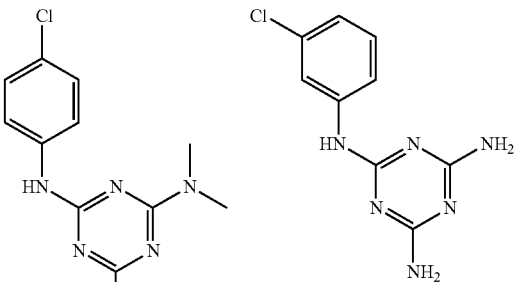
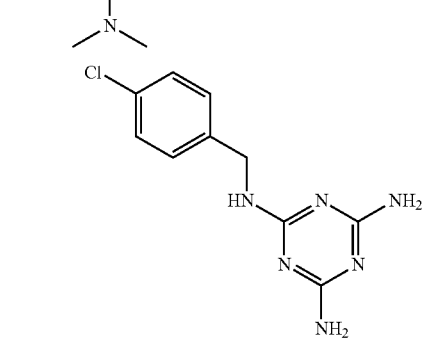
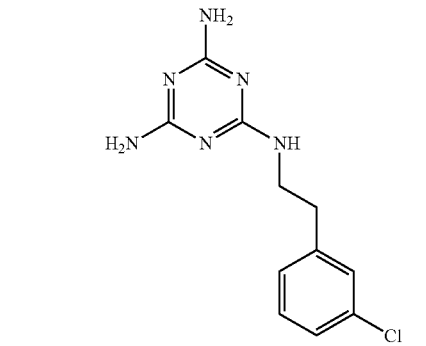
-continued
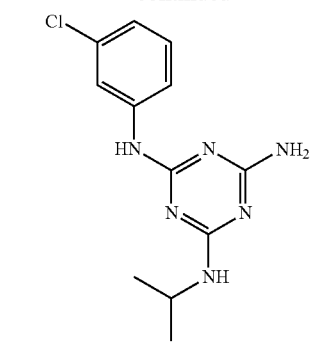
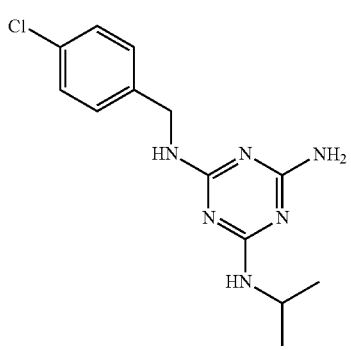
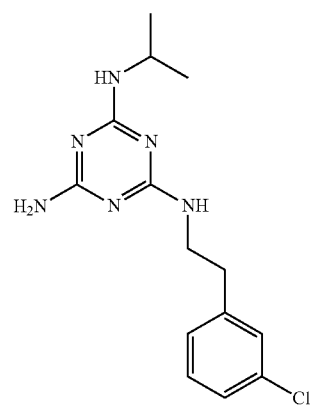
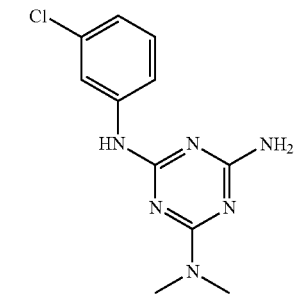
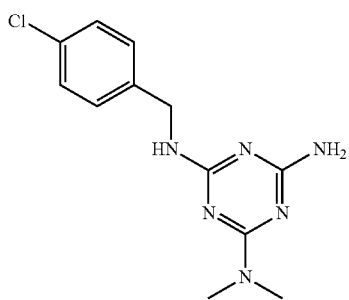

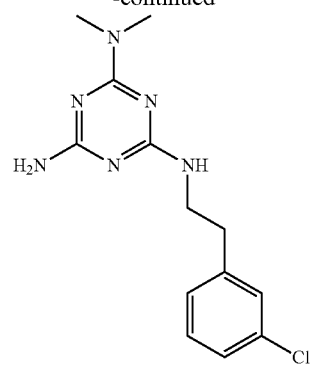
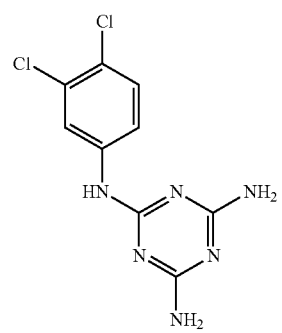
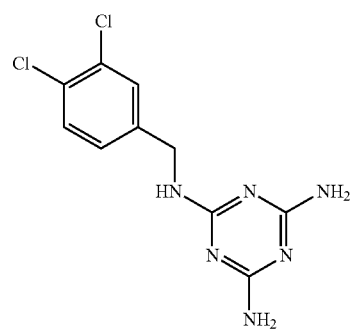
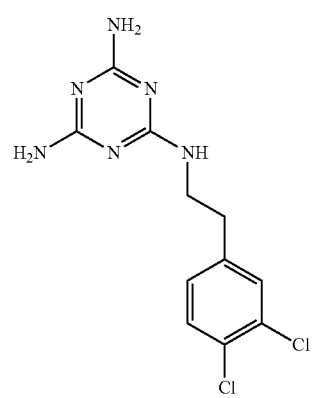
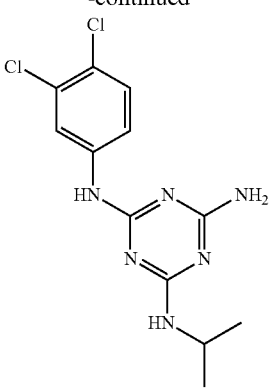
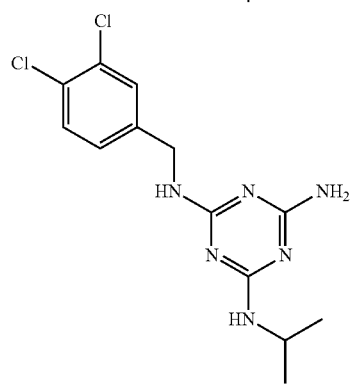
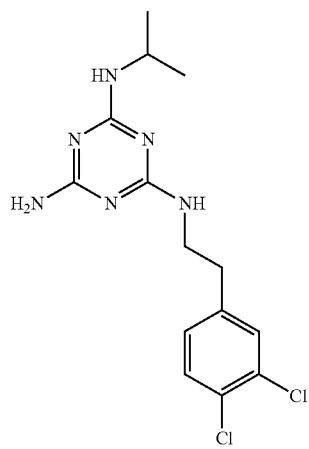
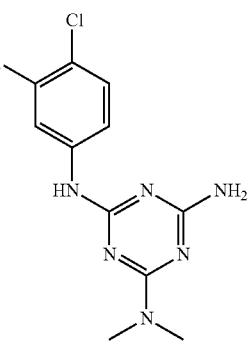

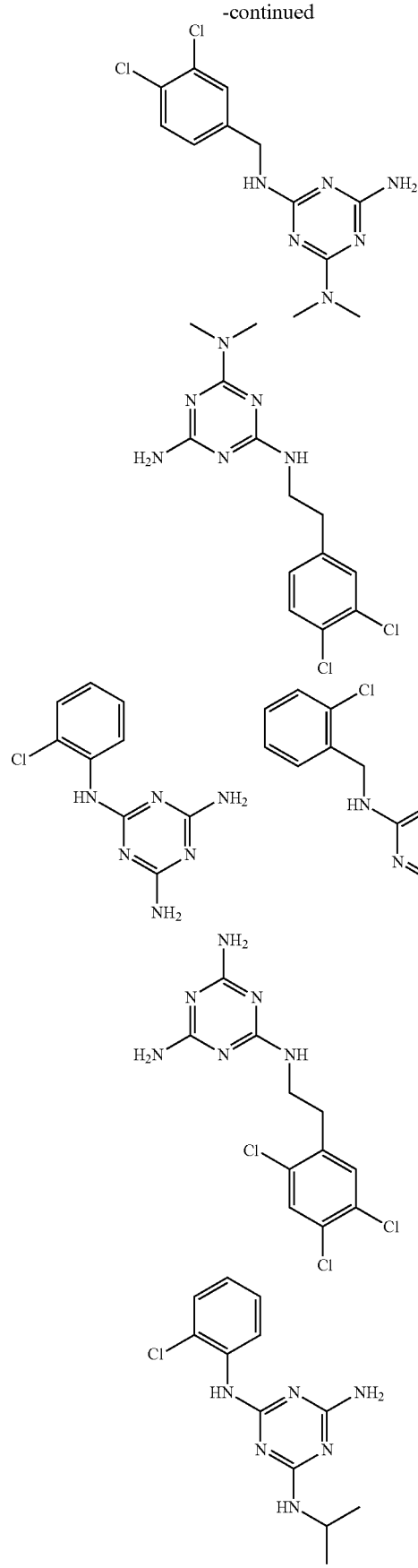
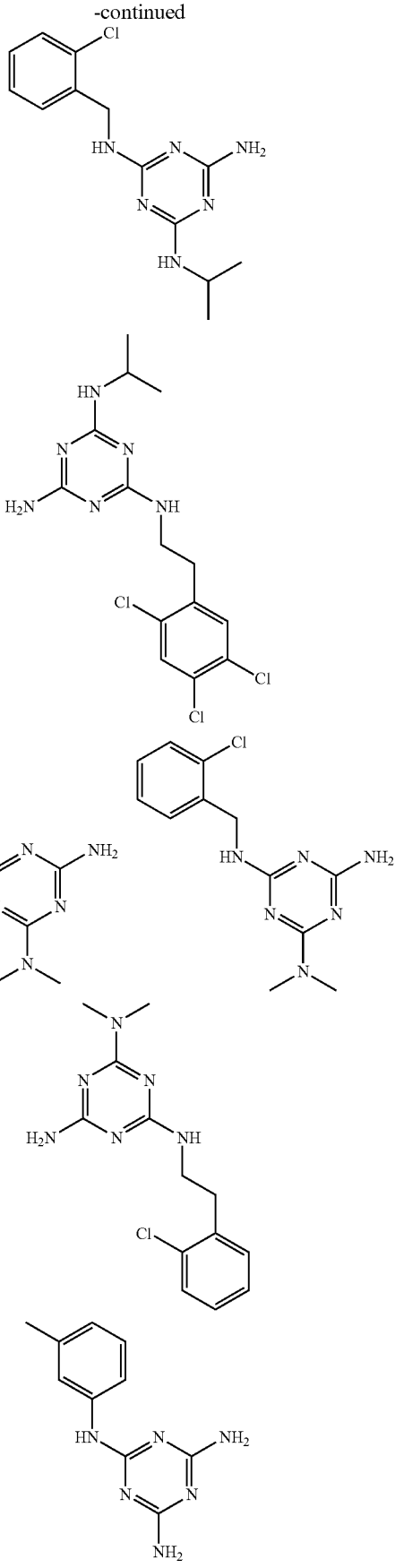

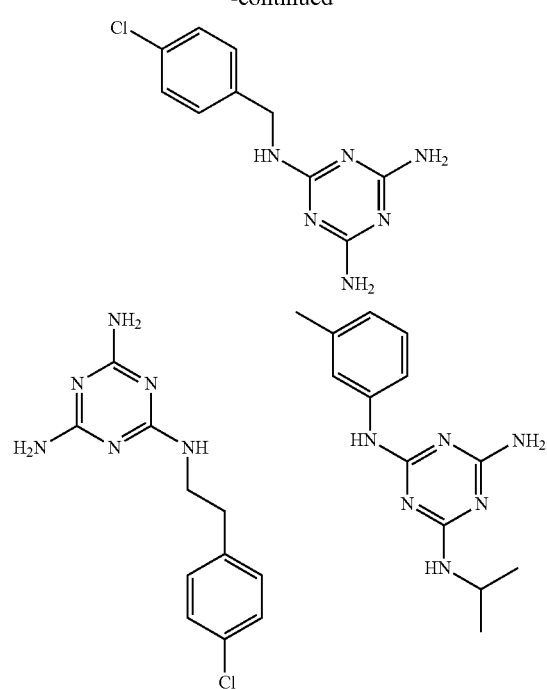
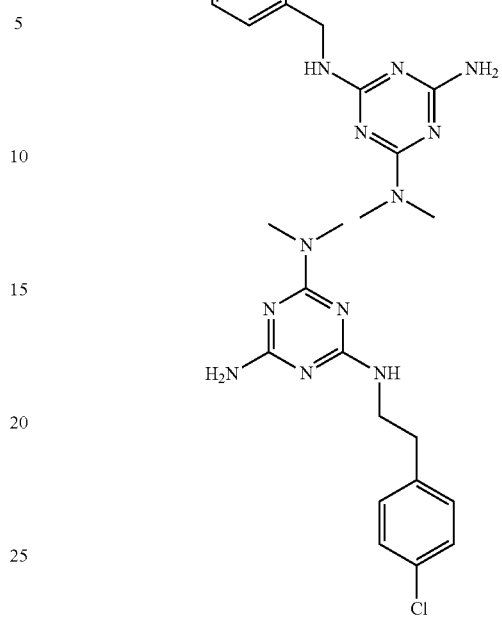
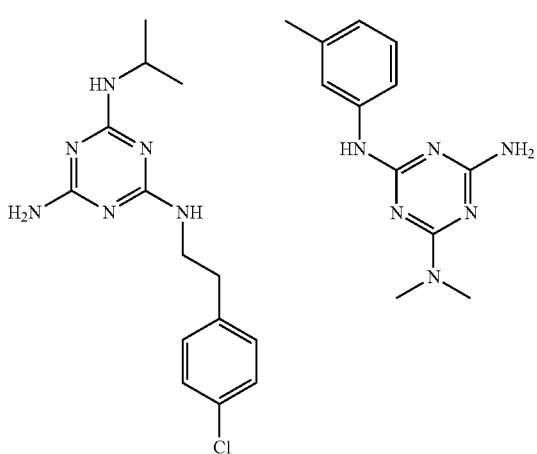

In other embodiments, dihydrotriazine compounds of Formula III may be used in connection with the compositions and methods of the disclosure. Substituent definitions, unless otherwise indicated, are the same as provided with reference to Formula I.

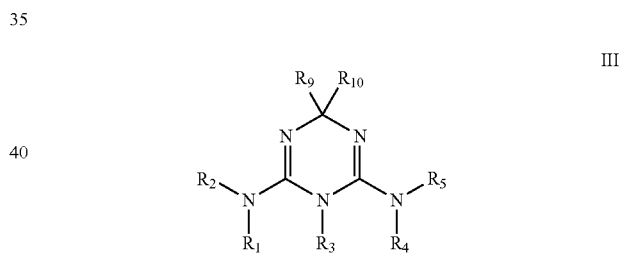

wherein:

$R_1$, $R_2$, $R_3$, $R_4$, $R_5$, $R_9$, and $R_{10}$, are independently selected from:

H, OH,

O—Rx, wherein Rx is alkyl, cycloalkyl, alkylcycloalkyl, acyl, ester, thioester;

optionally substituted alkyl (e.g., a $C_1$ to $C_{12}$ straight chain or branched chain alkyl optionally substituted with oxygen, silicon, sulphur or optionally substituted with OH, O-alkyl, SH, S-alkyl, $NH_2$, NH-alkyl); cycloalkyl (e.g., $C_3$ to $C_7$ cycloalkyl); alkylcycloalkyl (e.g., $C_4$ to $C_{12}$ alkylcycloalkyl); heterocycloalkyl (e.g., where the heterocycle comprises one or two hetero atoms selected from O, S, or N, including a $C_2$ to $C_6$ heterocycloalkyl); alkylheterocycloalkyl (e.g., where the heterocycle comprises one or two hetero atoms selected from O, S, or N, including a $C_3$ to $C_{11}$ alkylheterocycloalkyl, and including wherein when N is present in the heterocyclic ring, the nitrogen atom may be in the form of an amide, carbamate or urea); optionally substituted alkenyl (e.g., $C_1$ to $C_{12}$ straight chain or branched chain alkenyl optionally substituted with oxygen, silicon, sulphur or optionally substituted with OH, O-alkyl, SH, S-alkyl, NH$_2$, NH-alkyl); optionally substituted alkynyl (e.g., C$_1$ to C$_{12}$ straight chain or branched chain alkynyl optionally substituted with oxygen, silicon, sulphur or optionally substituted with OH, O-alkyl, SH, S-alkyl, NH$_2$, NH-alkyl);

optionally substituted aryl (e.g., phenyl, substituted phenyl, naphthyl, substituted naphthyl); optionally substituted alkylaryl (e.g., alkylphenyl, alkylsubstituted phenyl, alkylnaphthyl, alkylsubstituted naphthyl); optionally substituted heteroaryl (e.g., pyridyl, furanyl, thiophenyl, pyrrollyl, oxazolyl, isoxazolyl, thiazolyl, diazolyl, pyrazolyl, triazolyl all of which are optionally substituted); optionally substituted alkylheteroaryl; and or R$_1$ and R$_2$ may together form a 3 to 8 membered heterocyclic ring, including the nitrogen atoms to which they are attached;

or R$_4$ and R$_5$ may together form a ring selected from the group aziridine, pyrrolyl, imidazolyl, pyrazolyl, indolyl, indolinyl, pyrrolidinyl, piperazinyl and piperidyl, including the nitrogen atoms to which they are attached.

In certain embodiments, O—Rx may be selected from: O—C$_1$ to C$_8$ straight chain or branched chain alkyl; O—C$_3$ to C$_7$ cycloalkyl; O—C$_4$ to C$_8$ alkylcycloalkyl; O-acyl; O-esters; and O-thioesters.

In other embodiments, optional substitutions may include, e.g., OH, O-alkyl, SH, S-alkyl, NH$_2$, NH-alkyl. Further, an alkyl, alkenyl, alkynyl, etc. may be substituted with an oxygen, silicon, sulphur, etc. to form a heteroalkyl, heteroalkenyl, heteroalkynyl, etc.

In certain aspects, each of: R$_3$ or R$_3$, R$_4$, R$_5$, and R$_{10}$, or, R$_3$, R$_4$, R$_5$, R$_9$ and R$_{10}$, or R$_2$, R$_3$, R$_4$, R$_5$, R9 and R$_{10}$ may be independent selected from:

H, methyl, ethyl, propyl or isopropyl;
and each of the remaining substitutent groups: R$_1$, R$_2$, R$_4$, R$_5$, R$_9$, and R$_{10}$, or R$_1$, R$_2$, and R$_9$, or R$_1$ and R$_2$, or R$_1$, respectively, are independently selected from:

H; optionally substituted alkyl (e.g., C$_1$ to C$_{12}$ straight chain or branched chain alkyl optionally hetero substituted with oxygen, silicon, sulphur or optionally substituted with OH, O-alkyl, SH, S-alkyl, NH$_2$, NH-alkyl); optionally substituted alkenyl (e.g., C$_1$ to C$_{12}$ straight chain or branched chain alkenyl optionally hetero substituted with oxygen, silicon, sulphur or optionally substituted with OH, O-alkyl, SH, S-alkyl, NH$_2$, NH-alkyl); optionally substituted alkynyl (e.g., C$_1$ to C$_{12}$ straight chain or branched chain alkynyl optionally hetero substituted with oxygen, silicon, sulphur or optionally substituted with OH, O-alkyl, SH, S-alkyl, NH$_2$, NH-alkyl); cycloalkyl (e.g., C$_3$ to C$_7$ cycloalkyl); alkylcycloalkyl (e.g., C$_4$ to C$_{12}$ alkylcycloalkyl); heterocycloalkyl (e.g., where the heterocycle comprises one or two hetero atoms selected from O, S, or N, including C$_2$ to C$_6$ heterocycloalkyl); alkylheterocycloalkyl (e.g., where the heterocycle comprises one or two hetero atoms selected from O, S, or N, including C$_3$ to C$_{11}$ alkylheterocycloalkyl, and including wherein when N is present in the heterocyclic ring, the nitrogen atom may be in the form of an amide, carbamate or urea); aryl (e.g., phenyl, substituted phenyl, naphthyl, substituted naphthyl); alkylaryl (e.g., alkylphenyl, alkylsubstituted phenyl, alkylnaphthyl, alkylsubstituted naphthyl); heteroaryl (e.g., pyridyl, furanyl, thiophenyl, pyrrollyl, oxazolyl, isoxazolyl, thiazolyl, diazolyl, pyrazolyl, triazolyl all of which are optionally substituted); alkylheteroaryl;

or R$_1$ and R$_2$ may together form a 3 to 8 membered heterocyclic ring, including the nitrogen atoms to which they are attached;

or R$_4$ and R$_5$ may together form a ring selected from the group aziridine, pyrrolyl, imidazolyl, pyrazolyl, indolyl, indolinyl, pyrrolidinyl, piperazinyl and piperidyl, including the nitrogen atoms to which they are attached.

Exemplary compounds and substituents of R$_1$, R$_2$, R$_3$, R$_4$, R$_5$, R$_9$, and R$_{10}$ of Formula III are shown below. However, additional combinations of selections of substituents of R$_1$, R$_2$, R$_3$, R$_4$, R$_5$, R$_9$, and R$_{10}$ are envisioned.

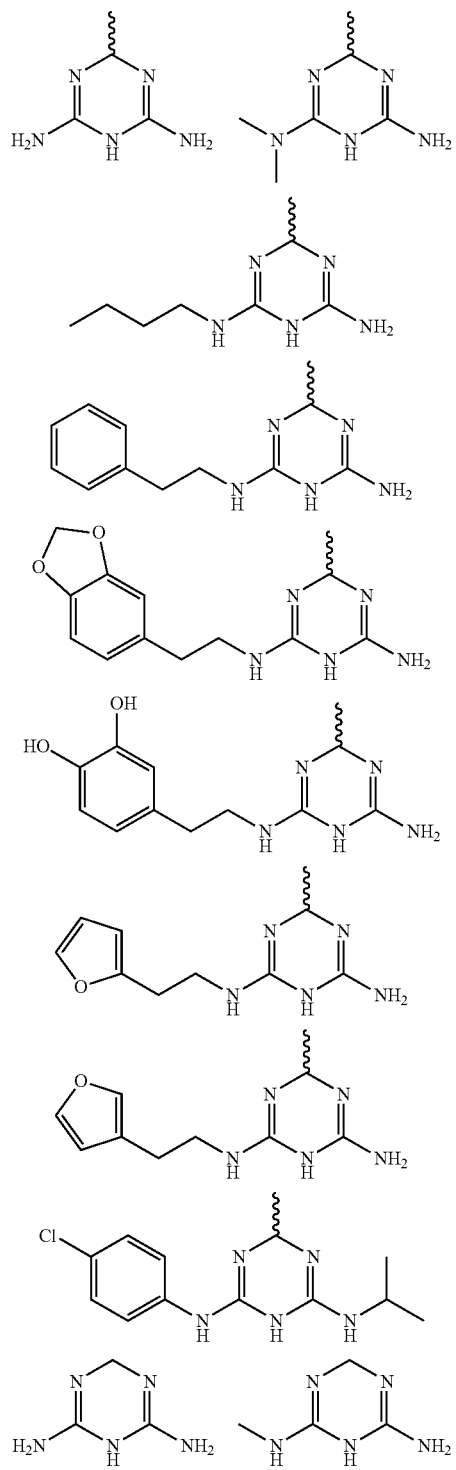

-continued
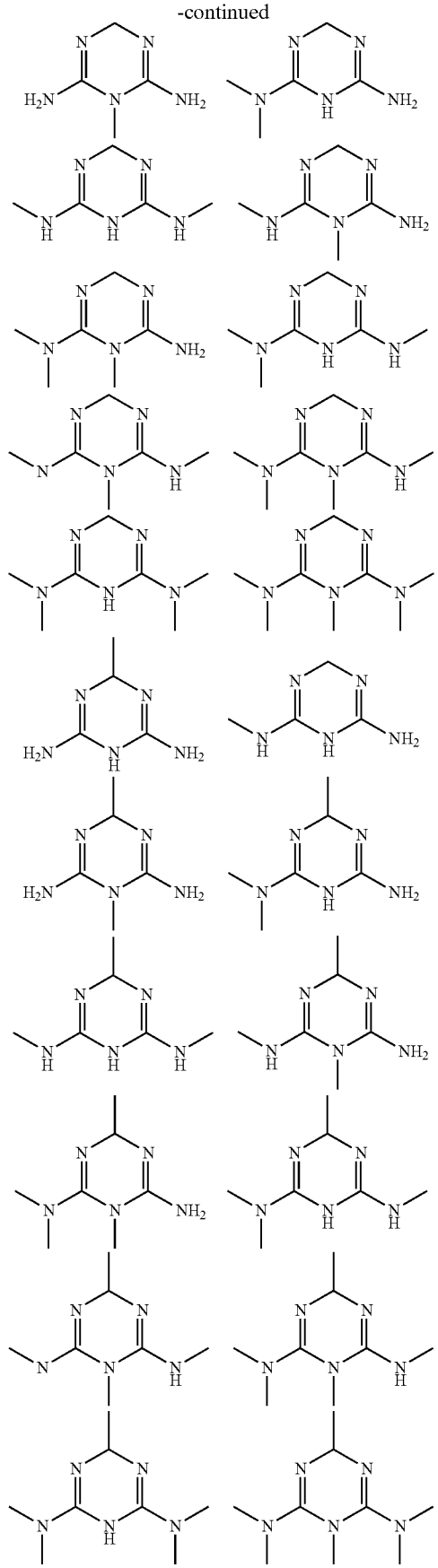
-continued
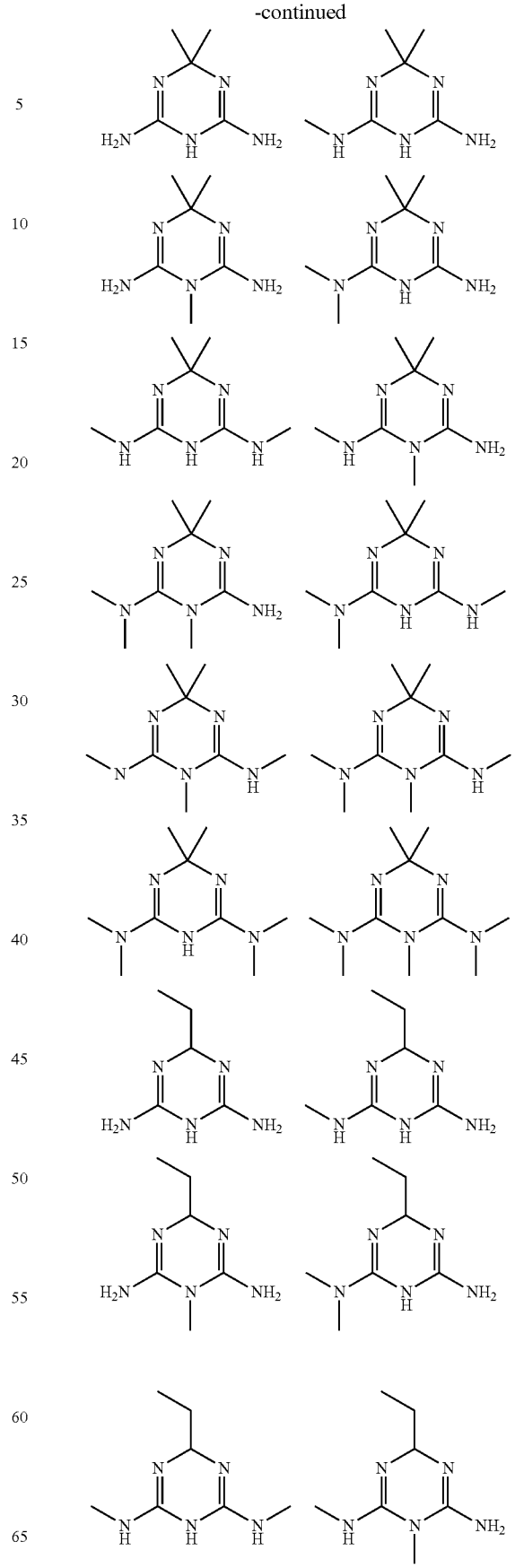

-continued
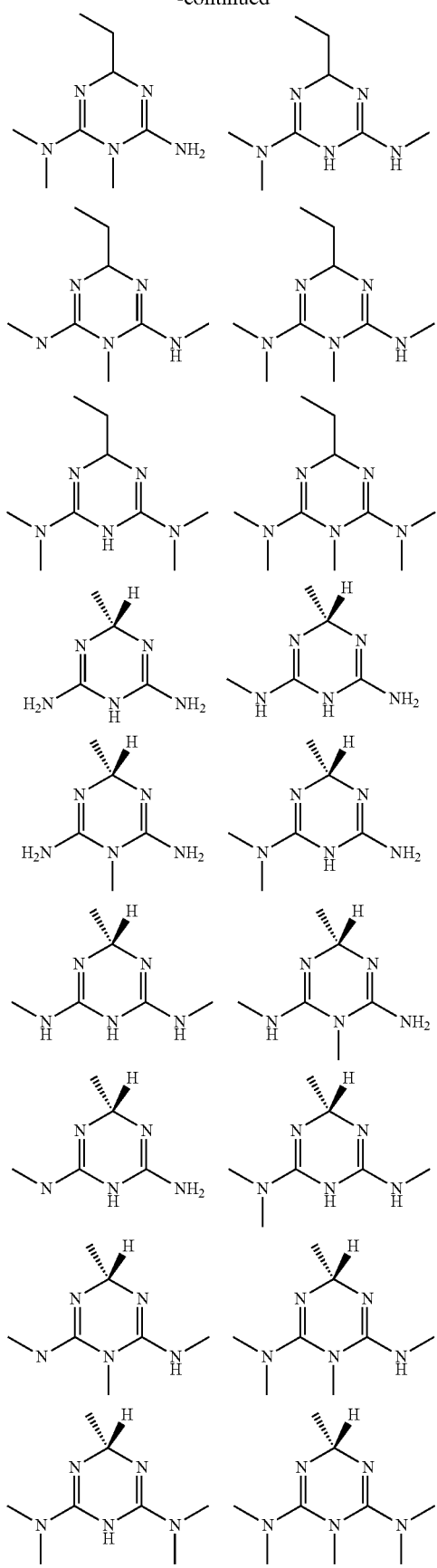
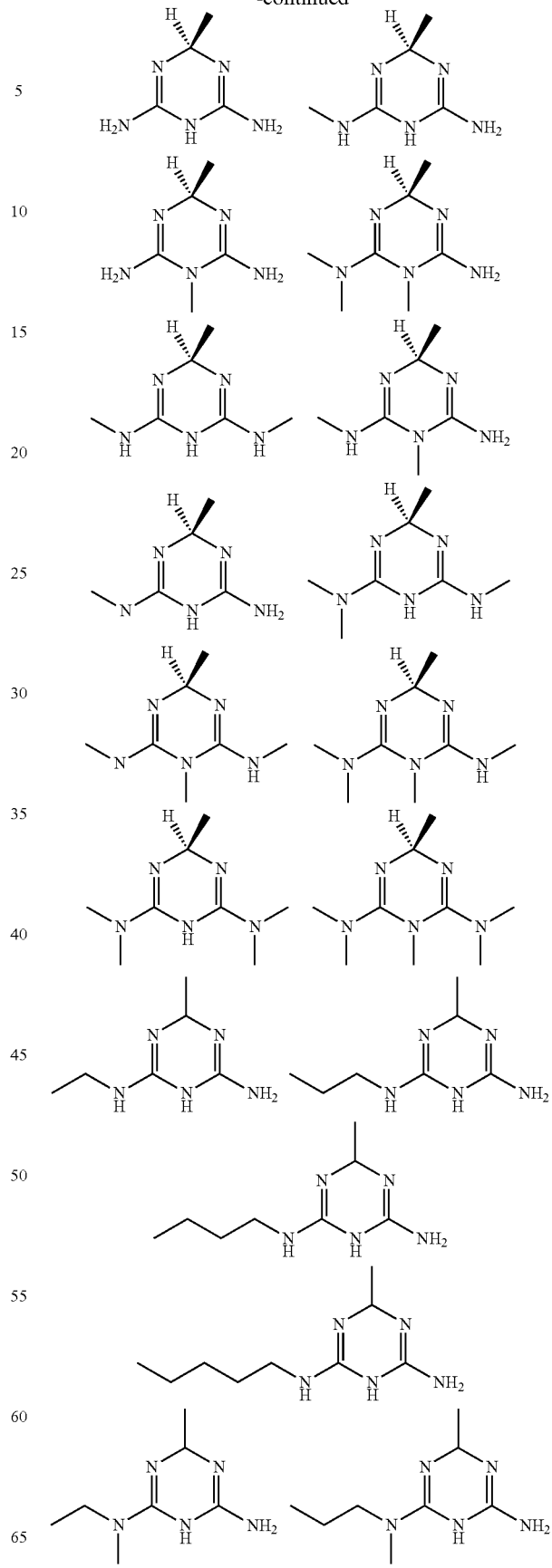

-continued
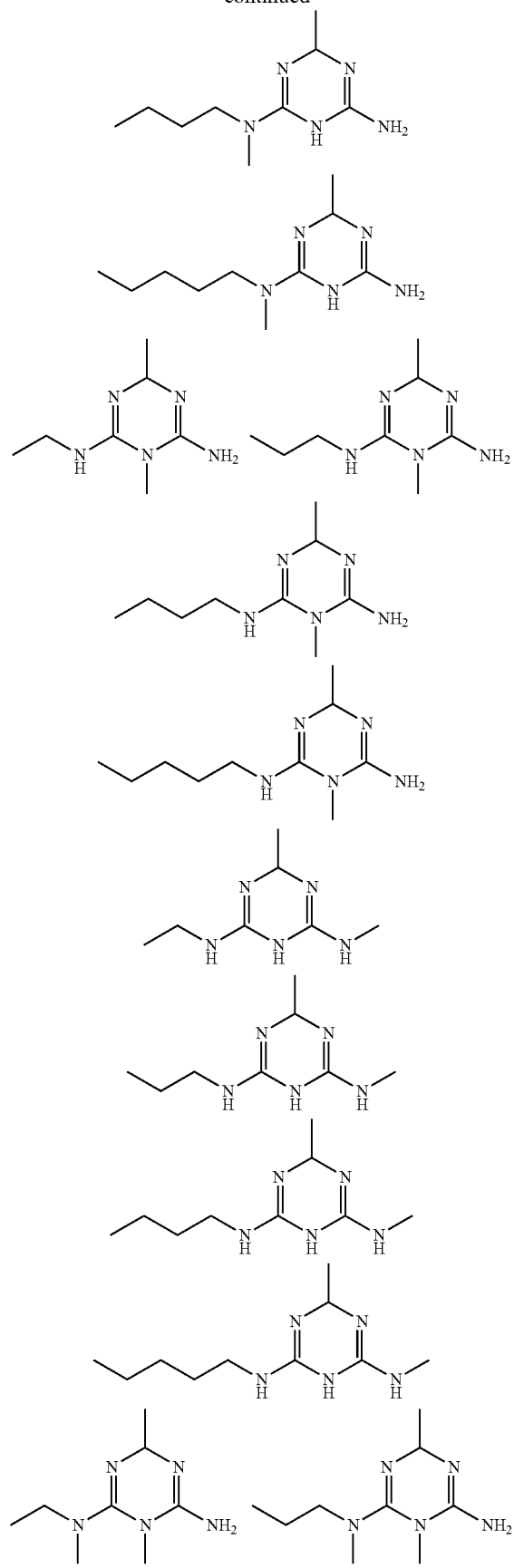
-continued
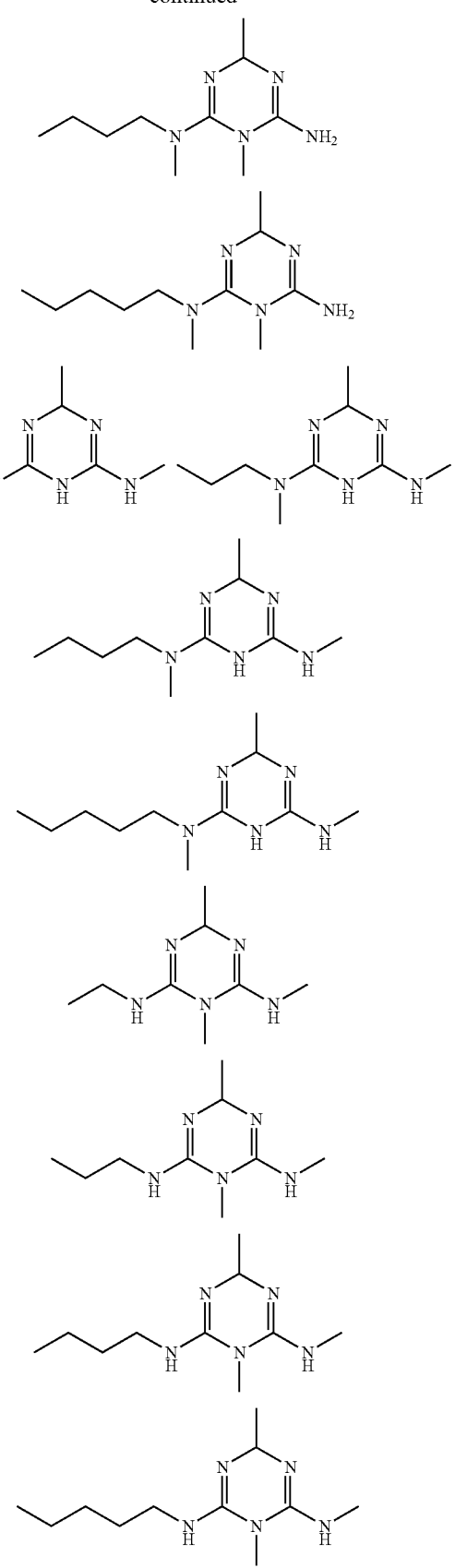

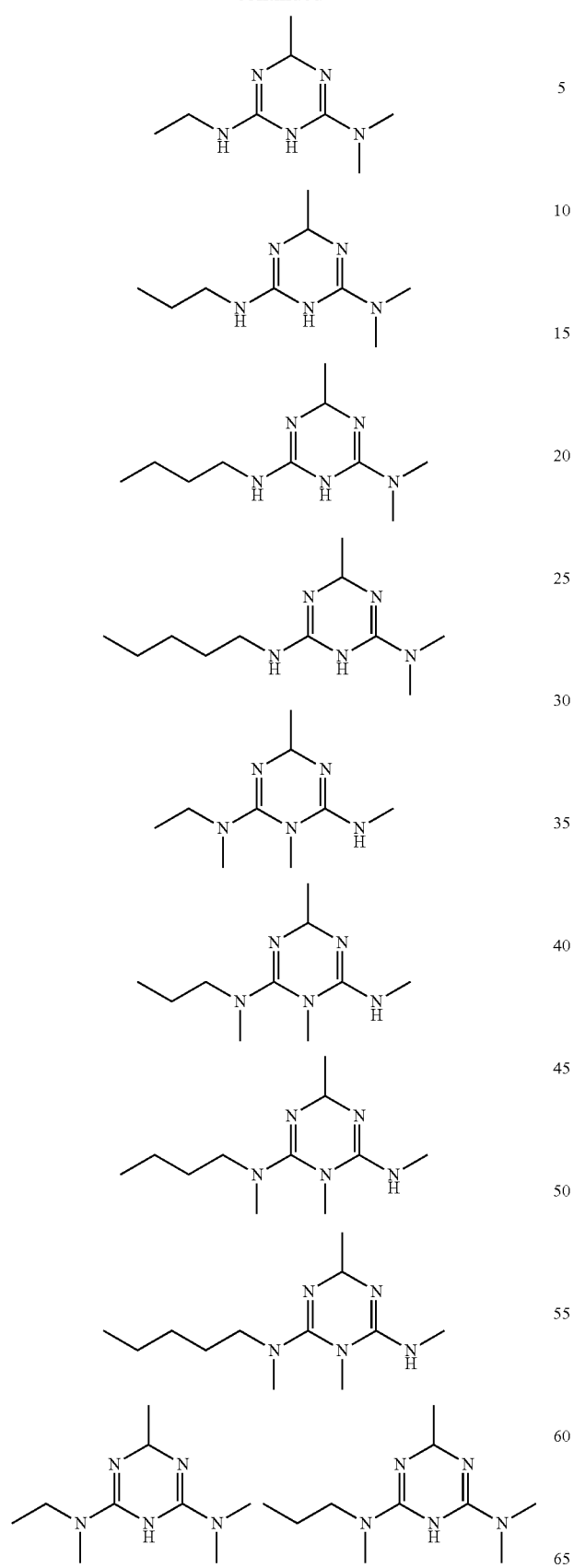
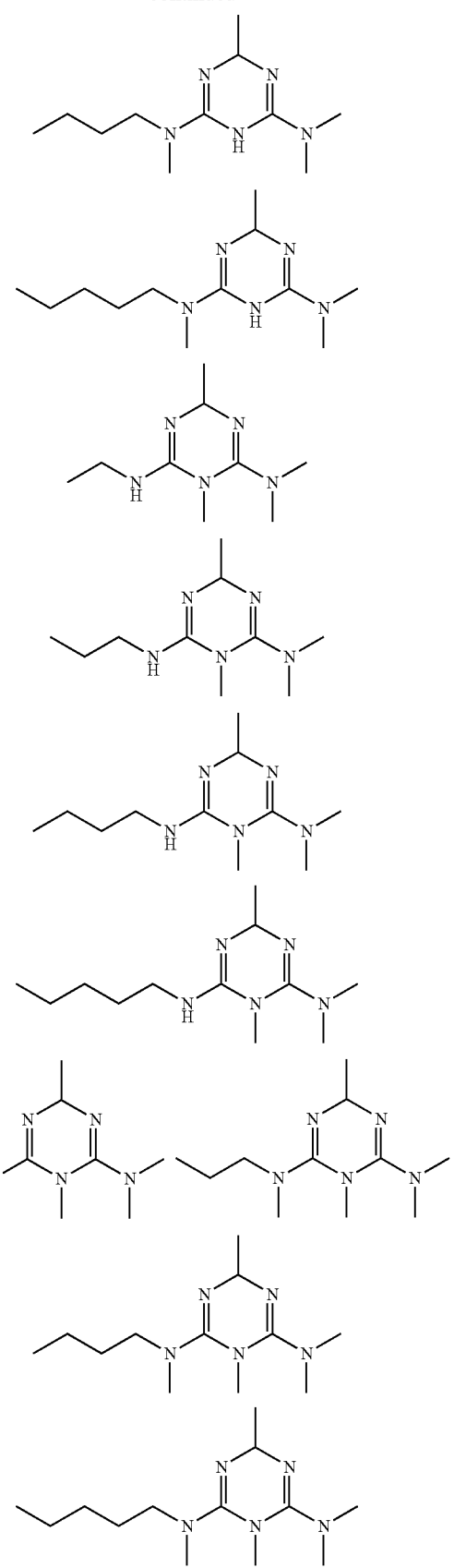

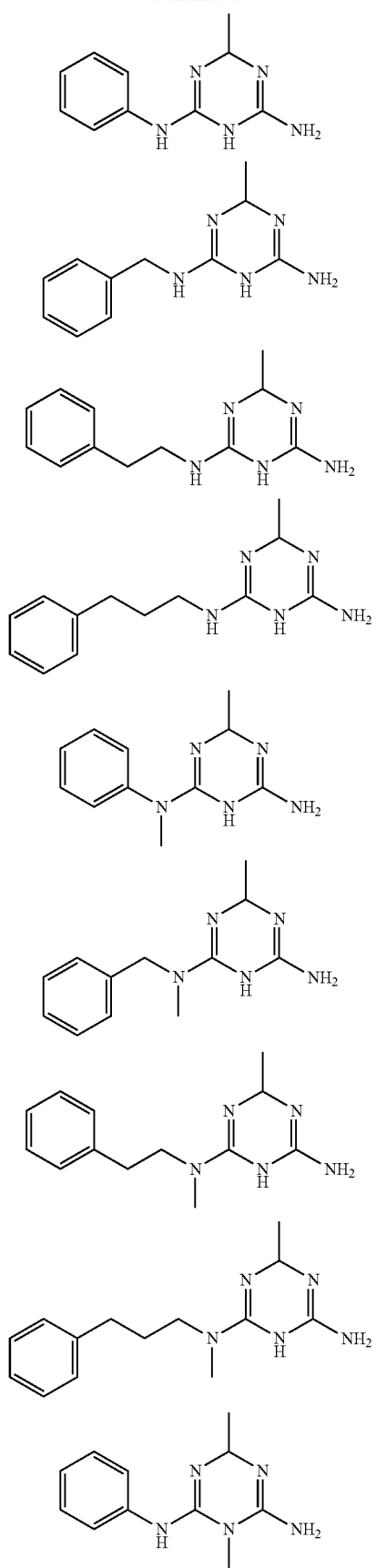
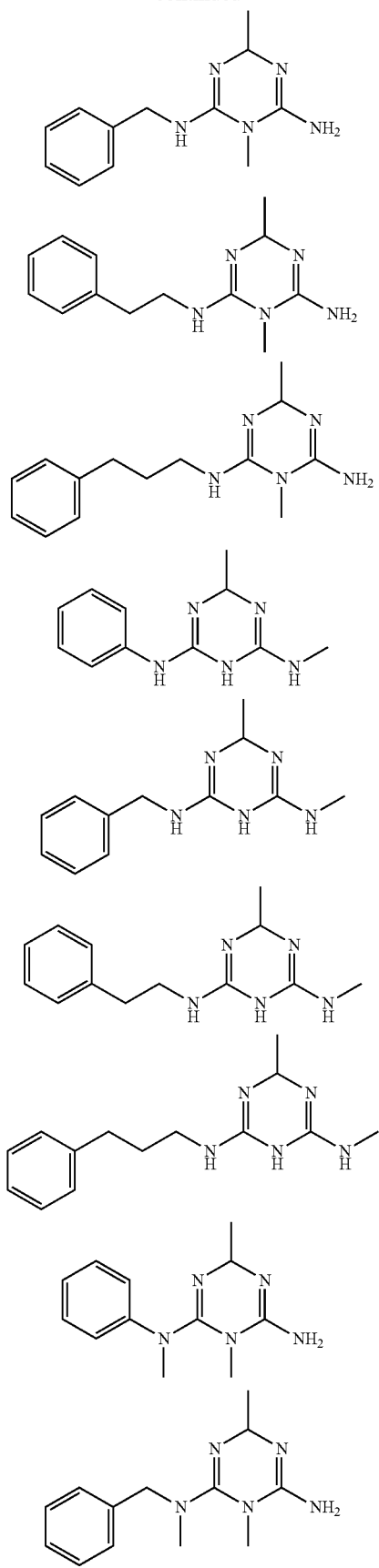

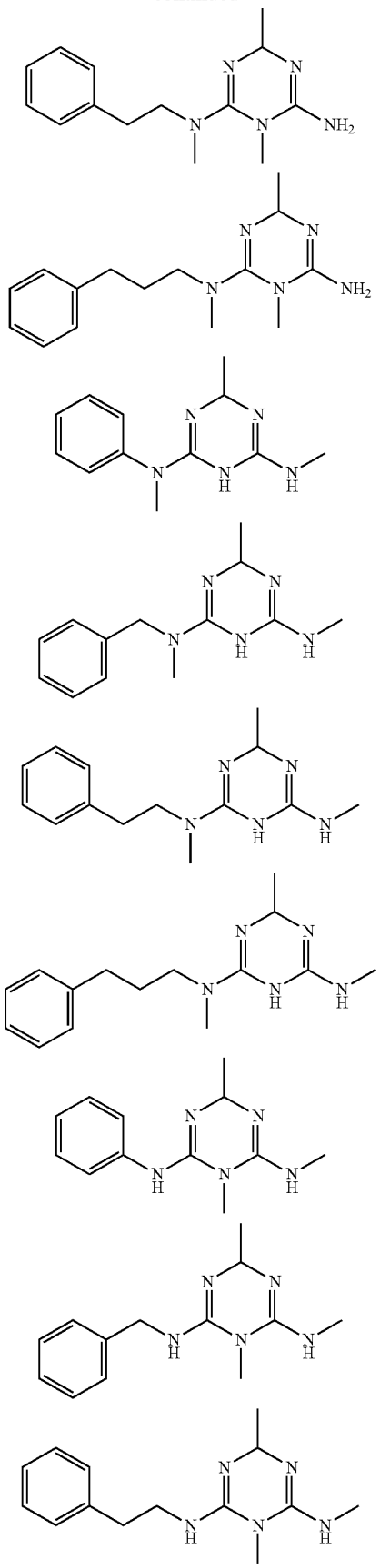
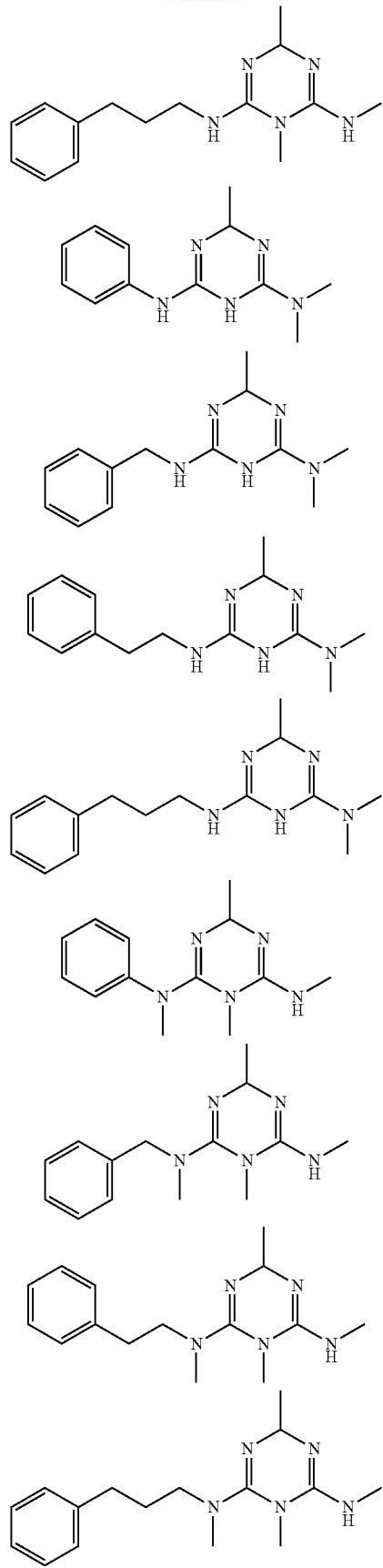

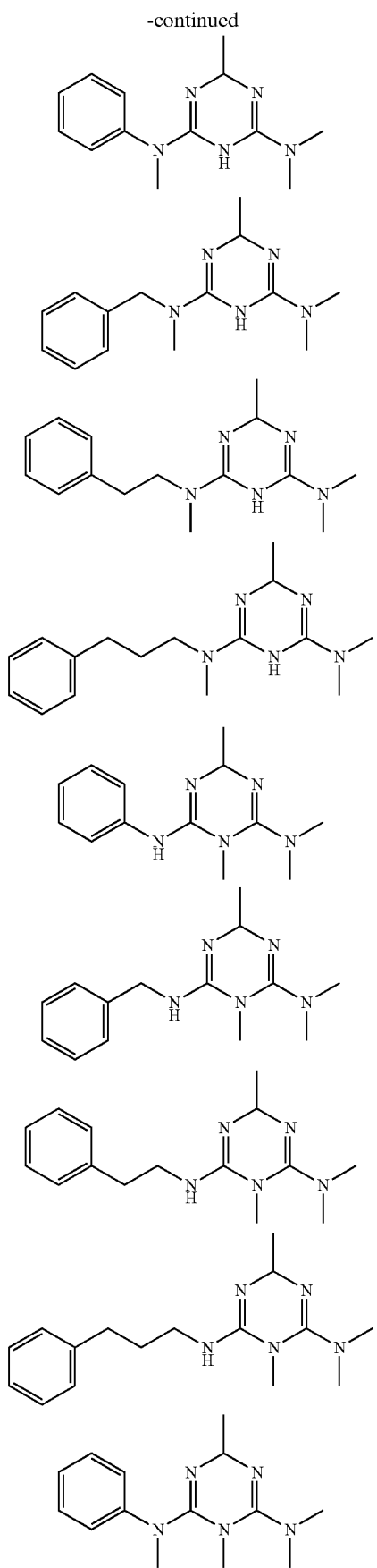
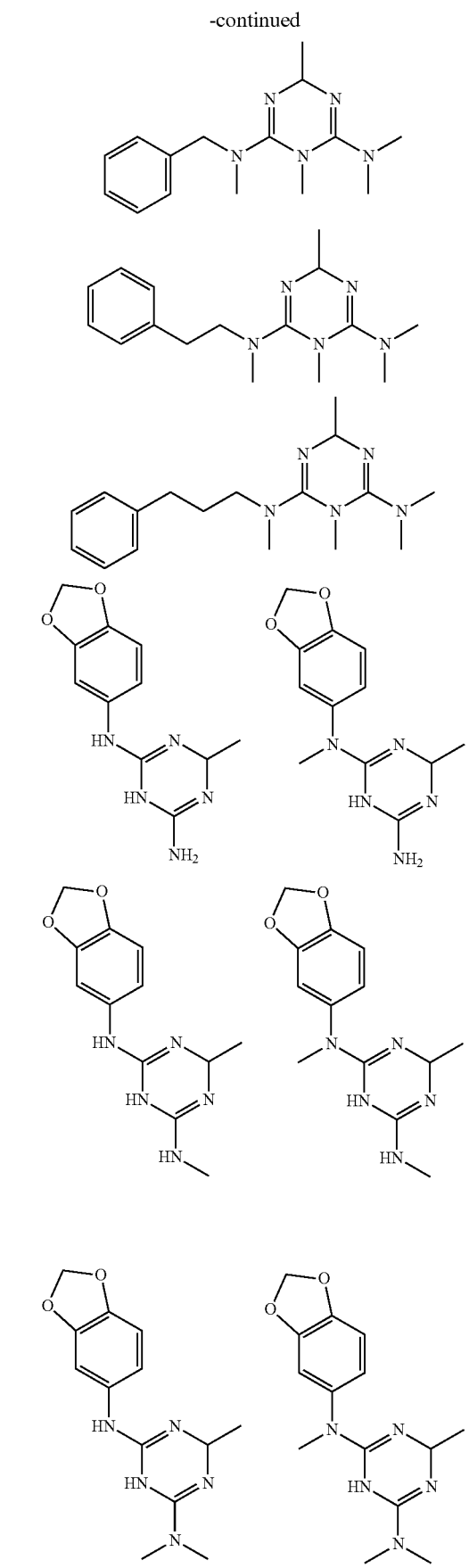

-continued
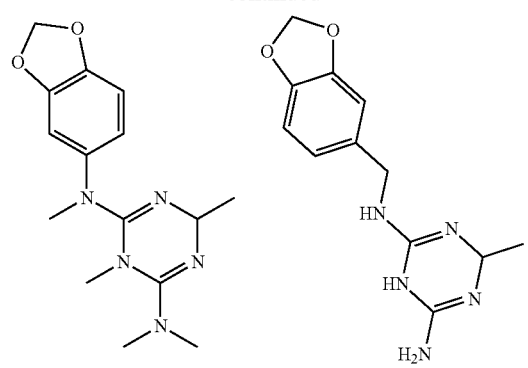
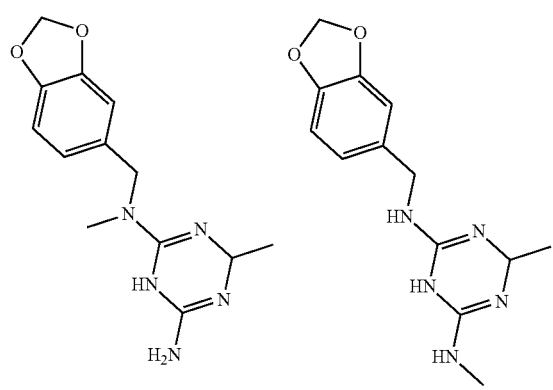
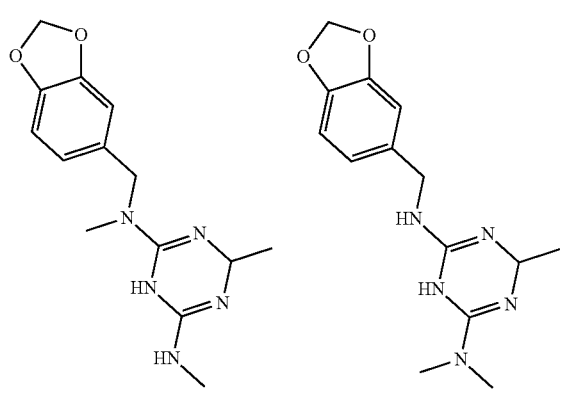
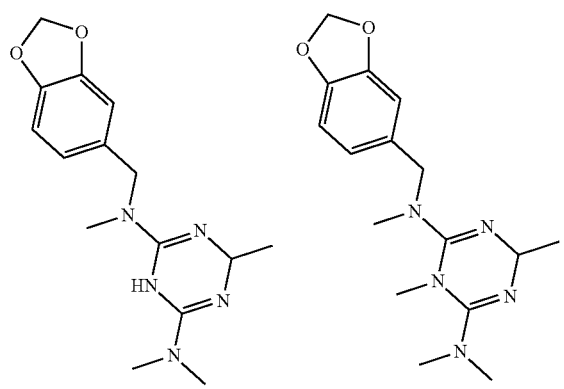
-continued
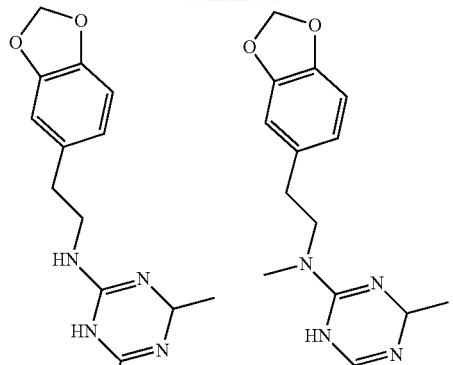
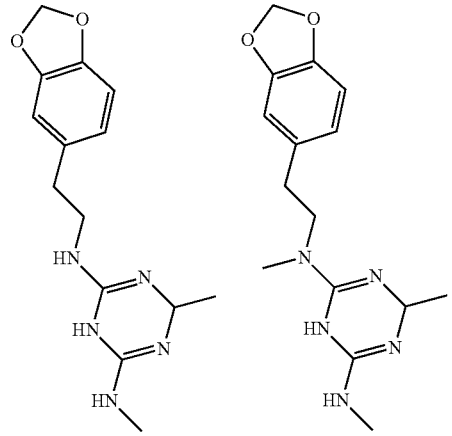
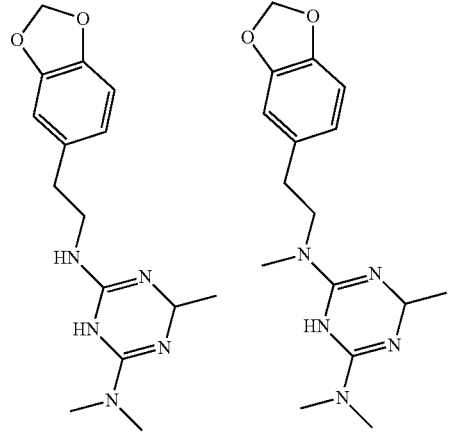
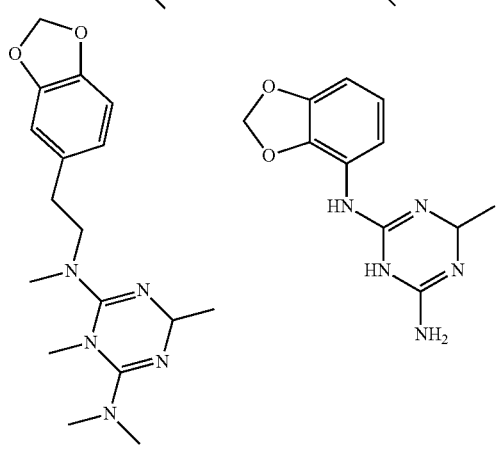

-continued
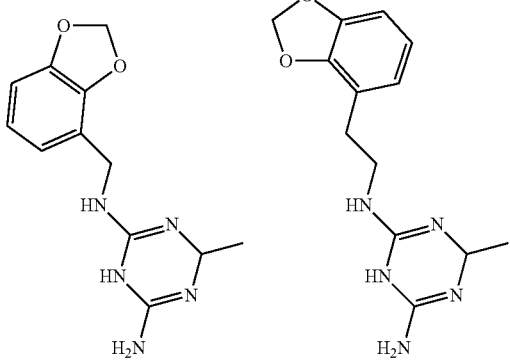
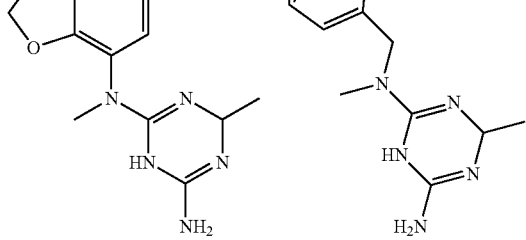
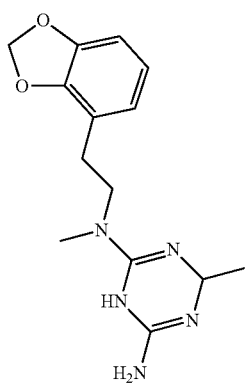
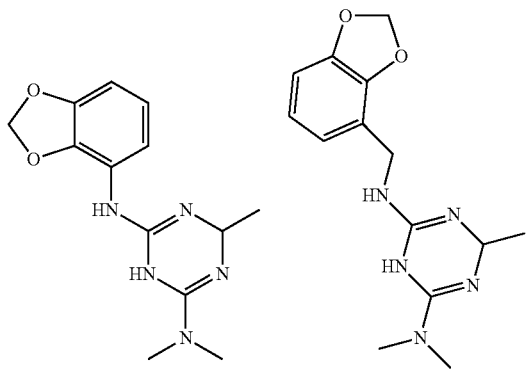
-continued
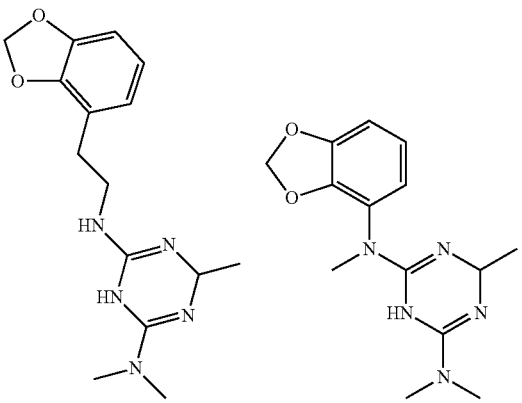
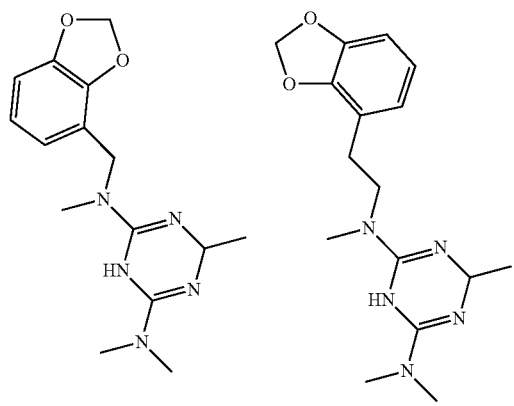
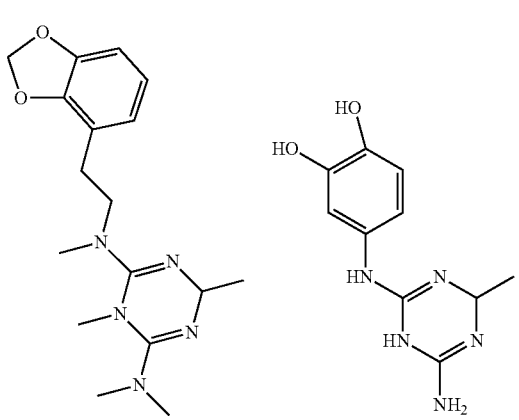
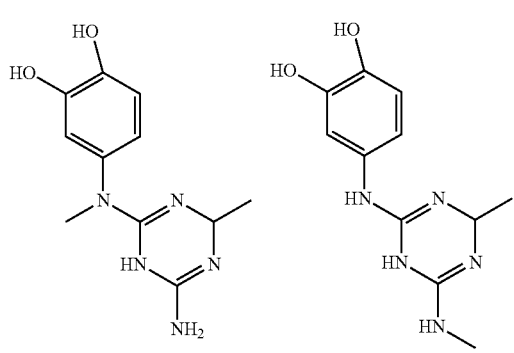

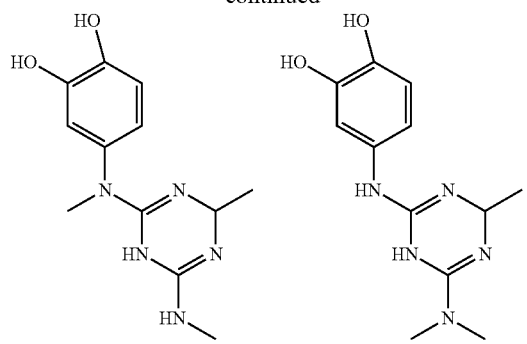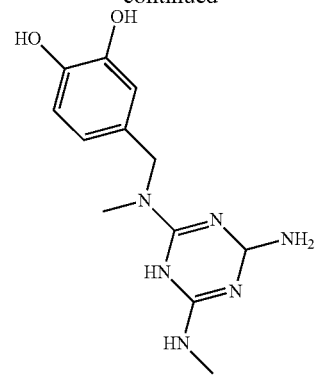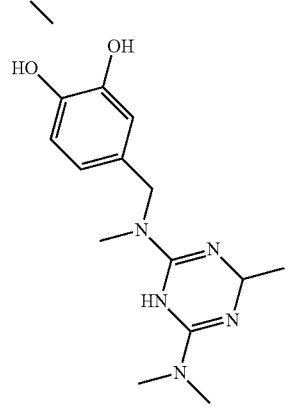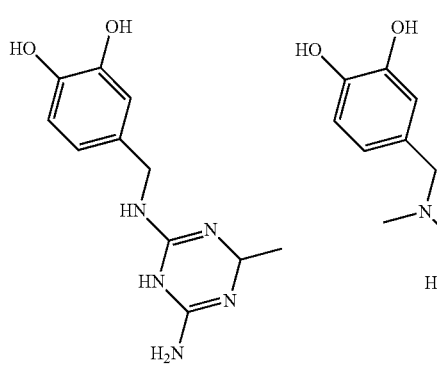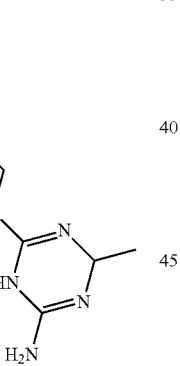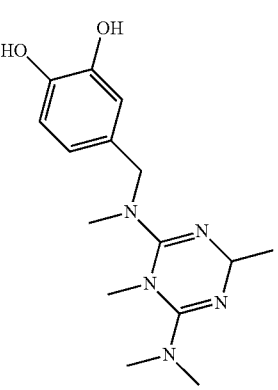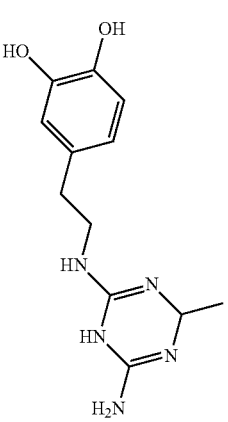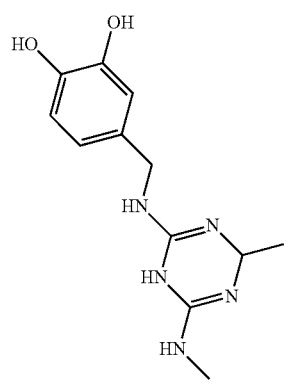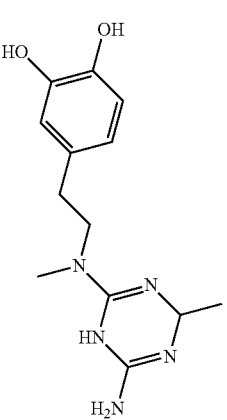

191
-continued
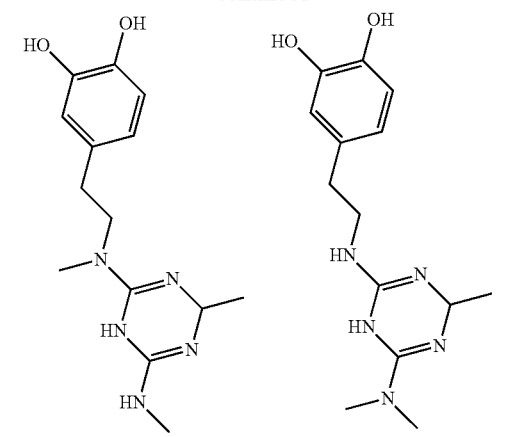
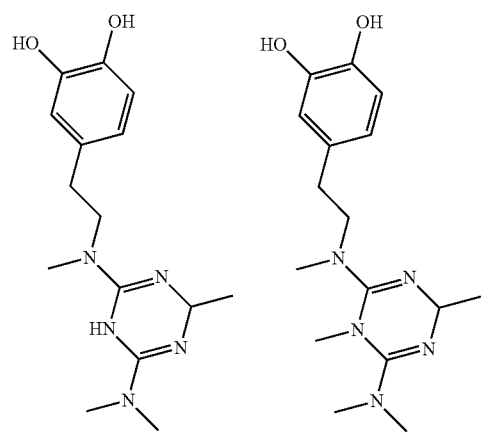
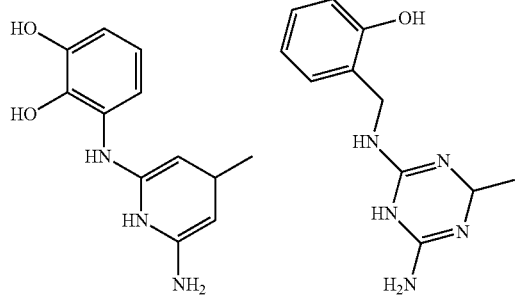
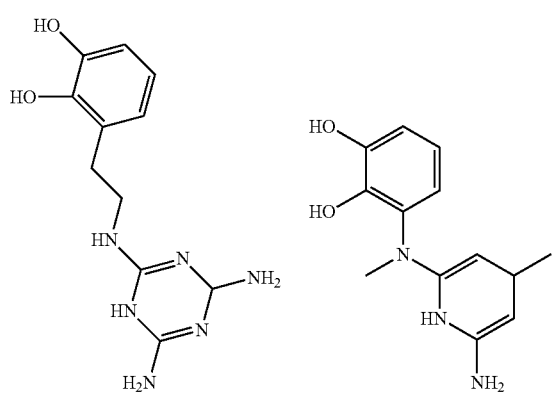
192
-continued
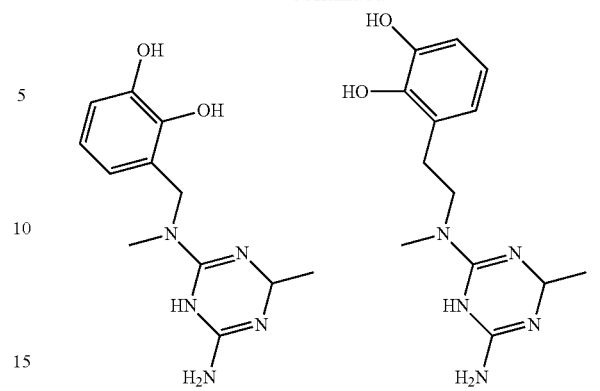
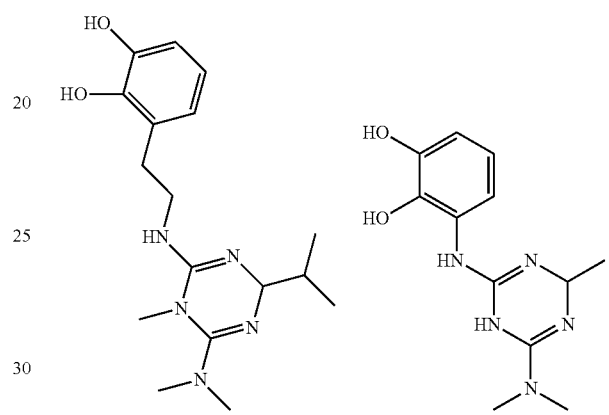
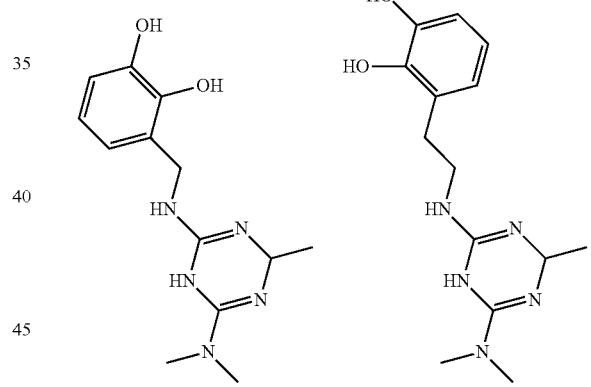
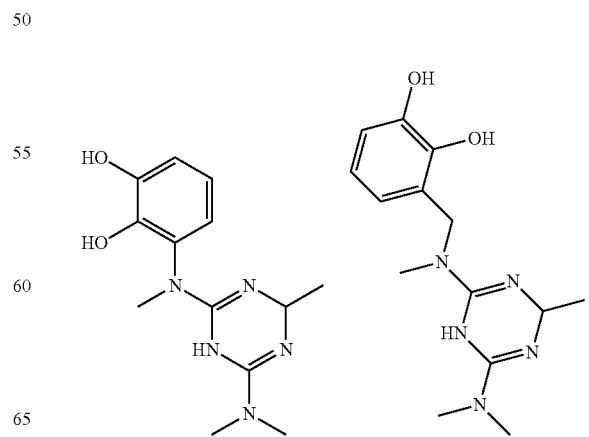

193
-continued
194
-continued
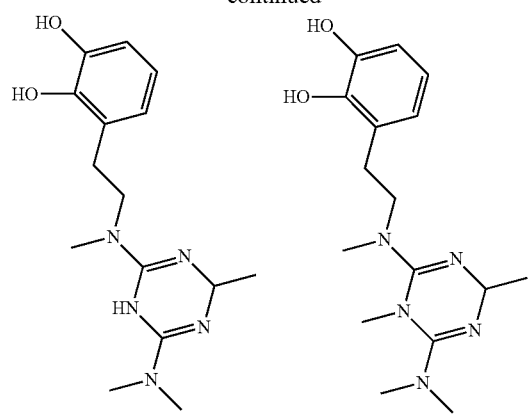
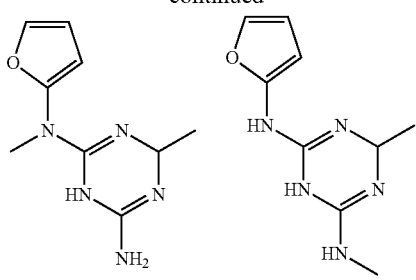
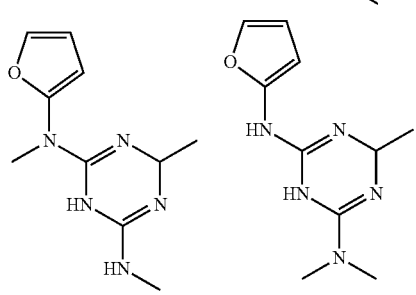
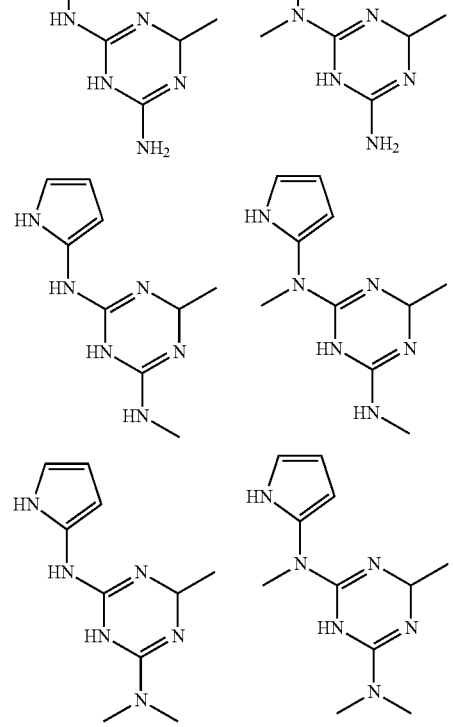
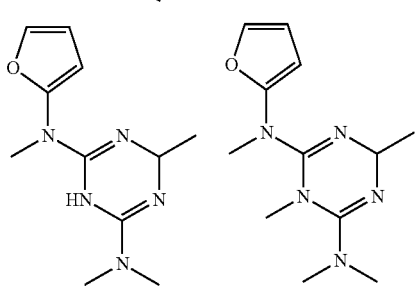
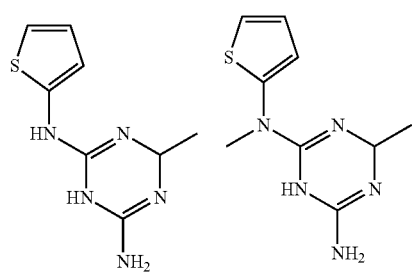
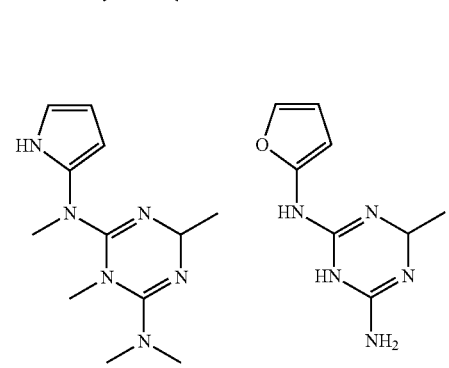
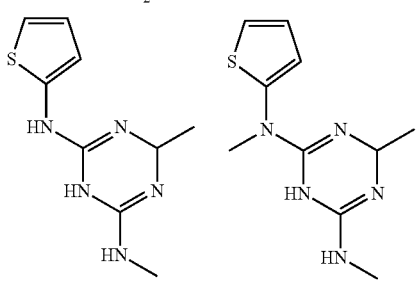
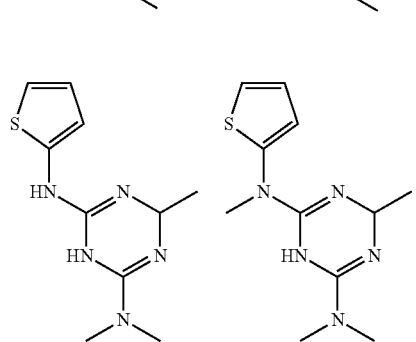

-continued
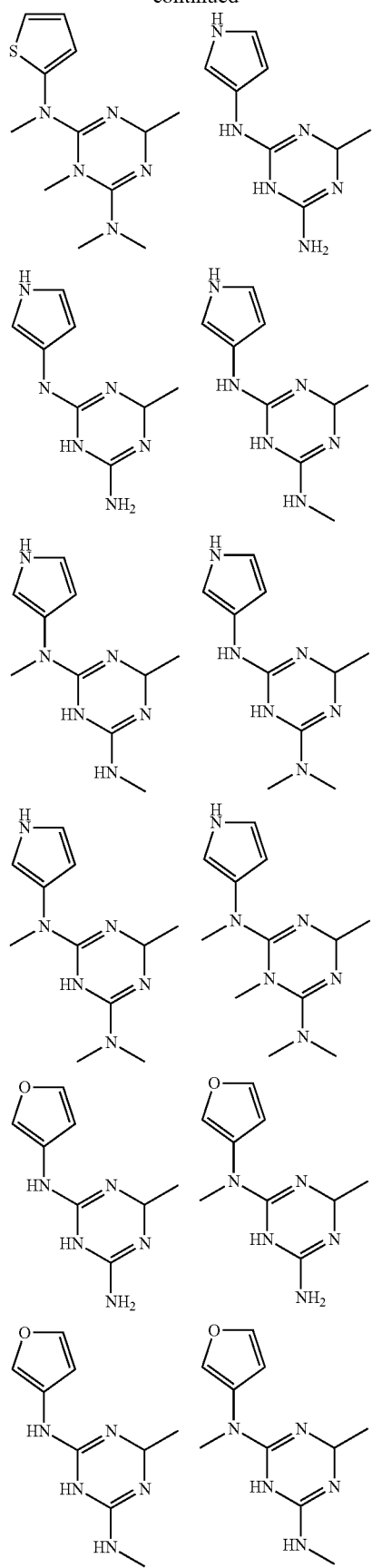
-continued
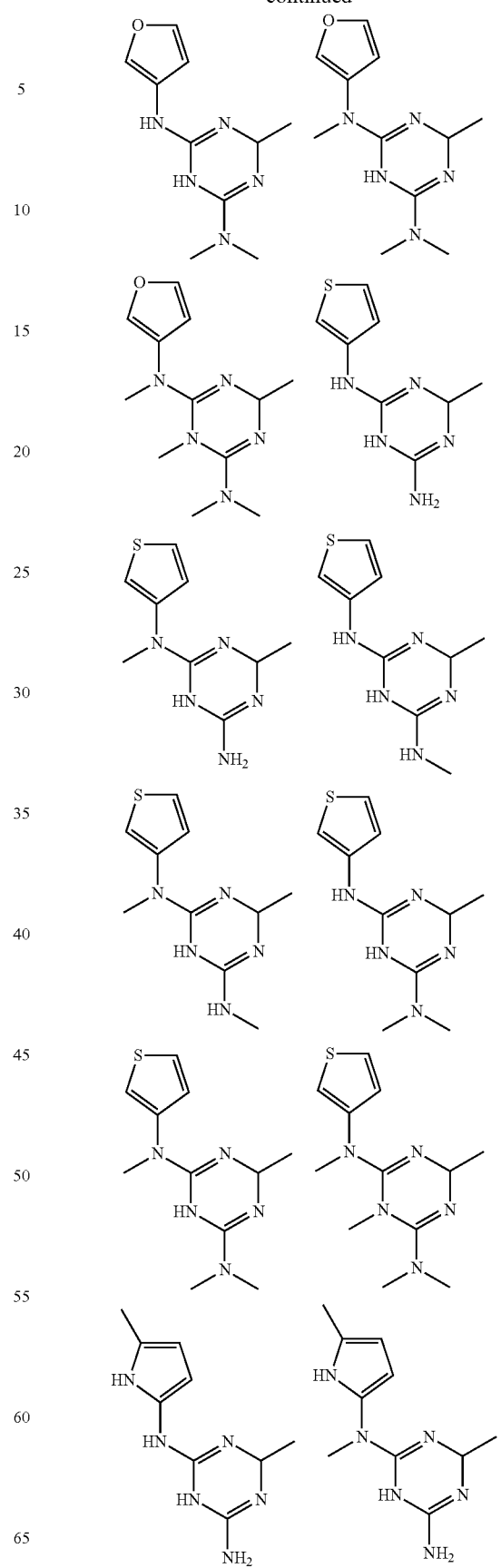

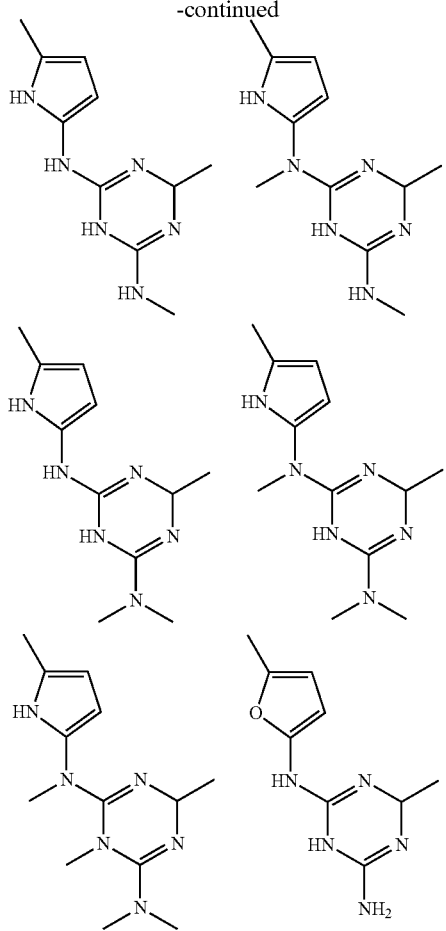
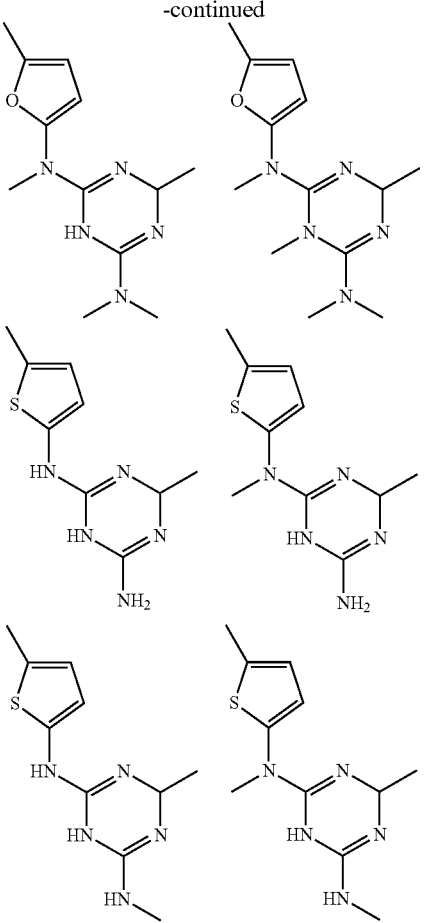
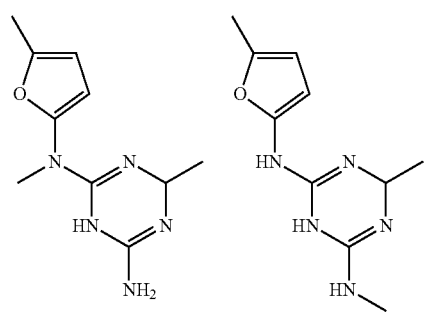
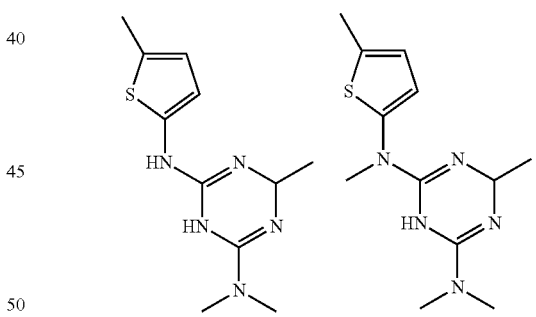
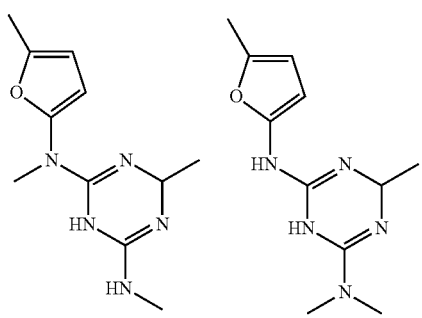
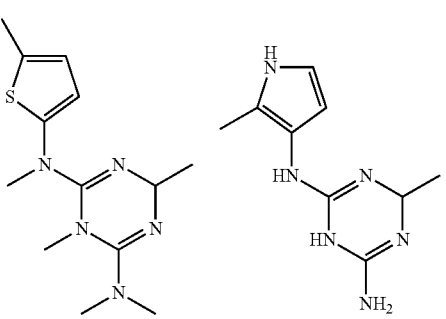

-continued
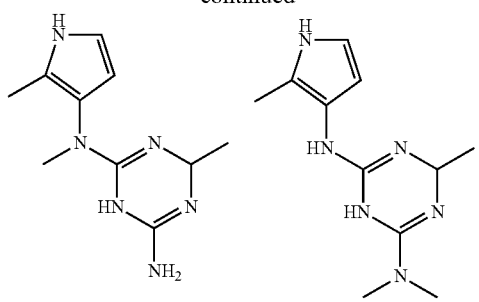
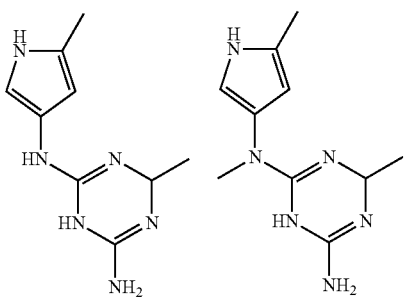
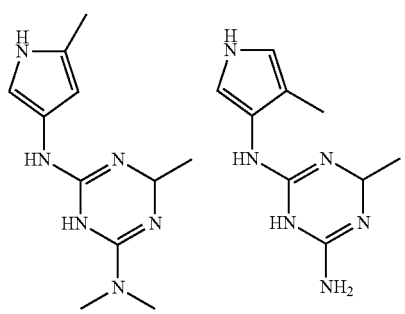
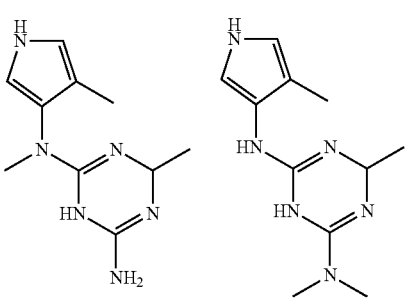
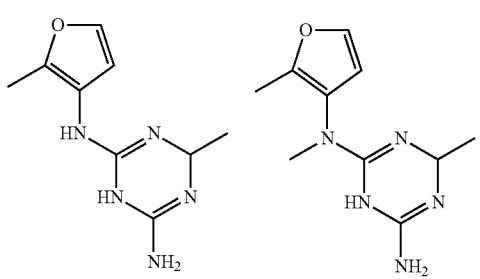
-continued
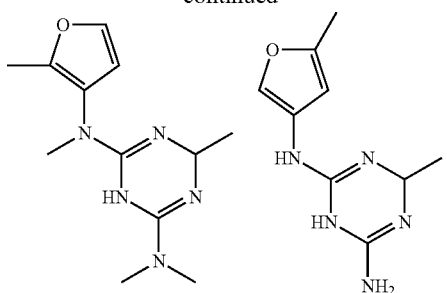
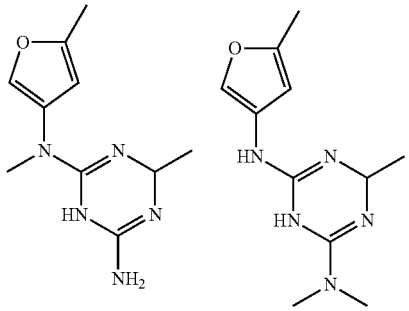
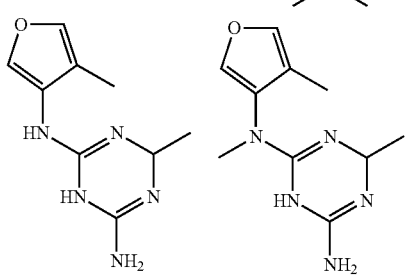
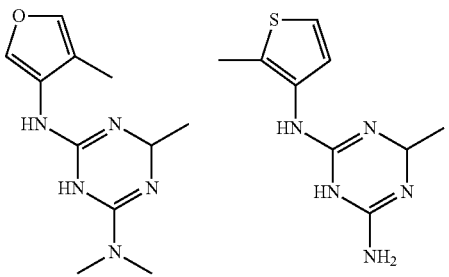
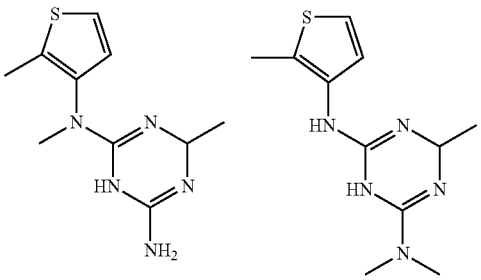
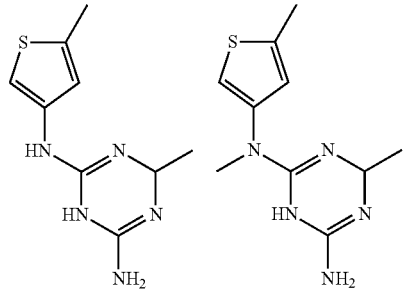

201
-continued
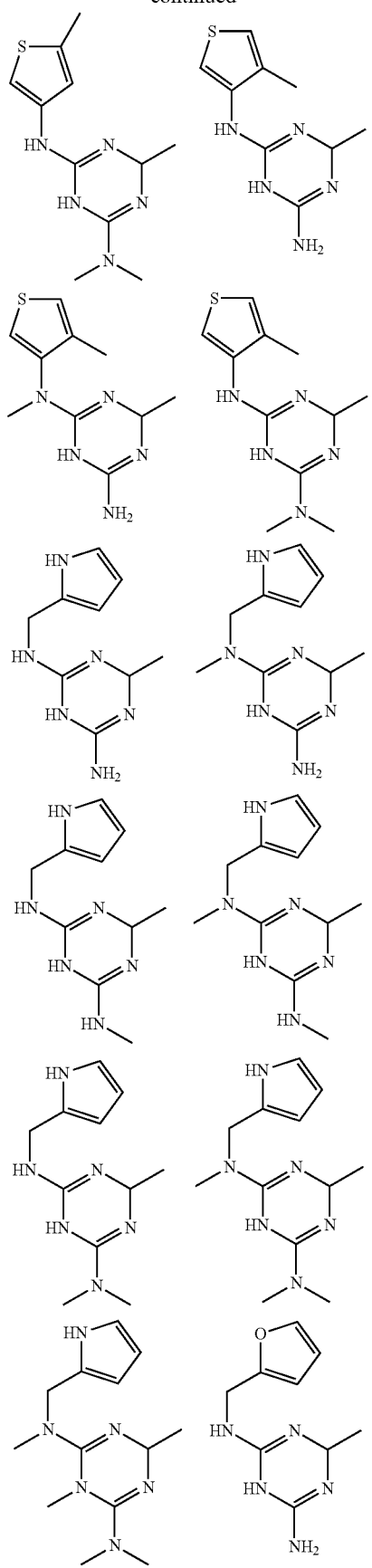
202
-continued
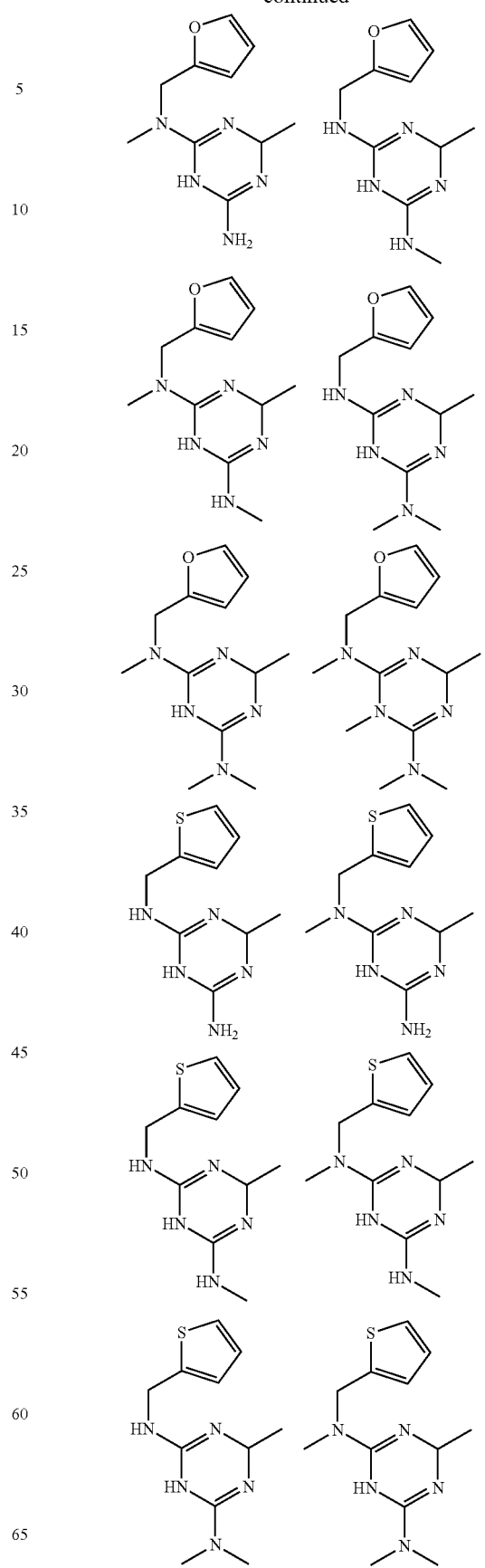

203
-continued
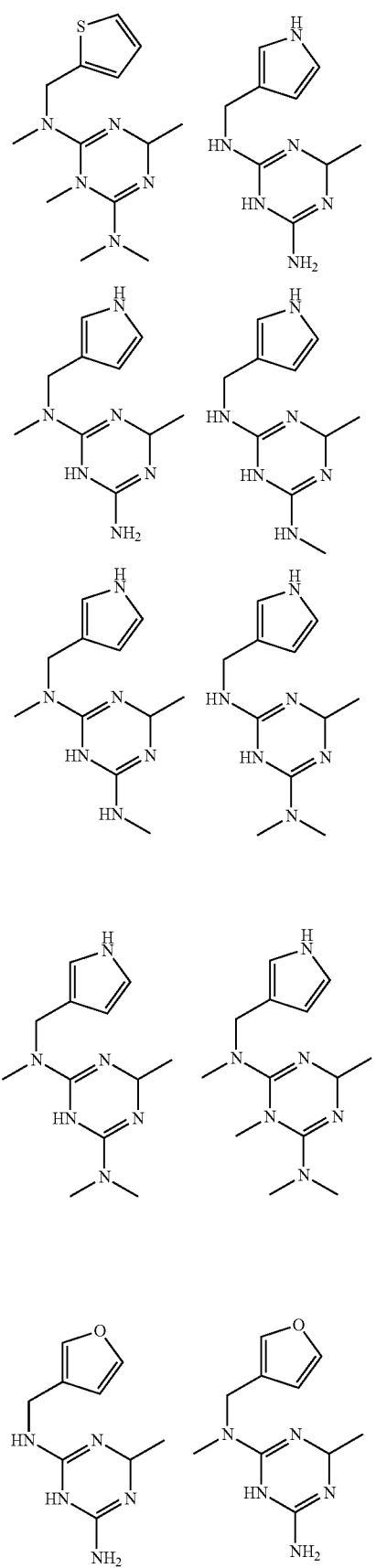
204
-continued
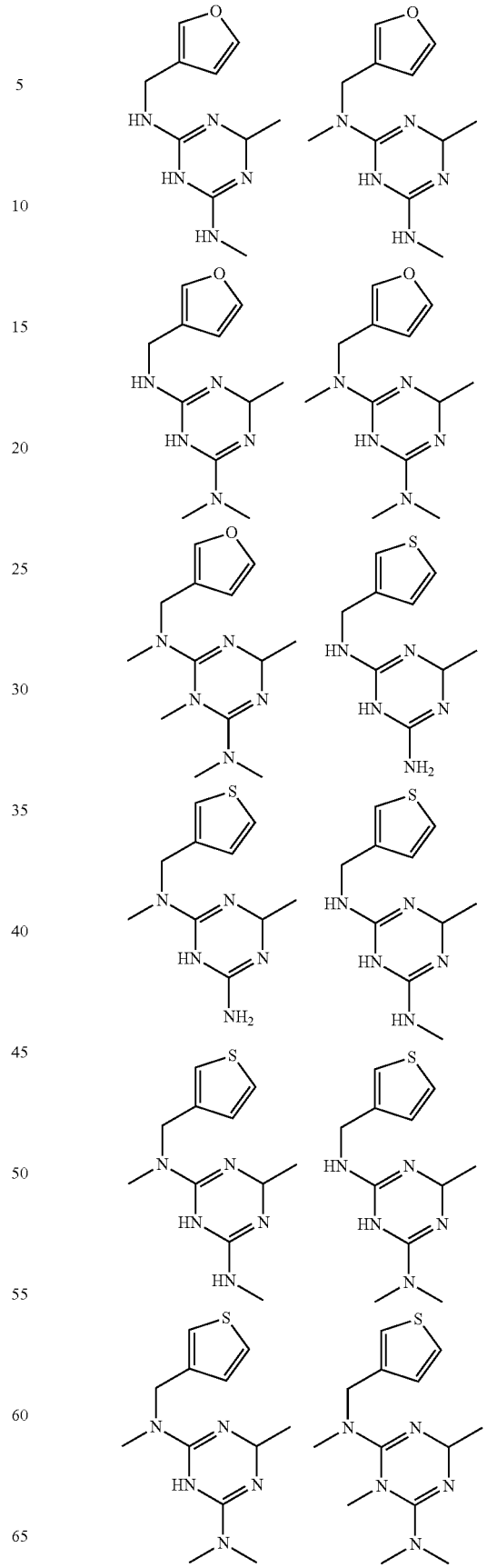

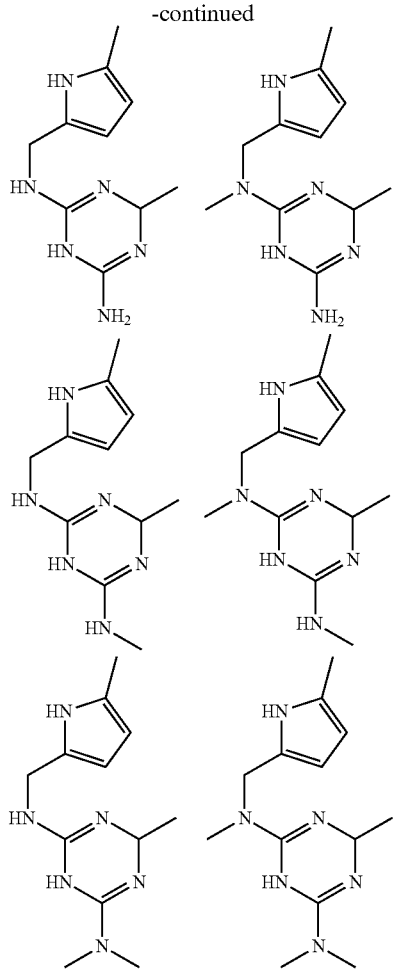
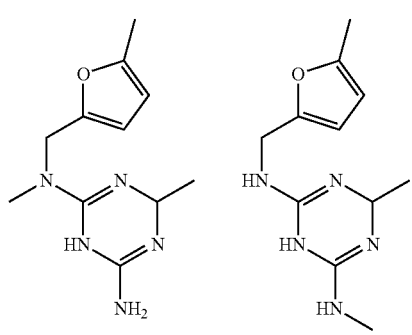
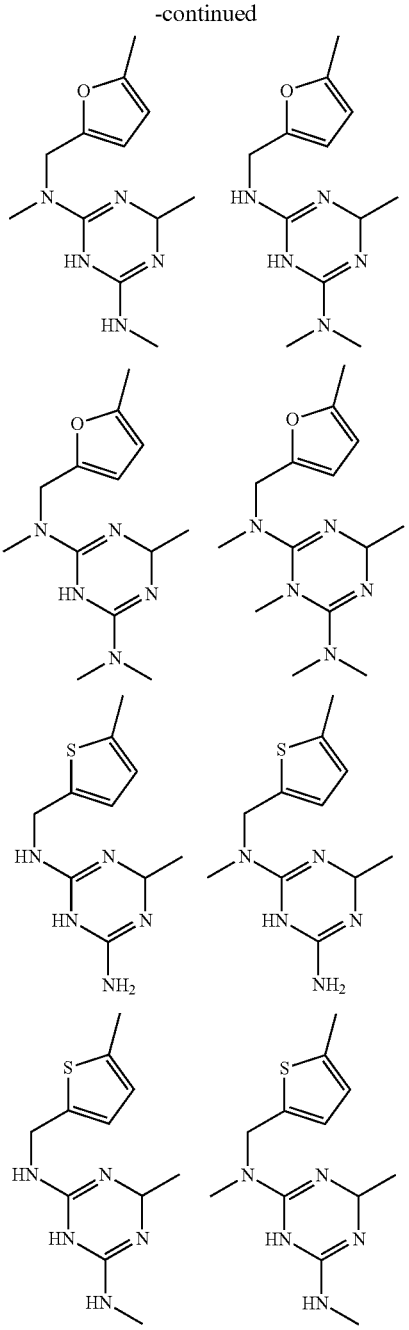

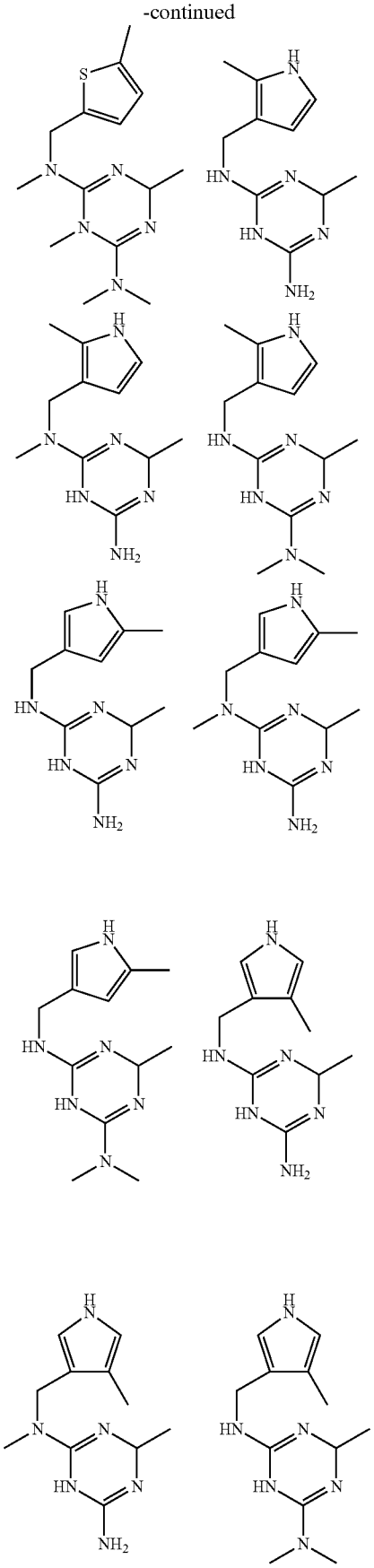
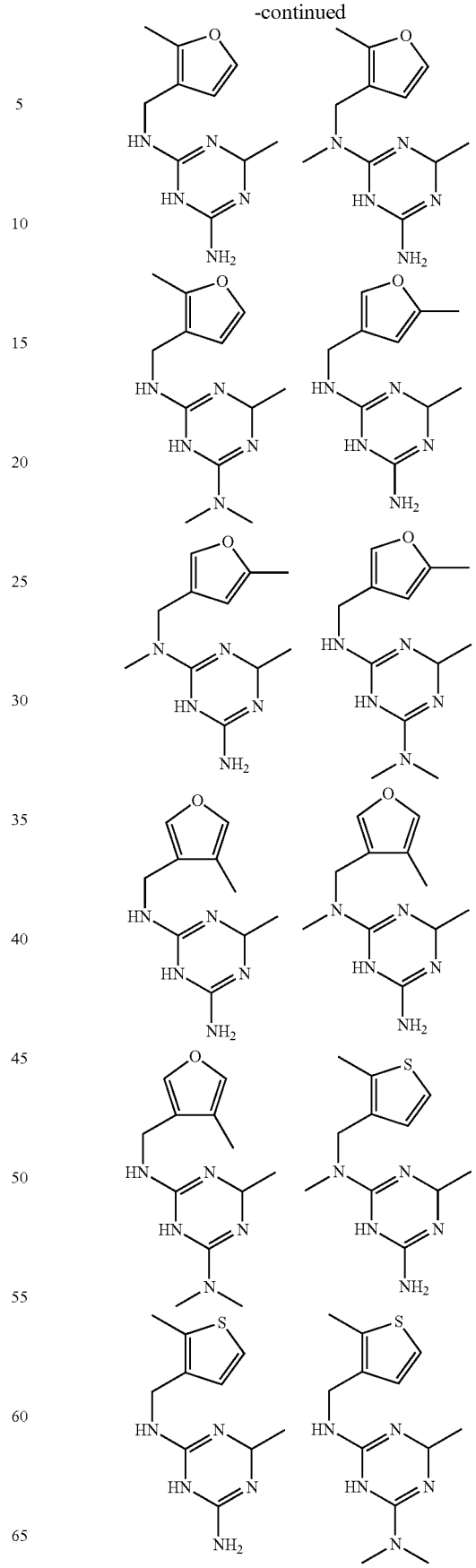

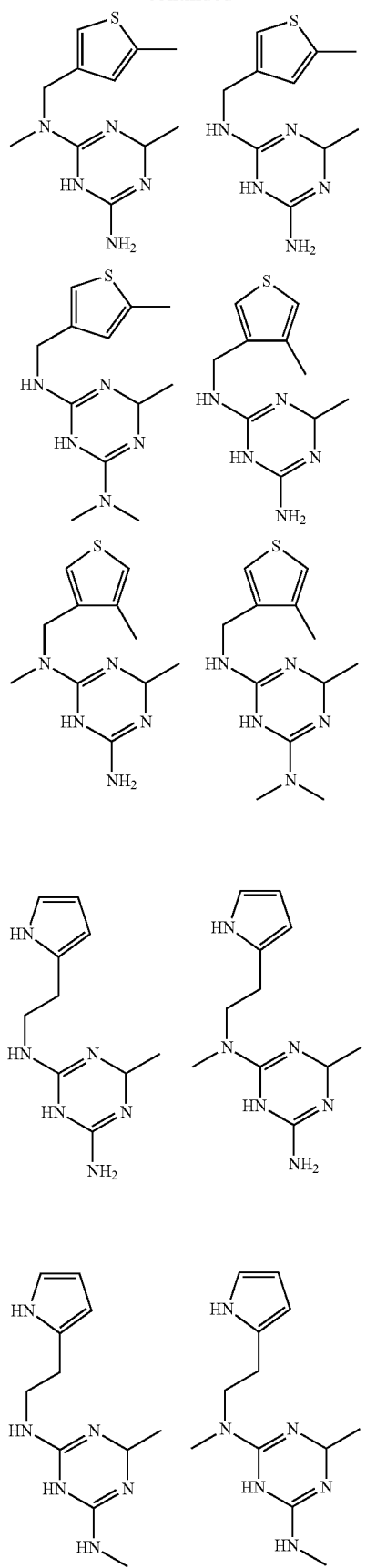
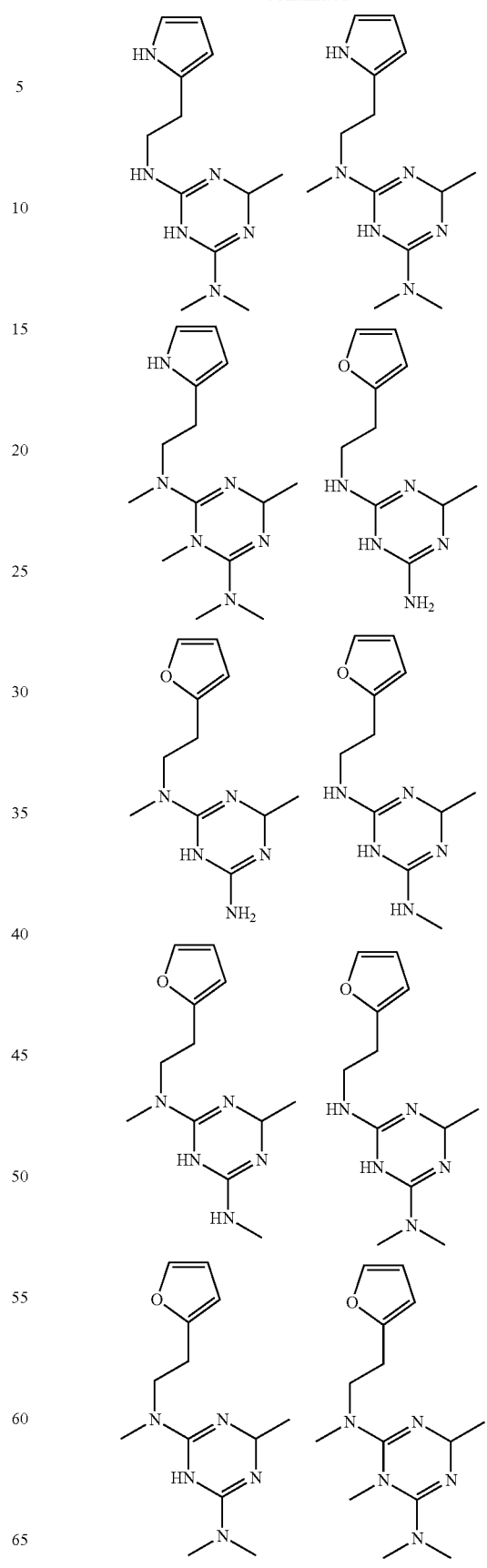

211
-continued
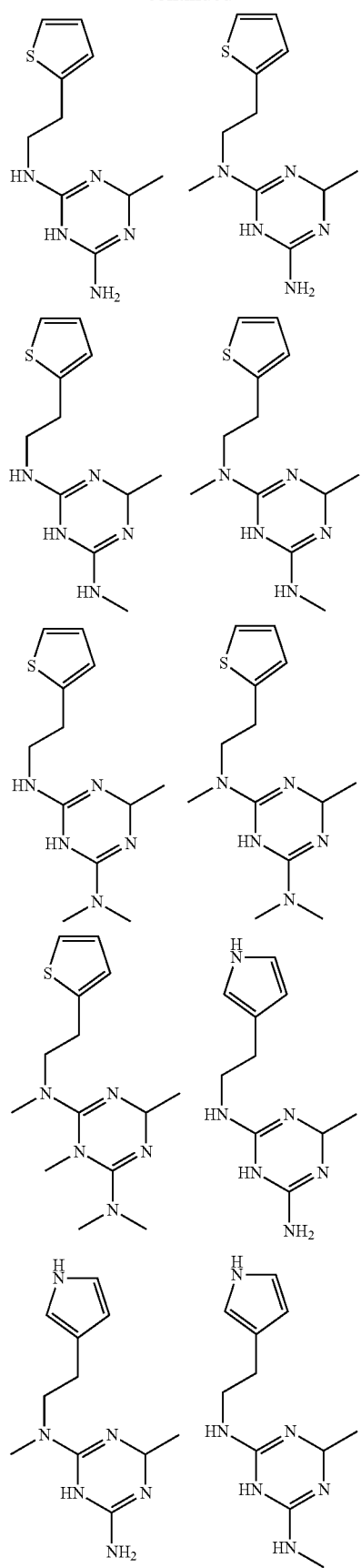
212
-continued
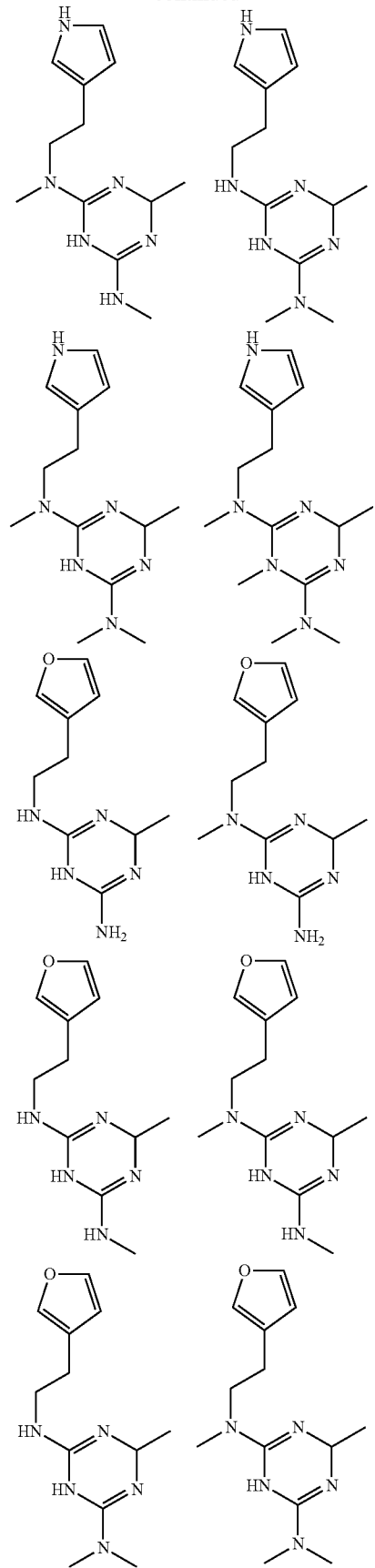

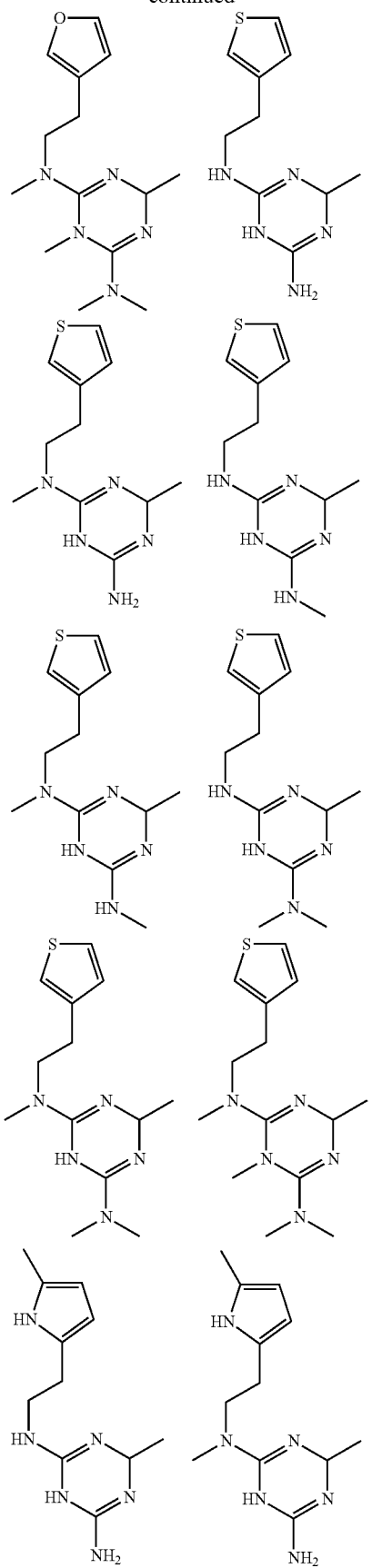
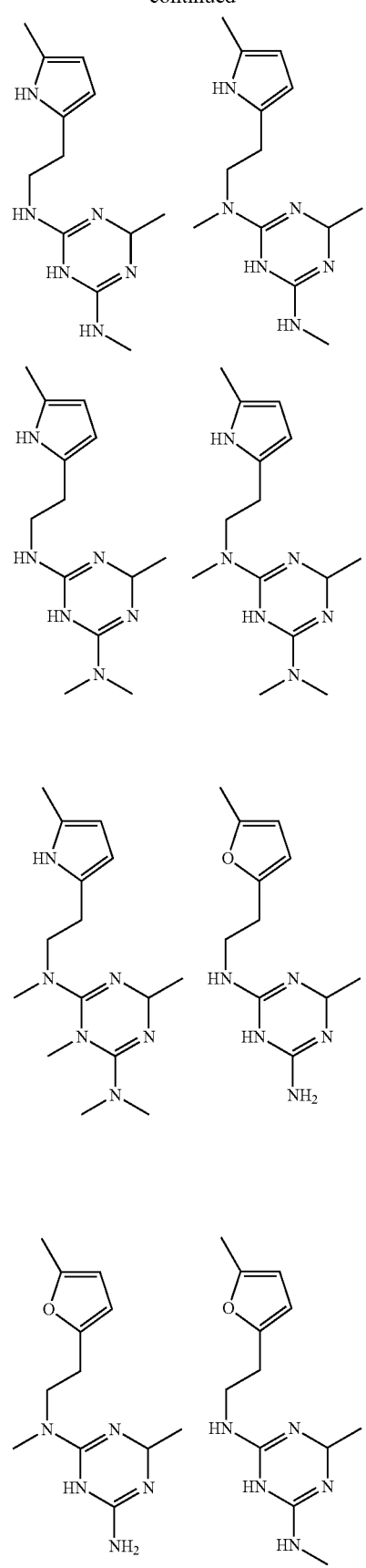

215
-continued
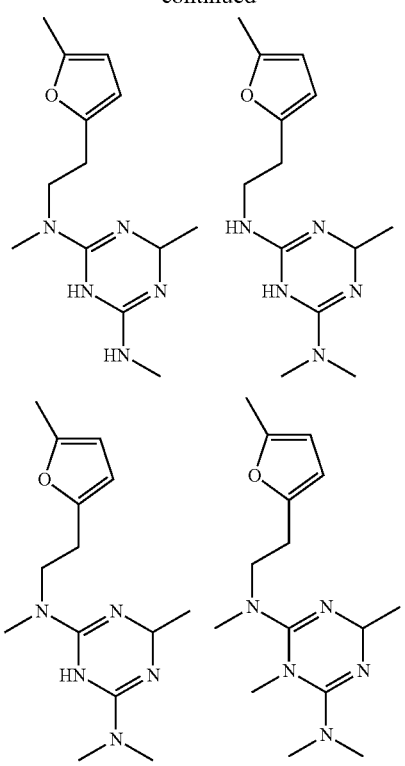
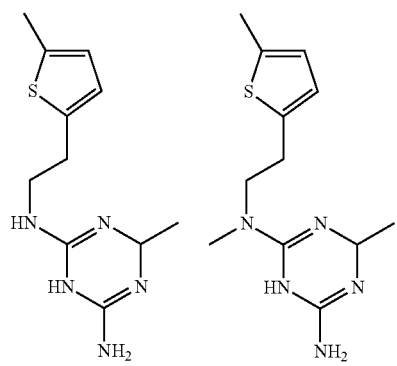
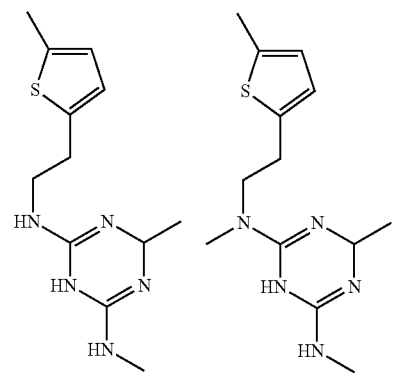
216
-continued
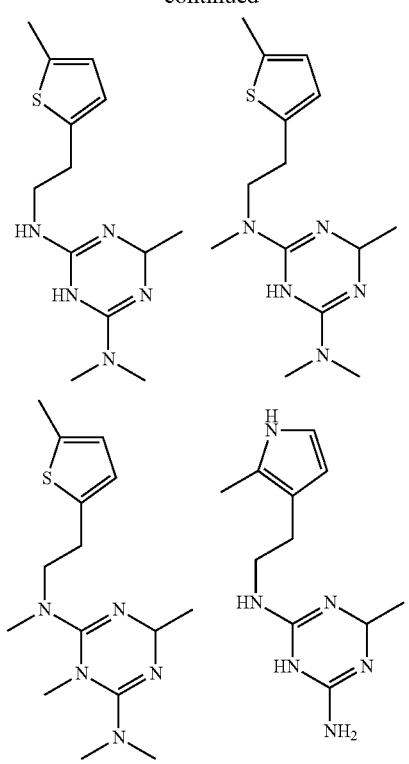
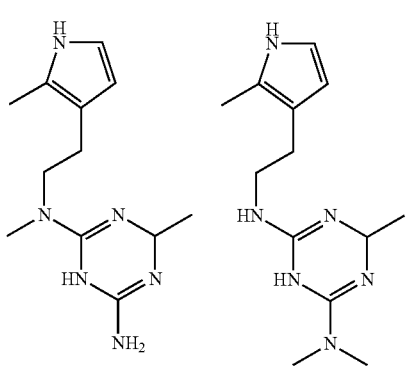
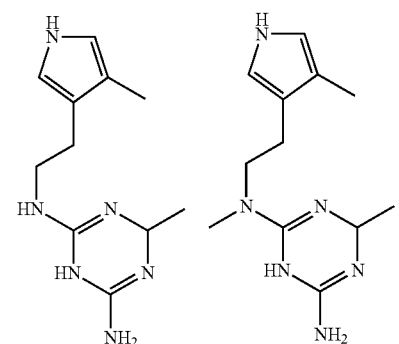

217
-continued
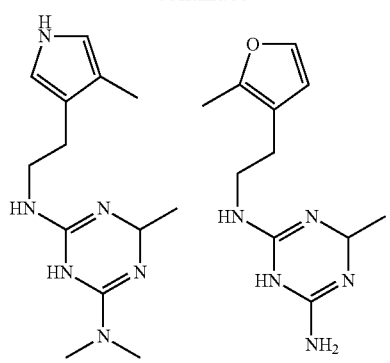
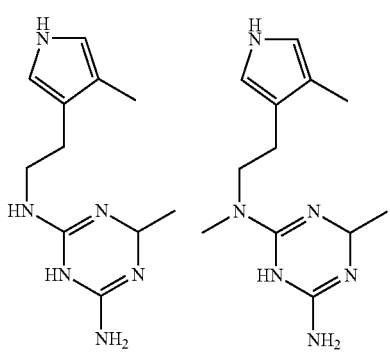
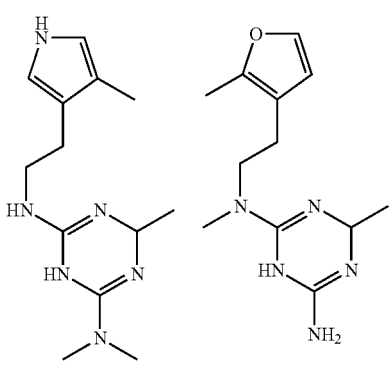
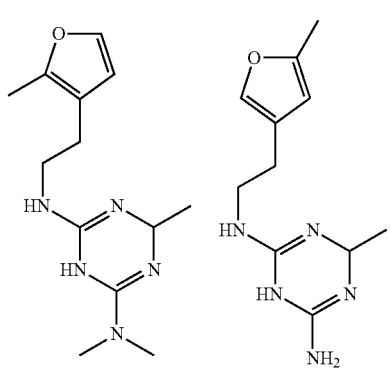
218
-continued
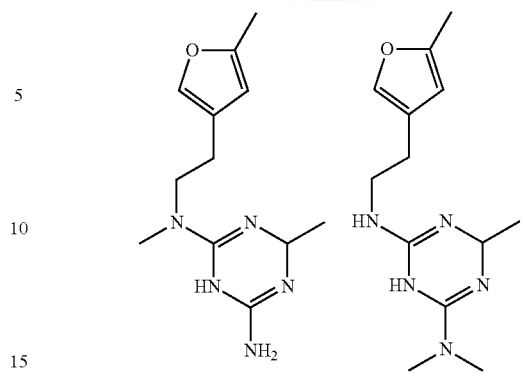
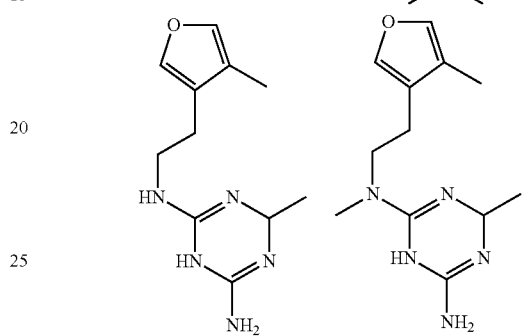
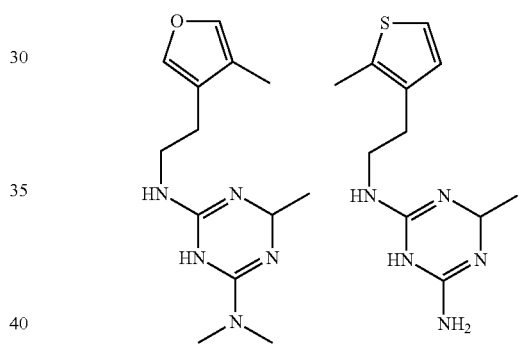
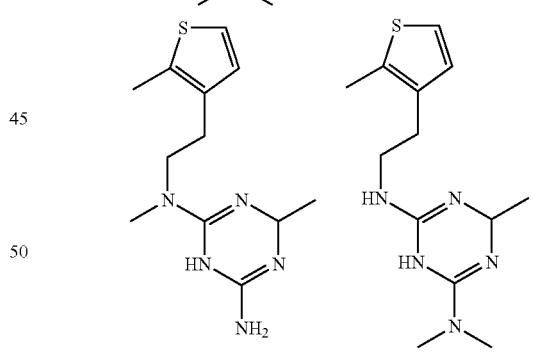
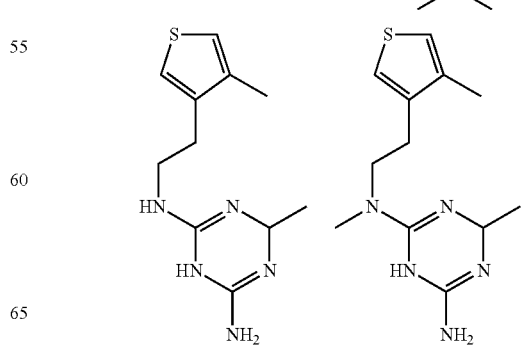

219
-continued
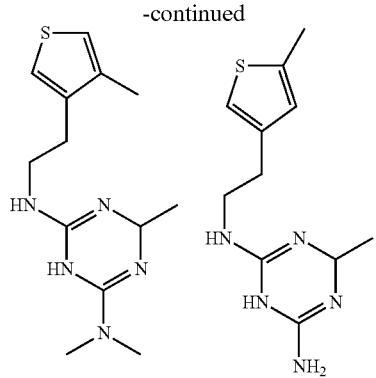
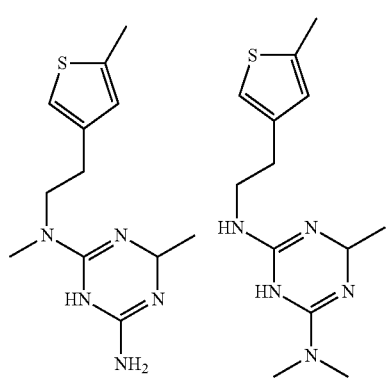
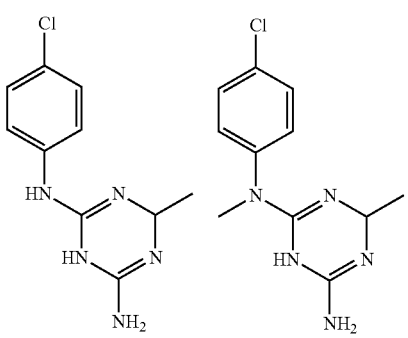
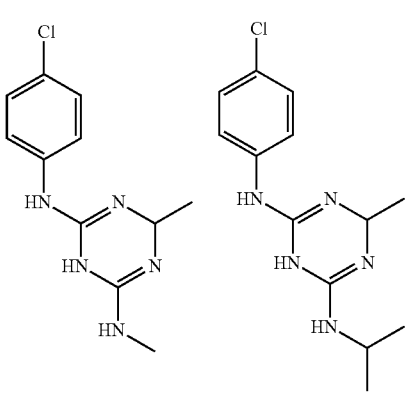
220
-continued
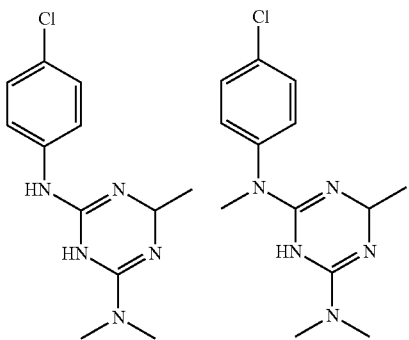
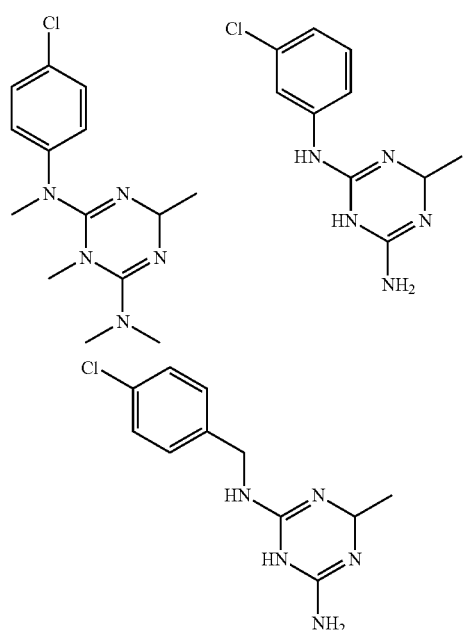
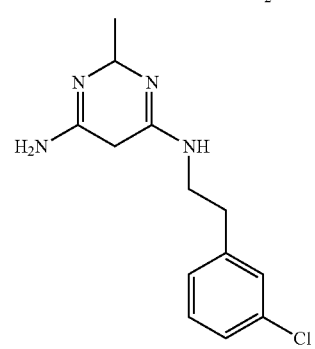
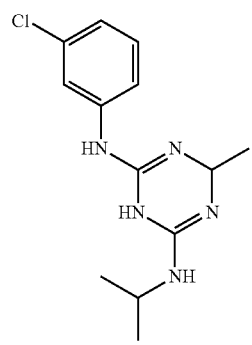

221
-continued
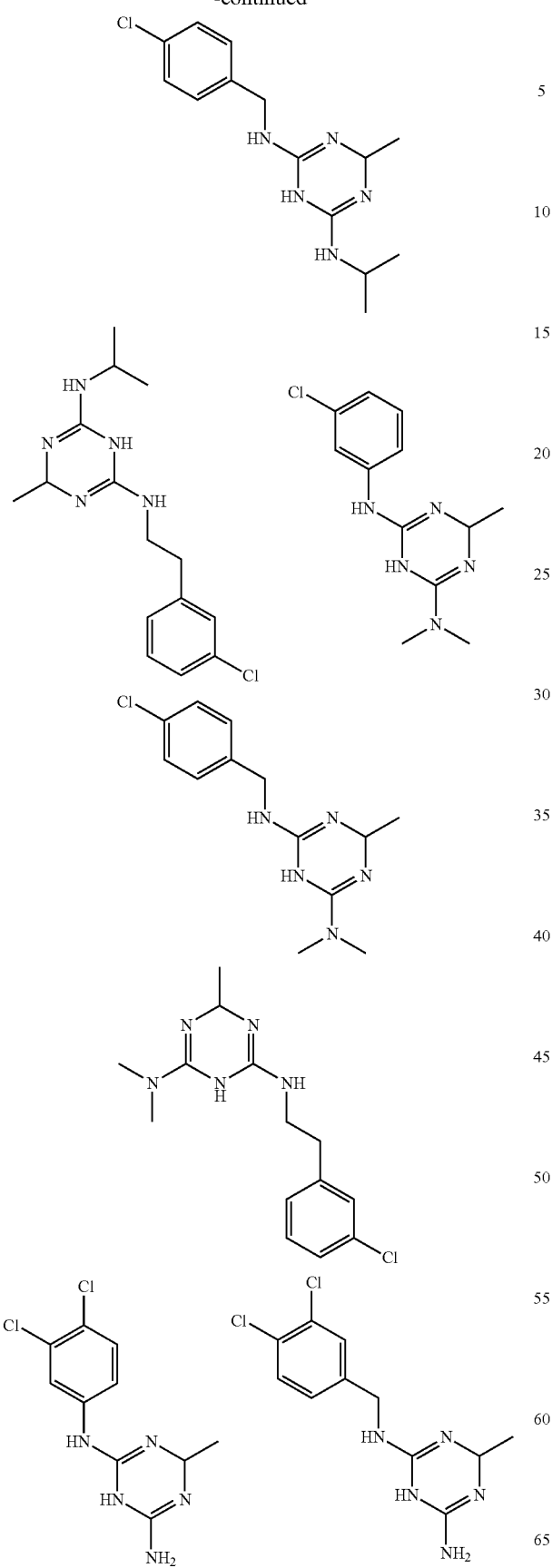
222
-continued
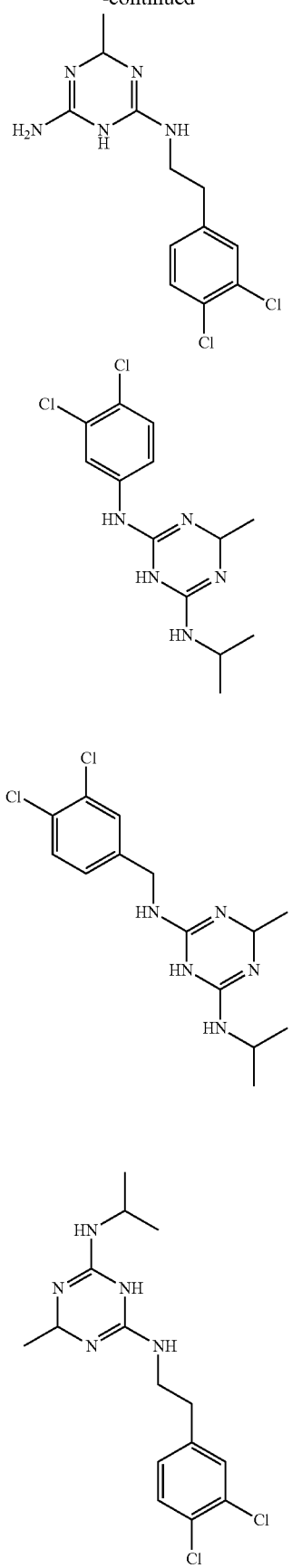

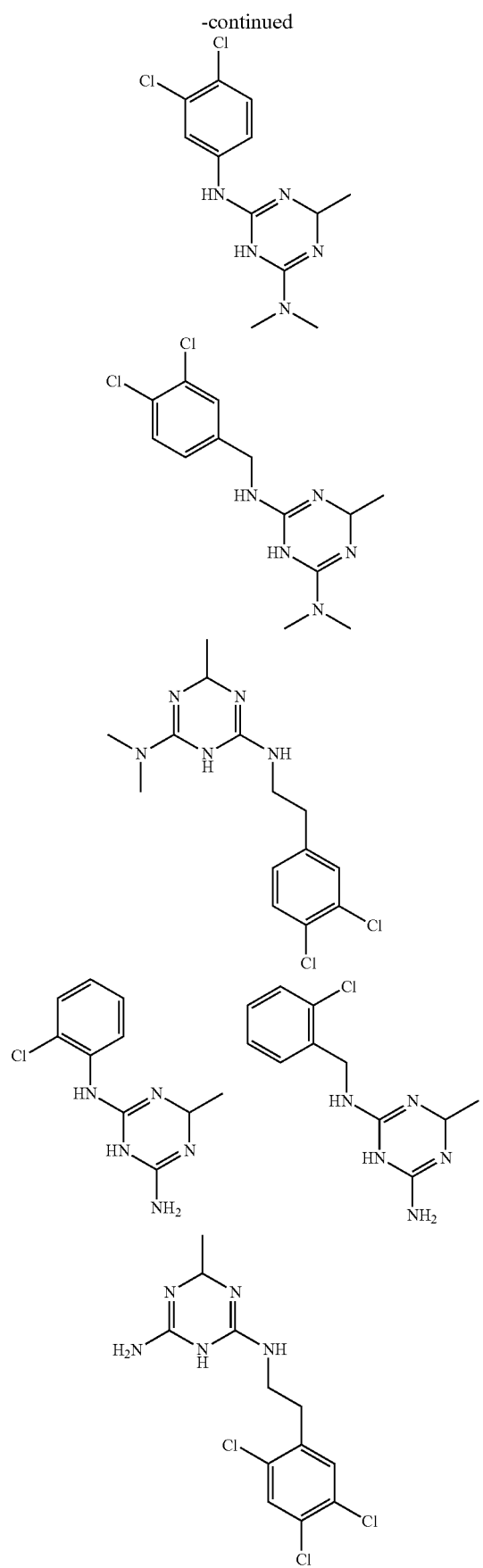

-continued

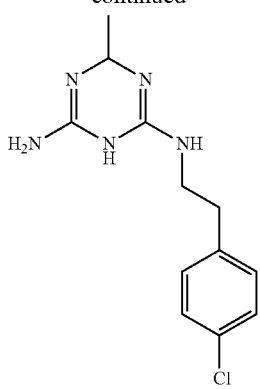

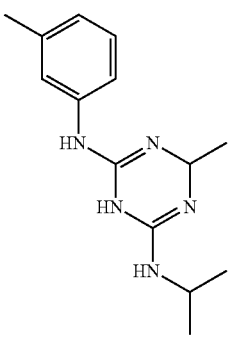
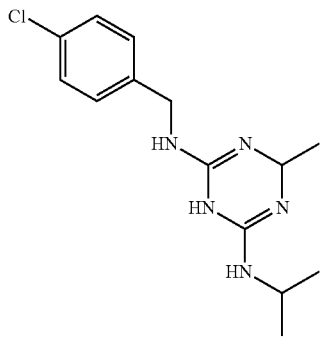

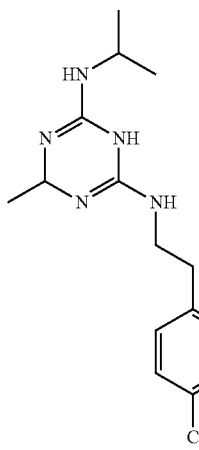
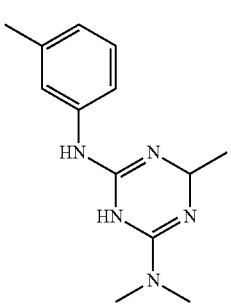

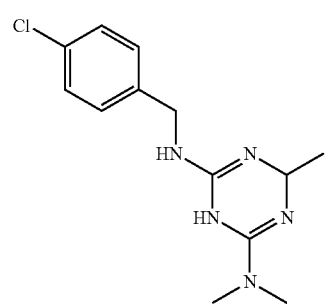

-continued

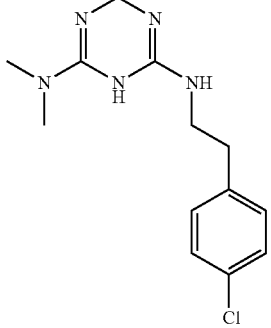

In other embodiments, 7-ring series compounds of Formula IV may be used in connection with the compositions and methods of the disclosure. Substituent definitions, unless otherwise indicated, are the same as provided with reference to Formula I.

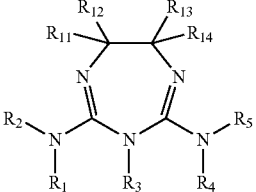

IV wherein:

wherein $R_3$, $R_4$, $R_5$, $R_6$, $R_7$, $R_8$ and $R_9$ are independently selected from H, methyl, ethyl, propyl or isopropyl;

and wherein $R_1$ and $R_2$, and are independently selected from:

H; optionally substituted alkyl (e.g., a $C_1$ to $C_{12}$ straight chain or branched chain alkyl optionally substituted with oxygen, silicon, sulphur or optionally substituted with OH, O-alkyl, SH, S-alkyl, $NH_2$, NH-alkyl); cycloalkyl (e.g., $C_3$ to $C_7$ cycloalkyl); alkylcycloalkyl (e.g., $C_4$ to $C_{12}$ alkylcycloalkyl); heterocycloalkyl (e.g., where the heterocycle comprises one or two hetero atoms selected from O, S, or N, including a $C_2$ to $C_6$ heterocycloalkyl); alkylheterocycloalkyl (e.g., where the heterocycle comprises one or two hetero atoms selected from O, S, or N, including a $C_3$ to $C_{11}$ alkylheterocycloalkyl, and including wherein when N is present in the heterocyclic ring, the nitrogen atom may be in the form of an amide, carbamate or urea); optionally substituted alkenyl (e.g., $C_1$ to $C_{12}$ straight chain or branched chain alkenyl optionally substituted with oxygen, silicon, sulphur or optionally substituted with OH, O-alkyl, SH, S-alkyl, $NH_2$, NH-alkyl); optionally substituted alkynyl (e.g., $C_1$ to $C_{12}$ straight chain or branched chain alkynyl optionally substituted with oxygen, silicon, sulphur or optionally substituted with OH, O-alkyl, SH, S-alkyl, $NH_2$, NH-alkyl);

optionally substituted aryl (e.g., phenyl, substituted phenyl, naphthyl, substituted naphthyl); optionally substituted alkylaryl (e.g., alkylphenyl, alkylsubstituted phenyl, alkylnaphthyl, alkylsubstituted naphthyl); optionally substituted heteroaryl (e.g., pyridyl, furanyl, thiophenyl, pyrrollyl, oxazolyl, isoxazolyl, thiazolyl, diazolyl, pyrazolyl, triazolyl all of which are optionally substituted); optionally substituted alkylheteroaryl; and or $R_1$ and $R_2$ may together form a 3 to 8 membered heterocyclic ring, including the nitrogen atoms to which they are attached.

In other embodiments, optional substitutions may include, e.g., OH, O-alkyl, SH, S-alkyl, $NH_2$, NH-alkyl. Further, an alkyl, alkenyl, alkynyl, etc. may be substituted with an oxygen, silicon, sulphur, etc. to form a heteroalkyl, heteroalkenyl, heteroalkynyl, etc.

In certain aspects, each of: $R_2$, $R_3$, $R_4$, $R_5$, $R_{11}$, $R_{12}$, $R_{13}$ and $R_{14}$ are independently selected from:

H, methyl, ethyl, propyl or isopropyl;

and $R_1$ is selected from:

H; optionally substituted alkyl (e.g., $C_1$ to $C_{12}$ straight chain or branched chain alkyl optionally hetero substituted with oxygen, silicon, sulphur or optionally substituted with OH, O-alkyl, SH, S-alkyl, $NH_2$, NH-alkyl); optionally substituted alkenyl (e.g., $C_1$ to $C_{12}$ straight chain or branched chain alkenyl optionally hetero substituted with oxygen, silicon, sulphur or optionally substituted with OH, O-alkyl, SH, S-alkyl, $NH_2$, NH-alkyl); optionally substituted alkynyl (e.g., $C_1$ to $C_{12}$ straight chain or branched chain alkynyl optionally hetero substituted with oxygen, silicon, sulphur or optionally substituted with OH, O-alkyl, SH, S-alkyl, $NH_2$, NH-alkyl); cycloalkyl (e.g., $C_3$ to $C_7$ cycloalkyl); alkylcycloalkyl (e.g., $C_4$ to $C_{12}$ alkylcycloalkyl); heterocycloalkyl (e.g., where the heterocycle comprises one or two hetero atoms selected from O, S, or N, including $C_2$ to $C_6$ heterocycloalkyl); alkylheterocycloalkyl (e.g., where the heterocycle comprises one or two hetero atoms selected from O, S, or N, including $C_3$ to $C_{11}$ alkylheterocycloalkyl, and including wherein when N is present in the heterocyclic ring, the nitrogen atom may be in the form of an amide, carbamate or urea); aryl (e.g., phenyl, substituted phenyl, naphthyl, substituted naphthyl); alkylaryl (e.g., alkylphenyl, alkylsubstituted phenyl, alkylnaphthyl, alkylsubstituted naphthyl); heteroaryl (e.g., pyridyl, furanyl, thiophenyl, pyrrollyl, oxazolyl, isoxazolyl, thiazolyl, diazolyl, pyrazolyl, triazolyl all of which are optionally substituted); alkylheteroaryl;

or $R_1$ and $R_2$ may together form a 3 to 8 membered heterocyclic ring, including the nitrogen atoms to which they are attached.

Exemplary compounds and substituents of $R_1$, $R_2$, $R_3$, $R_4$, $R_5$, $R_{11}$, $R_{12}$, $R_{13}$ and $R_{14}$ of Formula IV are shown below. However, additional combinations of selections of substituents of $R_1$, $R_2$, $R_3$, $R_4$, $R_5$, $R_{11}$, $R_{12}$, $R_{13}$ and $R_{14}$ are envisioned.

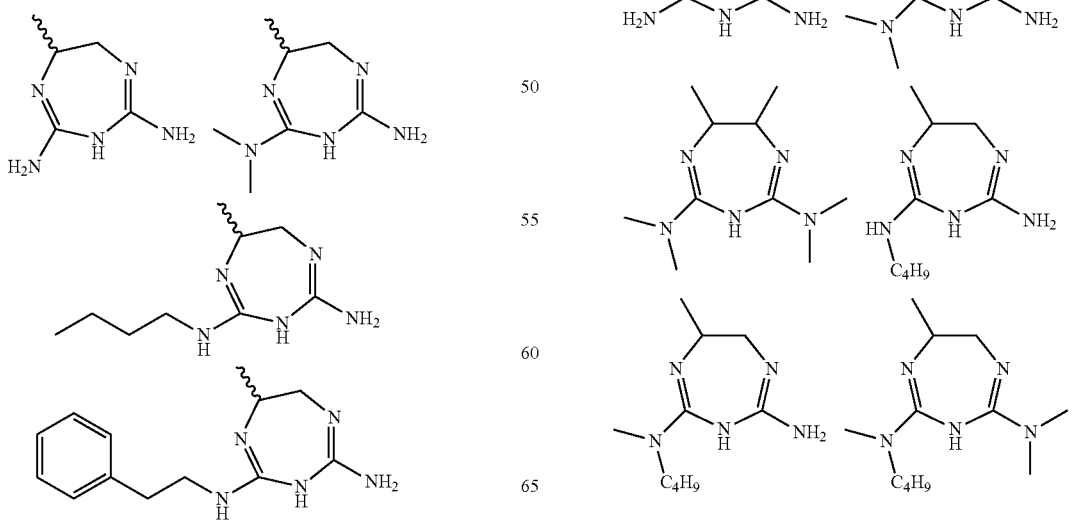

-continued

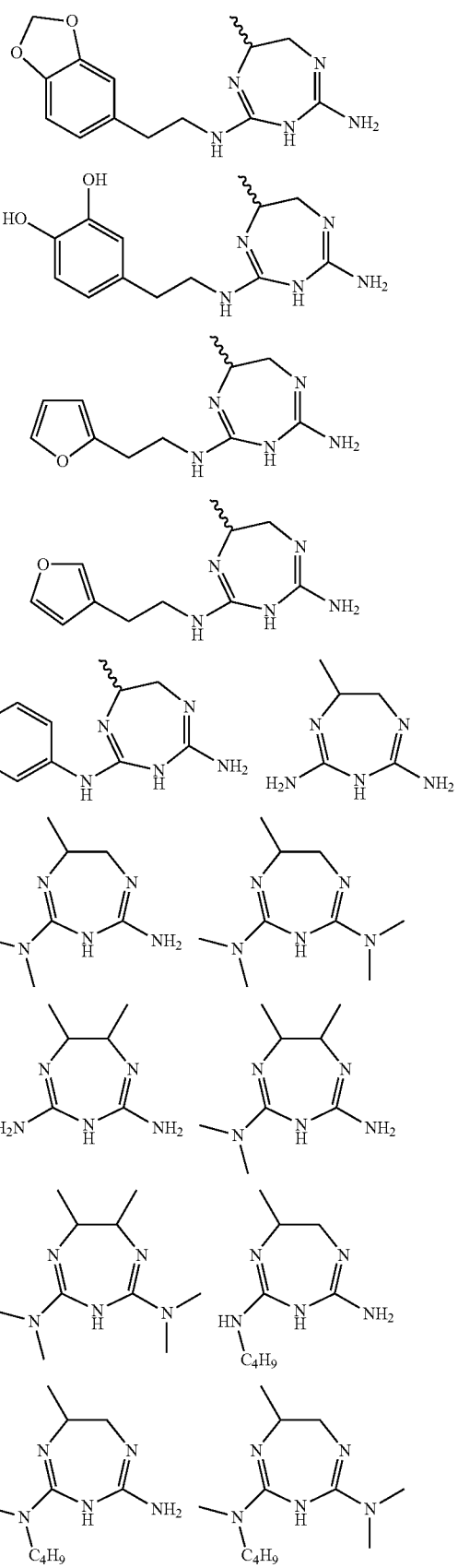

229
-continued
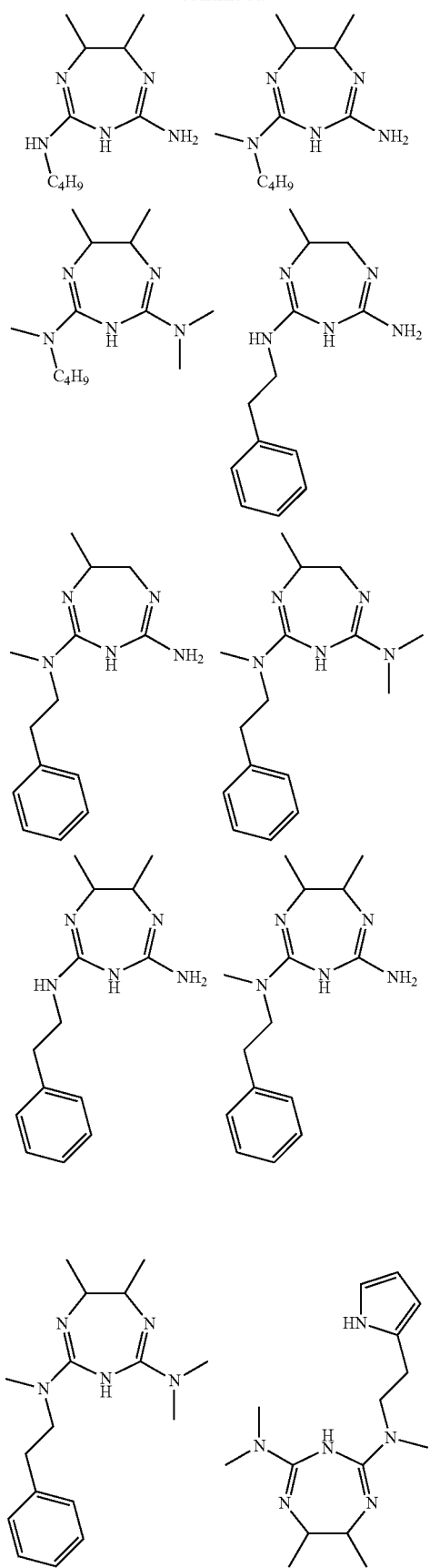
230
-continued
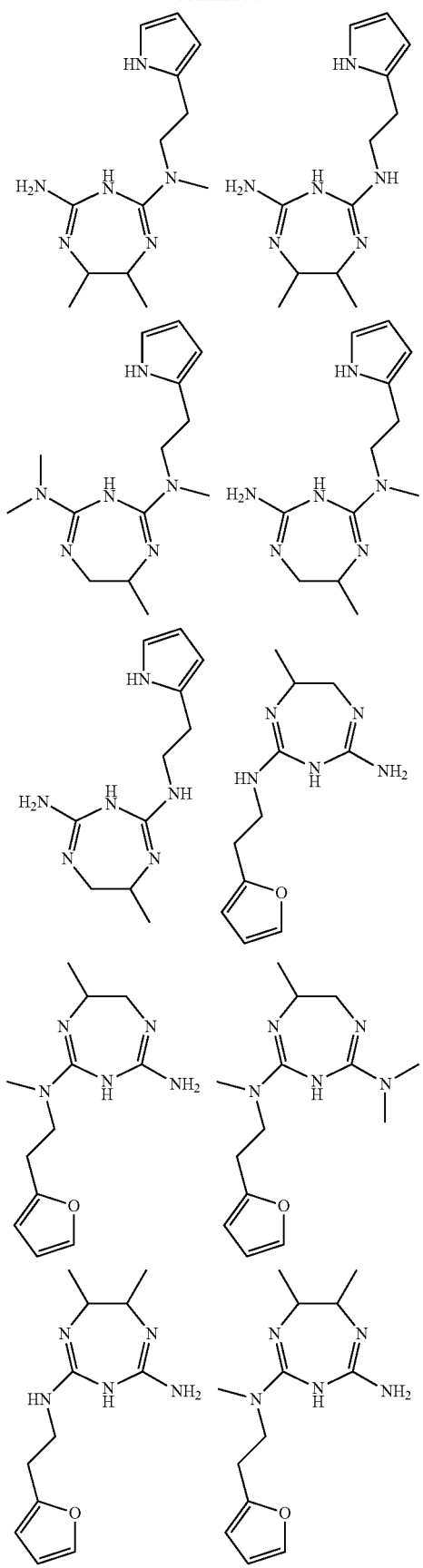

231
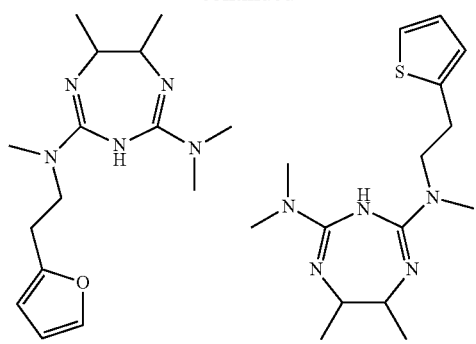
232
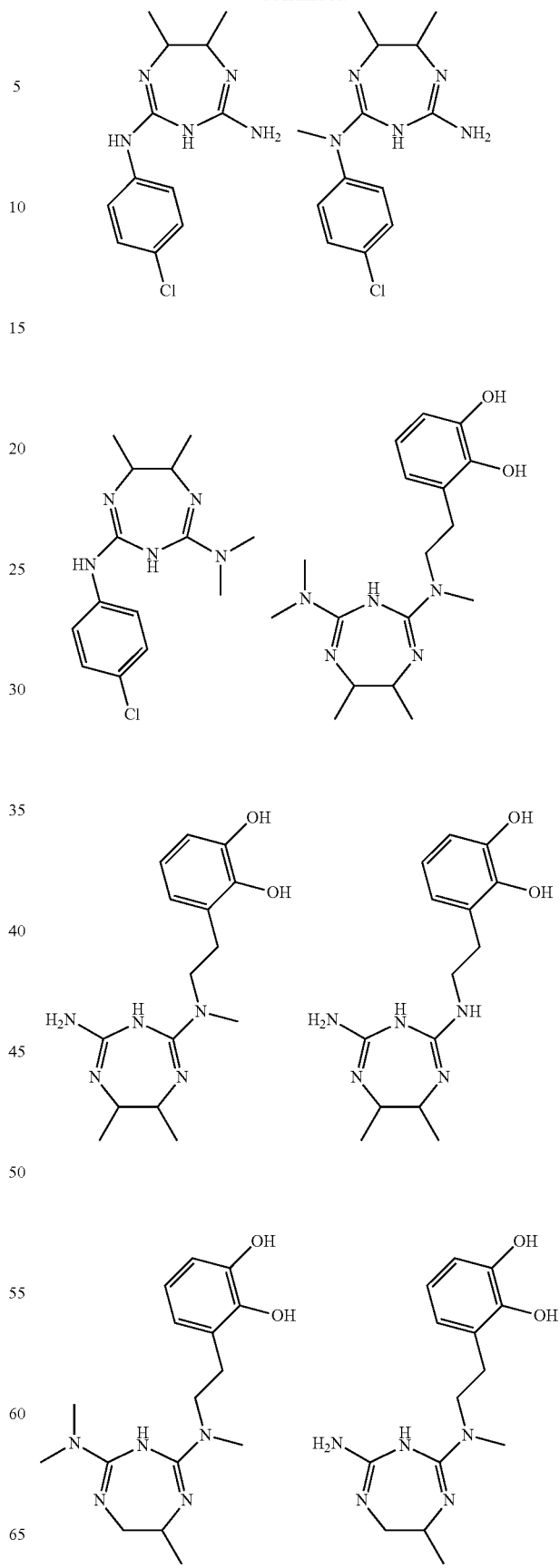

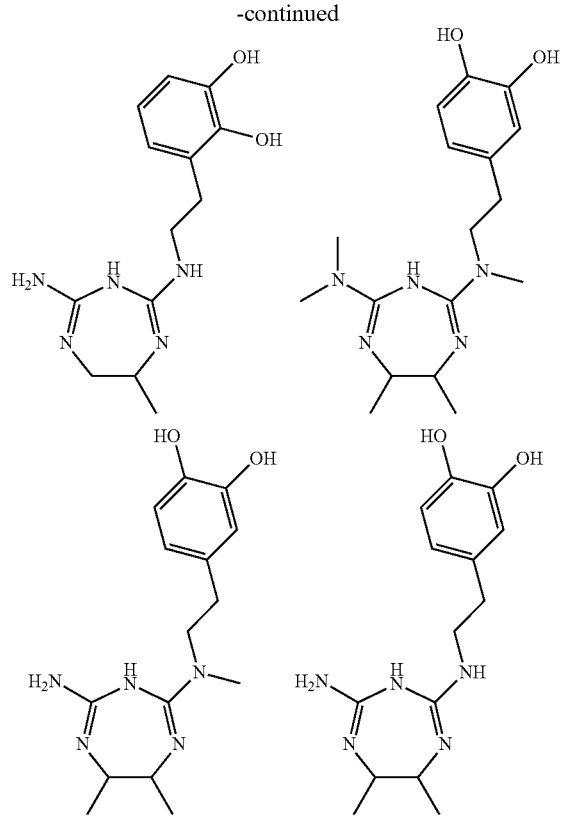
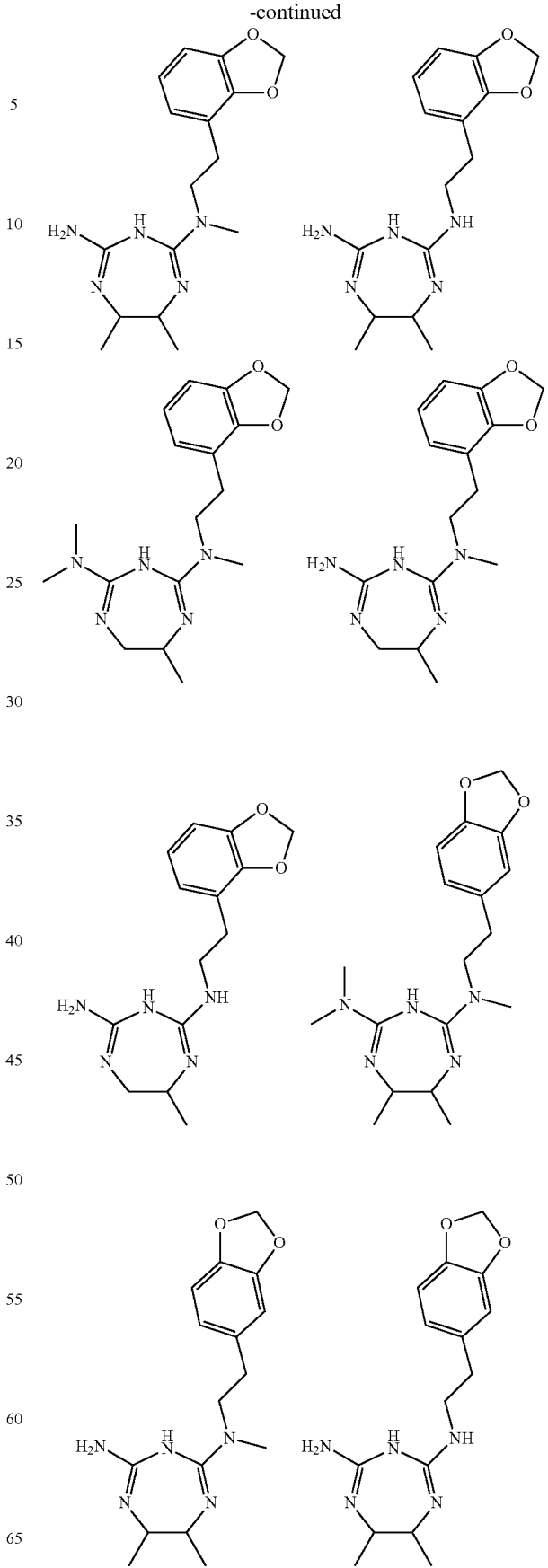

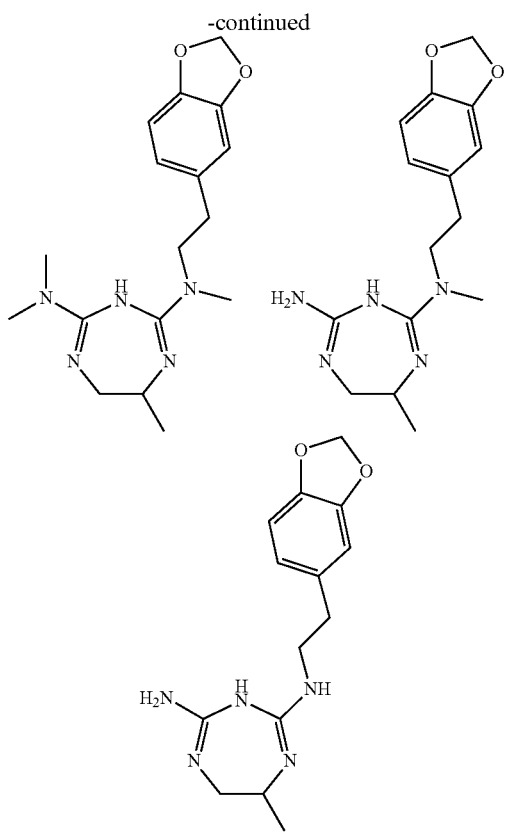

In certain embodiments, the compounds of Formulas I, IA, II, III or IV may include an asymmetric center or centers, and may be in the form of a composition of a racemic mixture, a diastereoisomeric mixture, a single enantiomer, an enantiomeric diastereomer, a meso compound, a pure epimer, or a mixture of epimers thereof, etc. Further, the compounds of Formulas I, IA, II, III or IV may have one or more double bonds, and may be in a form of a cis/trans, E/Z mixture or an E or Z geometric isomer thereof.

The compounds of Formulas I, IA, II, III, and IV may also be prepared as a salt form, e.g., pharmaceutically acceptable salts, including suitable acid forms, e.g., salt forms selected from hydrochloride, hydrobromide, acetate, propionate, butyrate, sulphate, hydrogen sulphate, sulphite, carbonate, hydrogen carbonate, phosphate, phosphinate, oxalate, hemi-oxalate, malonate, hemi-malonate, fumarate, hemi-fumarate, maleate, hemi-maleate, citrate, hemi-citrate, tartrate, hemi-tartrate, aspartate, glutamate, etc.

In one embodiment, the compounds of the disclosure may be prepared as a three component salt form including the components A, B, and C wherein:
  A is the protonated form of a natural or unnatural amino acid;
  B is the dianion of an acid; and
  C is the protonated form of a Compound of Formulas I, IA, II, III or IV.

In certain aspects, stoichiometric amounts of A, B, and C may be included wherein:
  A is the protonated form of a natural amino acid selected from alanine, aspartic acid, asparagine, arginine, glycine, glutamine, glutamic acid lysine, phenylalanine, tyrosine, serine, threonine, tryptophan, leucine, isoleucine, histidine, methionine, proline, cysteine, or cystine;
  B is the dianion of an acid selected from oxalic, malonic, citric, maleic, fumaric, tartaric, aspartic, glutamic acids and the like; and
  C is the protonated form of a compound of Formulas I, IA, II, III or IV.

Synthesis of the Compounds

Compounds described herein may be synthesized using standard synthetic techniques known to those of skill in the art or using methods known in the art in combination with methods described herein. In additions, solvents, temperatures and other reaction conditions presented herein may vary according to the practice and knowledge of those of skill in the art.

The starting material used for the synthesis of compounds described herein can be obtained from commercial sources, such as Aldrich Chemical Co. (Milwaukee, Wis.), Sigma Chemical Co. (St. Louis, Mo.), or the starting materials can be synthesized. The compounds described herein, and other related compounds having different substituents can be synthesized using techniques and materials known to those of skill in the art, such as described, for example, in March, ADVANCED ORGANIC CHEMISTRY 4th Ed., (Wiley 1992); Carey and Sundberg, ADVANCED ORGANIC CHEMISTRY 4th Ed., Vols. A and B (Plenum 2000, 2001), and Green and Wuts, PROTECTIVE GROUPS IN ORGANIC SYNTHESIS 3rd Ed., (Wiley 1999) (all of which are incorporated by reference in their entirety). General methods for the preparation of the compounds as disclosed herein may be derived from known reactions in the field, and the reactions may be modified by the use of appropriate reagents and conditions, as would be recognized by the skilled person, for the introduction of the various moieties found in the formulae as provided herein.

Additional biguanide and related heterocyclic compounds and synthesis methods and schemes for the compounds described herein can be found in U.S. application Ser. No. 12/593,479 (published as U.S. 2010/0130498); U.S. application Ser. No. 12/593,398 (published as U.S. 2010/0184796); U.S. Pat. No. 7,829,299; U.S. application Ser. No. 11/578,013 (published as U.S. 2010/0056621); U.S. Pat. No. 7,416,867; U.S. application Ser. No. 11/455,693 (published as U.S. 2007/0037212); U.S. application Ser. No. 13/059,730 (published as U.S. 2011/0143376), U.S. application Ser. No. 12/996,670 (published as U.S. 2011/0311991), U.S. Pat. No. 7,811,788; U.S. application Ser. No. 11/182,942 (published as U.S. 2006/0019346); U.S. application Ser. No. 12/993,542 (published as U.S. 2011/0086138), U.S. application Ser. No. 12/373,235 (published as U.S. 2010/0055209); International Application Ser. No. PCT/IL2007/000454 (published as WO 2007/116404); U.S. application Ser. No. 10/472,056 (published as U.S. 2004/0138189); U.S. Pat. No. 5,891,919; U.S. Pat. No. 6,376,657; U.S. application Ser. No. 11/554,982 (published as U.S. 2007/0104805); U.S. application Ser. No. 11/926,745 (published as U.S. 2008/0108604); International Application Ser. No. PCT/CA2009/001688 (published as WO 2010/060198); U.S. application Ser. No. 12/735,557 (published as U.S. 2010/0330205); International Application Ser. No. PCT/CA2007/001066 (published as WO 2008/000063); U.S. application Ser. No. 11/438,204 (published as U.S. 2006/0269617); U.S. application Ser. No. 10/563,713 (published as U.S. 2006/0172020); U.S. application Ser. No. 10/902,352 (published as U.S. 2006/0024335); U.S. application Ser. No. 10/538,038 (published as U.S. 2006/0275765), U.S. application Ser. No. 11/555,617 (published as U.S. 2008/0187936); U.S. application Ser. No. 12/739,264 (published as U.S. 2010/0316736); U.S. application Ser. No. 12/215,609 (published as U.S. 2009/0042813); U.S. application Ser. No. 11/893,088 (published as U.S. 2008/0050499); U.S. Pat. No. 7,807,204; U.S. application Ser. No. 11/811,166 (published as U.S. 2008/0003268); U.S. Pat. No. 6,376,657; International Application Ser. No. PCT/US2011/041183 (published as WO 2011/163183); International Application Ser. No. PCT/EP2011/059814 (published as WO 2011/157692); U.S. application Ser. No. 12/790,292 (published as U.S. 2011/0293753); International Application Ser. No. PCT/JP2009/071700 (published as WO 2010/076879); U.S. application Ser. No. 13/032,530 (published as U.S. 2011/0217394); International Application Ser. No. PCT/EP2011/000110 (published as WO 2011/085979); International Application Ser. No. PCT/US2010/058467 (published as WO 2011/068814); U.S. application Ser. No. 13/060,996 (published as U.S. 2011/0152361); U.S. application Ser. No. 12/09,253 (published as U.S. 2011/0124609); U.S. application Ser. No. 12/687,962 (published as U.S. 2011/0119499); and International Application Ser. No. PCT/EP2010/004623 (published as WO 2011/012298); each of which are incorporated by reference in their entirety.

Other known biguanide and related compounds include:

Chlorhexidine, a compound with antiseptic properties:

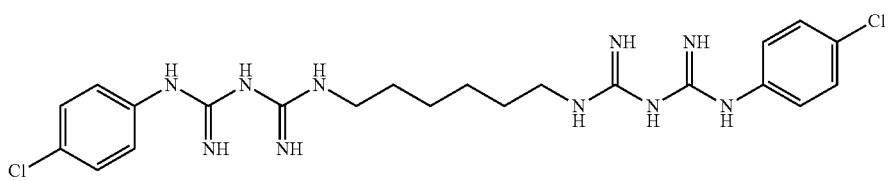 [SMILES: N=C(NCCCCCCNC(=N)NC(=N)Nc1ccc(Cl)cc1)NC(=N)Nc1ccc(Cl)cc1]

Cycloguanil, a compound with anti-malarial properties:

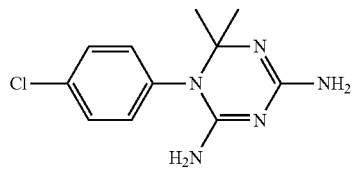 [SMILES: CC1(C)N=C(N)N=C(N)N1c1ccc(Cl)cc1]

Polyhexamethylene biguanide, a compound with antiseptic properties:

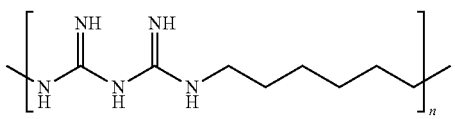

A compound designated JPC-2067-B, known as *Toxoplasma Gondi* Inhibitor:

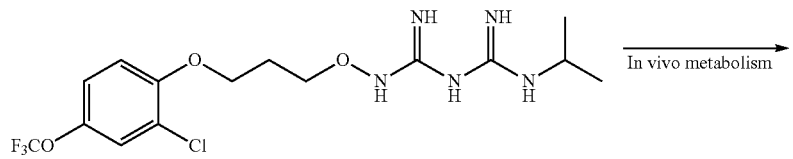

JPC-2056

In vivo metabolism

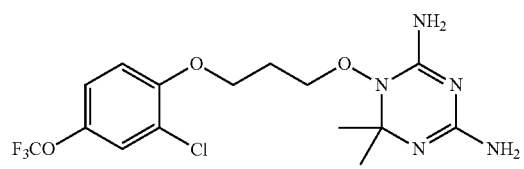

JPC-2067-B

These and other biguanide and related heterocyclic compounds are envisioned as within the scope of the disclosure. In further embodiments, a biguanide and related heterocyclic compound is metformin or a salt thereof.

Metformin

Metformin has low bioavailability in terms of circulating blood concentrations as compared to many other orally administered drugs. For example, metformin is reported to have an average systemic bioavailability of 30% to 60% while many comparably small molecules have bioavailability of greater than 60%. See, e.g., Tucker et al., "Metformin kinetics in healthy subjects and in patients with diabetes mellitus" Br. J. Clin. Pharmacol. 1981, 12(2) 235-246. It has been reported that administration of metformin increases release of GLP-1 from the L cells located in the gut. However, GLP-1 release from the L cells (and activation of enteroendocrine cells) is triggered by the luminal signals on the epithelial aspect of the gut. There are no known examples of blood-borne or circulating signals that can activate enteroendocrine cells to release their hormonal contents. Thus, it is contemplated that metformin does not act through its presence in the plasma circulation per se. Metformin may cause activation of enteroendocrine cells (e.g., by binding to a bitter receptor on the L cell or other enteroendocrine cell), including GLP-1 release from L cells through an interaction with the luminal or epithelial aspect of L cells.

Minimizing Systemic Exposure

Provided herein, in certain embodiments, are compositions of a biguanide or related heterocyclic compound, e.g., metformin or a salt thereof, adapted to minimize the systemic bioavailability of the compound, e.g., by delivery to the gut. In some embodiments, the compositions of a biguanide or related heterocyclic compound, e.g., metformin or a salt thereof, adapted for delivery to enteroendocrine cells described herein minimize metformin plasma absorption in a subject. In other embodiments, the compositions of a biguanide or related heterocyclic compound, e.g., metformin or a salt thereof, minimize plasma Cmax and/or AUC levels. In other embodiments, the compositions of a biguanide or related heterocyclic compound, e.g., metformin or a salt thereof, have negligible metformin plasma absorption, Cmax and/or AUC levels. It other embodiments, Cmax, and/or AUC levels of the biguanide or related heterocyclic compound, e.g., metformin or a salt thereof, are what was previously considered sub-therapeutic for the described compositions as compared to reported Cmax and/or AUC levels of known formulations of the compounds.

In preferred embodiments, the compositions described herein are adapted to reduce or minimize systemic bioavailability of the compound, e.g., minimize the circulating plasma concentration of the biguanide compound in the patient and/or reduce the average systemic bioavailability of the compound, e.g., when compared to a immediate release composition having an equivalent amount of the compound. In some embodiments, the minimized circulating plasma concentration is below about 5 µg/mL, 4 µg/mL, 3 µg/mL, 2 µg/mL, 1 µg/mL, 0.5 µg/mL or 0.25 µg/mL in subjects with normal or impaired renal function. In other embodiments, an adapted compound composition provides 70%, 60%, 50%, 40%, 30%, or 20% less relative bioavailability of the compound compared to an immediate release composition having the same amount of the compound.

Negligible or sub-therapeutic metformin plasma Cmax and/or AUC levels include 50%, 40%, 30%, 20% and 10% of reported Cmax and/or AUC levels of known metformin formulations (e.g., GLUMETZA, GLUCOPHAGE, GLUCOPHAGE XR, RIOMET, FORTAMET, OBIMET, GLUFORMIN, DIANBEN, DIABEX, DIAFORMIN, Metformin IR, Metformin SR, and the like). For example, a known extended release metformin formulation, GLUMETZA, has mean Cmax values that are 473±145, 868±223, 1171±297, and 1630±399 ng/mL for single doses of 500, 1000, 500, and 2500 mg, respectively. For AUC, the mean values for GLUMETZA are 3501±796, 6705±1918, 9299±2833, and 14161-4432 ng·hr/mL for single doses of 500, 1000, 1500, and 2500 mg, respectively (GLUMETZA product label).

In further embodiments, the compositions of metformin or a salt thereof have reduced average systemic bioavailability. Reduced average systemic bioavailability, in some embodiments, is lower average systemic bioavailability as compared to an immediate release metformin formulation (relative bioavailability) having an equivalent amount of metformin. In other embodiments, reduced average systemic bioavailability is when the average systemic bioavailability, e.g., relative bioavailability is less than 40%, 30%, less than 25%, less than 15%, less than 10% and less than 5%. In certain instances, the average systemic bioavailability is less than 15%.

To achieve these effects, delivery of metformin is designed for modified release that, for example, is retained in the gastro-intestinal tract, and/or releases metformin dosages in amounts that minimize plasma absorption. The delivery of metformin to one or more regions of the intestine is via any known method including, e.g., oral, rectal, nasogastric tube, parenterally injection such as intraluminal intestinal injection. In some instances, the delivery is oral. Oral delivery of metformin compositions are described in the modified release formulations section and include timed release systems, enteric coatings and pH dependent systems, gastro-retentive systems, floating systems, bioadhesive systems, swelling systems and the like. In some embodiments, the metformin compositions described herein utilize a multicomponent system where metformin is delivered to several places in the gastrointestinal tract such as the duodenum, jejunum, ileum, lower intestine or combinations thereof following administration. For example, a metformin composition can deliver to the small intestine by use of immediate release and timed or delayed (enteric) release components. Multicomponent systems of metformin compositions can be in unitary dosage forms such as bi- or tri- or multiple-layer tablets or multi-particulate forms such as encapsulated micro-tablets or as separate dosage forms, e.g., separate tablets taken together or at a periodic interval.

In some embodiments, a composition of metformin or a salt thereof adapted for delivery to one or more regions of the intestine comprises two components for delivering metformin where the first component is immediate release and the second component is an immediate release or timed release covered with an enteric coating. The second component releases after an onset desired pH, due to the enteric coating. pHs contemplated include about pH 5.0, about pH 5.5, about pH 6.0, about pH 6.5 and about pH 7.0. After an onset of a desired pH, the second component begins release. Second components that comprise immediate release metformin in about 15 minutes, about 20 minutes, about 25 minutes or about 30 minutes after the onset of the desired pH, while second components comprising timed, extended or slow release over the course of a longer time period such as about 1 hour, about 2 hours, about 3 hours, about 4 hours, about 5 hours, about 6 hours, about 7 hours or about 8 hours. The exemplary two component metformin delivery system can be, in some embodiments, a bilayer tablet. Three, four and additional components are contemplated within the embodiments. For example, a third or forth component may include a gastro-retentive component or one that delivers and releases metformin specifically to the lower intestine.

For compositions comprising metformin or a salt thereof, dosages of metformin can range from about 1 mg to about 2000 mg, about 10 mg to about 1500 mg, about 50 mg to about 1000 or about 100 mg or about 500 mg per day. In some instances, the dosage of metformin or a salt thereof is about 2000 mg, about 1500 about 1000 mg, about 800 mg, about 600 mg, about 500 mg, about 400 mg, about 300 mg, about 250 mg, about 200 mg, about 150 mg, about 100 mg, about 75 mg, about 50 mg, about 25 mg, about 10 mg or about 1 mg per day. In some embodiments, the dosage of metformin or a salt thereof is less than 400 mg. In some embodiments, the dosage of metformin or a salt thereof is 250 mg.

Salts of metformin include, but are not limited to, hydrochloride, phosphate, sulfate, hydrobromide, salicylate, maleate, benzoate, succinnate, ethanesulfonate, fumarate, glycolate, pamoate, oratate, acetate, isobutyrate, acetylsalicylate, nicotinic acid, adamantoate, zinc-chlorophylin, carboxylic acid, benzoic acid, dichloroacetic acid, theophylin-7-acetate, clofibrate, tartate, oxalate, tannate and hydroxyl acid salts. In certain instances, the metformin salt is metformin hydrochloride.

The compositions of metformin or a salt thereof adapted for delivery to one or more regions of the intestine, in some embodiments, are administered or combined with additional agents, such as anti-obesity and/or anti-diabetic agents described herein. Notable agents for combinations with the metformin compositions described herein include DPP-IV inhibitors (e.g., sitagliptin, saxagliptin, berberine, vildagliptin, linagliptin, alogliptin, and the like), thiazolidinediones (e.g., pioglitazone, rivoglitazone, rosiglitazone, troglitazone, and the like), sulfonylureas (e.g., glipzide, glibenclamide (glyburide), gliquidone, glyclopyramide, glimepiride, gliclazide, acetohexamide, carbutamide, chlorpropamide, tolbutamide, tolazamide, and the like), and Dual PPAR agonists (aleglitazar, muraglitazar, tesaglitazar, and the like).

In further embodiments, a chemosensory receptor modifier is administered with a biguanide or related heterocyclic compound to alter or change the activity of a receptor toward the compound. In yet further embodiments a chemosensory receptor enhancer is administered with a biguanide or related heterocyclic compound to enhance, potentiate or multiply the effect of the compound. In certain instances, modifiers and/or enhancers are administered prior to administration of a compound enhance, potentiate or multiply the effect of the compound. In other instances, modifiers and/or enhancers are administered with a compound together to enhance, potentiate or multiply the effect of the compound.

Modulators and enhancers can be specific to a chemoreceptor type and/or multiple chemoreceptor types. Specific chemoreceptor modulators and enhancers can include, but are not limited to, umami receptor modulators and enhancers, sweet receptor modulators and enhancers, bitter receptor modulators and enhancers, fat receptor modulators and enhancers, bile acid receptor modulators and enhancers, sour receptor modulators and enhancers, and the like.

In some embodiments, a bitter receptor enhancer is selected from enhancer compounds described herein or known in the art. Bitter receptor enhancers include, but are not limited to, sweet receptor ligands in sub-bitter quantities, i.e., quantities that do not elicit a bitter taste response. In some embodiments, a bitter receptor enhancer is a silver salt. Silver salts include silver acetate and silver lactate.

Combinations

The biguanide or related heterocyclic compounds can be administered alone or in combination with each other. Dosages for each biguanide or related heterocyclic compound can be determined via methods known in the art. Maximal response doses and maximum tolerated doses can be determined via animal and human experimental protocols as described herein. Additional relative dosages, represented as a percent of maximal response or of maximum tolerated dose, are easily obtained via the protocols.

In an exemplary dose-response experiment, biguanide or related heterocyclic compounds are individually administered in an animal model (e.g. diabetic or obese rat model) to determine the optimum doses for each biguanide or related heterocyclic compound. biguanide or related heterocyclic compounds are administered individually at increasing amounts (mg/kg/min), where each subject is administered a set mg/kg/min dose and the dose is maintained at this set level for a defined period. Blood samples are collected at frequent intervals (e.g., every 1, 2, or 5 minutes) throughout the period and assayed for hormone concentrations. Hormones assayed include CCK, GIP, GLP-1, oxyntomodulin, PYY, insulin, C-peptide, and GLP-2. 50% of maximal response dose and 50% of the maximum tolerated dose are determined for each biguanide or related heterocyclic compound.

In some embodiments, at least one biguanide or related heterocyclic compound is administered at a concentration that is 50% of the maximal response dose. In other embodiments, at least one biguanide or related heterocyclic compound is administered at a concentration that is 50% of the maximum tolerated dose. biguanide or related heterocyclic compound s can be administered as 5%, 10%, 20%, 25%, 30%, 35%, 40%, 45%, 50%, 55%, 60%, 65%, 70%, 75%, 80%, 85%, 90%, 95%, or 100%, of the maximum response or maximum tolerated dose, inclusive of all integers therein.

The combinations of biguanide or related heterocyclic compounds can be administered in a single composition or in multiple compositions. Multiple compositions may be administered simultaneously or at different times. The compositions may be administered in different delivery forms (i.e., tablets, powders, capsules, gels, liquids, nutritional supplements, edible food preparations (e.g., medical foods, bars, gels, sprinkles, gums, lozenges, candies, liquids, etc.) and in any combination of such forms.

In one non-limiting example, a tablet containing at least one biguanide or related heterocyclic compound is administered simultaneously with another tablet containing at least one biguanide or related heterocyclic compound to provide the desired dosage. In a further example, the two tablets are administered at different times. In another non-limiting example, a tablet containing the desired combination of biguanide or related heterocyclic compound(s) is administered to provide the full dosage. Any combination of delivery forms, compositions, and delivery times are contemplated herein.

The constituents of the compositions provided by the invention can be varied both with respect to the individual constituents and relative proportions of the constituents. In embodiments, the relative proportion of the constituents is optimized to produce the desired synergistic activity from the drug combination. For example, in a composition comprising, or a method comprising administering, two constituents, e.g., two biguanide or related heterocyclic compounds, or as another nonlimiting example, a biguanide or related heterocyclic compound and a chemosensory receptor ligand, the constituents can be present in ratios of or about, e.g., 1:1, 1:2, 1:3, 1:4, 1:5, 1:6, 1:7, 1:8, 1:9, 1:10, 1:15, 1:20, 1:25, 1:30, 1:35, 1:40, 1:45, 1:50, 1:60, 1:70, 1:80, 1:90, 1:100, 1:200, 1:300, 1:400, 1:500, 1:1000, etc. In a composition comprising, or a method comprising administering, three constituents, for example two biguanide or related heterocyclic compounds, and a metabolized chemosensory receptor ligand, the constituents can be present in ratios of or about, e.g., 1:1:1, 2:1:1, 2:2:1, 3:1:1, 3:3:1, 3:2:2, 3:3:2, 3:2:1, 4:1:1, 4:4:1, 4:2:2, 4:4:2, 4:2:3, 4:3:3, 4:4:3, 4:2:1, 5:1:1, 5:5:1, 5:2:1, 5:3:1, 5:3:2, 5:3:4, 5:5:2, 5:5:3, 5:5:4, 10:1:1, 10:10:1, etc.

When more than one biguanide or related heterocyclic compound is used in combination with at least one other chemosensory receptor ligand or compound, it is understood that the combination treatment regimen encompasses treatment regimens in which administration of one compound is initiated prior to, during, or after treatment with a second or additional agent in the combination, and continues until any time during treatment with any other agent in the combination or after termination of treatment with any other agent. Treatment regimens also include those in which the agents being used in combination are administered simultaneously or at different times and/or at decreasing or increasing intervals during the treatment period. Combination treatment includes periodic treatments that start and stop at various times to assist with the clinical management of the patient.

Indications

Among the conditions that are contemplated for treating using the compositions and methods of the embodiments herein are metabolic syndrome, diabetes type I, diabetes type II, obesity, binge eating, undesired food cravings, food addiction, a desire to reduce food intake or to lose weight or maintain weight loss, desire to maintain healthy weight, desire to maintain normal blood glucose metabolism, anorexia, pre-diabetes, glucose intolerance, gestational diabetes mellitus (GDM), impaired fasting glycemia, (IFG), post-prandial hyperglycemia, accelerated gastric emptying (dumping syndrome), delayed gastric emptying, dyslipidemia, post-prandial dyslipidemia, hyperlipidemia, hypertriglyceridemia, post hypertriglyceridemia, insulin resistance, bone loss disorders, osteopenia, osteoporosis, muscle wasting disease, muscle degenerative disorders, polycystic ovary syndrome (PCOS), non-alcoholic fatty liver disease (NAFL), non-alcoholic steatohepatitis (NASH), immune disorders of the gut (e.g., celiac disease), bowel irregularity, irritable bowel syndrome (IBS), or inflammatory bowel disease (IBD), including, e.g., ulcerative colitis, Crohn's disease, and short bowel syndrome, peripheral neuropathy (e.g., diabetic neuropathy). In certain embodiments, the methods comprise treating a subject having sadness, stress, grief, anxiety, anxiety disorder (e.g., generalized anxiety disorder, obsessive-compulsive disorder, panic disorder, post-traumatic stress disorder or social anxiety disorder or a mood disorder (e.g., depression, bipolar disorder, dysthymic disorder and cyclothymic disorder) by administering a composition comprising a biguanides or related heterocyclic compositions provided herein. In certain embodiments, the methods comprise methods of inducing feelings of happiness, well-being or contentment in subjects by administering a composition comprising biguanide or related heterocyclic composition provided herein.

Additionally, the compositions and methods described herein may be used for the dietary management of conditions listed above. In some embodiments, the compositions and methods provided herein are indicated for treatment, prevention and or maintenance of a metabolic disorder, disease or defect. Metabolic disorders, diseases or defects can include disorders, diseases or defects in energy homeostasis and disorders, diseases or defects in fuel homeostasis.

In certain embodiments, the compositions and methods provided herein are indicated for treatment, prevention and or maintenance of disorders, diseases and defects associated with energy homeostasis. Energy homeostasis generally relates to the signally pathways, molecules and hormones associated with food intake and energy expenditure. Disorders, diseases and defects associated with energy homeostasis include but are not limited to diabetes type I, diabetes type II, prediabetes, impaired fasting glycemia (IFG), impaired post-prandial glucose, and gestational diabetes. In some instances the compositions and methods provided herein are indicated for treatment, prevention and or maintenance of diabetes type I or type II.

In certain embodiments, the compositions and methods provided herein are indicated for treatment, prevention and or maintenance of disorders, diseases and defects associated with fuel homeostasis. Disorders, diseases and defects associated with fuel homeostasis include but is not limited to non-alcoholic fatty liver disease (NAFL), non-alcoholic steatohepatitis (NASH), hyperlipidemia, post hypertriglyceridemia, hypertriglyceridemia, insulin resistance and polycystic ovary syndrome (PCOS).

The embodiments also provide compositions and methods useful for treating conditions in which an increase in insulin secretion or control of glucose concentrations resulting from modulation of enteroendocrine cell hormones (e.g., GLP-1 or GIP) would be beneficial. These conditions include, but are not limited to, metabolic syndrome, diabetes type 1, diabetes type II, gestational diabetes, glucose intolerance, and related conditions including those in which patients suffer from glucose intolerance.

The embodiments also provide compositions and methods for modulating growth (proliferation), and/or generation (neogenesis), and/or prevention of cell death (apoptosis) of insulin producing and secreting cells (Beta cells) through the release of neural and hormonal signals emanating from the gut in response to luminal chemosensory stimulation. Gut hormones such as GLP-1, PYY, GLP-2 and gastrin have all been implicated in the process of beta cell preservation or beta cell mass expansion. In one aspect, chemosensory stimulation provides a hormonal signal coupled to a neural signal. The hormonal signal can occur before, after or at similar timeframes as the neural signal.

The embodiments also provide compositions and methods for treating conditions in which appetite suppression resulting from modulation of, e.g., PYY, oxyntomodulin, and/or CCK, would be beneficial. These conditions include, but are not limited to, obesity, binge eating, undesired food cravings, a desire to reduce food intake or to lose weight or maintain weight loss, and related conditions.

Further provided are compositions and methods for treating conditions in which proliferation of gut cells resulting from modulation of, e.g., GLP-2, would be beneficial, such as, short bowel syndrome, Crohn's disease, inflammatory bowel disease, ulcerative colitis, and other conditions resulting in bowel damage, including osteoporosis.

Methods of Treatment

Disorders of Glucose Metabolism

The embodiments described herein provide compositions and methods for treating and preventing disorders of glucose metabolism and their associated conditions.

For example, provided herein are methods for treating mammalian subjects with diabetes, including primary essential diabetes such as Type I Diabetes or Type II Diabetes (NIDDM) and secondary nonessential diabetes, comprising administering to the subject at least one biguanide or related heterocyclic compound as described herein. In accordance with the method of this invention a symptom of diabetes or the chance of developing a symptom of diabetes, such as atherosclerosis, obesity, hypertension, hyperlipidemia, fatty liver disease, nephropathy, neuropathy, retinopathy, foot ulceration and cataracts, each such symptom being associated with diabetes, can be reduced.

The methods and compositions provided by the invention are useful for preventing or ameliorating diseases and symptoms associated with hyperglycemia and insulin resistance or low insulin concentrations. While a cluster of signs and symptoms associated may coexist in an individual patient, it many cases only one symptom may dominate, due to individual differences in vulnerability of the many physiological systems affected by insulin resistance. Nonetheless, since hyperglycemia and insulin resistance are major contributors to many disease conditions, agents that address these cellular and molecular defects are useful for prevention or amelioration of virtually any symptom in any organ system that may be due to, or exacerbated by hyperglycemia and insulin resistance.

Metabolic syndrome is a cluster of metabolic abnormalities including abdominal obesity, insulin resistance, glucose intolerance, diabetes, hypertension and dyslipidemia. These abnormalities are known to be associated with an increased risk of vascular events.

In addition to the metabolic disorders related to insulin resistance indicated above, disease symptoms secondary to hyperglycemia also occur in patients with NIDDM. These include nephropathy, peripheral neuropathy, retinopathy, microvascular disease, ulceration of the extremities, and consequences of nonenzymatic glycosylation of proteins, e.g. damage to collagen and other connective tissues. Attenuation of hyperglycemia reduces the rate of onset and severity of these consequences of diabetes. Because compositions and methods of the invention help to reduce hyperglycemia in diabetes, they are useful for prevention and amelioration of complications of chronic hyperglycemia.

Elevated triglyceride and free fatty acid concentrations in blood affect a substantial fraction of the population and are an important risk factor for atherosclerosis and myocardial infarction. Provided herein are compositions and methods useful for reducing circulating triglycerides and free fatty acids in hyperlipidemic patients. Hyperlipidemic patients often also have elevated blood cholesterol concentrations, which also increase the risk of cardiovascular disease. Cholesterol-lowering drugs such as HMG-CoA reductase inhibitors ("statins") can be administered to hyperlipidemic patients in addition to biguanide or related heterocyclic compound compositions of the invention, optionally incorporated into the same pharmaceutical composition.

A substantial fraction of the population is affected by fatty liver disease, also known as nonalcoholic steatohepatitis (NASH); NASH is often associated with obesity and diabetes. Hepatic steatosis, the presence of droplets of triglycerides with hepatocytes, predisposes the liver to chronic inflammation (detected in biopsy samples as infiltration of inflammatory leukocytes), which can lead to fibrosis and cirrhosis. Fatty liver disease is generally detected by observation of elevated serum concentrations of liver-specific enzymes such as the transaminases ALT and AST, which serve as indices of hepatocyte injury, as well as by presentation of symptoms which include fatigue and pain in the region of the liver, though definitive diagnosis often requires a biopsy. The anticipated benefit is a reduction in liver inflammation and fat content, resulting in attenuation, halting, or reversal of the progression of NASH toward fibrosis and cirrhosis.

Hypoinsulinemia is a condition wherein lower than normal amounts of insulin circulate throughout the body and wherein obesity is generally not involved. This condition includes Type I diabetes.

Type 2 Diabetes or abnormal glucose metabolism may be caused by a variety of factors and may manifest heterogeneous symptoms. Previously, Type 2 Diabetes was regarded as a relatively distinct disease entity, but current understanding has revealed that Type 2 Diabetes (and its associated hyperglycemia or dysglycemia) is often a manifestation of a much broader underlying disorder, which includes the metabolic syndrome as noted above. This syndrome is sometimes referred to as Syndrome X, and is a cluster of cardiovascular disease risk factors that, in addition to glucose intolerance, includes hyperinsulinaemia, dyslipidaemia, hypertension, visceral obesity, hypercoagulability, and microalbuminuria.

Also provided herein are compositions and methods for treating obesity, comprising administering to the subject at least one biguanide or related heterocyclic compound as described herein in an amount effective to treat the condition. The agent can be administered orally, and alternatively, other routes of administration that can be used in accordance with this invention include rectally, and parenterally, by injection (e.g., by intraluminal intestinal injection).

Both human and non-human mammalian subjects can be treated in accordance with the methods of this invention. In embodiments, the present invention provides compositions and methods for preventing or treating diabetes in a wide range of subject mammals, in particular, a human patient that has, has had, is suspected of having, or who is predisposed to developing diabetes. Diabetes mellitus is selected from the group consisting of insulin-dependent diabetes mellitus (IDDM or type I diabetes) and non-insulin-dependent diabetes mellitus (NIDDM, or type II diabetes). Examples of disorders related to diabetes mellitus have been described and include, but are not limited to, impaired glucose tolerance (IGT); maturity-onset diabetes of youth (MODY); leprechaunism (insulin receptor mutation), tropical diabetes, diabetes secondary to a pancreatic disease or surgery; diabetes associated with a genetic syndrome (e.g., Prader-Willi syndrome); pancreatitis; diabetes secondary to endocrinopathies; adipositas; and metabolic syndrome (syndrome X).

Diabetic subjects appropriate for treating using the compositions and methods provided by the invention can be easily recognized by the physician, and are characterized by, e.g., fasting hyperglycemia, impaired glucose tolerance, glycosylated hemoglobin, and, in some instances, ketoacidosis associated with trauma or illness. Hyperglycemia or high blood sugar is a condition in which an excessive amount of glucose circulates in the blood plasma. This is generally a blood glucose level of 10+ mmol/L, but symptoms and effects may not start to become noticeable until later numbers such as 15-20+ mmol/L. NIDDM patients have an abnormally high blood glucose concentration when fasting and delayed cellular uptake of glucose following meals or after a diagnostic test known as the glucose tolerance test. NIDDM is diagnosed based on recognized criteria (American Diabetes Association, Physician's Guide to Insulin-Dependent (Type I) Diabetes, 1988; American Diabetes Association, Physician's Guide to Non-Insulin-Dependent (Type II) Diabetes, 1988). The optimal dose of a particular biguanide or related heterocyclic compound composition for a particular subject can be determined in the clinical setting by a skilled clinician.

Chronic Kidney Disease, Diabetic Nephropathy, Macular Degeneration and Diabetes-Associated Conditions The compositions and methods provided herein can be used to prevent or treat kidney diseases. Diabetes is the most common cause of chronic kidney disease and kidney failure, accounting for nearly 44 percent of new cases. Even when diabetes is controlled, the disease can lead to chronic kidney disease and kidney failure. Most people with diabetes do not develop chronic kidney disease that is severe enough to progress to kidney failure. Nearly 24 million people in the United States have diabetes, and nearly 180,000 people are living with kidney failure as a result of diabetes. High blood pressure, or hypertension, is a major factor in the development of kidney problems in people with diabetes.

Accumulation of the glomerular mesangial extracellular matrix (ECM) leading to glomerulosclerosis is a common finding in diabetic nephropathy and other chronic kidney diseases. Several lines of evidence indicate that ECM accumulation in such chronic renal diseases results from both increased synthesis and decreased degradation of ECM components and it is widely accepted that ECM degradation in glomeruli and glomerular cells is mediated by a plasminogen activator-plasmin-matrix metalloproteinase-2 (MMP)-2 cascade. In addition, a variety of studies have reported decreased plasminogen activator (PA) activity, decreased plasmin activity, or increased concentrations of PA inhibitor 1 (PAI-1; the major PA inhibitor), in glomeruli obtained from animals with experimentally induced glomerular injuries known to result in mesangial matrix accumulation (Baricos, et al., "Extracellular Matrix Degradation by Cultured Mesangial Cells: Mediators and Modulators" (2003) Exp. Biol. Med. 228:1018-1022).

Macular degeneration (AMD) is the loss of photoreceptors in the portion of the central retina, termed the macula, responsible for high-acuity vision. Degeneration of the macula is associated with abnormal deposition of extracellular matrix components and other debris in the membrane between the retinal pigment epithelium and the vascular choroid. This debris-like material is termed drusen. Drusen is observed with a funduscopic eye examination. Normal eyes may have maculas free of drusen, yet drusen may be abundant in the retinal periphery. The presence of soft drusen in the macula, in the absence of any loss of macular vision, is considered an early stage of AMD.

Choroidal neovascularization (CNV) commonly occurs in macular degeneration in addition to other ocular disorders and is associated with proliferation of choroidal endothelial cells, overproduction of extracellular matrix, and formation of a fibrovascular subretinal membrane. Retinal pigment epithelium cell proliferation and production of angiogenic factors appears to effect choroidal neovascularization.

Diabetic retinopathy (DR) is an ocular disorder that develops in diabetes due to thickening of capillary basement membranes and lack of contact between pericytes and endothelial cells of the capillaries. Loss of pericytes increases leakage of the capillaries and leads to breakdown of the blood-retina barrier.

Proliferative vitreoretinopathy is associated with cellular proliferation of cellular and fibrotic membranes within the vitreous membranes and on the surfaces of the retina. Retinal pigment epithelium cell proliferation and migration is common with this ocular disorder. The membranes associated with proliferative vitreoretinopathy contain extracellular matrix components such as collagen types I, II, and IV and fibronectin, and become progressively fibrotic.

Compositions of the embodiments described herein can be, as needed, administered in combination with one or more standard therapeutic treatments known in the art. For example, for treatment of diabetic nephropathy, compounds of the present invention can be administered in combination with, for example, ACE inhibitors, angiotensin II receptor blockers (ARBS) or any other conventional therapy such as, for example, glucose management.

Obesity and Eating Disorders

Further provided herein are compositions and methods that can be used for weight loss or to prevent or treat obesity. Central obesity, characterized by its high waist to hip ratio, is an important risk for metabolic syndrome. Metabolic syndrome, as described above, is a combination of medical disorders which often includes diabetes mellitus type 2, high blood pressure, high blood cholesterol, and triglyceride concentrations (Grundy S M (2004), J. Clin. Endocrinol. Metab. 89(6): 2595-600). Obesity and other eating disorders are described in, e.g., U.S. Pat. App. Pub. No. 2009/0062193, "Compositions and Methods for the Control, Prevention and Treatment of Obesity and Eating Disorders."

"Overweight" and "obesity" are both labels for ranges of weight that are greater than what is generally considered healthy for a given height. The terms also identify ranges of weight that have been shown to increase the likelihood of certain diseases and other health problems. An adult who has a BMI of between 25 and 25.9 is generally considered overweight. An adult who has a BMI of 30 or higher is generally considered obese. However, anyone who needs or wishes to reduce body weight or prevent body weight gain can be considered to be overweight or obese. Morbid obesity typically refers to a state in which the BMI is 40 or greater. In embodiments of the methods described herein, subjects have a BMI of less than about 40. In embodiments of the methods described herein, subjects have a BMI of less than about 35. In embodiments of the methods described herein, subjects have a BMI of less than about 35 but greater than about 30. In other embodiments, subjects have a BMI of less than about 30 but greater than about 27. In other embodiments, subjects have a BMI of less than about 27 but greater than about 25. In embodiments, the subject may be suffering from or be susceptible to a condition associated with eating such as binge eating or food cravings.

Conditions, disorders or diseases relating to mental health, such as sadness, stress, grief, anxiety, anxiety disorder (e.g., generalized anxiety disorder, obsessive-compulsive disorder, panic disorder, post-traumatic stress disorder or social anxiety disorder or a mood disorder (e.g., depression, bipolar disorder, dysthymic disorder and cyclothymic disorder), may be diagnosed by mental health professionals. Similarly, measures of feelings of happiness, well-being or contentment may be made by mental health professionals.

A "subject" may include any mammal, including humans. A "subject" may also include other mammals kept as pets or livestock (e.g., dogs, cats, horses, cows, sheep, pigs, goats). Subjects who may benefit from the methods provided herein may be overweight or obese; however, they may also be lean. Subjects who may benefit from the methods provided herein may be desirous of losing weight or may have an eating disorder, such as binge eating, or an eating condition, such as food cravings. Subjects who may benefit from the methods provided herein may be desirous of modifying food preferences. They may have a metabolic disorder or condition in addition to these conditions. Exemplary metabolic disorders include diabetes, metabolic syndrome, insulin-resistance, and dyslipidemia. Subjects can be of any age. Accordingly, these disorders can be found in young adults and adults (e.g., those aged 65 or under) as well as infants, children, adolescents, and the elderly (e.g., those over the age of 65).

By "metabolic rate" is meant the amount of energy liberated/expended per unit of time. Metabolism per unit time can be estimated by food consumption, energy released as heat, or oxygen used in metabolic processes. It is generally desirable to have a higher metabolic rate when one wants to lose weight. For example, a person with a high metabolic rate may be able to expend more energy (and burn more calories) to perform an activity than a person with a low metabolic rate for that activity.

As used herein, "lean mass" or "lean body mass" refers to muscle and bone. Lean body mass does not necessarily indicate fat free mass. Lean body mass contains a small percentage of fat (roughly 3%) within the central nervous system (brain and spinal cord), marrow of bones, and internal organs. Lean body mass is measured in terms of density. Methods of measuring fat mass and lean mass include, but are not limited to, underwater weighing, air displacement plethysmograph, x-ray, dual-energy x-ray absorptiometry (DEXA) scans, MRIs and CT scans. In one embodiment, fat mass and lean mass is measured using underwater weighing.

By "fat distribution" is meant the location of fat deposits in the body. Such locations of fat deposition include subcutaneous, visceral and ectopic fat depots.

By "subcutaneous fat" is meant the deposit of lipids just below the skin's surface. The amount of subcutaneous fat in a subject can be measured using any method available for the measurement of subcutaneous fat. Methods of measuring subcutaneous fat are known in the art, for example, those described in U.S. Pat. No. 6,530,886.

By "visceral fat" is meant the deposit of fat as intra-abdominal adipose tissue. Visceral fat surrounds vital organs and can be metabolized by the liver to produce blood cholesterol. Visceral fat has been associated with increased risks of conditions such as polycystic ovary syndrome, metabolic syndrome and cardiovascular diseases.

By "ectopic fat storage" is meant lipid deposits within and around tissues and organs that constitute the lean body mass (e.g., skeletal muscle, heart, liver, pancreas, kidneys, blood vessels). Generally, ectopic fat storage is an accumulation of lipids outside classical adipose tissue depots in the body.

Fat mass can be expressed as a percentage of the total body mass. In some aspects, the fat mass is reduced by at least 1%, at least 5%, at least 10%, at least 15%, at least 20%, or at least 25% over the course of a treatment. In one aspect, the subject's lean mass is not decreased over the course of a treatment.

In another aspect, the subject's lean mass is maintained or increased over the course of a treatment. In another aspect, the subject is on a reduced calorie diet or restricted diet. By "reduced calorie diet" is meant that the subject is ingesting fewer calories per day than compared to the same subject's normal diet. In one instance, the subject is consuming at least 50 fewer calories per day. In other instances, the subject is consuming at least 100, 150 200, 250, 300, 400, 500, 600, 700, 800, 900, 1000 fewer calories per day. In some embodiments, the method involves the metabolism of visceral fat or ectopic fat or both at a rate of at least about 5%, 10%, 15%, 20%, 25%, 30%, 40%, or 50%, greater than for subcutaneous fat. In one aspect, the methods result in a favorable fat distribution. In one embodiment, favorable fat distribution is an increased ratio of subcutaneous fat to visceral fat, ectopic fat, or both. In one aspect, the method involves an increase in lean body mass, for example, as a result of an increase in muscle cell mass. In one embodiment, the amount of subcutaneous fat is reduced in a subject by at least about 5%. In certain embodiments, the amount of subcutaneous fat is reduced by at least about 10%, 15%, 20%, 25%, 30% 40%, or 50% compared to the subject prior to administration of a biguanide or related heterocyclic compound composition.

The methods described herein can be used to reduce the amount of visceral fat in a subject. In one instance, the visceral fat is reduced in a subject by at least about 5%. In other instances, the visceral fat is reduced in a subject by at least about 10%, 15%, 20%, 25%, 30% 40%, or 50% compared to the subject prior to administration of a biguanide or related heterocyclic compound composition. Visceral fat can be measured through any means available to determine the amount of visceral fat in a subject. Such methods include, for example, abdominal tomography by means of CT scanning and MRI. Other methods for determining visceral fat are described, for example, in U.S. Pat. Nos. 6,864,415, 6,850,797, and 6,487,445.

In one embodiment, a method for preventing the accumulation of ectopic fat or reducing the amount of ectopic fat in a subject is provided, wherein the method comprises administering, to a subject in need thereof, a biguanide or related heterocyclic compound composition effective to prevent accumulation of ectopic fat or to reduce the amount of ectopic fat in the subject. It is understood that a treatment can be a series of individual doses, or a treatment regimen, provided to the subject over a period of time. In one instance, the amount of ectopic fat is reduced in a subject by at least about 5% compared to the untreated subject. In other instances, the amount of ectopic fat is reduced by at least about 10%, 15%, 20%, 25%, 30% 40%, or 50%. Alternatively, the amount of ectopic fat is proportionally reduced 5%, 10%, 15%, 20%, 25%, 30%, 40%, 50%, 60%, 70%, 80%, 90%, or 100% in comparison to subcutaneous fat in a subject. Ectopic fat can be measured in a subject using any method available for measuring ectopic fat.

In another embodiment, methods for altering anthropometric parameters, e.g., waist circumference, hip circumference, and waist-to-hip ratio are provided. Waist circumference is a measure of abdominal obesity. In one embodiment, methods for reducing waist circumference of a subject are provided, wherein the method comprises administering, to a subject in need thereof, a biguanide or related heterocyclic compound composition in an amount effective to reduce the waist circumference of the subject. In one embodiment, the waist circumference of the subject is reduced by at least about 1%. In certain embodiments, the waist circumference of the subject is reduced by at least about 2%, 3%, 4%, 5%, 6%, 7%, 8%. 9% or 10% compared to the subject prior to administration of a biguanide or related heterocyclic compound composition provided herein. In one embodiment, the waist circumference of the subject is reduced by at least about 1 cm. In other embodiments, the waist circumference of the subject is reduced by at least about 2 cm, 3 cm, 4 cm, 5 cm, or 6 cm compared to the subject prior to administration of a biguanide or related heterocyclic compound composition.

In another embodiment, methods for reducing hip circumference of a subject are provided, wherein the method comprises administering, to a subject in need thereof, a biguanide or related heterocyclic compound composition provided herein in an amount effective to reduce the hip circumference of the subject. In one embodiment, the hip circumference of the subject is reduced by at least about 1%. In certain embodiments, the waist circumference of the subject is reduced by at least about 2%, 3%, 4%, 5%, or 6% compared to the subject prior to administration of a biguanide or related heterocyclic compound composition. In one embodiment, the waist circumference of the subject is reduced by at least about 1 cm. In certain embodiments, the waist circumference of the subject is reduced by at least about 2 cm, 3 cm, 4 cm, 5 cm, or 6 cm compared to the subject prior to administration of a biguanide or related heterocyclic compound composition.

Also provided are methods to reduce weight in a morbidly obese subject by first reducing the subject's weight to a level below that of being morbidly obese, then administering an effective amount of a biguanide or related heterocyclic compound composition to further reduce the subject's weight. Methods for reducing a subject's weight to being below that of morbid obesity include reducing caloric intake, increasing physical activity, drug therapy, bariatric surgery, such as gastric bypass surgery, or any combinations of the preceding methods. In one aspect, administering the treatment results in reduced caloric intake, which further reduces the weight of the subject. In another embodiment, methods are provided for reducing the body mass index (BMI) in a subject having a BMI of 40 or less by administering a biguanide or related heterocyclic compound composition in an amount and regimen effective to further reduce the subject's weight. In another embodiment, methods are provided for reducing the body mass index (BMI) in a subject having a BMI of 35 or less by administering a biguanide or related heterocyclic compound composition in an amount and regimen effective to further reduce the subject's weight.

In embodiments, methods for reducing the risk of developing metabolic disorders are provided, where the method comprises administering to the subject a biguanide or related heterocyclic compound composition in an amount effective to reduce the weight or control the blood glucose of a subject. Also provided herein, are methods for maintaining a healthy or normal weight and/or glucose concentrations, where the method comprises administering to the subject a biguanide or related heterocyclic compound composition in an amount effective maintaining a healthy or normal weight and/or glucose concentrations.

In another embodiment, methods for controlling or modifying eating behaviors are provided, wherein the methods comprise administering, to a subject in need thereof, a biguanide or related heterocyclic compound composition effective to control or modify an eating behavior by the subject. In one embodiment, methods for controlling binge eating are provided, where the methods comprise administering, to a subject in need thereof, a biguanide or related heterocyclic compound composition in an amount effect to control or curb binge eating by the subject. In one embodiment, a biguanide or related heterocyclic compound composition is administered at times of the day when the subject is most likely to binge eat. In one aspect, binge eating is characterized by 1) eating, in a discrete period of time (e.g., within any 2-hour period), an amount of food that is definitely larger than most people would eat during a similar period of time and under similar circumstances and 2) a sense of lack of control over eating during the episode (e.g., a feeling that one cannot stop eating or control what or how much one is eating). The reduction of binge eating includes a reduction in the frequency of binge eating episodes, the duration of binge eating episodes, the total amount consumed during a binge eating episode, difficulty in resisting the onset of a binge eating episode, and any combination thereof, as compared to as compared to such frequency, duration, amount and resistance in the absence of the biguanide or related heterocyclic compound composition. For example, in one embodiment, a method may comprise a reduction in the frequency of binge eating episodes. In another embodiment, a method may comprise a reduction in the duration of binge eating episodes. In yet another embodiment, a method may comprise a reduction in the total amount consumed during a binge-eating episode. In yet another embodiment, a method may comprise a reduction in difficulty resisting the onset of a binge-eating episode.

Some of the signs of binge eating include eating large amounts of food when not physically hungry, rapid eating, hiding of food because the person feels embarrassed about how much he or she is eating, eating until uncomfortably full, or any combination thereof. Many binge eaters are emotional eaters, i.e. their binge eating is triggered by their emotional state (e.g., some binge eaters eat when they are sad, some eat when they are happy, and some eat when they are under stress). A large number of binge eaters suffer from anxiety disorders, such as obsessive-compulsive disorder; impulse control problems; or personality disorders, such as borderline personality disorder or depression. In one embodiment, the binge eating is in response to stressed conditions. Other binge eaters are substance abusers, such as drug abusers or alcohol abusers. Not everyone who has a binge eating disorder is overweight, such as those binge eaters diagnosed with bulimia.

Subjects who binge eat often do so at particular times of the day, and thus treatment should be adjusted according to when the subject is most likely to binge eat. For example, if the subject binge eats mostly after 7 p.m. at night, the subject should be administered a biguanide or related heterocyclic compound composition at or shortly before 7 p.m. In one embodiment, the subject is administered a biguanide or related heterocyclic compound composition at the time they are susceptible to binge eating. In certain embodiments, the subject is administered a biguanide or related heterocyclic compound composition at least about 5 minutes, at least about 15 minutes, at least about 30 minutes, at least about 45 minutes, at least about 1 hour, at least about 1 hour and 30 minutes, or at least about 2 hours before they are susceptible to binge eating. An effective amount of a biguanide or related heterocyclic compound composition in this embodiment is an amount effective to curb or control the subject's desire to binge eat. Therefore, the effective amount of a biguanide or related heterocyclic compound composition will change dependent upon the subject and the level of their desire to binge eat. Furthermore, if a subject's desire to binge eat is less at one point in the day than at another, the dosage can be adjusted accordingly to provide a lower dose at the times of the day the subject has a lower desire to binge eat, and to provide a higher dose at the times of the day the subject has a higher desire to binge eat. In one embodiment, the subject is administered a peak dosage of a biguanide or related heterocyclic compound composition at the time they have a high desire to binge eat. In certain embodiments, the subject is administered a peak dosage of a biguanide or related heterocyclic compound composition at least about 5 minutes, at least about 15 minutes, at least about 30 minutes, at least about 45 minutes, at least about 1 hour, at least about 1 hour and 30 minutes, or at least about 2 hours before they have a high desire to binge eat.

In another embodiment, methods for modifying food preferences in a subject are provided, wherein methods comprise administering, to a subject in need thereof, a biguanide or related heterocyclic compound composition in an amount effective to modify food preferences in the subject. The chemosensory receptor targeted by a composition can influence the subject's desire to eat the corresponding food.

The modifications in food preferences may include a decrease in a preference for such foods, a decrease in the amount of intake of such foods, an enhancement of a preference of one food type over another food type, changes in frequency of cravings for such foods, duration of cravings for such foods, intensity of cravings for such foods, difficulty in resisting cravings for such foods, frequency of eating in response to cravings for such foods, and any combination thereof, as compared to such frequency, duration, intensity, or resistance in the absence of treatment. In yet another embodiment, a method may comprise reducing a subject's preference for sweet foods, savory foods, high fat foods, salty foods, sour foods, and any combination thereof.

In one embodiment, a method may comprise reducing a subject's frequency of cravings for sweet foods, savory foods, high fat foods, salty foods, sour foods, and any combination thereof. In another embodiment, a method may comprise reducing a subject's duration of cravings for sweet foods savory foods, high fat foods, salty foods, sour foods, and any combination thereof, etc. In yet another embodiment, a method may comprise reducing a subject's intensity of cravings for sweet foods, savory foods, high fat foods, salty foods, sour foods, and any combination thereof. In yet another embodiment, a method may comprise reducing a subject's difficulty in resisting cravings for sweet foods, savory foods, high fat foods, salty foods, sour foods, and any combination thereof. In yet another embodiment, a method may comprise reducing a subject's frequency of eating in response to cravings for sweet foods, savory foods, high fat foods, salty foods, sour foods, and any combination thereof. In yet another embodiment, a method may comprise reducing a subject's intake of sweet foods, savory foods, high fat foods, salty foods, sour foods, and any combination thereof.

Treatment of Bowel Damage

The compositions and methods provided herein can be used for the treatment of short bowel syndrome and compromised intestinal function (e.g., small bowel resection, colitis, enteritis, inflammatory bowel syndrome, ischemic bowel, and chemotherapeutic injury to the intestine). Short bowel syndrome refers to the collection of symptoms caused by intestinal resection. Its symptoms include intractable diarrhea, dehydration, malabsorption of macronutrients, weight loss, malabsorption of vitamins and trace elements and malnutrition. GLP-2 is known to slow gastric emptying, increase intestinal transit time and inhibit sham feeding-induced gastric acid secretion. Patients with jejunostomy often have impaired meal-stimulated GLP-2 responses, and thus impaired absorption. Administration of GLP-2 in patients with jejunostomy has been shown to improve intestinal absorption of energy and intestinal wet weight absorption as well as prolong gastric emptying of solids and liquids. See Jeppesen, P. B., 2003, "Clinical significance of GLP-2 in short-bowel syndrome," Journal of Nutrition 133 (11): 3721-4. GLP-2 is also reported to stimulate intestinal growth in addition to inhibiting gastric secretion and gastric motility. Burrin et al., 2001, "Glucagon-like peptide 2: a nutrient-responsive gut growth factor," Journal of Nutrition 131 (3): 709. Modulation of GLP-2 secretion through the administration of the compositions described herein can provide for the treatment of short bowel syndrome and compromised intestinal function, including but not limited to, small bowel resection, colitis, enteritis, inflammatory bowel syndrome, ischemic bowel, and chemotherapeutic injury to the intestine.

Delivery to Specific Intestinal Locations

The density of L-cells increases along the length of the intestine with the lowest density at the level of the duodenum and greatest in the rectum. There is an approximately 80-fold increase in L-cell density from the duodenum to rectum as assessed by peptide YY content. See Adrian et al., Gastroenterology 1985; 89:1070-77. Given that nutrients or bile salts would not be expected to reach the colon much less the rectum, the mechanism of these L-cells in the regulation of metabolism is not completely clear. While speculative, it is possible that products produced by the colonic flora could inform the gut of the microbial mass and composition via L-cell sensors and in turn this information could be relayed to the CNS via hormonal and neural signals emanating from the colonic and rectal area which is innervated quite differently than the small intestine. Regardless of the role of neuroendocrine cells in the colon and rectum, the basis of this invention is to stimulate these cells wherever they may be (for example, different individuals, and patients with diabetes, might be expected to have different distributions and numbers of these cells) via the presentation of one or more stimuli of taste and/or nutrient receptors and other stimulants for the purpose of treating metabolic disorders.

The upper intestine has different EECs than the lower intestine. For example, CCK and GIP are released from the upper and not typically from the lower intestine, corresponding to I- and K-cells predominantly being located in the upper gut. Conversely, L-cells are located predominantly in the lower intestine. Hormonal release patterns are not only chemosensory receptor ligand- and combination-specific but also site-specific in the intestine.

In embodiments, it is contemplated that sensing and/or metabolism of nutrients in the upper intestine amplifies certain responses from the lower intestine. Moreover, L-cells located in the upper intestine can behave differently than those in the lower region providing another level control for targeting biguanide or related heterocyclic compounds. For example, in embodiments, certain biguanide or related heterocyclic compound combinations or biguanide and chemosensory receptor ligand combinations delivered to the upper intestine may be more favorable to a hormonal release pattern for the treatment of one disorder, e.g., diabetes, whereas that same combination delivered to the lower intestine may be more appropriate for a different disorder, e.g., obesity. It is also contemplated that the same combination can produce a more favorable hormonal profile when presented to both the upper and lower intestine.

Thus, the embodiments described herein provide a treatment method comprising a combination of biguanide or related heterocyclic compounds that is engineered to deliver certain of the biguanide or related heterocyclic compounds to one or more locations of the intestine, for example, to optimize hormonal patterns achieved.

In some of the embodiments provided herein, the biguanide or related heterocyclic compounds are delivered to one or more regions of the intestine. In some of the embodiments provided herein, the biguanide or related heterocyclic compounds are delivered to one or more regions downstream or distal of the stomach. In certain embodiments, the biguanide or related heterocyclic compounds are delivered to one or more regions of the upper intestine. In certain embodiments, the biguanide or related heterocyclic compounds are delivered to the duodenum, jejunum, ileum, or a combination thereof. In certain embodiments, the biguanide or related heterocyclic compounds are delivered to one or more regions of the lower intestine. In certain embodiments, the biguanide or related heterocyclic compounds are delivered to the caecum, colon, rectum, or a combination thereof. In yet other embodiments, the biguanide or related heterocyclic compounds are delivered downstream or distal of the duodenum. In additional embodiments, the biguanide or related heterocyclic compounds are delivered downstream or distal of the jejunum.

In yet other embodiments, biguanide or related heterocyclic compounds are delivered to one or more regions of the upper intestine and one or more regions of the lower intestine. For example, biguanide or related heterocyclic compounds can be delivered to the duodenum and the colon. In another non-limiting example, biguanide or related heterocyclic compounds can be delivered to the duodenum, jejunum, ileum and colon. More embodiments are described under Formulations.

Administration of biguanide or related heterocyclic compounds to certain regions or locations of the intestine is achieved by any known method. In certain embodiments, enteral administration of biguanide or related heterocyclic compounds is performed, e.g., in rodents or man. Intubation/cannulation is performed in lightly anaesthetized patients with silastic tubing. Tubing is placed in the post-pyloric region and in the rectum and advanced as deeply as possible. These locations are explored separately and together as foods sensed in the upper intestine can provide signals to the lower intestine and vice versa. In certain embodiments, biguanide or related heterocyclic compounds are formulated in a modified release composition for oral delivery that delivers the biguanide or related heterocyclic compounds to targeted regions or locations of the intestine. In yet other embodiments, biguanide or related heterocyclic compounds are formulated for rectal delivery as a suppository, douche, wash, or the like for delivery to targeted regions or locations of the intestinal tract, e.g., rectum or colon.

When delivery of biguanide or related heterocyclic compounds is to two or more regions of the gastrointestinal tract, the compounds delivered may be in any proportion and manner. In some embodiments, certain biguanide or related heterocyclic compounds are be targeted and delivered to specific regions, such as for example, one compound to the ileum and another compound to the colon or, in another example, compound(s) to the stomach, different compound(s) to the duodenum and other compound(s) to the colon. In certain embodiments, biguanide or related heterocyclic compounds are delivered in certain proportions in each region of the gut.

Administration
Combination Therapies

The compositions of the embodiments described herein may be co-administered with known therapies for the treatment of any of the conditions described herein. Co-administration can also provide for additive or synergistic effects, resulting in the need for lower dosages of a known therapy, the compositions described herein, or both. Additional benefits of co-administration include the reduction in toxicities associated with any of the known therapies.

Co-administration includes simultaneous administration in separate compositions, administration at different times in separate compositions, or administration in a composition in which both agents are present. Thus, in some embodiments, compositions described herein and a known therapy are administered in a single treatment. In some embodiments, the compositions described herein and a known therapy are admixed in a resulting composition. In some embodiments, compositions described herein and the known therapy are administered in separate compositions or administrations.

Administration of compositions described herein and known therapies described herein may be by any suitable means. Administration of a composition described herein and a second compound (e.g., diabetes drug or obesity drug) may be by any suitable means. If the compositions described herein and a second compound are administered as separate compositions, they may be administered by the same route or by different routes. If the compositions described herein and a second compound are administered in a single composition, they may be administered by any suitable route such as, for example, oral administration. In certain embodiments, compositions of biguanide or related heterocyclic compound and second compounds can be administered to the same region or different regions of the gastrointestinal tract. For example, biguanide or related heterocyclic compounds can be administered in combination with an anti-diabetic drug to be delivered to the duodenum, jejunum, ileum, or colon.

Therapies, drugs and compounds useful for the treatment of diabetes, metabolic syndrome (including glucose intolerance, insulin resistance, and dyslipidemia), and/or diseases or conditions associated therewith may be administered with the biguanide or related heterocyclic compounds. Diabetic therapies drugs and compounds include, but are not limited to, those that decrease triglyceride concentrations, decrease glucose concentrations, and/or modulate insulin (e.g. stimulate insulin production, mimic insulin, enhance glucose-dependent insulin secretion, suppress glucagon secretion or action, improve insulin action or insulin sensitizers, or are exogenous forms of insulin).

Drugs that decrease triglyceride level include but are not limited to ascorbic acid, asparaginase, clofibrate, colestipol, fenofibrate mevastatin, pravastatin, simvastatin, fluvastatin, or omega-3 fatty acid. Drugs that decrease LDL cholesterol level include but are not limited to clofibrate, gemfibrozil, and fenofibrate, nicotinic acid, mevinolin, mevastatin, pravastatin, simvastatin, fluvastatin, lovastatin, cholestyrine, colestipol or probucol.

In another aspect, compositions of the embodiments described herein may be administered in combination with glucose-lowering compounds.

The medication classes of thiazolidinediones (also called glitazones), sulfonylureas, meglitinides, biguanides, alpha-glucosidase inhibitors, DPP-IV inhibitors, and incretin mimetics have been used as adjunctive therapies for hyperglycemia and diabetes mellitus (type 2) and related diseases.

Drugs that decrease glucose level include but are not limited to glipizides, glyburides, exenatide (Byetta®), incretins, sitagliptin (Januvia®), pioglitizone, glimepiride, rosiglitazone, metformin, vildagliptin, saxagliptin (Onglyza™), sulfonylureas, meglitinide (e.g., Prandin®) glucosidase inhibitor, biguanides (e.g., Glucophage®), repaglinide, acarbose, troglitazone, nateglinide, natural, synthetic or recombinant insulin and derivatives thereof, and amylin and amylin derivatives.

When administered sequentially, the combination may be administered in two or more administrations. In an alternative embodiment, it is possible to administer one or more biguanide or related heterocyclic compounds and one or more additional active ingredients by different routes. The skilled artisan will also recognize that a variety of active ingredients may be administered in combination with one or more biguanide or related heterocyclic compounds that may act to augment or synergistically enhance the control prevention, amelioration, attenuation, or treatment of obesity or eating disorders or conditions.

According to the methods provided herein, when co-administered with at least one other obesity reducing (or anti-obesity) or weight reducing drug, a biguanide or related heterocyclic compound(s) may be: (1) co-formulated and administered or delivered simultaneously in a combined formulation; (2) delivered by alternation or in parallel as separate formulations; or (3) by any other combination therapy regimen known in the art. When delivered in alternation therapy, the methods provided may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

In certain embodiments, compositions provided herein may be used with other commercially available diet aids or other anti-obesity agents, such as, by way of example, PYY and PYY agonists, GLP-1 and GLP-1 agonists, a DPP-IV inhibitor, CCK and CCK agonists, exendin and exendin agonists, GIP and GIP agonists, amylin and amylin agonists, ghrelin modulators (e.g., inhibitors such as but not limited to Cortistatin-8, AEZ-123 (JMV2959) under development by AEterna Zentaris Inc., [D-Arg(1),D-Phe(5),D-Trp(7,9),Leu(11)]-substance P, D-Lys3-GHRP-6, YIL-781 and YIL870 under development by Bayer (see, e.g., Esler et al. (2007) *Endocrinology* 148:5175-85), and EX-1350 under development by Elixer Pharmaceuticals) and leptin and leptin agonists. In certain instances, biguanide or related heterocyclic compound compositions provided herein are used in combination with amylin, arylin agonists or mimetics. Exemplary amylin agonists or mimetics include pramlintide and related compounds. In certain instances, biguanide or related heterocyclic compound compositions provided herein are used in combination with leptin, leptin agonists or mimetics. Additional leptin agonists or mimetics can be identified using the methods described by U.S. Pat. No. 7,247,427 which is incorporated by reference herein. In further instances, biguanide or related heterocyclic compound compositions provided herein increase leptin sensitivity and increase effectiveness of leptin, leptin agonists or mimetics.

Additional anti-obesity agents for use in the methods provided that are in current development are also of interest in the methods of the present invention. Other anti-obesity agents include alone or any combination of phentermine, fenfluramine, sibutramine, rimonabant, topiramate, zonisamide bupropion, naltrexone, lorcaserin, and orlistat. Therapies, drugs and compounds useful for the treatment of weight loss, binge eating, food addictions and cravings may be administered with the compositions described herein. For example, the subject may further be administered at least one other drug which is known to suppress hunger or control appetite. Such therapies drugs and compounds include but are not limited to phenteramines such as Meridia® and Xenical®. Additional therapies, drugs and compounds are known in the art and contemplated herein.

As such, in one aspect, the biguanide or related heterocyclic compounds may be used as part of a combination therapy for the control, prevention or treatment of obesity or eating disorders or conditions. Compounds used as part of a combination therapy to treat obesity or reduce weight include, but are not limited to, central nervous system agents that affect neurotransmitters or neural ion channels, including antidepressants (bupropion), noradrenalin reuptake inhibitors (GW320659), selective serotonin 2c receptor agonists, selective 5HT 2c receptor agonists, antiseizure agents (topiramate, zonisamide), some dopamine antagonists, and cannabinoid-1 receptor antagonists (CB-1 receptor antagonists) (rimonabant); leptin/insulin/central nervous system pathway agents, including leptin analogues, leptin transport and/or leptin receptor promoters, ciliary neurotrophic factor (Axokine), neuropeptide Y and agouti-related peptide antagonists, pro-opiomelanocortin and cocaine and amphetamine regulated transcript promoters, .alpha.-melanocyte-stimulating hormone analogues, melanocoritin-4 receptor agonists, and agents that affect insulin metabolism/activity, which include protein-tyrosine phosphatase-1B inhibitors, peroxisome proliferator activated receptor-.gamma. receptor antagonists, short-acting bromocriptine (ergoset), somatostatin agonists (octreotide), and adiponectin/Acrp30 (Famoxin or Fatty Acid Metabolic Oxidation Inducer); gastrointestinal-neural pathway agents, including those that increase cholecystokinin activity (CCK), PYY activity, NPY activity, and PP activity, increase glucagon-like peptide-1 activity (exendin 4, liraglutide, dipeptidyl peptidase IV inhibitors), and those that decrease ghrelin activity, as well as amylin analogues (pramlintide); agents that may increase resting metabolic rate (selective β-3 stimulators/agonist, uncoupling protein homologues, and thyroid receptor agonists); other more diverse agents, including melanin concentrating hormone antagonists, phytostanol analogues, functional oils, P57, amylase inhibitors, growth hormone fragments, synthetic analogues of dehydroepiandrosterone sulfate, antagonists of adipocyte 11B-hydroxysteroid dehydrogenase type 1 activity, corticotropin-releasing hormone agonists, inhibitors of fatty acid synthesis (cerulenin and C75), carboxypeptidase inhibitors, indanone/indanols, aminosterols (trodusquemine/trodulamine), and other gastrointestinal lipase inhibitors (ATL962); amphetamines, such as dextroamphetamine; other sympathomimetic adrenergic agents, including phentermine, benzphetamine, phendimetrazine, mazindol, and diethylpropion.

Other compounds include ecopipam; oxyntomodulin (OM); inhibitors of glucose-dependent insulinotropic polypeptide (GIP); gastrin-releasing peptide; neuromedin B; enterostatin; amfebutamone, SR-58611; CP-045598; AOD-0604; QC-BT16; rGLP-1; 1426 (HMR-1426); N-5984; ISIS-113715; solabegron; SR-147778; Org-34517; melanotan-II; cetilistat; c-2735; c-5093; c-2624; APD-356; radafaxine; fluasterone; GP-389255; 856464; S-2367; AVE-1625; T-71; oleoyl-estrone; peptide YY [3-36] intranasal; androgen receptor agonists; PYY 3-36; DOV-102677; tagatose; SLV-319; 1954 (Aventis Pharma AG); oxyntomodulin, Thiakis; bromocriptine, PLIVA; diabetes/hyperlipidemia therapy, Yissum; CKD-502; thyroid receptor beta agonists; beta-3 adrenoceptor agonist; CDK-A agonists; galanin antagonist; dopamine D1/D2 agonists; melanocortin modulators; verongamine; neuropeptide Y antagonists; melanin-concentrating hormone receptor antagonists; dual PPAR alpha/gamma agonists; CGEN-P-4; kinase inhibitors; human MCH receptor antagonists; GHS-R antagonists; ghrelin receptor agonists; DG70 inhibitors; cotinine; CRF-BP inhibitors; urocortin agonists; UCL-2000; impentamine; .beta.-3 adrenergic receptor; pentapeptide MC4 agonists; trodusquemine; GT-2016; C-75; CPOP; MCH-1 receptor antagonists; RED-103004; aminosterols; orexin-1 antagonists; neuropeptide Y5 receptor antagonists; DRF-4158; PT-15; PTPase inhibitors; A37215; SA-0204; glycolipid metabolites; MC-4 agonist; produlestan; PTP-1B inhibitors; GT-2394; neuropeptide Y5 antagonists; melanocortin receptor modulators; MLN-4760; PPAR gamma/delta dual agonists; NPY5RA-972; 5-HT2C receptor agonist; neuropeptide Y5 receptor antagonists (phenyl urea analogs); AGRP/MC4 antagonists; neuropeptide Y5 antagonists (benzimidazole); glucocorticoid antagonists; MCHR1 antagonists; Acetyl-CoA carboxylase inhibitors; R-1496; HOB1 modulators; NOX-B 11; peptide YY 3-36 (eligen); 5-HT 1 modulators; pancreatic lipase inhibitors; GRC-1087; CB-1 antagonists; MCH-1 antagonists; LY-448100; bombesin BRS3 agonists; ghrelin antagonists; MC4 antagonists; stearoyl-CoA desaturase modulators; H3 histamine antagonists; PPARpan agonists; EP-01492; hormone-sensitive lipase inhibitors; fatty acid-binding protein 4 inhibitors; thiolactone derivatives; protein tyrosine phosphatase 1B inhibitors; MCH-1 antagonist; P-64; PPAR gamma ligands; melanin concentrating hormone antagonists; thiazole gastroprokinetics; PA-452; T-226296; A-331440; immunodrug vaccines; diabetes/obesity therapeutics (Bioagency, Biofrontera Discovery GmbH); P-7 (Genfit); DT-011 M; PTP1B inhibitor; anti-diabetic peptide conjugates; KATP agonists; obesity therapeutics (Lexicon); 5-HT2 agonists; MCH-1 receptor antagonists; GMAD-1/GMAD-2; STG-a-MD; neuropeptide Y antagonist; angiogenesis inhibitors; G protein-coupled receptor agonists; nicotinic therapeutics (ChemGenex); anti-obesity agents (Abbott); neuropeptide Y modulators; melanin concentrating hormone; GW-594884A; MC-4R agonist; histamine H3 antagonists; orphan GPCR modulators; MITO-3108; NLC-002; HE-2300; IGF/IBP-2-13; 5-HT2C agonists; ML-22952; neuropeptide Y receptor antagonists; AZ-40140; anti-obesity therapy (Nisshin Flour); GNTI; melanocortin receptor modulators; alpha-amylase inhibitors; neuropeptide Y1 antagonist; beta-3 adrenoceptor agonists; ob gene products (Eli Lilly & Co.); SWR-0342-SA; beta-3 adrenoceptor agonist; SWR-0335; SP-18904; oral insulin mimetics; beta 3 adrenoceptor agonists; NPY-1 antagonists; .beta.-3 agonists; obesity therapeutics (7TM Pharma); 11 beta-hydroxysteroid dehydrogenase (HSD)1 inhibitors; QRX-431; E-6776; RI-450; melanocortin-4 antagonists; melanocortin 4 receptor agonists; obesity therapeutics (CuraGen); leptin mimetics; A-74498; second-generation leptin; NBI-103; CL-314698; CP-114271; beta-3 adrenoceptor agonists; NMI-8739; UCL-1283; BMS-192548; CP-94253; PD-160170; nicotinic agonist; LG-100754; SB-226552; LY-355124; CKD-711; L-751250; PPAR inhibitors; G-protein therapeutics; obesity therapy (Amylin Pharmaceuticals Inc.); BW-1229; monoclonal antibody (ObeSys/CAT); L-742791; (S)-sibutramine; MBU-23; YM-268; BTS-78050; tubby-like protein genes; genomics (eating disorders; Allelix/Lilly); MS-706; GI-264879A; GW-409890; FR-79620 analogs; obesity therapy (Hybrigenics SA); ICI-198157; ESP-A; 5-HT2C agonists; PD-170292; AIT-202; LG-100641; GI-181771; anti-obesity therapeutics (Genzyme); leptin modulator; GHRH mimetics; obesity therapy (Yamanouchi Pharmaceutical Co. Ltd.); SB-251023; CP-331684; BIBO-3304; cholesten-3-ones; LY-362884; BRL-48962; NPY-1 antagonists; A-71378; ®-didesmethylsibutramine; amide derivatives; obesity therapeutics (Bristol-Myers Squibb Co.); obesity therapeutics (Ligand Pharmaceuticals Inc.); LY-226936; NPY antagonists; CCK-A agonists; FPL-14294; PD-145942; ZA-7114; CL-316243; SR-58878; R-1065; BIBP-3226; HP-228; talibegron; FR-165914; AZM-008; AZM-016; AZM-120; AZM-090; vomeropherin; BMS-187257; D-3800; AZM-131; gene discovery (Axys/Glaxo); BRL-26830A; SX-013; ERR modulators; adipsin; AC-253; A-71623; A-68552; BMS-210285; TAK-677; MPV-1743; obesity therapeutics (Modex); GI-248573; AZM-134; AZM-127; AZM-083; AZM-132; AZM-115; exopipam; SSR-125180; obesity therapeutics (Melacure Therapeutics AB); BRL-35135; SR-146131; P-57; AZM-140; CGP-71583A; RF-1051; BMS-196085; manifaxine; beta-3 agonists; DMNJ (Korea Research Institute of Bioscience and Biotechnology); BVT-5182; LY-255582; SNX-024; galanin antagonists; neurokinin-3 antagonists; dexfenfluramine; mazindol; diethylpropion; phendimetrazine; benzphetamine; amfebutmone; sertraline; metformin; AOD-9604; ATL-062; BVT-933; GT389-255; SLV319; HE-2500; PEG-axokine; L-796568; and ABT-239.

In some embodiments, compounds for use in combination with a biguanide or related heterocyclic compound composition provided herein include rimonabant, sibutramine, orlistat, PYY or an analog thereof, CB-1 antagonist, leptin, phentermine, and exendin analogs. Exemplary dosing ranges include phentermine resin (30 mg in the morning), fenfluramine hydrochloride (20 mg three times a day), and a combination of phentermine resin (15 mg in the morning) and fenfluramine hydrochloride (30 mg before the evening meal), and sibutramine (10-20 mg). Weintraub et al. (1984) Arch. Intern. Med. 144:1143-1148.

In further embodiments, compounds for use in combination with a biguanide or related heterocyclic compound composition provided herein include GPR119 agonists (e.g., anandamide; AR-231, 453; MBX-2982; Oleoylethanolamide; PSN-365,963; PSN-632,408; palmitoylethanolamide), GPR120 agonists (e.g., omega-3 fatty acids including, but not limited to, α-linolenic acid, docosapentaenoic acid, docosahexaenoic acid, eicosatrienoic acid, eicosatetraenoic acid, eicosapentaenoic acid, heneicosapentaenoic acid, hexadecatrienoic acid, stearidonic acid, tetracosahexaenoic acid and tetracosapentaenoic acid), and GPR 40 agonists (e.g., free fatty acids including short-, medium-, and long-chain saturated and unsaturated fatty acids).

In some embodiments, a biguanide or related heterocyclic compound composition provided herein is used as an adjunctive therapy to a bariatric surgical procedure. Bariatric surgery is a procedure for weight loss and relates to modifications with the gastrointestinal tract and includes such procedures as gastric banding, sleeve gastrectomy, GI bypass procedure (e.g., roux en Y, biliary duodenal bypass, loop gastric bypass), intragastric balloon, vertical banded, gastroplasty, endoluminal sleeve, biliopancreatic diversion, and the like. In certain instances, a biguanide or related heterocyclic compound composition is adjunctive to gastric banding. In certain instances, a biguanide or related heterocyclic compound composition is adjunctive to GI bypass procedures. In yet other instances, a biguanide or related heterocyclic compound composition is adjunctive to sleeve gastrectomy. In certain embodiments, a biguanide or related heterocyclic compound composition as an adjunctive therapy to bariatric surgery is administered prior to the bariatric procedure. In certain embodiments, a biguanide or related heterocyclic compound composition as an adjunctive therapy to bariatric surgery is administered after the bariatric procedure. In certain instances, when used as adjunctive therapy, the dosage and amounts of a biguanide or related heterocyclic compound composition may be adjusted as needed with respect to the bariatric procedure. For example, amounts of a biguanide or related heterocyclic compound composition administered as an adjunct therapy to a bariatric procedure may be reduced by one-half of normal dosages or as directed by a medical professional.

Combination therapy can be exploited, for example, in modulating metabolic syndrome (or treating metabolic syndrome and its related symptoms, complications and disorders), wherein biguanide or related heterocyclic compound compositions provided herein can be effectively used in combination with, for example, the active agents discussed above for modulating, preventing or treating diabetes, obesity, hyperlipidemia, atherosclerosis, and/or their respective related symptoms, complications and disorders.

Formulations

Formulations for the compositions provided herein include those suitable for oral or rectal administration, and administration although the most suitable route can depend upon for example the condition and disorder of the recipient. The formulations can conveniently be presented in unit dosage form and can be prepared by any of the methods well known in the art of pharmacy. All methods include the step of bringing into association the active ingredient with the carrier which constitutes one or more accessory ingredients.

Formulations suitable for oral administration can be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion.

Composition preparations which can be used orally include tablets, push-fit capsules made of gelatin, as well as soft, sealed capsules made of gelatin and a plasticizer, such as glycerol or sorbitol. Tablets can be made by compression or molding, optionally with one or more accessory ingredients. Compressed tablets can be prepared by compressing in a suitable machine the active ingredient in a free-flowing form such as a powder or granules, optionally mixed with binders (e.g., povidone, gelatin, hydroxypropylmethyl cellulose), inert diluents, preservative, disintegrant (e.g., sodium starch glycolate, cross-linked povidone, cross-linked sodium carboxymethyl cellulose) or lubricating, surface active or dispersing agents. Molded tablets can be made by molding in a suitable machine a mixture of the powdered compound moistened with an inert liquid diluent. The tablets can optionally be coated or scored and can be formulated so as to provide slow or controlled release of the active ingredient therein. Tablets can optionally be provided with an enteric coating, to provide release in parts of the gut other than the stomach. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or Dragee coatings for identification or to characterize different combinations of active compound doses.

For buccal or sublingual administration, the compositions can take the form of tablets, lozenges, pastilles, or gels formulated in conventional manner. Such compositions can comprise the active ingredient in a flavored basis such as sucrose and acacia or tragacanth. Such compositions can be formulated to delivery biguanide or related heterocyclic compounds to a desired area in the gastrointestinal system.

It should be understood that in addition to the ingredients particularly mentioned above, the compounds and compositions described herein can include other agents conventional in the art having regard to the type of formulation in question, for example those suitable for oral administration can include flavoring agents.

The compositions described herein can also contain biguanide or related heterocyclic compounds in a form suitable for oral use, for example, as tablets, troches, lozenges, aqueous or oily suspensions, dispersible powders or granules, emulsions, hard or soft capsules, or syrups or elixirs. Compositions intended for oral use can be prepared according to any method known to the art for the manufacture of pharmaceutical compositions, and such compositions can contain one or more agents selected from, by way of non-limiting example, sweetening agents, flavoring agents, coloring agents and preserving agents in order to provide pharmaceutically elegant and palatable preparations.

Tablets contain the active ingredient in admixture with pharmaceutically acceptable excipients which are suitable for the manufacture of tablets. These excipients can be, for example, inert diluents, such as calcium carbonate, sodium carbonate, lactose, calcium phosphate or sodium phosphate; granulating and disintegrating agents, such as microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets can be un-coated or coated by known techniques to mask the taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, or cellulose acetate butyrate can be employed as appropriate. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

In various embodiments, the biguanide or related heterocyclic compound compositions provided herein are in liquid form. Liquid forms include, by way of non-limiting example, neat liquids, solutions, suspensions, dispersions, colloids, foams and the like. In certain instances, liquid forms contain also a nutritional component or base (e.g., derived from milk, yogurt, shake, or juice). In some aspects, the biguanide or related heterocyclic compounds are micronized or as nanoparticles in the liquid form. In certain instances, the biguanide or related heterocyclic compounds are coated to mask the tastant properties. In other instances, the biguanide or related heterocyclic compounds are coated to modify delivery to the intestine and colon.

Aqueous solutions or suspensions contain the active ingredient(s) in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents can be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous solutions or suspensions can also contain one or more preservatives, for example ethyl, or n-propyl p-hydroxybenzoate, one or more coloring agents, one or more flavoring agents, and one or more sweetening agents, such as sucrose, saccharin or aspartame. In certain instances, the flavoring agents are biguanide or related heterocyclic compounds.

Oily suspensions can be formulated by suspending the active ingredient(s) in a vegetable oil, for example arachis oil, olive oil, sesame oil or coconut oil, or in mineral oil such as liquid paraffin. The oily suspensions can contain a thickening agent, for example beeswax, hard paraffin or cetyl alcohol. Sweetening agents such as those set forth above, and flavoring agents can be added to provide a palatable oral preparation. These compositions can be preserved by the addition of an anti-oxidant such as butylated hydroxyanisol or alpha-tocopherol.

Dispersible powders and granules suitable for preparation of an aqueous solutions or suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, can also be present. These compositions can be preserved by the addition of an anti-oxidant such as ascorbic acid.

Compositions can also be in the form of an oil-in-water emulsion. The oily phase can be a vegetable oil, for example olive oil or arachis oil, or a mineral oil, for example liquid paraffin or mixtures of these. Suitable emulsifying agents can be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions can also contain sweetening agents, flavoring agents, preservatives and antioxidants.

Syrups and elixirs can be formulated with sweetening agents, for example glycerol, propylene glycol, sorbitol or sucrose. Such formulations can also contain a demulcent, a preservative, flavoring and coloring agents and antioxidant.

Compositions can also be formulated in rectal compositions such as suppositories or retention enemas, e.g., containing conventional suppository bases such as cocoa butter, polyethylene glycol, or other glycerides. These compositions can be prepared by mixing the inhibitors with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

The composition can, for example, be in a form suitable for oral administration as a tablet, capsule, cachet, pill, lozenge, powder or granule, sustained release formulations, solution, liquid, or suspension. The pharmaceutical composition can be in unit dosage forms suitable for single administration of precise dosages. The pharmaceutical composition will include a conventional pharmaceutical carrier or excipient and the compound according to the invention as an active ingredient. In addition, it can include other medicinal or pharmaceutical agents, carriers, adjuvants, etc.

Suitable carriers include inert diluents or fillers, water and various organic solvents. The compositions can, if desired, contain additional ingredients such as flavorings, binders, excipients and the like. Thus for oral administration, tablets containing various excipients, such as citric acid can be employed together with various disintegrants such as starch or other cellulosic material, alginic acid and certain complex silicates and with binding agents such as sucrose, gelatin and acacia. Additionally, lubricating agents such as magnesium stearate, sodium lauryl sulfate and talc are often useful for tableting purposes. Other reagents such as an inhibitor, surfactant or solubilizer, plasticizer, stabilizer, viscosity increasing agent, or film forming agent can also be added. Solid compositions of a similar type can also be employed in soft and hard filled gelatin capsules. Materials include lactose or milk sugar and high molecular weight polyethylene glycols. When aqueous suspensions or elixirs are desired for oral administration the active compound therein can be combined with various sweetening or flavoring agents, coloring matters or dyes and, if desired, emulsifying agents or suspending agents, together with diluents such as water, ethanol, propylene glycol, glycerin, or combinations thereof.

Also contemplated within the invention are food compositions, including medical food compositions and formulations containing the compositions of the invention described herein, as well as nutritional or dietary supplements incorporating the compositions of the invention. Foods, such as medical foods, incorporating biguanide or related heterocyclic compound compositions include edible forms such as bars, candies, powders, gels, snacks, soups, and liquids. Chewing gums are also contemplated within the scope of food compositions. Medical food biguanide or related heterocyclic compound compositions can be formulated to control the amounts and types of biguanide or related heterocyclic compound(s) as well as the content of other edible additives and ingredients (e.g., carbohydrates, proteins, fats, fillers, excipients). Exemplary medical food compositions include, but are not limited to, bars with defined and/or limited biguanide or related heterocyclic compounds. Food compositions can be packaged ready-to-serve or ready-to-consume where a set amount of biguanide or related heterocyclic compound is present at a predefined dosage. Examples include frozen food products, yoghurts, shakes and the like. In another aspect, food compositions can be "semi-finished" where an individual assembles various components such as flavorings, sauces, extracts, etc. into a finished consumable product, e.g., soup base, pre-packaged noodles, dessert gelatin. The biguanide or related heterocyclic compounds can be present in one or more components of a semi-finished food composition adapted for mixing in biguanide or related heterocyclic compound(s) during food preparation or sprinkling them on the finished, prepared food.

Modified Release Formulations

In various embodiments, the methods and compositions directed to the biguanide or related heterocyclic compound are provided in the form of controlled, sustained, or extended release formulations, known collectively as "modified release" formulations. Compositions can be administered by modified release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566. Such dosage forms can be used to provide modified release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable modified release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

Many strategies can be pursued to obtain modified release in which the rate of release outweighs, if any, the rate of metabolism of the compound and/or the location of the release is controlled. For example, modified release can be obtained by the appropriate selection of formulation parameters and ingredients (e.g., appropriate controlled release compositions and coatings). Examples include single or multiple unit tablet or capsule compositions, oil solutions, suspensions, emulsions, microcapsules, microspheres, nanoparticles, patches, and liposomes. The release mechanism can be controlled such that the compounds are released at period intervals, the release could be simultaneous, a delayed release of one of the agents of the combination can be affected, when the early release of one particular agent is preferred over the other, or the location of the release is controlled. Different delivery systems described herein can also be combined to release at an onset of multiple period intervals (e.g., about 30 minutes, about 120 minutes, about 180 minutes and about 240 minutes after oral administration) or at different locations (e.g., release in the lower intestine tract, upper intestine tract, the duodenum, jejunum, ileum, caecum, colon, and/or rectum) or a combination thereof. For example, a pH dependent system can be combined with a timed release system or any other system described herein to achieve a desired release profile.

In some embodiments, the modified release systems are formulated to release a the compound at a duration of about 75 minutes, about 80 minutes, about 90 minutes, about 100 minutes, about 110 minutes, about 120 minutes, about 130 minutes, about 140 minutes, about 150 minutes, about 160 minutes, about 170 minutes, about 180 minutes, about 190 minutes, about 200 minutes, about 210 minutes, about 220 minutes, about 230 minutes, about 240 minutes, about 250 minutes, about 260 minutes, about 270 minutes, about 280 minutes, about 290 minutes, about 300 minutes, about 310 minutes, about 320 minutes, about 330 minutes, about 340 minutes, about 350 minutes, about 360 minutes, about 370 minutes, about 380 minutes, about 390 minutes, about 400, about 400, about 410, or about 420 minutes subsequent to onset of the release. In embodiments with multiple releases, modified release systems are formulated to release at more than one durations of time at different time points.

In various embodiments, the compound compositions(s) are provided in the form of modified release formulations coupled with an immediate release component in a unitary dosage form. The immediate release component can be formulated by any known method such as a layer that envelops the modified release component or the like. Exemplary ratios of immediate release ("IR") of an active agent to a modified release ("MR") of an active agent are about 10% IR to about 90% MR, about 15% IR to about 85% MR, about 20% IR to about 80% MR, about 25% IR to about 75% MR, about 30% IR to about 70% MR, about 35% IR to about 65% MR, about 40% IR to about 60% MR, about 45% IR to about 55% MR, or about 50% IR to about 50% MR. In certain embodiments, the immediate release of an active agent to modified release of an active agent is about 25% IR to about 75% MR. In certain embodiments, the immediate release of an active agent to modified release of an active agent is about 20% IR to about 80% MR. Unitary dosage forms with an IR and MR component include any known formulation including bilayer tablets, coated pellets, and the like.

Timed Release Systems

In one embodiment, the release mechanism is a "timed" or temporal release ("TR") system that releases an active agent, for example a biguanide or related heterocyclic compound(s), at certain timepoints subsequent to administration. Timed release systems are well known in the art and suitable timed release system can include any known excipient and/or coating. For example, excipients in a matrix, layer or coating can delay release of an active agent by slowing diffusion of the active agent into an environment. Suitable timed release excipients, include but are not limited to, acacia (gum arabic), agar, aluminum magnesium silicate, alginates (sodium alginate), sodium stearate, bladderwrack, bentonite, carbomer, carrageenan, Carbopol, cellulose, microcrystalline cellulose, ceratonia, chondrus, dextrose, furcellaran, gelatin, Ghatti gum, guar gum, galactomannan, hectorite, lactose, sucrose, maltodextrin, mannitol, sorbitol, honey, maize starch, wheat starch, rice starch, potato starch, gelatin, sterculia gum, xanthum gum, Glyceryl behenate (e.g., Compritol 888 ato), Gylceryl distearate (e.g. Precirol ato 5), polyethylene glycol (e.g., PEG 200-4500), polyethylene oxide, adipic acid, gum tragacanth, ethyl cellulose (e.g., ethyl cellulose 100), ethylhydroxyethyl cellulose, ethylmethyl cellulose, methyl cellulose, hydroxyethyl cellulose, hydroxyethylmethyl cellulose (e.g., K100LV, K4M, K15M), hydroxypropyl cellulose, poly(hydroxyethyl methacrylate), cellulose acetate (e.g. cellulose acetate CA-398-10 NF), cellulose acetate phthalate, cellulose acetate propionate, cellulose acetate butyrate, hydroxypropyl methyl cellulose acetate succinate, hydroxypropyl methyl cellulose phthalate, cellulose butyrate, cellulose nitrate, oxypolygelatin, pectin, polygeline, povidone, propylene carbonate, polyandrides, methyl vinyl ether/maleic anhydride copolymer (PVM/MA), poly(methoxyethyl methacrylate), poly (methoxyethoxyethyl methacrylate), hydroxypropyl cellulose, hydroxypropylmethyl cellulose, sodium carboxymethyl-cellulose (CMC), silicon dioxide, vinyl polymers, e.g. polyvinyl pyrrolidones (PVP: povidone), polyvinyl acetates, or polyvinyl acetate phthalates and mixtures, Kollidon SR, acryl derivatives (e.g. polyacrylates, e.g. cross-linked polyacrylates, methycrylic acid copolymers), Splenda® (dextrose, maltodextrin and sucralose) or combinations thereof. The timed release excipient may be in a matrix with active agent, in another compartment or layer of the formulation, as part of the coating, or any combination thereof. Varying amounts of one or more timed release excipients may be used to achieve a designated release time.

In some embodiments, the timed release systems are formulated to release a biguanide or related heterocyclic compound(s) at an onset of about 75 minutes, about 80 minutes, about 90 minutes, about 100 minutes, about 110 minutes, about 120 minutes, about 130 minutes, about 140 minutes, about 150 minutes, about 160 minutes, about 170 minutes, about 180 minutes, about 190 minutes, about 200 minutes, about 210 minutes, about 220 minutes, about 230 minutes, about 240 minutes, about 250 minutes, about 260 minutes, about 270 minutes, about 280 minutes, about 290 minutes, about 300 minutes, about 310 minutes, about 320 minutes, about 330 minutes, about 340 minutes, about 350 minutes, about 360 minutes, about 370 minutes, about 380 minutes, about 390 minutes, about 400, about 400, about 410, or about 420 minutes subsequent to administration. In embodiments with multiple releases, timed release systems are formulated to release at more than one time point. In certain embodiments, the timed release systems are formulated to release at an onset of about 120 minutes, about 180 minutes and about 240 minutes after administration. In certain embodiments of the timed release systems are formulated to release at an onset of about 5 to about 45 minutes, about 105 to about 135 minutes, about 165 to about 195 minutes, about 225 to about 255 minutes or a combination of times thereof following administration to a subject.

In various embodiments, the methods and compositions directed to biguanide or related heterocyclic compound(s) are provided in the form of timed release formulations coupled with an immediate release component in a unitary dosage form. The immediate release component can be a can be formulated by any known method such as a layer that envelops the timed release component or the like. The timed release component can be formulated to release at exemplary times previously described. Exemplary ratios of immediate release ("IR") of an active agent to a timed release ("TR") of an active agent are about 10% IR to about 90% TR, about 15% IR to about 85% TR, about 20% IR to about 80% TR, about 25% IR to about 75% TR, about 30% IR to about 70% TR, about 35% IR to about 65% TR, about 40% IR to about 60% TR, about 45% IR to about 55% TR, or about 50% IR to about 50% TR. In certain embodiments, the immediate release of an active agent to timed release of an active agent is about 25% IR to about 75% TR. In certain embodiments, the immediate release of an active agent to timed release of an active agent is about 20% IR to about 80% TR.

Enteric Coatings and pH Dependent Systems

The formulation may also be coated with an enteric coating, which protects an active agent, for example a biguanide or related heterocyclic compound(s), from degradation in an acidic environment, such as the stomach, and allows a delayed release into a target area, for example the duodenum, for uptake.

The enteric coating may be, as a non-limiting example, wax or wax like substance, such as carnauba wax, fatty alcohols, hydrogenated vegetable oils, zein, shellac, sucrose, Arabic gum, gelatin, dextrin, *psyllium* husk powder, polymethacrylates, anionic polymethacrylates, mixtures of poly(methacrylic acid, methyl methacrylate), polymers or copolymers derived from acrylic and/or methacrylic acid esters, cellulose acetate phthalate, cellulose acetate trimelliate, hydroxypropyl methylcellulose phthalate (HPMCP), cellulose propionate phthalate, cellulose acetate maleate, polyvinyl alcohol phthalate, hydroxypropyl methylcellulose acetate succinate (HPMCAS), hydroxypropyl methylcellulose hexahydrophthalate, polyvinyl acetate phthalate, mixtures of poly(methacrylic acid, ethyl acrylate), ethylcellulose, methylcellulose, propylcellulose, chitosan succinate, chitosan succinate, polyvinyl acetate phthalate (PVAP), polyvinyl acetate polymers carboxymethylethyl cellulose and compatible mixtures thereof. In addition, an inactive intermediate film may be provided between the active agent, for example, a biguanide or related heterocyclic compound(s), and the enteric coating to prevent interaction of the active agent with the enteric coating.

The enteric coatings can be formulated to release the active agent, for example, a biguanide or related heterocyclic compound(s), at a desired pH using combinations of enteric polymers. It is well-known that different locations of the gastrointestinal system have specific pHs. For example, the duodenum may correspond to a pH 5.5 environment and the jejunum may correspond to pH 6.0 environment. In some embodiments, the enteric coatings are formulated to release a biguanide or related heterocyclic compound(s) at an onset of a pH including about pH 5, about pH 5.5, about pH 6, about pH 6.5, or about pH 7. In embodiments with multiple releases, the enteric coatings are formulated to release at an onset of two or more pH values. In certain embodiments, the enteric coatings are formulated to release at an onset of pH 5.5, 6.0, 6.5 and 7.0. In certain embodiments, the enteric coatings are formulated to release at an onset of pH 5.5, 6.0 and 6.5. In certain embodiments, the enteric coatings are formulated to release at the duodenum, jejunum, ileum, and lower intestine. In yet other embodiments, the enteric coatings are used in combination with other release systems such as a timed release system.

In yet other embodiments, the enteric coatings are used in combination with an immediate release/modified release unitary dosage forms. For example, an unitary dosage form, such as a bilayer tablet with a 20% IR/80% MR component of biguanide or related heterocyclic compound(s) can be coated with an enteric coating that releases at pH 6.5 so that the release is delayed until the dosage form reaches a pH of 6.5, thereby releasing the IR component immediately and the MR component according to its MR release properties. In certain instances, the enteric coatings are used in combination with an immediate release/timed release unitary dosage forms.

Microcapsule Gastroretentive Systems

The microcapsules gastroretentive systems described in U.S. Pat. Nos. 6,022,562, 5,846,566 and 5,603,957, can be used in the sustained release delivery methods described herein. Microparticles of an active agent or drug are coated by spraying with a material consisting of a mixture of a film-forming polymer derivative, a hydrophobic plasticizer, a functional agent and a nitrogen-containing polymer. The resulting microcapsules are less than or equal to 1000 microns (gm) in size, and in certain cases such microcapsules are between 100 and 500 microns. These microcapsules remain in the small intestine for at least 5 hours.

Film-forming polymer derivatives used in such microcapsules include, but are not limited to, ethylcellulose, cellulose acetate, and non-hydrosoluble cellulose derivates. The nitrogen-containing polymers include, but are not limited to, polyacrylamide, poly-N-vinylamide, poly-N-vinyl-lactam and polyvinylpyrrolidone. The plasticizer used in such microcapsule include, but are not limited to, glycerol esters, phthalates, citrates, sebacates, cetylalcohol esters, castor oil and cutin. The surface-active and/or lubricating agent used in such microcapsule include, but are not limited to, anionic surfactants, such as by way of example the alkali metal or alkaline-earth metal salts of fatty acids, stearic acid and/or oleic acid, nonionic surfactants, such as by way of example, polyoxyethylenated esters of sorbitan and/or polyoxyethylenated esters of sorbitan and/or polyoxyethylenated derivatives of castor oil; and/or lubricants such as stearates, such as by way of example, calcium, magnesium, aluminum stearate, zinc stearate, stearylfumarate, sodium stearylfimarate, and glyceryl behenate.

Other Modified Release/Gastroretentive Systems

The following exemplary modified release and gastroretentive systems are useful for the biguanide or related heterocyclic compound compositions. In one non-limiting example, chitosan and mixtures of chitosan with carboxymethylcellulose sodium (CMC-Na) have been used as vehicles for the sustained release of active ingredients, as described by Inouye et al., Drug Design and Delivery 1: 297-305, 1987. Mixtures of these compounds and agents of the combinations of the invention, when compressed under 200 kg/cm2, form a tablet from which the active agent is slowly released upon administration to a patient. The release profile can be changed by varying the ratios of chitosan, CMC-Na, and active agent(s). The tablets can also contain other additives, including lactose, CaHPO4 dihydrate, sucrose, crystalline cellulose, or croscarmellose sodium.

In another non-limiting example, Baichwal, in U.S. Pat. No. 6,245,356, describes sustained release oral, solid dosage forms that includes agglomerated particles of a therapeutically active medicament in amorphous form, a gelling agent, an ionizable gel strength enhancing agent and an inert diluent. The gelling agent can be a mixture of a xanthan gum and a locust bean gum capable of cross-linking with the xanthan gum when the gums are exposed to an environmental fluid. Preferably, the ionizable gel enhancing agent acts to enhance the strength of cross-linking between the xanthan gum and the locust bean gum and thereby prolonging the release of the medicament component of the formulation. In addition to xanthan gum and locust bean gum, acceptable gelling agents that may also be used include those gelling agents well known in the art. Examples include naturally occurring or modified naturally occurring gums such as alginates, carrageenan, pectin, guar gum, modified starch, hydroxypropylmethylcellulose, methylcellulose, and other cellulosic materials or polymers, such as, for example, sodium carboxymethylcellulose and hydroxypropyl cellulose, and mixtures of the foregoing.

In another non-limiting formulation useful for the combinations of the invention, Baichwal and Staniforth in U.S. Pat. No. 5,135,757 describe a free-flowing slow release granulation for use as a pharmaceutical excipient that includes from about 20 to about 70 percent or more by weight of a hydrophilic material that includes a heteropolysaccharide (such as, for example, xanthan gum or a derivative thereof) and a polysaccharide material capable of cross-linking the heteropolysaccharide (such as, for example, galactomannans, and most preferably locust bean gum) in the presence of aqueous solutions, and from about 30 to about 80 percent by weight of an inert pharmaceutical-filler (such as, for example, lactose, dextrose, sucrose, sorbitol, xylitol, fructose or mixtures thereof). After mixing the excipient with a tricyclic compound/corticosteroid combination, or combination agent, of the invention, the mixture is directly compressed into solid dosage forms such as tablets. The tablets thus formed slowly release the medicament when ingested and exposed to gastric fluids. By varying the amount of excipient relative to the medicament, a slow release profile can be attained.

In another non-limiting example, Shell, in U.S. Pat. No. 5,007,790, describes sustained-release oral drug-dosage forms that release a active ingredient in solution at a rate controlled by the solubility of the active ingredient. The dosage form comprises a tablet or capsule that includes a plurality of particles of a dispersion of a limited solubility active ingredient in a hydrophilic, water-swellable, cross-linked polymer that maintains its physical integrity over the dosing lifetime but thereafter rapidly dissolves. Once ingested, the particles swell to promote gastric retention and permit the gastric fluid to penetrate the particles, dissolve active ingredient and leach it from the particles, assuring that active ingredient reaches the stomach in the solution state which is less injurious to the stomach than solid-state active ingredient. The programmed eventual dissolution of the polymer depends upon the nature of the polymer and the degree of crosslinking The polymer is nonfibrillar and substantially water soluble in its uncrosslinked state, and the degree of crosslinking is sufficient to enable the polymer to remain insoluble for the desired time period, normally at least from about 4 hours to 8 hours up to 12 hours, with the choice depending upon the active ingredient incorporated and the medical treatment involved. Examples of suitable crosslinked polymers that may be used in the invention are gelatin, albumin, sodium alginate, carboxymethyl cellulose, polyvinyl alcohol, and chitin. Depending upon the polymer, crosslinking may be achieved by thermal or radiation treatment or through the use of crosslinking agents such as aldehydes, polyamino acids, metal ions and the like.

In an additional non-limiting example, Silicone microspheres for pH-controlled gastrointestinal drug delivery have been described by Carelli et al., Int. J. Pharmaceutics 179: 73-83, 1999. The microspheres are pH-sensitive semi-interpenetrating polymer hydrogels made of varying proportions of poly(methacrylic acid-co-methylmethacrylate) (Eudragit L100 or Eudragit S 100) and crosslinked polyethylene glycol 8000 that are encapsulated into silicone microspheres. Slow-release formulations can include a coating which is not readily water-soluble but which is slowly attacked and removed by water, or through which water can slowly permeate. Thus, for example, the combinations of the invention can be spray-coated with a solution of a binder under continuously fluidizing conditions, such as describe by Kitamori et al., U.S. Pat. No. 4,036,948. Examples of water-soluble binders include pregelatinized starch (e.g., pregelatinized corn starch, pregelatinized white potato starch), pregelatinized modified starch, water-soluble celluloses (e.g. hydroxypropyl-cellulose, hydroxymethyl-cellulose, hydroxypropylmethyl-cellulose, carboxymethyl-cellulose), polyvinylpyrrolidone, polyvinyl alcohol, dextrin, gum arabicum and gelatin, organic solvent-soluble binders, such as cellulose derivatives (e.g., cellulose acetate phthalate, hydroxypropylmethyl-cellulose phthalate, ethylcellulose).

Combinations of the invention, or a component thereof, with sustained release properties can also be formulated by spray drying techniques. Yet another form of sustained release combinations can be prepared by microencapsulation of combination agent particles in membranes which act as microdialysis cells. In such a formulation, gastric fluid permeates the microcapsule walls and swells the microcapsule, allowing the active agent(s) to dialyze out (see, for example, Tsuei et al., U.S. Pat. No. 5,589,194). One commercially available sustained-release system of this kind consists of microcapsules having membranes of acacia gum/gelatine/ethyl alcohol. This product is available from Eurand Limited (France) under the trade name Diffucaps™. Microcapsules so formulated can be carried in a conventional gelatine capsule or tableted. A bilayer tablet can be formulated for a combination of the invention in which different custom granulations are made for each agent of the combination and the two agents are compressed on a bi-layer press to form a single tablet.

When desired, formulations can be prepared with enteric coatings adapted for sustained or controlled release administration of the active ingredient. A common type of controlled-release formulation that may be used for the purposes of the present invention comprises an inert core, such as a sugar sphere, coated with an inner active ingredient-containing layer and an outer membrane layer controlling active ingredient release from the inner layer. Other formulations for targeted release of compounds in the gastrointestinal tract are also known in the art and contemplated for use with the invention described herein. Exemplary systems for targeting delivery of a substance to the upper and/or lower gastrointestinal tract include the formulations of the TIMERx® system. This controlled release formulation system provides for altered temporal release (SyncroDose™) as well as biphasic release (Geminex®). (See, for example, Staniforth & Baichwal, TIMERx®: novel polysaccharide composites for controlled/programmed release of active ingredients in the gastrointestinal tract, Expert Opin. Drug Deliv., 2(3): 587-89 (2005)). Using formulations such as these for the invention described herein, compositions can be created which target the upper gastrointestinal tract, the lower gastrointestinal tract, or both, in addition to temporally controlling the release of such compounds in any of these locations.

One non-limiting example of a lower GI delivery formulation comprises a tablet for lower GI delivery. The inner composition of the tablet comprises about 0.01% weight to about 10.0% by weight of a suitable active ingredient; about 50% by weight to about 98% by weight of a hydrocolloid gum obtainable from higher plants; and about 2% by weight to about 50% by weight of a pharmaceutically acceptable excipient such as a binder. Other optional materials may be present that will assist in establishing the desired characteristics of the pharmaceutical composition. These include materials that may enhance absorption of the active ingredient in the lower GI, may protect the active ingredient against degradation, may prevent dissolution, and the like. Optionally surrounding the inner composition of the tablet is a coating that is preferably of enteric polymeric material.

The formulation is designed to take advantage of (1) the protective characteristics of the hydrocolloid obtainable from higher plants in the upper GI and (2) the disintegrative characteristics of the hydrocolloid in the lower GI. Thus, the inner composition of the tablet may be one of several designs: (a) it may be a matrix of a therapeutically effective amount of the active ingredient uniformly dispersed throughout in combination with a high percentage of the hydrocolloid and a generally lesser amount of other excipients; (b) it may have a core, in which the active ingredient is concentrated, surrounded by a layer of material that is free of the active ingredient and that has a high percentage of the hydrocolloid and a generally lesser amount of other excipients; (c) it may have a concentration gradient of the active ingredient such that there is a greater amount in the core of the tablet with lesser amounts in multiple layers surrounding the core and very little or no active ingredient in the outer layer. Whether the design of the tablet is that of (a), (b) or (c) above, the specificity for regional delivery to the lower GI is enhanced by enterically coating the tablet with an appropriate enteric coating material.

Hydrocolloids are obtainable from higher plants. By "higher plant" is meant an organism of the vegetable kingdom that lacks the power of locomotion, has cellulose cell walls, grows by synthesis of inorganic substances and includes the vascular plants (or tracheophytes) of the division Spermatophyta, particularly those of the class Angiospermae. The gums may be extracted from the roots, legumes, pods, berries, bark, etc. Representative hydrocolloid gums obtainable from higher plants include guar gum, gum tragacanth, karaya gum (also referred to as kadaya gum) and locust bean gum (also referred to as carob). Others may be readily apparent to one of skill in the art. See, for example, "The Chemistry of Plant Gums and Mucilages" by Smith and Montgomery from ACS Monograph Series, No. 141, 1959, Reinhold Publishing Company and the 18th edition of the Merck Index. A particularly convenient and useful hydrocolloid is guar gum which is a neutral polysaccharide and consists of long galactomannan molecules with some side chain attachments. The hydrocolloids used in the patient invention generally have high viscosity exhibited upon hydration, are normally linear (at least about 50% by weight of the compound is the backbone chain), and will normally have high molecular weight, usually about $3 \times 10^5$ daltons, more usually greater than about $1 \times 10^6$ daltons. Generally, the hydrocolloid comes as a powdered hydrocolloid gum and exhibits a viscosity at a 1% concentration in a neutral aqueous solution of at least about 75 centipoise per second (cps) at 25° C. after 24 hours, using a Brookfield viscometer (model LDF) with a number 3 spindle at 90 rpms, preferably at least $1 \times 10^3$ cps and most preferably at least about $2 \times 10^3$ cps. Generally, the viscosity increases with increasing molecular weight. See Meer Corporation, "An Introduction to Polyhydrocolloids." Hydrocolloid gums most useful are those where the hydrocolloid is a polysaccharide hydrocolloid which is chemically designated as galactomannan. Galactomannans are polysaccharides consisting of long chains of (1-04)-I3-D-mannopyranosyl units to which single unit side chains of α-D-galactopyranosyl are joined by (1-06) linkages. Galactomannans are found in a variety of plants but differ in molecular size and the number of D-galactosyl side chains. The galactomannans useful in this invention are commonly found in the endosperms of the leguminosae.

Galactomannan can be obtained, for example, from the *cyamopsis tetragonolobus*, commonly referred to as guar. This exhibits a percentage mannose residue of about 64% with a percent galactose residue of about 36%. Commercially available guar gum is about 66-82% galactomannan polysaccharide with impurities making up the remainder of the composition. According to the National Formulary (NF) standards the guar gum may contain up to 15% w water, up to 10% w protein, up to 7% w acid insoluble material and up to about 1.5% ash. Sources of commercially available guar gum are Aqualon Company, Wilmington, Del.; Meer Corporation, Cincinnati, Ohio; Stein Hall & Company and TIC Gums, Inc., Belcamp, Md.

Other hydrocolloids are known in the art. See for example "The Chemistry of Plant Gums and Mucilages" by Smith and Montgomery from the A.C.S. Monograph series, #141, 1959, Reinhold Publishing Co. and the Eighteenth Edition of The Merck Index. In general, the amount of the hydrocolloid that will be used is an amount that allows the composition to traverse the upper GI tract without significant disintegration and without releasing significant amounts of active ingredient in the upper GI tract, i.e. to provide a delayed-release profile. Generally, that amount of hydrocolloid will be more than about 50% but less than about 98%. Depending on individual variability, whether a patient has eaten or has fasted, and other factors, a tablet will traverse the stomach and upper intestinal tract in about 3 to 6 hours. During this time, little active ingredient (less than 20%, preferably less than 10%) is released from the tablet of this invention. Once the tablet reaches the lower GI, the release of the active ingredient is triggered by enzymatic degradation of the galactomannan gum.

One non-limiting example of a formulation for upper gastrointestinal delivery comprises a free-flowing slow release granulation for use as a pharmaceutical excipient that includes from about 20 to about 70 percent or more by weight of a hydrophilic material that includes a heteropolysaccharide (such as, for example, xanthan gum or a derivative thereof) and a polysaccharide material capable of cross-linking the heteropolysaccharide (such as, for example, galactomannans, and most preferably locust bean gum) in the presence of aqueous solutions, and from about 30 to about 80 percent by weight of an inert pharmaceutical-filler (such as, for example, lactose, dextrose, sucrose, sorbitol, xylitol, fructose or mixtures thereof). After mixing the excipient with the compounds of the invention, the mixture is directly compressed into solid dosage forms such as tablets. The tablets thus formed slowly release the medicament when ingested and exposed to gastric fluids. By varying the amount of excipient relative to the medicament, a slow release profile can be attained.

One non-limiting example of a sustained gastrointestinal delivery formulation comprises a plurality of particles of a dispersion of a limited solubility active ingredient in a hydrophilic, water-swellable, crosslinked polymer that maintains its physical integrity over the dosing lifetime but thereafter rapidly dissolves. Once ingested, the particles swell to promote gastric retention and permit the gastric fluid to penetrate the particles, dissolve active ingredient and leach it from the particles, assuring that active ingredient reaches the stomach in the solution state which is less injurious to the stomach than solid-state active ingredient. The programmed eventual dissolution of the polymer depends upon the nature of the polymer and the degree of crosslinking The polymer is nonfibrillar and substantially water soluble in its uncrosslinked state, and the degree of crosslinking is sufficient to enable the polymer to remain insoluble for the desired time period. Examples of suitable crosslinked polymers that may be used in the invention are gelatin, albumin, sodium alginate, carboxymethyl cellulose, polyvinyl alcohol, and chitin. Depending upon the polymer, crosslinking may be achieved by thermal or radiation treatment or through the use of crosslinking agents such as aldehydes, polyamino acids, metal ions and the like.

In another non-limiting example, Villa et al., in U.S. Pat. No. 6,773,720, describes a modified-release system containing an inner lipophilic matrix where an active ingredient is inglobated and an outer hydrophilic matrix in which the lipophilic matrix is dispersed. An active ingredient, such as a biguanide or related heterocyclic compound, is first inglobated in a low melting lipophlilic excipient or mixture of excipients while heating to soften and/or melt the excipient itself, which thereby incorporates the active ingredient by simple dispersion. After cooling at room temperature, an inert matrix forms, which can be reduced in size to obtain matrix granules containing the active ingredient particles. The inert matrix granules are subsequently mixed together with one or more hydrophilic water-swellable excipients. In this respect, when the composition is contacted with biological fluids, a high viscosity swollen layer is formed, which coordinates the solvent molecules and acts as a barrier to penetration of the aqueous fluid itself inside the new structure. Said barrier antagonizes the staring "burst effect" caused by dissolution of the active ingredient inglobated inside the inert matrix, which is in its turn inside the hydrophilic matrix. One commercially available system of this type is from Cosmo Technologies Limited (Italy) under the trade name MMX® technology. The lipophilic/hydrophilic matrices can be further enterically coated for pH specific delivery.

Formulations for upper intestinal delivery, lower intestinal delivery or both are known in the art. Targeting of active ingredients to various regions of the gut is described, e.g., in The Encyclopedia of Pharmaceutical Technology, by James Swarbrick and James Boylan, Informa Health Care, 1999, at pp. 287-308. Any suitable formulation for gastrointestinal delivery for site-specific delivery and/or specific temporal delivery (i.e. delayed, controlled, extended, or sustained release) can be used with the invention and is contemplated herein. In one non-limiting example, a single composition comprises a first formulation for delivery of at least one the compound to the upper gastrointestinal tract and a second formulation for delivery of at least one compound to the lower gastrointestinal tract. Thus, a single composition can provide for delivery of one or more biguanide or related heterocyclic compound(s) to the upper and lower gastrointestinal tract. Additional non-limiting examples include compositions having formulations for delivery of at least one the compounds to the upper gastrointestinal tract and compositions having formulations for delivery of at least one the compounds to the lower gastrointestinal tract. As described herein, different combinations of the compounds can be formulated for treatment of specific conditions and for delivery to specific locations in the intestinal tract.

Any of the delivery systems described herein may be used in combination with others to achieve multiple releases and/or specific release profiles. In some embodiments, the active agent(s) is in a formulation that achieves multiple releases in the gastrointestinal locations following administration. In certain embodiments, the active agent(s) is in a multiple release formulation that releases at an onset of about 120 minutes, about 180 minutes, about 240 minutes, or combinations thereof following administration. In certain embodiments, the active agent(s) is in a multiple release formulation that releases at an onset of about 75 minutes, about 105 to about 135 minutes, about 165 to about 195 minutes, about 225 to about 255 minutes, or combinations thereof following administration. In certain embodiments, the active agent(s) is in a multiple release formulation that releases in the duodenum, jejunum, ileum, lower intestine or combinations thereof following administration. In yet other embodiments, the active agent(s) is in a multiple release formulation that releases at an onset of about pH 5.5, about pH 6.0, at about pH 6.5, about pH 7.0, or combinations thereof following administration. In yet other embodiments, the active agent(s) is in a multiple release formulation that releases in ranges at about pH 5.0 to about pH 6.0, about pH 6.0 to about pH 7.0, about pH 7.0 to about pH 8.0, or combinations thereof following administration. In yet other embodiments, the active agent(s) is in a multiple release formulation that releases a fraction or portion of the active agent(s) as an immediate release with the rest of the active agent(s) released by a modified manner described herein.

Excipients

Any of the compositions or formulations described herein include any commonly used excipients in pharmaceutics and are selected on the basis of compatibility with the active agent(s) and release profile properties of the desired dosage form. Excipients include, but are not limited to, binders, fillers, flow aids/glidents, disintegrants, lubricants, stabilizers, surfactants, and the like. A summary of excipients described herein, may be found, for example in Remington: The Science and Practice of Pharmacy, Nineteeth Ed (Easton, Pa.: Mack Publishing Company, 1995); Hoover, John E., Remington's Pharmaceutical Sciences, (Easton, Pa.: Mack Publishing Co 1975); Liberman, H. A. and Lachman, L., Eds., Pharmaceutical Dosage Forms (New York, N.Y.: Marcel Decker 1980); and Pharmaceutical Dosage Forms and Drug Delivery Systems, Seventh Ed (Lippincott Williams & Wilkins 1999), herein incorporated by reference in their entirety.

Binders impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

Disintegrants facilitate breakup or disintegration of oral solid dosage forms after administration. Examples of disintegrants include a starch, e.g., a natural starch such as corn starch or potato starch, a pregelatinized starch such as National 1551 or Amijel®, or sodium starch glycolate such as Promogel® or Explotab®; a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a resin such as a cation-exchange resin; citrus pulp; sodium lauryl sulfate; sodium lauryl sulfate in combination starch; and the like.

Lubricants are compounds which prevent, reduce or inhibit adhesion or friction of materials. Exemplary lubricants include, e.g., stearic acid; calcium hydroxide; talc; sodium stearyl fumerate; a hydrocarbon such as mineral oil, hydrogenated castor oil or hydrogenated vegetable oil such as hydrogenated soybean oil (Sterotex®); higher fatty acids and their alkali-metal and alkaline earth metal salts, such as aluminum, calcium, magnesium, zinc; stearic acid, sodium stearates, magnesium stearates, glycerol, talc, waxes, Stearowet® boric acid, sodium benzoate, sodium acetate, sodium chloride, leucine, a polyethylene glycol or a methoxypolyethylene glycol such as Carbowax™, ethylene oxide polymers, sodium oleate, glyceryl behenate (E.g. Compritol 888 Ato), glyceryl disterate (Precirol Ato 5), polyethylene glycol, magnesium or sodium lauryl sulfate, colloidal silica such as Syloid™, Carb-O-Sil®, DL-leucine, a starch such as corn starch, silicone oil, a surfactant, and the like.

Flow-aids or glidants improve the flow characteristics of powder mixtures. Such compounds include, e.g., colloidal silicon dioxide such as Cab-o-sil®; tribasic calcium phosphate, talc, corn starch, DL-leucine, sodium lauryl sulfate, magnesium stearate, calcium stearate, sodium stearate, kaolin, and micronized amorphous silicon dioxide (Syloid®) and the like.

Plasticizers aid in coating of oral solid dosage forms. Exemplary plasticizers include, but are not limited to, triethyl citrate, triacetin (glyceryl triacetate), acetyl triethyl citrate, polyethylene glycols (PEG 4000, PEG 6000, PEG 8000), Carbowax 400 (polyethylene glycol 400), diethyl phthalate, diethyl sebacate, acetyltriethylcitrate, oleic acid, glyceralmonosterate, tributyl citrate, acetylated monoglycerides, glycerol, fatty acid esters, propylene glycol, and dibutyl phthalate and the like.

The aforementioned excipients are given as examples only and are not meant to include all possible choices. Other suitable excipient classes include coloring agents, granulating agents, preservatives, anti-foaming agents, solubulizers and the like. Additionally, many excipients can have more than one role or function, or can be classified in more than one group; the classifications are descriptive only, and are not intended to limit any use of a particular excipient.

Methods for Evaluating Treatment
Hormonal Profiles

Administration of biguanide or related heterocyclic compound composition(s) provided herein modulates hormone concentrations and/or concentrations of hormones including, but not limited to, GLP-1, GLP-2, GIP, oxyntomodulin, PYY, CCK, glycentin, insulin, glucagon, ghrelin, amylin, C-peptide and uroguanylin. Sampling of hormones can be performed frequently during the administration of compounds. Test animals and subjects can be studied with and without systemic inhibition of dipeptidyl-peptidase IV (DPP-IV) to augment the circulating half-life of the relevant hormones that can be degraded by DPP-IV.

By way of example, certain embodiments of the methods described herein provide for glucose lowering, wherein hormonal profiles suited for treating elevated blood glucose are composed of, but not limited to: 1) GLP-1 with circulating concentrations over 1.5-fold basal concentrations; 2) GIP with circulating concentrations over 1.5-fold basal concentrations and 3) PYY 3-36 circulating concentrations over 1.5-fold basal concentrations.

In another example, certain embodiments of the methods described herein provide for weight loss, wherein hormonal profiles suited for weight loss are composed of, but not limited to: 1) PYY with circulating concentrations over 3-fold basal concentrations; 2) Oxyntomodulin with circulating concentrations over 2-fold basal concentrations; 3) GPL-1 with circulating concentrations over 3-fold basal concentrations; and 4) CCK with circulating concentrations over 2-fold basal concentrations.

In another example, certain embodiments of the methods described, hormonal profiles include: 1) PYY (total) with circulating concentrations over 3-fold basal concentrations; and 2) GLP-1 (active) with circulating concentrations over 3-fold basal concentrations.

In certain embodiments described herein, methods are provided for modulating hormone concentrations in a subject comprising the administration of a composition comprising a biguanide or related heterocyclic compound, said composition being adapted to deliver said compound to one or more regions of the intestine of said subject. In some embodiments, administration of biguanide or related heterocyclic compound composition(s) as provided herein modulates circulating hormone concentrations of at least one, at least two, at least three, at least four, at least five, at least six, at least seven, at least eight, at least nine, at least ten, at least eleven, at least twelve, or at least thirteen hormones. In certain embodiments, administration of biguanide or related heterocyclic compound composition(s) as provided herein increases circulating hormone concentrations of at least one, at least two, at least three, at least four, at least five, at least six, at least seven, at least eight, at least nine, at least ten, at least eleven, at least twelve, or at least thirteen hormones. In certain embodiments, administration of biguanide or related heterocyclic compound composition(s) as provided herein decreases circulating hormone concentrations of at least one, at least two, at least three, at least four, at least five, at least six, at least at least seven hormones. In some embodiments, administration of biguanide or related heterocyclic compound compositions modulates GLP-1. In some embodiments, administration of biguanide or related heterocyclic compound compositions modulates GLP-2. In some embodiments, administration of biguanide or related heterocyclic compound compositions modulates GIP. In some embodiments, administration of biguanide or related heterocyclic compound compositions modulates oxyntomodulin. In some embodiments, administration of biguanide or related heterocyclic compound compositions modulates PYY. In some embodiments, administration of biguanide or related heterocyclic compound compositions modulates CCK. In some embodiments, administration of biguanide or related heterocyclic compound compositions modulates glycentin. In some embodiments, administration of biguanide or related heterocyclic compound compositions modulates insulin. In some embodiments, administration of biguanide or related heterocyclic compound compositions modulates glucagon. In some embodiments, administration of biguanide or related heterocyclic compound compositions modulates, ghrelin. In some embodiments, administration of biguanide or related heterocyclic compound compositions modulates amylin. In some embodiments, administration of biguanide or related heterocyclic compound compositions modulates insulin. In some embodiments, administration of biguanide or related heterocyclic compound compositions modulates C-peptide. In some embodiments, administration of biguanide or related heterocyclic compound compositions modulates uroguanylin.

Hormone Assays

In embodiments, the levels of hormones assayed in association with the methods of the invention, including, but not limited to, GLP-1, GLP-2, GIP, oxyntomodulin, PYY, CCK, glycentin, insulin, glucagon, ghrelin, amylin, uroguanylin, C-peptide and/or combinations thereof are detected according to standard methods described in the literature. For example, proteins can be measured by immunological assays, and transcription products by nucleic acid amplification techniques. Functional assays described in the art can also be used as appropriate. In embodiments, samples assayed comprise cultured cells, patient cell or tissue samples, patient body fluids, e.g., blood or plasma, etc. Similarly, the levels of analytes (e.g., glucose, triglycerides, HDL, LDL, apoB and the like) assayed in association with the methods of the invention are detected according to any known method.

For example, immunofluorescence can be used to assay for GLP-1. Cells can be grown on matrigel-coated cover slips to confluent monolayers in 12-well plates at 37° C., fixed in 4% paraformaldehyde in phosphate-buffered saline (PBS) and incubated with primary antiserum (e.g., rabbit anti-alpha gustducin, 1:150; Santa Cruz Biotechnology, and rabbit anti-GLP-1, Phoenix) overnight at 4° C. following permeabilization with 0.4% Triton-X in PBS for 10 minutes and blocking for 1 hour at room temperature. Following three washing steps with blocking buffer, the appropriate secondary antibody is applied (AlexaFluor 488 anti-rabbit immunoglobulin, 1:1000; Molecular Probes) for 1 hour at room temperature. After three washing steps, the cells can be fixed in Vectashield medium and the immunofluorescence visualized.

GLP-1 RNA isolated from cells can be assayed using RT-PCR. RT-PCR RNA isolation from cells can be performed using standard methodology. The RT-PCR reaction can be performed in a volume of 50 µl in a Peltier thermal cycler (PTC-225 DNA Engine Tetrad Cycler; MJ Research), using published primer sequences (Integrated DNA Technologies). Reverse transcription can be performed at 50° C. for 30 minutes; after an initial activation step at 95° C. for 15 minutes. PCR can be performed by denaturing at 94° C. for 1 minute, annealing at 55° C. for 1 minute and extension at 72° C. for 1 minute for 40 cycles, followed by a final extension step at 72° C. for 10 minutes. Negative controls can be included as appropriate, for example, by substituting water for the omitted reverse transcriptase or template. The control can be RNA isolated from, e.g., rat lingual epithelium. PCR products can be separated in 2% agarose gel with ethidium bromide, and visualized under UV light.

Radioimmunoassay (RIA) for total GLP-1 in patient blood samples can be performed as described in the art, e.g., by Laferrere, et al., 2007, "Incretin Levels and Effect are Markedly Enhanced 1 Month after Roux-en-Y Gastric Bypass Surgery in Obese Patients with Type 2 Diabetes, Diabetes Care 30(7):1709-1716 (using commercially available materials obtained from Phoenix Pharmaceutical, Belmont, Calif.). The authors describe measuring the effect of GIP and GLP-1 on secretion of insulin by measuring the difference in insulin secretion (area under the curve, or AUC) in response to an oral glucose tolerance test and to an isoglycemic intravenous glucose test.

Measurement of plasma concentrations of GLP-1, GIP, glucagon, insulin, C peptide, pancreatic peptide, nonesterified fatty acids, glutamic acid decarboxylase antibodies, and islet antigen antibodies, is described, e.g., by Toft-Nielsen, et al., 2001, "Determinants of the Impaired Secretion of Glucagon-Like Peptide-1 in Type 2 Diabetic Patients," J. Clin. End. Met. 86(8):3717-3723. The authors describe the use of radioimmunoassay for GLP-1 to measure plasma concentrations of amidated GLP-1-(7-36), using antibody code no. 89390. This assay measures the sum of GLP-1-(7-36) and its metabolite GLP-1-(9-36). The authors describe measurement of GIP using C-terminally directed antibody code no. R65 (RIA), that reacts 100% with a human GIP but not with 8-kDA GIP.

GLP-1 and PYY can be directly assayed in the supernatant from venous effluents as described by, e.g., Claustre, et al. (1999, "Stimulatory effect of β-adrenergic agonists on ileal L cell secretion and modulation by α-adrenergic activation, J. Endocrin. 162:271-8). (See also Plaisancie' et al., 1994, "Regulation of glucagon-like peptide-1-(7-36) amide secretion by intestinal neurotransmitters and hormones in the isolated vascularly perfused rat colon," Endocrinology 135:2398-2403 and Plaisancie' et al., 1995, "Release of peptide YY by neurotransmitters and gut hormones in the isolated, vascularly perfused rat colon," Scandinavian Journal of Gastroenterology 30:568-574.) In this method, the 199D anti-GLP-1 antibody is used at a 1:250 000 dilution. This antibody reacts 100% with GLP-1-(7-36) amide, 84% with GLP-1-(1-36) amide, and less than 0.1% with GLP-1-(1-37), GLP-1-(7-37), GLP-2, and glucagon. PYY is assayed with the A4D anti-porcine PYY antiserum at a 1:800 000 dilution.

Methods for assaying GLP-1 and GIP are also described elsewhere in the art, e.g., by Jang, et al., PNAS, 2007.

PYY can also be assayed in blood using a radioimmunoassay as described by, e.g., Weickert, et al., 2006, "Soy isoflavones increase preprandial peptide YY (PYY), but have no effect on ghrelin and body weight in healthy postmenopausal women" Journal of Negative Results in BioMedicine, 5:11. Blood is collected in ice-chilled EDTA tubes for the analysis of glucose, ghrelin, and PYY. Following centrifugation at 1600 g for 10 minutes at 4° C., aliquots were immediately frozen at −20° C. until assayed. All samples from individual subjects were measured in the same assay. The authors described measuring immunoreactive total ghrelin was measured by a commercially available radioimmunoassay (Phoenix Pharmaceuticals, Mountain View, Calif., USA). (See also Weickert, et al., 2006, "Cereal fiber improves whole-body insulin sensitivity in overweight and obese women," Diabetes Care 29:775-780). Immunoreactive total human PYY is measured by a commercially available radioimmunoassay (LINCO Research, Missouri, USA), using 1251-labeled bioactive PYY as tracer and a PYY antiserum to determine the level of active PYY by the double antibody/PEG technique. The PYY antibody is raised in guinea pigs and recognizes both the PYY 1-36 and PYY 3-36 (active) forms of human PYY.

SGLT-1, the intestinal sodium-dependent glucose transporter 1, is a protein involved in providing glucose to the body. It has been reported to be expressed in response to sugar in the lumen of the gut, through a pathway involving T1R3 (Margolskee, et al., 2007 "T1R3 and gustducin in gut sense sugars to regulate expression of Na+-glucose cotransporter 1," Proc Natl Acad Sci USA 104, 15075-15080"). Expression of SGLT-1 can be detected as described, e.g., by Margolskee, et al., for example, using quantitative PCR and Western Blotting methods known in the art. Measurement of glucose transport has been described in the literature, e.g., by Dyer, et al., 1997, Gut 41:56-9 and Dyer, et al., 2003, Eur. J. Biochem 270:3377-88. Measurement of glucose transport in brush border membrane vesicles can be made, e.g., by initiating D-glucose uptake by the addition of 100 μl of incubation medium containing 100 mM NaSCN (or KSCN), 100 mM mannitol, 20 mM Hepes/Tris (pH 7.4), 0.1 mM MgSO4, 0.02% (wt/vol) NaN3, and 0.1 mM D-[U14C] glucose to BBMV (100 μg of protein). The reaction is stopped after 3 sec by addition of 1 ml of ice-cold stop buffer, containing 150 mM KSCN, 20 mM Hepes/Tris (pH 7.4), 0.1 mM MgSO4, 0.02% (wt/vol) NaN3, and 0.1 mM phlorizin. A 0.9-ml portion of the reaction mixture is removed and filtered under vacuum through a 0.22-μm pore cellulose acetate/nitrate filter (GSTF02500; Millipore, Bedford, Mass.). The filter is washed five times with 1 ml of stop buffer, and the radioactivity retained on the filter is measured by liquid scintillation counting.

Evaluation of Treatment of Diabetes

The effect of a biguanide or related heterocyclic compound treatment of the invention on aspects of diabetic disease can be evaluated according to methods known in the art and common practiced by physicians treating diabetic subjects.

Efficacy of treatment of diabetes/metabolic syndrome and diabetes-associated conditions with the compositions and methods described herein can be assessed using assays and methodologies known in the art. By way of example, quantitative assessment of renal function and parameters of renal dysfunction are well known in the art. Examples of assays for the determination of renal function/dysfunction include serum creatinine level; creatinine clearance rate; cystatin C clearance rate, 24-hour urinary creatinine clearance, 24-hour urinary protein secretion; Glomerular filtration rate (GFR); urinary albumin creatinine ratio (ACR); albumin excretion rate (AER); and renal biopsy.

Quantitative assessment of pancreatic function and parameters of pancreatic dysfunction or insufficiency are also well known in the art. Examples of assays for the determination of pancreas function/dysfunction include evaluating pancreatic functions using biological and/or physiological parameters such as assessment of islets of Langerhans size, growth and/or secreting activity, beta-cells size, growth and/or secreting activity, insulin secretion and circulating blood levels, glucose blood levels, imaging of the pancreas, and pancreas biopsy, glucose uptake studies by oral glucose challenge, assessment of cytokine profiles, blood-gas analysis, extent of blood-perfusion of tissues, and angiogenesis within tissues.

Additional assays for treatment of diabetes and diabetes-associated conditions are known in the art and are contemplated herein.

Evaluation of Treatment of Obesity and Eating Disorders

In treatment of obesity it is desired that weight and/or fat is reduced in a subject. By reducing weight it is meant that the subject loses a portion of his/her total body weight over the course of treatment (whether the course of treatment be days, weeks, months or years). Alternatively, reducing weight can be defined as a decrease in proportion of fat mass to lean mass (in other words, the subject has lost fat mass, but maintained or gained lean mass, without necessarily a corresponding loss in total body weight). An effective amount of a biguanide or related heterocyclic compound treatment administered in this embodiment is an amount effective to reduce a subject's body weight over the course of the treatment, or alternatively an amount effective to reduce the subject's percentage of fat mass over the course of the treatment. In certain embodiments, the subject's body weight is reduced, over the course of treatment, by at least about 1%, by at least about 5%, by at least about 10%, by at least about 15%, or by at least about 20%. Alternatively, the subject's percentage of fat mass is reduced, over the course of treatment, by at least 1%, at least 5%, at least 10%, at least 15%, at least 20%, or at least 25%.

Total body weight and fat content can be measured at the end of the dietary period. In rats, a frequently used method to determine total body fat is to surgically remove and weigh the retroperitoneal fat pad, a body of fat located in the retroperitoneum, the area between the posterior abdominal wall and the posterior parietal peritoneum. The pad weight is considered to be directly related to percent body fat of the animal. Since the relationship between body weight and body fat in rats is linear, obese animals have a correspondingly higher percent of body fat and retroperitoneal fat pad weight.

In embodiments wherein methods of treating, reducing, or preventing food cravings in a subject are provided, food cravings can be measured by using a questionnaire, whether known in the art or created by the person studying the food cravings. Such a questionnaire would preferably rank the level of food cravings on a numerical scale, with the subject marking 0 if they have no food cravings, and marking (if on a scale of 1-10) 10 if the subject has severe food cravings. The questionnaire would preferably also include questions as to what types of food the subject is craving.

Binge eating can be determined or measured using a questionnaire and a Binge Eating Scale (BES). Binge eating severity can be divided into three categories (mild, moderate, and severe) based on the total BES score (calculated by summing the scores for each individual item). Accordingly, methods are provided for reducing the BES score of a subject comprising administering to a subject in need thereof a biguanide or related heterocyclic compound treatment in an amount effective to reduce the BES score of the subject. In some embodiments, administration of a biguanide or related heterocyclic compound treatment changes the BES category of the subject, for example, from severe to moderate, from severe to mild, or from moderate to mild.

Pre-Treatment Evaluation of Patient Hormonal Profile

In some embodiments, patients are pre-evaluated for expression of metabolic hormones using methods described herein. The therapy provided to the individual can thus be targeted to his or her specific needs. In embodiments, a patient's hormonal profile is pre-evaluated and depending on the changes that the physician desires to affect, a certain biguanide or related heterocyclic compound/metabolite combination is administered. The evaluation process can be repeated and the treatment adjusted accordingly at any time during or following treatment.

Definitions

"Chemosensory receptor" as used herein includes, e.g., the G-protein coupled receptors (GPCRs) that are expressed in the gastrointestinal tract of a subject. Chemosensory receptors include the taste receptor family and are further categorized according to their taste characteristics. They include sweet receptors, umami receptors (also known as savory receptors), bitter receptors, fat receptors, bile acid receptors, salty receptors, and sour receptors. A chemosensory receptor can be any receptor associated with chemosensory sensation or chemosensory ligand triggered signal transduction, e.g., via taste receptors or taste related receptors present in taste bud, gastrointestinal tract, etc.

"Activity," or "functional effects" in the context of the disclosed ligands and assays for testing compounds that modulate a chemosensory receptor, e.g., enhance a chemosensory receptor family member mediated signal transduction such as sweet, umami, bitter, fat, bile acid, sour or salty receptor functional effects or activity, includes the determination of any parameter that is indirectly or directly under the influence of the particular chemosensory receptor. It includes, without any limitation, ligand binding, changes in ion flux, membrane potential, current flow, transcription, G protein binding, GPCR phosphorylation or dephosphorylation, signal transduction, receptor-ligand interactions, second messenger concentrations (e.g., cAMP, cGMP, IP3, or intracellular Ca2+), in vitro, in vivo, and ex vivo and also includes other physiologic effects such as increases or decreases of neurotransmitter or hormone release and the measurement of the downstream physiological effects of such release.

The term "determining the functional effect" or receptor "activity" means assays for a compound that increases or decreases a parameter that is indirectly or directly under the influence of a chemosensory receptor, e.g., functional, physical and chemical effects. Such parameters also include secretion of hormones such as GIP, GLP-1, GLP-2, oxyntomodulin, insulin, glucagon, insulin peptide C, peptide YY, and CCK. Such functional effects can be measured by any means known to those skilled in the art, e.g., changes in spectroscopic characteristics (e.g., fluorescence, absorbance, refractive index), hydrodynamic (e.g., shape), chromatographic, or solubility properties, patch clamping, voltage-sensitive dyes, whole cell currents, radioisotope efflux, inducible markers, oocyte chemosensory receptor, e.g., TIR gene expression; tissue culture cell chemosensory receptor, e.g., TIR expression; transcriptional activation of chemosensory receptor, e.g., T1R genes; ligand binding assays; voltage, membrane potential and conductance changes; ion flux assays; changes in intracellular second messengers such as cAMP, cGMP, and inositol triphosphate (IP3); changes in intracellular calcium levels; neurotransmitter release, and the like. Also included are assays to determine increases or decreases in hormone or neurotransmitter secretion and/or activity. Changes in hormone or neurotransmitter secretion and/or activity can also be determined indirectly by the physiological effects caused by changes in the secretion of hormone or neurotransmitter. Functional and physical parameters that can be used to determine the functional effect or receptor activity include, but is not limited to, appetite suppression and weight loss.

Chemosensory receptor ligands include metabolized chemosensory receptor ligands that can be metabolized as an energy source, e.g. food or metabolites, as well as nonmetabolized chemosensory receptor ligands that are not metabolized as an energy source, e.g. tastants. The term nonmetabolized chemosensory receptor ligands, as used herein, includes chemosensory receptor ligands that are metabolized to a small degree but are not metabolized substantially. That is, nonmetabolized chemosensory receptor ligand includes ligands that have insignificant caloric value. Chemosensory receptor ligands include agonists, antagonists, modifiers, and enhancers as well as other compounds that modulate chemosensory receptors. Many chemosensory receptor ligands are known in the art and have been reported in the literature.

"Tastants" as used herein refers to any ligand that induces a flavor or taste in a subject, including sweet, sour, salty, bitter, umami and others. Tastants are also generally non-metabolized in the sense that they have no significant caloric value.

"Metabolites" as used herein are metabolized chemosensory receptor ligands such as, for example, glucose, glutamate salts, fatty acids and bile acids. In certain aspects, metabolites can be derived from a food source. Metabolites can be administered as part of a chemosensory receptor ligand composition or separately.

Antagonists/inhibitors are compounds that, e.g., bind to, partially or totally block stimulation, decrease, prevent, delay activation, inactivate, desensitize, or down-regulate chemosensory receptor and/or taste transduction. Agonists/activators are compounds that, e.g., bind to, stimulate, increase, open, activate, facilitate, enhance activation, sensitize, or up regulate chemosensory receptor signal transduction.

Modifiers include compounds that, e.g., alter, directly or indirectly, the activity of a receptor or the interaction of a receptor with its ligands, e.g., receptor ligands, biguanide or related heterocyclic compounds, and optionally bind to or interact with activators or inhibitors; G Proteins; kinases (e.g., homologs of rhodopsin kinase and beta adrenergic receptor kinases that are involved in deactivation and desensitization of a receptor); and arresting, which also deactivate and desensitize receptors. Modifiers include genetically modified versions of chemosensory receptors, e.g., TIR family members, e.g., with altered activity, as well as naturally occurring and synthetic ligands, antagonists, agonists, small chemical molecules and the like. In the present invention this includes, without any limitation, sweet receptor ligands, umami receptor ligands, bitter receptor ligands, fatty acid ligands, bile receptor ligands, (agonists or antagonists). Modifiers also include compounds that allosterically bind to a receptor and change receptor activity. Modifiers also include enhancers. Depending on the structure, functional and activity properties, modifiers can enhance, potentiate, induce and/or block the physiological activity other chemosensory receptor ligands.

Enhancers as used herein are a type of modifier and refer to chemosensory receptor ligands that enhance, potentiate or multiply the effect of another chemosensory receptor ligand. For example, a sweet receptor enhancer can increase or multiply the sweetness of a chemosensory receptor ligand composition, when used in combination with a sweet receptor ligand (e.g., a sweetener, such as sucrose, fructose, glucose, saccharine, aspartame, sucralose, etc.). While a sweet receptor enhancer may or may not have sweet properties at some combinations when used in the absence of a sweet receptor ligand, sweet receptor enhancement occurs when the sweet receptor enhancer is used in combination with another sweet receptor ligand with the result that the resulting sweetness perceived in a subject is greater than the additive effects attributable to the sweet receptor enhancer's own sweet properties (if any), plus the sweetness attributable to the presence of the sweet receptor ligand.

The terms "gastrointestinal tract" and "gut," as used herein, refer to the stomach and intestines. The "small" or "upper" intestine includes the duodenum, jejunum and ileum and the "large" or "lower" intestine includes the caecum, colon and rectum. "Beyond the stomach" refers to the small and lower intestines.

"Treating" or "treatment" of any condition, disease or disorder refers, in some embodiments, to ameliorating the disease, disorder, or condition (i.e., arresting or reducing the development of the disease, disorder, or condition, or at least one of the clinical symptoms thereof). In other embodiments "treating" or "treatment" refers to ameliorating at least one physical parameter, which may or may not be discernible by the subject, including physical parameters that are undesired but not clinically significant. In yet other embodiments, "treating" or "treatment" refers to inhibiting the disease, disorder, or condition, either physically, (e.g., stabilization of a discernible symptom), physiologically, (e.g., stabilization of a physical parameter) or both. In yet other embodiments, "treating" or "treatment" refers to preventing or to delaying the onset of the disease, disorder, or condition.

"Therapeutically effective amount" or "effective amount" means the amount of a composition, compound, therapy, or course of treatment that, when administered to a subject for treating a disease, disorder, or condition, is sufficient to effect such treatment for the disease, disorder, or condition. The "therapeutically effective amount" will vary depending on the composition, the compound, the therapy, the course of treatment, the disease, disorder, or condition, and its severity and the age, weight, etc., of the subject to be treated.

When the compounds (e.g., compounds of formulae I-IV as well as other compounds having a described chemical structure) described herein include one or more chiral centers, the stereochemistry of such chiral centers can independently be in the R or S configuration, or a mixture of the two. The chiral centers can be further designated as R or S or R,S or d,D, l,L or d,l, D,L. Correspondingly, the amide, guanidine, biguanide and related heterocyclic compounds of the invention, if they can be present in optically active form, can actually be present in the form of a racemic mixture of enantiomers, or in the form of either of the separate enantiomers in substantially isolated and purified form, or as a mixture comprising any relative proportions of the enantiomers.

When the amide, guanidine, biguanide and related heterocyclic compounds of the invention, if they can be present in geometrically isomeric forms around, for example, the guanide bond, then they can actually be present in the form of a mixture of geometric isomers comprising any relative proportions of the isomers, or in some cases in the form of either of the separate geometric isomers in substantially isolated and purified form.

When the compounds (e.g., compounds of formulae I-IV as well as other compounds having a described chemical structure) described herein include one or more isolated or linearly conjugated double bonds, the geometry around such double bonds can be independently a cis/trans, E/Z mixture or an E or Z geometric isomer thereof.

"Alkyl" means a straight or branched chain, saturated monovalent hydrocarbon radical. By way of example, the hydrocarbon chain may have from one to twenty carbons, one to sixteen carbons, one to fourteen carbons, one to twelve carbons, one to ten carbons, one to eight carbons, one to six carbons, one to four carbons, etc. "Lower alkyl" may refer to alkyls having, e.g., one to six carbons, one to four carbons, etc. In certain examples, an straight chain alkyl may have from one to six carbon atoms and a branched alkyl three to six carbon atoms, e.g., methyl, ethyl, propyl, 2-propyl, butyl (including all isomeric forms), pentyl (including all isomeric forms), and the like. "Me" means methyl, "Et" means ethyl, and "iPr" means isopropyl.

"Aryl" means a monovalent monocyclic or bicyclic aromatic hydrocarbon radical, e.g., having from of 6 to 20 or 6 to 10 ring atoms e.g., phenyl or naphthyl.

"Alkylaryl" means a -(alkylene)-R radical where R is aryl as defined above.

"Cycloalkyl" means a cyclic saturated or partially saturated monovalent hydrocarbon radical (or an alicyclic radical). By way of example, the cycloalkyl may have from three to twenty carbon atoms, from three to sixteen carbon atoms, from three to fourteen carbon atoms, from three to twelve carbon atoms, from three to ten carbon atoms, from three to eight carbon atoms, from three to six carbon atoms, etc., wherein one or two carbon atoms may be replaced by an oxo group, e.g., adamantanyl, cyclopropyl, cyclobutyl, cyclopentyl, cyclohexyl, cyclohexenyl, indanyl and the like.

"Alkylcycloalkyl" means a -(alkylene)-R radical where R is cycloalkyl as defined above; e.g., cyclopropylmethyl, cyclobutylmethyl, cyclopentylethyl, or cyclohexylmethyl, and the like.

"Heterocyclyl" or "heterocycloalkyl" means a saturated or unsaturated monovalent monocyclic group, in which one or two ring atoms are heteroatom selected from N, O, or S, the remaining ring atoms being C. The heterocyclyl ring is optionally fused to a (one) aryl or heteroaryl ring as defined herein. The heterocyclyl ring fused to monocyclic aryl or heteroaryl ring is also referred to in this Application as "bicyclic heterocyclyl" ring. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydropyranyl, thiomorpholino, and the like. When the heterocyclyl ring is unsaturated it can contain one or two ring double bonds. When the heterocyclyl group contains at least one nitrogen atom, it is also referred to herein as heterocycloamino and is a subset of the heterocyclyl group. When the heterocyclyl group is a saturated ring and is not fused to aryl or heteroaryl ring as stated above, it is also referred to herein as saturated monocyclic heterocyclyl.

"Alkylheterocycloalkyl" means a -(alkylene)-R radical where R is heterocyclyl ring as defined above e.g., tetrayhydrofuranylmethyl, piperazinylmethyl, morpholinylethyl, and the like.

"Heteroaryl" means a monovalent monocyclic or bicyclic aromatic radical, where one or more, preferably one, two, or three, ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, diazolyl, pyrazolyl, triazolyl, benzothiazolyl, benzoxazolyl, quinolinyl, isoquinolinyl, pyridinyl, pyrimidinyl, pyrazinyl, pyridazinyl, tetrazolyl, and the like.

"Oxo" or "carbonyl" means =(O) group or C=O group, respectively.

The term "substituted" means that the referenced group is substituted with one or more additional group(s) individually and independently selected from groups described herein. In some embodiments, an optional substituent is selected from oxo, halogen, —CN, —NH2, —OH, —NH(CH3), —N(CH3)2, alkyl (including straight chain, branched and/or unsaturated alkyl), substituted or unsubstituted cycloalkyl, substituted or unsubstituted heterocycloalkyl, fluoroalkyl, substituted or unsubstituted heteroalkyl, substituted or unsubstituted alkoxy, fluoroalkoxy, —S-alkyl, —S(O)$_2$-alkyl, —CONH((substituted or unsubstituted alkyl) or (substituted or unsubstituted phenyl)), —CON(H or alkyl)$_2$, —OCON(substituted or unsubstituted alkyl)$_2$, —NHCONH((substituted or unsubstituted alkyl) or (substituted or unsubstituted phenyl)), —NHCOalkyl, —N(substituted or unsubstituted alkyl)CO(substituted or unsubstituted alkyl), —NHCOO(substituted or unsubstituted alkyl), —C(OH)(substituted or unsubstituted alkyl)2, and —C(NH2)(substituted or unsubstituted alkyl)2. In some embodiments, by way of example, an optional substituent is selected from oxo, fluorine, chlorine, bromine, iodine, —CN, —NH2, —OH, —NH(CH3), —N(CH3)2, —CH3, —CH2CH3, —CH(CH3)2, —CF3, —CH2CF3, —OCH3, —OCH2CH3, —OCH(CH3)2, —OCF3, —OCH2CF3, —S(O)2-CH3, —CONH2, —CONHCH3, —NHCONHCH3, —COCH3, —COOH and the like. In some embodiments, substituted groups are substituted with one, two or three of the preceding groups. In some embodiments, substituted groups are substituted with one or two of the preceding groups. In some embodiments, substituted groups are substituted with one of the preceding groups. Further, unless stated to the contrary, a formula with chemical bonds shown only as solid lines and not as wedges or dashed lines contemplates each possible isomer, e.g., each enantiomer and diastereomer, and a mixture of isomers, such as racemic or scalemic mixtures.

In some embodiments, a compound of the disclosure (e.g., compounds of Formulae I-IV as well as other compounds having a described chemical structure) is present in a composition as a salt. In some embodiments, salts are obtained by reacting a compound of the disclosure with acids. In some other embodiments, pharmaceutically acceptable salts are obtained by reacting a compound of the disclosure with a base. In other embodiments, the compounds are used as free-acid or free-base form in the manufacture of the compositions described herein. The type of salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, the biguanide or related heterocyclic compound described herein are reacted with an organic base, such as, but not limited to, ethanolamine, diethanolamine, triethanolamine, tromethamine, N-methylglucamine, dicyclohexylamine, tris(hydroxymethyl)methylamine. In other cases, the compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

The term "amino acid" includes any one of the twenty naturally-occurring amino acids or the D-form of any one of the naturally-occurring amino acids. In addition, the term "amino acid" also includes other non-naturally occurring amino acids besides the D-amino acids, which are functional equivalents of the naturally-occurring amino acids. Such non-naturally-occurring amino acids include, for example, norleucine ("Nle"), norvaline ("Nva"), L- or D-naphthalanine, ornithine ("Orn"), homoarginine (homoArg) and others well known in the peptide art, such as those described in M. Bodanzsky, "Principles of Peptide Synthesis," 1st and 2nd Revised Ed., Springer-Verlag, New York, N.Y., 1984 and 1993, and Stewart and Young, "Solid Phase Peptide Synthesis," 2nd Ed., Pierce Chemical Co., Rockford, Ill., 1984, both of which are incorporated herein by reference.

Amino acids and amino acid analogs can be purchased commercially (Sigma Chemical Co.; Advanced Chemtech) or synthesized using methods known in the art.

In the scope of the embodiments, compounds described herein (e.g., compounds of formula I-V and the like) include further forms of the compounds such as pharmaceutically acceptable salts, solvates (including hydrates), amorphous phases, partially crystalline and crystalline forms (including all polymorphs), prodrugs, metabolites, N-oxides, isotopically-labeled, epimers, pure epimers, epimer mixtures, enantiomers including but not limited to single enantiomers and enantiomeric diastereomers, meso compounds, stereoisomers, racemic mixtures and diasteroisomeric mixtures. Compounds described herein having one or more double bonds include cis/trans isomers, E/Z isomers and geometric isomers. Compounds described herein can be prepared as a pharmaceutically acceptable salts formed when an acidic proton present in the parent compound either is replaced by a metal ion, for example an alkali metal ion, an alkaline earth ion, or an aluminum ion; or coordinates with an organic base. In addition, the salt forms of the disclosed compounds can be prepared using salts of the starting materials or intermediates.

In some embodiments, the compounds described herein include solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol.

In some embodiments, the compounds described herein possess one or more stereocenters and each center exists independently in either the R or S configuration. The compounds presented herein include all diastereomeric, enantiomeric, and epimeric forms as well as the appropriate mixtures thereof.

In some embodiments, sites on the compounds disclosed herein are susceptible to various metabolic reactions. Therefore incorporation of appropriate substituents at the places of metabolic reactions will reduce, minimize or eliminate the metabolic pathways. In specific embodiments, the appropriate substituent to decrease or eliminate the susceptibility of the aromatic ring to metabolic reactions is, by way of example only, a halogen, deuterium or an alkyl group.

In some embodiments, the compounds described herein are isotopically-labeled, which are identical to those recited in the various formulae and structures presented herein, but for the fact that one or more atoms are replaced by an atom having an atomic mass or mass number different from the atomic mass or mass number usually found in nature. In some embodiments, one or more hydrogen atoms are replaced with deuterium. In some embodiments, metabolic sites on the compounds described herein are deuterated. In some embodiments, substitution with deuterium affords certain therapeutic advantages resulting from greater metabolic stability, such as, for example, increased in vivo half-life or reduced dosage requirements. Throughout the specification, groups and substituents thereof can be chosen by one skilled in the field to provide stable moieties and compounds.

EXAMPLES

Example 1

Exemplary Metformin Composition and its Administration.

| Composition A | | | |
|---|---|---|---|
| Chemosensory Receptor Ligand | Per oral solid dosage form (mg) | Dose (mg) | B.i.d. Daily Total |
| Metformin HCl | 50 | 200 | 400 |

A single oral solid dosage form (e.g., tablet, pill, capsule, and the like) includes the listed component(s). A single dose for administration is a set of 4 units of the oral solid dosage form (e.g., 4 tablets or 4 capsules). Each of the 4 units contains identical active component(s); however each individual unit is formulated for release at a different pH: pH 5.5, pH 6.0 or pH 6.5. One unit releases approximately 20% of its components in about 15 to about 60 mins after encountering an intestinal pH of approximately 5.5, and releases the remaining 80% of its components in about 2 hrs. Another unit releases approximately 20% of its components in about 15 to about 60 mins after encountering an intestinal pH of approximately 6.0, and releases the remaining 80% of its components in about 4 hrs. A third unit releases approximately 20% of its components in about 15 to about 60 mins after encountering an intestinal pH of approximately 6.5, and releases the remaining 80% of its components in about 4 hrs. A fourth unit releases approximately 20% of its components in about 15 to about 60 mins after encountering an intestinal pH of approximately 6.0, and releases the remaining 80% of its components in about 7 hrs. B.i.d. dosing occurs at mealtime, typically breakfast or the first meal of the day and dinner or the third meal of the day.

Bilayer Tablet of Composition A

The biguanide or related heterocyclic compound of Composition A (metformin) are formulated into bilayer tablet cores with the excipients as indicated in the following table (expressed in proportional units).

|  | IR | CR7 | CR4 | CR2 |
|---|---|---|---|---|
| Metformin HCl | 60.29 | 65.2 | 65.2 | 65.2 |
| Prosol HD90 | 28.71 | 9.6 | 12.0 | 15.6 |
| Pruv | 3.0 | 3.0 | 3.0 | 3.0 |
| Croscarmelose Sodium | 4.0 | — | — | — |
| Methocel K4M | — | 11.0 | 8.6 | 5.0 |
| Klucel EXF | 4.0 | 4.0 | 4.0 | 4.0 |

The IR column of the above table refers to 20% of the mass of the bilayer tablet that releases its contents in about 15 to about 60 minutes. CR2, CR4, and CR7 refer to the remaining 80% of the components that release over approximately 2, 4 or 7 hrs. A bilayer tablet core has an IR compound and one of the CR, CR4 or CR7 components. The purity of all ingredients is >99.8% and the concentrations of all impurities for all ingredients are significantly below the limits set under International Conference on Harmonisation (ICH) guidance.

The bilayer tablet cores are coated with the following coating compositions for release at the indicated pH in the following table (expressed in proportional units).

| Composition | IR/CR 2 hr pH 5.5 | IR/CR 4 hr pH 6.0 | IR/CR 4 hr pH 6.5 | IR/CR 7 hr pH 6.0 |
|---|---|---|---|---|
| Eudragit L30 D55 | 833.4 | 750.06 | 625.05 | 750.06 |
| Eudragit FS 30D | 0 | 83.34 | 208.35 | 83.34 |
| Talc | | | 125.0 | |
| Triethylcitrate | | | 25.0 | |
| Water | | | 1016 | |

Example 2

Exemplary Metformin Composition Combined with Additional Chemosensory Receptor Ligands and its Administration.

| Composition D | | | |
|---|---|---|---|
| Chemosensory Receptor Ligand | Per oral solid dosage form (mg) | Dose (mg) | B.i.d. Daily Total |
| Rebaudioside A | 200 | 800 | 1600 |
| Stevioside | 100 | 400 | 800 |
| Sucralose | 100 | 400 | 800 |
| Metformin HCl | 25 | 100 | 200 |
| L-Glutamine | 50 | 200 | 400 |

A single oral solid dosage form (e.g., tablet, pill, capsule, and the like) includes the listed components. A single dose for administration is a set of 4 units of the oral solid dosage form (e.g., 4 tablets or 4 capsules). Each of the 4 units contains identical active components; however each individual unit is formulated for release at a different pH: pH 5.5, pH 6.0 or pH 6.5. One unit releases approximately 20% of its components in about 15 to about 60 mins after encountering an intestinal pH of approximately 5.5, and releases the remaining 80% of its components in about 2 hrs. Another unit releases approximately 20% of its components in about 15 to about 60 mins after encountering an intestinal pH of approximately 6.0, and releases the remaining 80% of its components in about 4 hrs. A third unit releases approximately 20% of its components in about 15 to about 60 mins after encountering an intestinal pH of approximately 6.5, and releases the remaining 80% of its components in about 4 hrs. A fourth unit releases approximately 20% of its components in about 15 to about 60 mins after encountering an intestinal pH of approximately 6.0, and releases the remaining 80% of its components in about 7 hrs. B.i.d. dosing occurs at mealtime, typically breakfast or the first meal of the day and dinner or the third meal of the day.

Bilayer Tablet of Composition B

The chemosensory receptor ligands of Composition B (Rebaudioside A, stevioside, sucralose, Metformin HCl and L-glutamine) are formulated into bilayer tablet cores with the excipients as indicated in the following table (expressed in proportional units).

|  | IR | CR7 | CR4 | CR2 |
|---|---|---|---|---|
| Stevioside | 12.65 | 13.72 | 13.72 | 13.72 |
| Sucralose | 12.65 | 13.72 | 13.72 | 13.72 |
| Metformin HCl | 3.17 | 3.43 | 3.43 | 3.43 |
| L-Glutamine | 6.35 | 6.86 | 6.86 | 6.86 |
| Reb A | 25.38 | 27.45 | 27.45 | 27.45 |
| Prosol HD90 | 28.71 | 9.6 | 12.0 | 15.6 |
| Pruv | 3.0 | 3.0 | 3.0 | 3.0 |
| Croscarmelose Sodium | 4.0 | — | — | — |
| Methocel K4M | — | 11.0 | 8.6 | 5.0 |
| Klucel EXF | 4.0 | 4.0 | 4.0 | 4.0 |

The IR column of the above table refers to 20% of the mass of the bilayer tablet that releases its contents in about 15 to about 60 minutes. CR2, CR4, and CR7 refer to the remaining 80% of the components that release over approximately 2, 4 or 7 hrs. A bilayer tablet core has an IR compound and one of the CR, CR4 or CR7 components. With the exception of stevioside (>90 purity), the purity of all ingredients is >99.8% and the concentrations of all impurities for all ingredients are significantly below the limits set under International Conference on Harmonisation (ICH) guidance.

The bilayer tablet cores are coated with the following coating compositions for release at the indicated pH in the following table (expressed in proportional units).

| Composition | IR/CR 2 hr pH 5.5 | IR/CR 4 hr pH 6.0 | IR/CR 4 hr pH 6.5 | IR/CR 7 hr pH 6.0 |
|---|---|---|---|---|
| Eudragit L30 D55 | 833.4 | 750.06 | 625.05 | 750.06 |
| Eudragit FS 30D | 0 | 83.34 | 208.35 | 83.34 |
| Talc | | | 125.0 | |
| Triethylcitrate | | | 25.0 | |
| Water | | | 1016 | |

Example 3

Exemplary Metformin Bilayer Tablet Composition and its Administration.

| Composition C | | | |
|---|---|---|---|
| Chemosensory Receptor Ligand | Per layer IR Layer/Enteric layer (mg) | Total Dose (mg) | B.i.d. Daily Total |
| Metformin HCl | 50/200 | 250 | 500 |

The biguanide or related heterocyclic compound of Composition C (metformin) is formulated into bilayer tablet cores with the excipients as indicated in the following table (expressed in proportional units).

|  | IR | CR4 |
|---|---|---|
| Metformin HCl | 60.29 | 65.2 |
| Prosol HD90 | 28.71 | 12.0 |
| Pruv | 3.0 | 3.0 |
| Croscarmelose Sodium | 4.0 | — |
| Methocel K4M | — | 8.6 |
| Klucel EXF | 4.0 | 4.0 |

The IR column of the above table refers to the immediate release component of the bilayer tablet that releases its contents (20% metformin) in about 15 to about 60 minutes. CR4 refer to the remaining 80% of the metformin that release over approximately 4 hrs. The purity of all ingredients is >99.8% and the concentrations of all impurities for all ingredients are significantly below the limits set under International Conference on Harmonisation (ICH) guidance.

Both the immediate release and extended release tablet cores of the bilayer tablet are coated with the one of following coating compositions for release at the indicated pH in the following table (expressed in proportional units).

| Composition | pH 5.5 | pH 6.0 | pH 6.5 | pH 6.0 |
|---|---|---|---|---|
| Eudragit L30 D55 | 833.4 | 750.06 | 625.05 | 750.06 |
| Eudragit FS 30D | 0 | 83.34 | 208.35 | 83.34 |
| Talc | | | 125.0 | |
| Triethylcitrate | | | 25.0 | |
| Water | | | 1016 | |

Example 4

Plasma Absorption of Metformin is Unnecessary for Enteroendocrine Production of PYY, GLP-1A and GLP-1T and Reduction of Glucose and Insulin Example 4.1 Materials and Methods Population: Approximately 18 eligible male and female subjects, 18 to 65 years of age, with a BMI of 25.0 to 35.0 kg/m$^2$, were randomized in this study. To be eligible, each subject also met the following criteria: (a) was not breast-feeding; (b) had a negative pregnancy test result (human chorionic gonadotropin, beta subunit); (c) surgically sterile, postmenopausal, or if of childbearing potential, practiced appropriate birth control during the entire duration of the study; (d) had a physical examination with no clinically significant abnormalities, including but not limited to the following conditions: (i) Hepatic disease; (ii) Renal disease; (iii) gastrointestinal disease; (iv) Endocrine disorder, including diabetes; (v) Cardiovascular disease; (vi) Seizure disorder; (vii) Organ transplantation; and (viii) Chronic infection; and (e) an ability to understand and willingness to adhere to protocol requirements.

Formulations

A metformin formulation that results in plasma absorption, EFB0026, (500 mg metformin, no coating; labeled "Metformin" in the figures) and, a metformin formulation that minimizes plasma absorption, EFB0027, (500 mg metformin with pH 6.5 enteric coating; labeled "Re-Metformin" in the figures) were supplied to the site as bulk tablets packaged in screw cap containers labeled with container number and lot number. All study medications were stored in cool and dry conditions as indicated on the label, and used only as directed by study personnel.

Administration

Study medication was dispensed by an unblinded site pharmacist or study personnel according a randomization scheme at Visits 2 and 4. At the end of Visits 2 and 4, subjects were discharged from the clinic with assigned study medications and with instructions for self-administration until they returned for their next study visit (Visit 3 or 5).

Study medication was administered orally as intact tablets (swallowed whole, not chewed or crushed), and with water. The first dose and the last two doses of study medication for each treatment period were administered to subjects by qualified study site personnel (first dose at Visits 2 and 4 and last two doses at Visits 3 and 5). Subjects self-administered the assigned study medications according to instructions until they returned for their next study visit (Visit 3 or 5).

Study site personnel contacted subjects by telephone on the second day of dosing of each treatment period to assess compliance and adverse events through non-directed questioning. If the subject was experiencing significant gastrointestinal symptoms, at the Investigator's discretion, subjects were instructed not to dose escalate. Instructions for self-administration of study medications were as follows:

Take one tablet by mouth with some water tonight before bedtime, one tomorrow morning, and one tomorrow night before bedtime Study site personnel will telephone you tomorrow (Day 2) to remind you to increase your dose for the next day (Day 3) to two tablets in the morning and two tablets before bedtime and, for the following day (Day 4), two tablets on the morning before you return later that day for your next visit When you take your tablets, swallow them whole by mouth with water, and do not crush or chew your tablets.

The procedures performed during the study are listed in the following three tables below.

TABLE 1

Study Plan (Protocol LCPOC6)

| | | Treatment Period 1 | | | Treatment Period 2 | | | |
| --- | --- | --- | --- | --- | --- | --- | --- | --- |
| Evaluation | Screen | Baseline of Period 1 Visit 2 | Day 2 of Treatment Period Phone Call [1] | End of Period 1 Visit 3 | Baseline of Period 2 Visit 4 | Day 2 of Treatment Period Phone Call [1] | End of Period 2/Study Termination Visit 5 | Early Termination |
| Fast (≥8 Hours Overnight) | X | X | | X | X | | X | |
| Informed Consent | X | | | | | | | |
| Complete Medical History | X | | | | | | | |
| Physical Examination and Height | X | | | | | | | |
| Body Weight and Vital Signs | X | X | | X | X | | X | X |
| Chemistry, Hematology, Urinalysis | X | | | | | | X | X |
| Pregnancy Test (Females) [2] | X | | | | | | X | X |
| Randomization | | X | | | | | | |
| Timed Blood Sampling [3] | | X | | X | X | | X | |
| Study Medication Administration [4] | | X | | X | X | | X | |
| Dispense Study Medication | | X | | | X | | | |
| Study Medication Compliance Assessment and Collection | | | | X | | | X | |
| Dose Escalation Phone Call | | | X | | | X | | |
| Concomitant Medications Assessment | X | X | | X | X | | X | X |

[1] Phone calls to assess compliance and adverse events through non-directed questioning and to remind subjects to dose escalate
[2] Pregnancy test required on all female subjects unless subject has had a hysterectomy or is postmenopausal.
[3] GLP-1, PYY, plasma glucose, insulin, and triglycerides at Visits 2 and 4; GLP-1, PYY, plasma glucose, insulin, triglycerides and metformin at Visits 3 and 5. After meal challenge at Visit 2 and Visit 4. Evening dose on Day 4 and morning dose on Day 5 at Visit 3 and Visit 5.

TABLE 2

Schedule of Standardized Breakfast and Blood Sampling Profile at Visit 2 and Visit 4

| Time (minutes) | Collect 6-mL blood samples [1] | Standardized Breakfast Administration [2] |
| --- | --- | --- |
| −15 | X | |
| −5 | X | |
| 0 | | X |
| 30 | X | |
| 45 | X | |
| 60 | X | |
| 90 | X | |
| 120 | X | |
| 150 | X | |
| 180 | X | |
| 210 | X | |
| 240 | X | |
| 270 | X | |
| 300 | X | |
| 330 | X | |

[1] 6-mL blood volume total per sampling time point for assessment of PYY, GLP-1, plasma glucose, insulin, and triglycerides.
[2] Subjects are to be instructed to consume the standardized breakfast within 20 minutes.

TABLE 3

Day 5 Schedule of Dosing, Standardized Breakfast
and Blood Sampling Profile at Visit 3 and Visit 5

| Time (minutes) | Collect 6-mL blood samples [1] | Standardized Breakfast Administration [2] | Dose Study Medication | Collect 2-mL blood sample [3] |
|---|---|---|---|---|
| −245 | | | | X |
| −240 | | | X | |
| −120 | | | | X |
| −15 | X | | | |
| −5 | X | | | X |
| 0 | | X | | |
| 30 | X | | | X |
| 45 | X | | | X |
| 60 | X | | | X |
| 90 | X | | | X |
| 120 | X | | | X |
| 150 | X | | | X |
| 180 | X | | | X |
| 210 | X | | | X |
| 240 | X | | | X |
| 270 | X | | | X |
| 300 | X | | | X |
| 330 | X | | | X |
| 360 | | | | X |
| 420 | | | | X |
| 480 | | | | X |

[1] 6-mL blood volume total per sampling time point for assessment of PYY, GLP-1, plasma glucose, insulin, and triglycerides.
[2] Subjects are to be instructed to consume the standardized breakfast within 20 minutes.
[3] 2-mL blood volume total per sampling time point for assessment of metformin.

Study Procedures

Visit 1 Screening Procedures

At Visit 1, subjects arrived at the clinic after fasting overnight for at least 8 hours and the following procedures were performed:

Signed Informed Consent form was obtained
Subject eligibility based on inclusion and exclusion criteria was assessed
Complete medical history, including menopausal status (females) was taken
Concomitant medications were reviewed
Physical examination was performed
Body weight and height were measured
Vital signs (sitting systolic and diastolic blood pressure, heart rate, and body temperature) were measured
Blood sample (fasting samples) for clinical chemistry and hematology was collected
Urine for urinalysis was collected
For female subjects of childbearing potential, serum or urine pregnancy test was performed Individuals were disqualified if results of any laboratory test are abnormal and clinically significant as judged by the investigator or medical monitors. Individuals with an abnormal test may have been re-evaluated for study enrollment within 2 weeks of Screening by having that test repeated once with acceptable results as judged by the investigator and medical monitor (or designees).

When all of the screening results were available, individuals were notified by telephone or other means of their eligibility status. Those who qualified were eligible return to the clinical study site within 14 days from the start of Screening to be enrolled and randomized at Visit 2.

Visit 2 (Baseline of Treatment Period 1): Enrollment and Randomization

Subjects arrived at the clinic the evening prior to the standardized meal challenge. The following procedures were performed:

Study eligibility was confirmed
Treatment sequence for eligible subjects were randomized
Concomitant medications and adverse events were reviewed
Vital signs (sitting systolic and diastolic blood pressure, heart rate, and body temperature) and body weight were measured
At t=0 min, subjects began consumption of the −1000 kcal standardized breakfast which was completely consumed within 20 minutes
Fourteen 6-mL blood samples were drawn at the following time-points relative to administration of the standardized breakfast for PYY, GLP-1, glucose, insulin and triglycerides (see Table 2): t=−15, −5, 30, 45, 60, 90, 120, 150, 180, 210, 240, 270, 300, and 330 min
The first dose of randomized study medication (1 tablet) was administered by site personnel following the last blood draw at 330 minutes
Subjects were dispensed with assigned study medication and instructions to self-administer the assigned study medication until their next clinic visit
Subjects returned to the study site with the remainder of their study medications on the fourth day of the treatment period for Visit 3

On Day 2 of the treatment period, study site personnel made a scheduled telephone call to address any questions, to evaluate study medication administration, and to remind the subject to increase the dose on Day 3 of treatment.

Visit 3 (End of Treatment Period 1)

Subjects arrived at the clinic the evening prior to the standardized meal challenge on the fourth day of the first treatment period, before the evening dose. The following procedures were performed at Visit 3:

Concomitant medications and adverse events were reviewed
Vital signs (sitting systolic and diastolic blood pressure, heart rate, and body temperature) and body weight were measured
Dinner for the fourth day of the first treatment period was provided to subjects at the study site
The evening dose for the fourth day of the treatment period was administered after dinner at the study site
All unused study medications from subjects after their evening dose were collected
At t=−240 min the next morning, subjects were administered the last dose of assigned study medication for the first treatment period
At t=−0 min, subjects began consumption of the −1000 kcal standardized breakfast which should be completely consumed within 20 minutes
Blood was drawn at t=−245, −120, −15, −5, 30, 45, 60, 90, 120, 150, 180, 210, 240, 270, 300, 330, 360, 420, and 480 min relative to administration of the standardized breakfast, for metformin, and PYY, GLP-1, glucose, insulin and triglycerides (see Table 3 for details)
Lunch may have been provided to subjects after the 360 min blood draw
Subjects were discharged from the site after finishing Visit 3 procedures, and returned to the site for Visit 4 after a washout period of at least 7 but no more than 14 days for baseline assessment of Treatment Period 2

Visit 4 (Baseline of Treatment Period 2)

Subjects arrived at the clinic the evening prior to the standardized meal challenge. The following procedures were performed:

Concomitant medications and adverse events were reviewed

Vital signs (sitting systolic and diastolic blood pressure, heart rate, and body temperature) and body weight were measured At t=0 min, subjects began consumption of the −1000 kcal standardized breakfast, which was completely consumed within 20 minutes Fourteen 6-mL blood samples were drawn at the following time-points relative to administration of the standardized breakfast for PYY, GLP-1, glucose, insulin and triglycerides (see Table 2): t=−15, −5, 30, 45, 60, 90, 120, 150, 180, 210, 240, 270, 300, and 330 min The first dose of randomized study medication for the second treatment period (1 tablet) was administered by site personnel following the last blood draw at 330 minutes Subjects were dispensed the assigned study medication for the second treatment period with instructions to self-administer the study medication until their next clinic visit Subjects returned to the study site with the remainder of their study medication on the fourth day of the second treatment period for Visit 5

On Day 2 of the treatment period, study site personnel made a scheduled telephone call to address any questions, to evaluate study medication administration, and to remind the subject to increase the dose on Day 3 of treatment.

Visit 5 (End of Treatment Period 2): Study Termination

Subjects arrived at the clinic before the evening dose of the fourth day of the second treatment period. The following procedures were performed at Visit 5:

Concomitant medications and adverse events were reviewed

Vital signs (sitting systolic and diastolic blood pressure, heart rate, and body temperature) and body weight were measured Dinner for the fourth day of the second treatment period was provided to subjects at the study site The evening dose for Day 4 of the second treatment period was administered after dinner at the study site All unused study medications from subjects after their evening dose were collected Blood sample for clinical chemistry, hematology, and serum pregnancy test (females of childbearing potential) was collected Urine for urinalysis was collected At t=−240 min the next morning, subjects were administered the last dose of assigned study medication for the second treatment period At t=−0 min, subjects began consumption of the −1000 kcal standardized breakfast which was completely consumed within 20 minutes Blood was collected at t=−245, −120, −15, −5, 30, 45, 60, 90, 120, 150, 180, 210, 240, 270, 300, 330, 360, 420, and 480 min relative to administration of the standardized breakfast, for metformin, and PYY, GLP-1, glucose, insulin and triglycerides (see Appendix 3 for details)

Lunch may have been provided after the 360 min blood draw

Subjects who complete all study procedures at Visit 5 were considered study completers.

Early Termination

Subjects who withdrew from the study prior to completion of Visit 5 completed early termination procedures in a timely manner, as follows:

Review of adverse events (AEs) and concomitant medications

Measurement of body weight

Measurement of vital signs (sitting systolic and diastolic blood pressure, heart rate, and body temperature)

Collection of used and unused study medication

Blood sample collection for clinical chemistry, hematology, and serum pregnancy test (females of childbearing potential)

Collection of urine samples for urinalysis

Pharmacodynamic Assessments

Blood samples were collected according to the schedules presented in Tables 1, 2, and 3, and as described above. Fasting and postprandial plasma concentrations of gut hormones GLP-1 and PYY, as well as concentrations of plasma glucose, insulin, and triglycerides were measured by analytical methods. Blood samples from each visit was processed and stored at −70° C. for future exploratory analysis of additional hormones.

Pharmacokinetic Assessments

Blood samples were collected according to the schedules presented in Tables 1, 2, and 3, and as described above. Plasma metformin concentrations were measured by analytical methods. Blood samples from each visit was processed and stored at −70° C. for future exploratory analysis of additional hormones.

Clinical Laboratory Evaluations

Samples were collected according to the schedules presented in Tables 1, 2 and 3, and in the preceding section.

Chemistry

Chemistry assessments included the following: urea nitrogen, creatinine, total protein, albumin, uric acid, total bilirubin, alkaline phosphatase, alanine aminotransferase, aspartate aminotransferase, gamma glutamyltranspeptidase, creatine phosphokinase, glucose, sodium, potassium, chloride, bicarbonate, phosphorus, lactate, and calcium (or other routine chemistry panels as approved by the sponsor).

Hematology

Hematology assessments included the following: red cell count, hemoglobin, hematocrit, white cell count, platelets, differential count, mean cell volume, mean corpuscular hemoglobin, and mean corpuscular hemoglobin concentration (or other routine hematology assessments as approved by the sponsor).

Urinalysis

Urinalysis assessments included the following: pH, specific gravity, glucose, blood, ketones, and protein (or other routine urinalysis as approved by the sponsor).

Pregnancy Testing

All female subjects, regardless of childbearing status (unless subject is postmenopausal or has had a hysterectomy), provided blood or urine for pregnancy tests. Study medication was not administered unless a negative result is obtained.

Vital Signs and Other Observations Related to Safety

Clinically significant abnormalities in vital signs and other observations related to safety were followed up by the investigator and evaluated with additional tests if necessary, until the underlying cause is diagnosed or resolution occurred.

Vital Signs

Vital sign measurements included sitting systolic and diastolic blood pressure, heart rate, and body temperature. Vital signs were measured after the subject rested for approximately 5 minutes and with the subject in a sitting position. The blood pressure measurement was repeated after at least 30 seconds and the average of the two readings recorded.

Example 4.2: Results

Figure 2:
FIG. 2 shows the events during the treatment period of the study described in Example 5.

The study design and event timeline are shown in FIGS. 1-2. Shown in Tables 4 and 5 below are the resulting subject disposition and population (Table 4) and the demographic and baseline characteristics of 18 subjects (Table 5).

TABLE 4

Subject Disposition and Population

| Parameter | Result |
| --- | --- |
| Randomized | 18 |
| Completed | 17 |
| Withdrawal (positive drug test) | 1 |
| Evaluable Population | 16 |

2 subjects excluded from evaluable population; 1 withdrawn and 1 could not complete test meal at end of Treatment Period 2

TABLE 5

Demographic and Baseline Characteristics (n = 18)

| Parameter | Result |
| --- | --- |
| Gender (M/F) | 9/9 |
| Mean Age (yr) ± SD | 44 ± 10 |
| Race | 9 caucasian, 7 hispanic, 2 black |
| Mean BMI (kg/m2) ± SD | 29.3 ± 2.8 |

Figure 3:
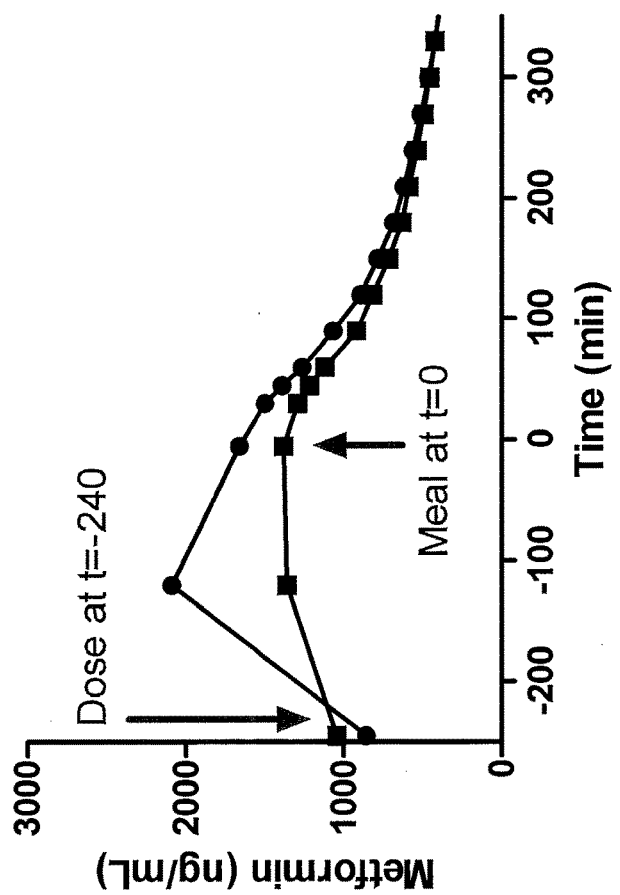
FIG. 3 shows the plasma concentration of Metformin (●) and Re-Metformin (■) (x-axis; ng/mL) as a function of time (y-axis; min) after ingestion at t=−240 and after a meal at t=0 min.

FIG. 3 demonstrates that ingestion of Re-Metformin minimizes adsorption of Metformin in the plasma compared to Metformin. The area under the curve (AUC) and Cmax values for Re-Metformin and Metformin are provided in Table 6 below.

| Metformin Plasma Pharmacokinetics | | |
| --- | --- | --- |
| | LS Mean Ratio ReMet/Metformin | P Value |
| Abs AUC | 0.83 | 0.02 |
| Abs Cmax | 0.73 | 0.003 |
| Incremental Cmax | 0.45 | <0.001 |

Figure 4A:
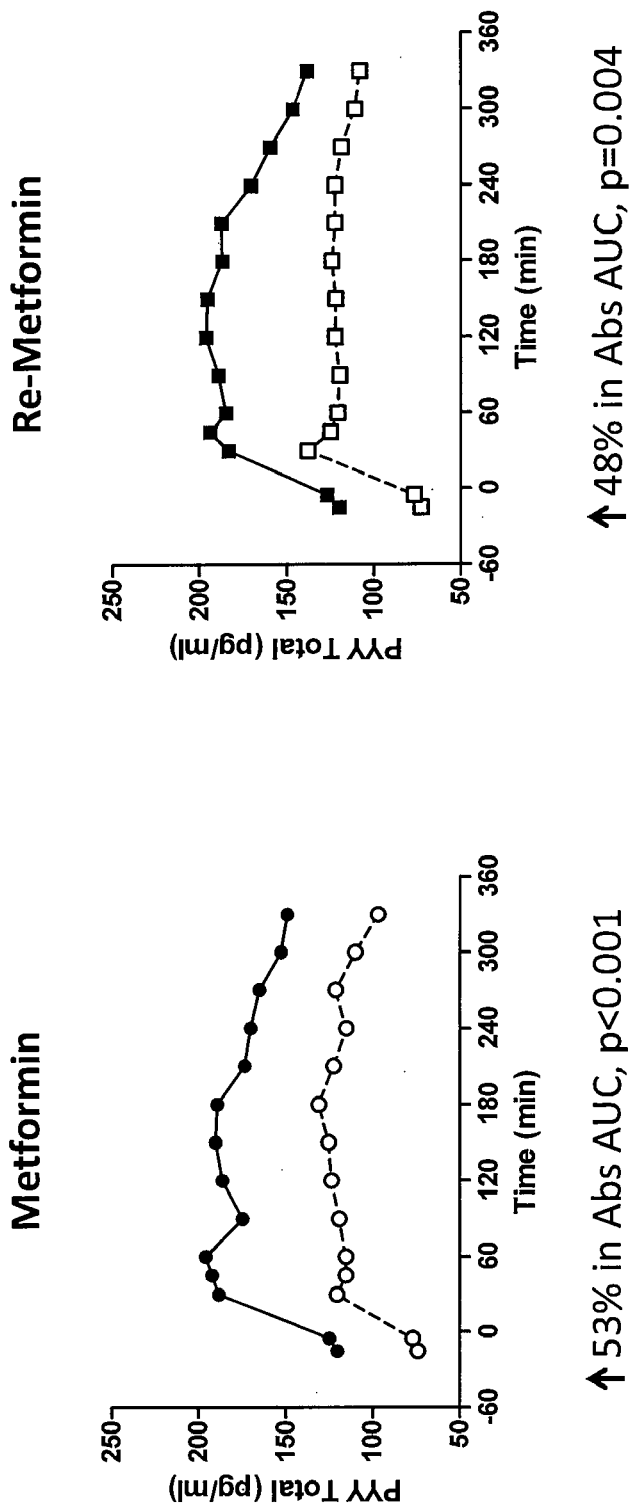
FIG. 4A shows the plasma concentration of PYY (x-axis; pg/mL) as a function of time (y-axis; min) in subjects at baseline (□,○) or after ingestion of either Metformin (●) or Re-Metformin (■) and after a meal at t=0 min.
Figure 4B:
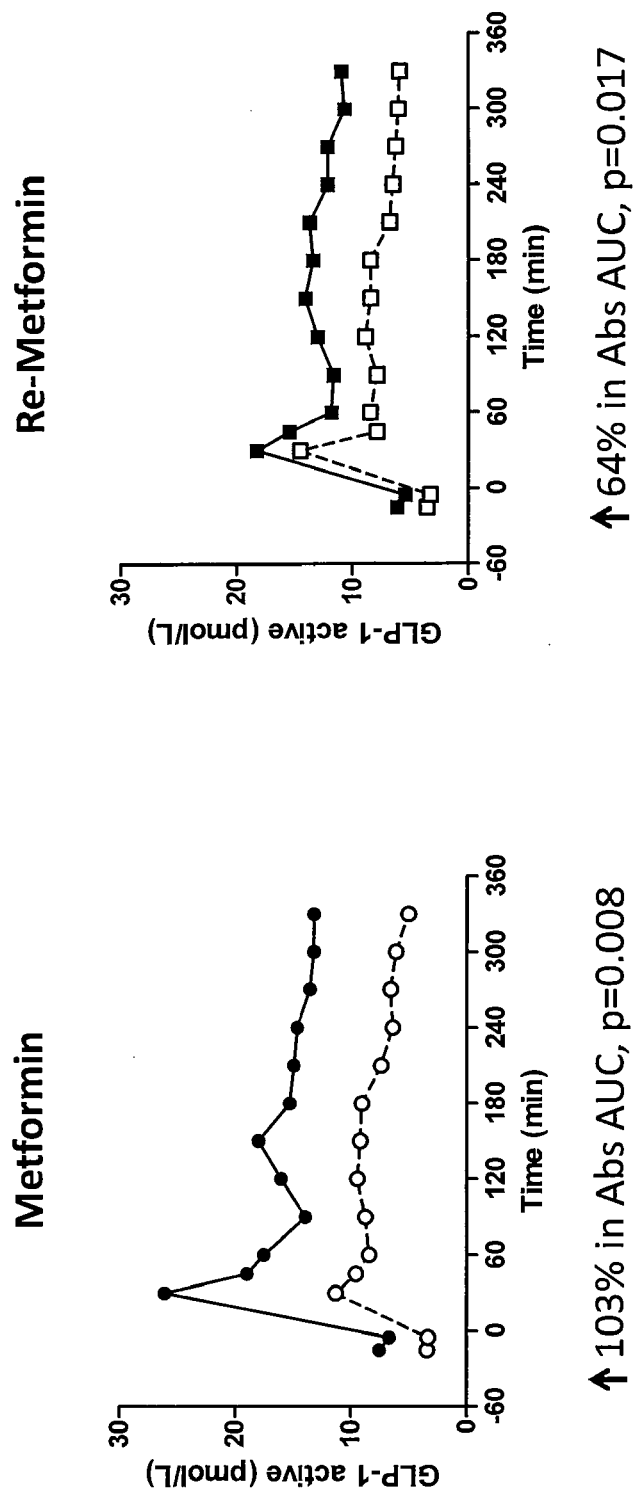
FIG. 4B shows the plasma concentration of active GLP-1(x-axis; GLP-1A pmol/L) as a function of time (y-axis; min) in subjects at baseline (□,○) or after ingestion of either Metformin (●) or Re-Metformin (■) and after a meal at t=0 min.
Figure 5A:
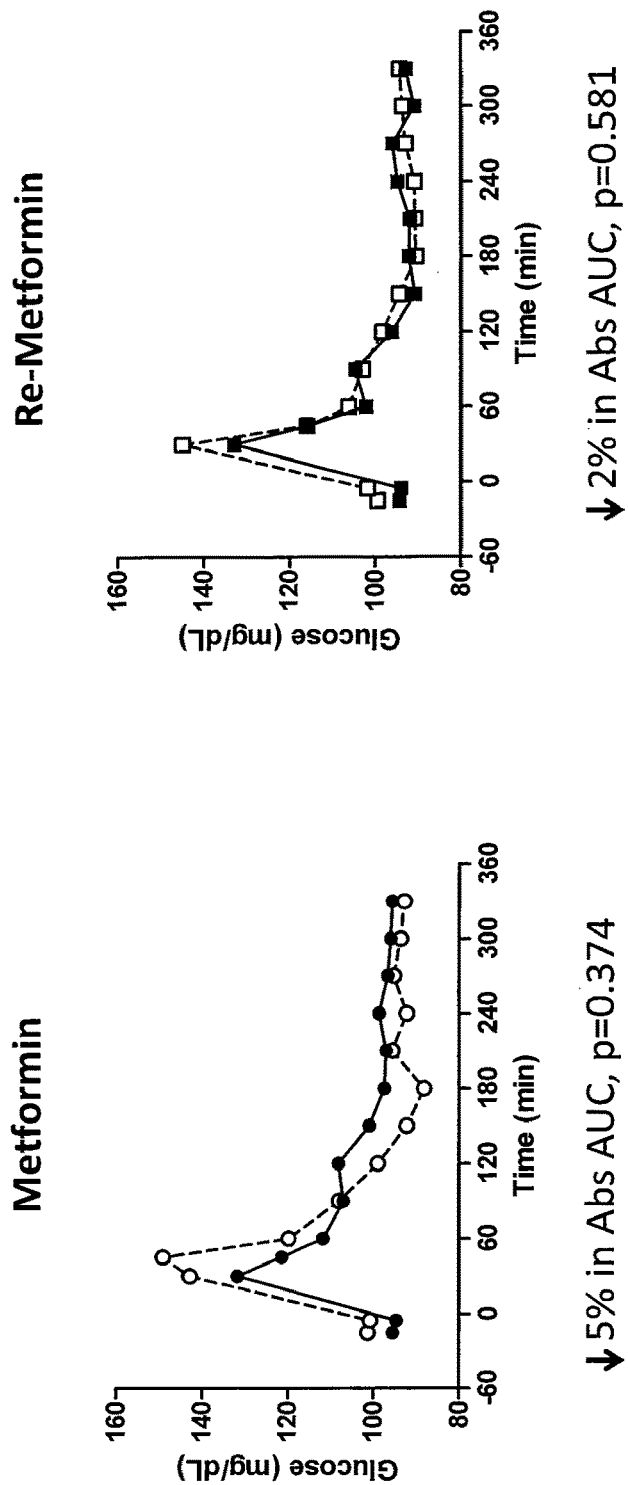
FIG. 5A shows the plasma concentration of glucose (x-axis; mg/dL) as a function of time (y-axis; min) in subjects at baseline (□,○) or after ingestion of either Metformin (●) or Re-Metformin (■) and after a meal at t=0 min.
Figure 5B:
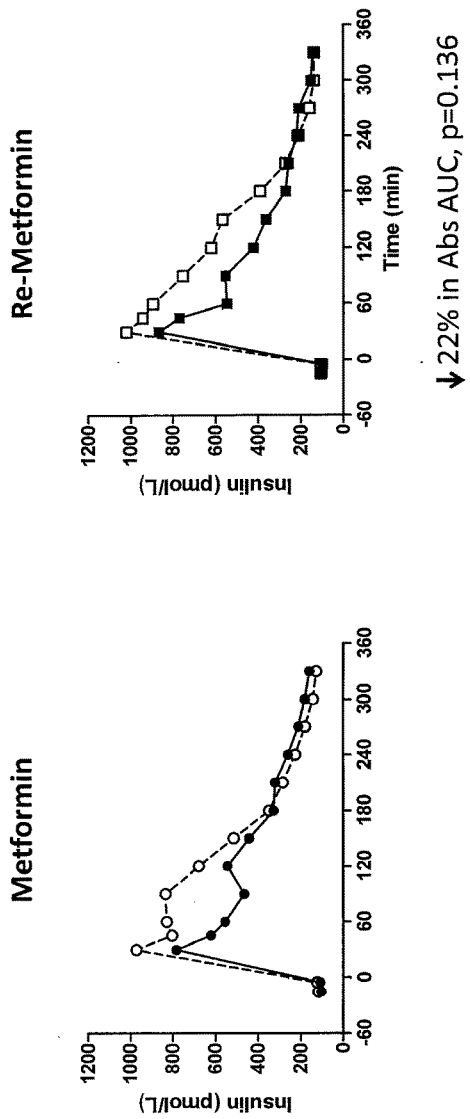
FIG. 5B shows the plasma concentration of insulin (x-axis; pmol/L) as a function of time (y-axis; min) in subjects at baseline (□,○) or after ingestion of either Metformin (●) or Re-Metformin (■) and after a meal at t=0 min. For FIGS. 5A-5B, percent decrease in Abs AUC is compared to baseline values.
Figure 6:
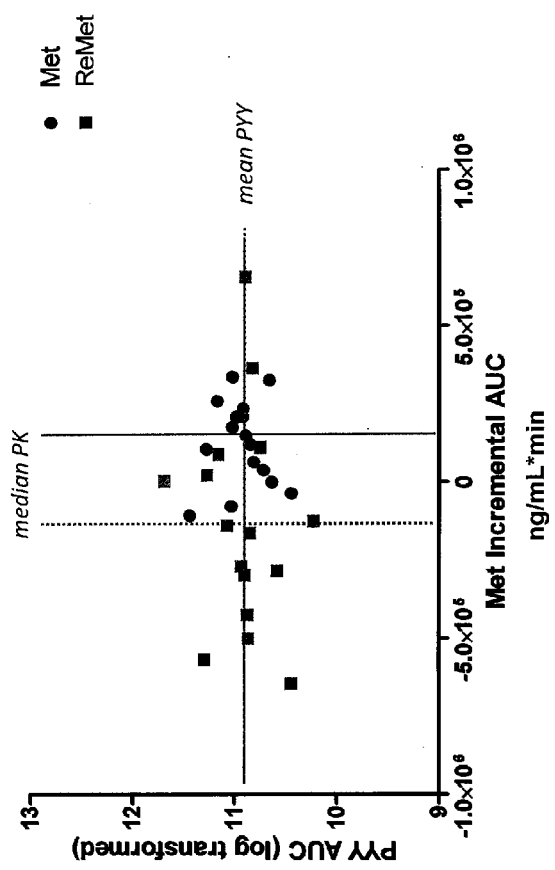
FIG. 6 is a graph that shows the area under the curve of PYY (x-axis; log transformed) as a function of the area under the curve of metformin (ng/mL*min) after ingestion of Metformin (●) and Re-Metformin (■).
Figure 7B:
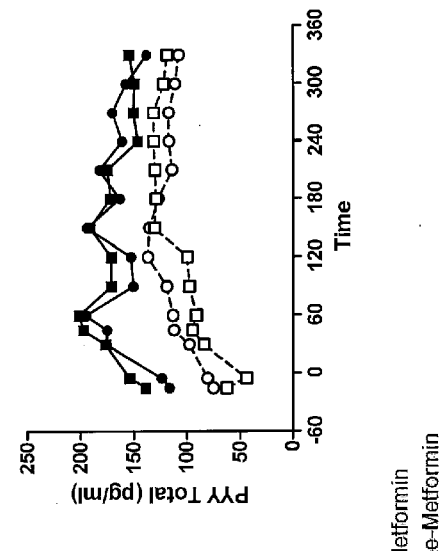
FIG. 7B shows the plasma concentration of PYY (x-axis; pg/mL) as a function of time (y-axis; min) in subjects at baseline (□,○) or after ingestion of either Metformin (●) or Re-Metformin (■) and after a meal at t=0 min.
Figure 7A:
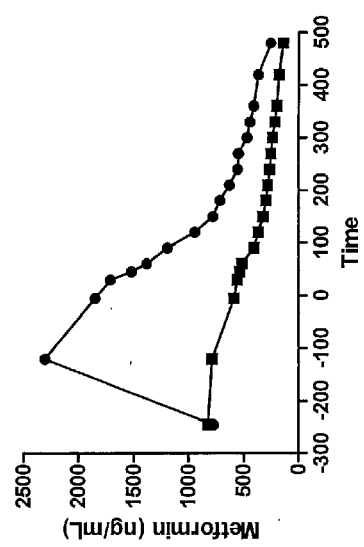
FIG. 7A shows the plasma concentration of Metformin (●) and Re-Metformin (■) (x-axis; ng/mL) as a function of time (y-axis; min) after ingestion at t=−240 and after a meal at t=0 min.
Figure 8:
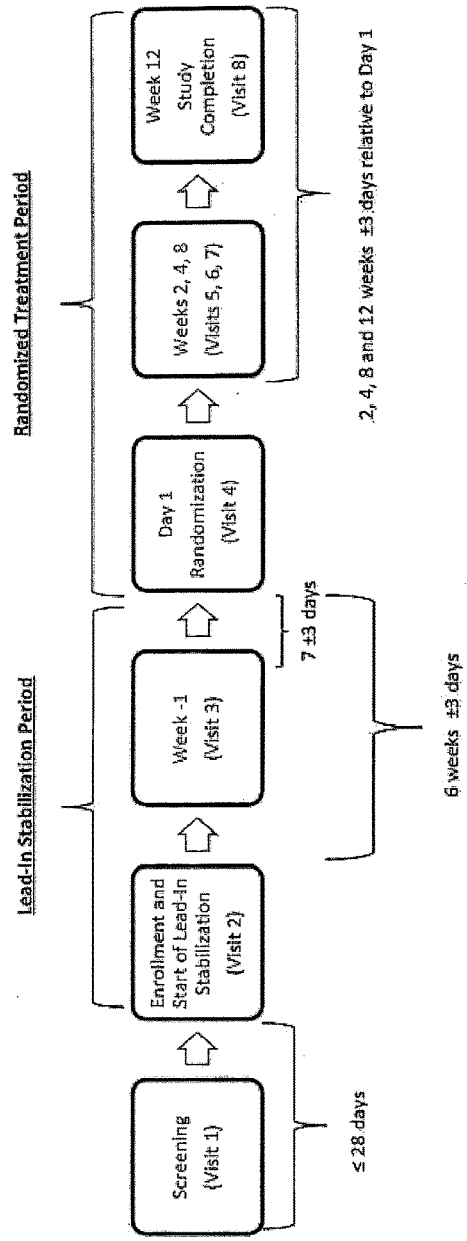
FIG. 8 is a flow diagram of a 12-week, randomized, double-blind, placebo-controlled, parallel-group, multi-center study to determine the safety and efficacy of twice daily administration of Re-Metformin in subjects with type 2 diabetes mellitus

FIG. 4A-C shows an increase in meal-enhanced gut hormones in 16 subjects after treatment of Re-Metformin comparable to that of Metformin, although treatment with Re-Metformin minimized the systemic level of metformin compared to Metformin (FIG. 3). Additionally, FIGS. 5A-B show a reduction in meal-enhanced glucose and insulin after treatment with Re-Metformin in 16 subjects comparable to that of Metformin. FIG. 6 shows that treatment with Re-Metformin results in a similar PYY response as Metformin, but has a lower systemic exposure. FIGS. 7A-B show that the Metformin PK/PD relationship was dissociable in at least one patient.

Example 5

Evaluate Efficacy of Compounds Formulated for Release in the Lower Intestine, Including Those which May be Accompanied by Poor Absorption.

Key measurements to be taken include plasma concentrations of test compounds, influence on GLP-1 levels, influence on PYY levels, differences in glucose levels from an acute glucose tolerance test as well as insulin levels and differences in composition of intestinal microbiota as measured by 16S RNA based sequencing or chip analysis.

Materials and Methods (Adapted from: Dao T-M A, Waget A, Klopp P, Serino M, Vachoux C, Pechere L, Drucker D J, Champion S, Barthélemy S, Barra Y, Burcelin R, Sérée E. *Resveratrol Increases Glucose Induced GLP-1 Secretion in Mice: A Mechanism which Contributes to the Glycemic Control PLoS One* 2011; 6(6): e20700).

Representative Test Compound Formulation and Dosage

Two versions of the representative test compounds may be prepared, namely a regular version of 200 micron particle size solid material and a coated version, designed to release material in the lower intestine at pH 6.5, of 200 micron particle size. Each is formulated with an appropriate carrier (including but not limited to polysorbate 20 and polyglyceryl-3-dioleate). For some experiments the representative test compound is mixed with the diet for animal experiments at a dose ranging from of 1 mg/Kg/day to 60 mgs/kg/day. For other experiments a dose ranging from 1 mg/kg to 60 mgs/kg was formulated for delivery by oral gavage in either a solution or a as a uniform suspension of fine particles.

In addition, a 500 mg GLUCOPHAGE® XR (metformin hydrochloride) Extended-Release tablet with a target 6% enteric coating at pH 6.5 for release in the lower intestine is evaluated; as compared to standard non-coated GLUCOPHAGE® XR (metformin hydrochloride) Extended-Release tablet.

Animals and Treatment

General Methods

Eight week-old male C57Bl/6J wild type mice (Charles River are housed under specific pathogen-free conditions in individual ventilated cages with a 12-/12-hour light (10 p.m.)/dark (10 a.m.) cycle and with free access to water and food. Mice are maintained on a normal chow diet (energy content: 12% fat, 28% protein, and 60% carbohydrate), or a high-fat diet (energy content: roughly 72% fat comprising corn oil and lard, 28% protein, and, 1% carbohydrate) for five weeks. This diet induces diabetes before the onset of obesity (see, Cani P D, Amar J, Iglesias M A, Poggi M, Knauf C, et al. (2007) "Metabolic endotoxemia initiates obesity and insulin resistance." *Diabetes* 56: 1761-1772; Cani P D, Bibiloni R, Knauf C, Waget A, Neyrinck A M, et al. (2008) "Changes in gut microbiota control metabolic endotoxemia-induced inflammation in high-fat diet-induced obesity and diabetes in mice." *Diabetes* 57: 1470-1481; Knauf C, Cani P D, Ait-Belgnaoui A, Benani A, Dray C, et al. (2008) "Brain glucagon-like peptide 1 signaling controls the onset of high-fat diet-induced insulin resistance and reduces energy expenditure." *Endocrinology* 149: 4768-4777; Cani P D, Neyrinck A M, Fava F, Knauf C, Burcelin R G, et al. (2007) "Selective increases of bifidobacteria in gut microflora improve high-fat-diet-induced diabetes in mice through a mechanism associated with endotoxaemia." *Diabetologia* 50: 2374-2383.) Food intake, body weight, and glucose tolerance are measured by standard methods as previously described (Riant E, Waget A, Cogo H, Arnal J, Burcelin R, et al. (2009) "Estrogens protect against high-fat diet-induced insulin resistance and glucose intolerance in mice." *Endocrinology* 150: 2109-2117). All animal experimental procedures are carried out in an AAALAC qualified facility and are further approved by the local animal ethical committee. Statistical significance was typically achieved by having n=6 or greater in each arm of each study, including controls.

Acute Experiments

For acute experiments the representative test compounds are formulated for oral gavage as described above and are administered twice daily over a period of 24 to 48 hrs.

Chronic Experiments

For chronic experiments the representative test compounds are formulated in chow as described above and are administered with chow on a twice daily basis over a 28 day period. Where analysis of intestinal microbiota are part of the protocol, faeces are collected from each mouse in all arms of study at end of day 1, end of day 28 and conserved for later analysis/shipping by flash freezing at −80° C. In addition, at the end of the experiment, caeca are dissected from each mouse, collected and conserved for later analysis/shipping by flash freezing at −80° C.

Oral Glucose Tolerance Test and Insulin Assays

An oral glucose tolerance test (OGTT, 2 g/kg of glucose) is performed in mice previously fasted for 6 h after acute or chronic treatment. Blood glucose concentrations are monitored from the tip of the tail vein with a standard portable glucometer (Onetouch from Life Scan or equivalent) at −30, 0, 30, 60, 90 and 120 min after oral glucose administration, as previously described. Area under the curve (AUC) (30-90) is calculated for each group of mice. Plasma insulin concentration is determined by ELISA (for example Mercodia, Uppsala, Sweden) by using 10 µl of plasma from normal chow and HFD representative test article treated mice.

GLP-1 Measurement in Plasma from Portal Vein Blood Samples

For plasma portal vein GLP-1 quantification, mice (in fed state) are rapidly anesthetized by intra-peritoneal injection (0.1 ml/10 mg body weight) of Ketamine (Vibrac) and Xylazine hydrochloride 2% RompunH (Bayer) in sodium chloride (0.9%; 2:1:7 v/v/v), dissected and the portal vein blood samples are collected in EDTA tubes (Sarstedt, Numbrecht, Germany) containing a cocktail of enzyme inhibitors including a DPP-4 inhibitor (Linco Research, St Charles, Mo., USA). Concentrations of GLP-1 (7-36) amide are determined using an ELISA method (Glucagon-Like-Peptide-1 active ELISA kit, Millipore).

PK Measurements by LC-MS or LC-MS/MS

An appropriately sensitive assay is established for each of the representative test compounds in either plasma or whole blood, using either a PE Sciex 4000, a PE Sciex 5000 (triple quadrupole tandem mass spectrometers) or a Thermo LCQ ion trap mass spectrometer. Blood samples are collected from the tail vein of each mouse at defined intervals on day 1 of the studies (both chronic and acute) and day 28 of the studies (chronic only), mixed with a cocktail of enzyme inhibitors plus EDTA then analyzed directly (LC/MS/MS).

RNA Extraction and Real Time PCR

Total RNA was isolated from tissues using Trizol reagent (Life Technologies) and quantified by NanoDrop (NanoDrop technologies Inc.). Total RNA (1 g) is reverse transcribed using Moloney murine leukemia virus reverse transcriptase (Life Technologies) and random primers at 42° C. for 1 h. The expression of target genes is determined using the Stratagene Mx 3005p. The mRNA concentration of target genes is normalized to levels of β2-actin mRNA and the results are expressed as relative expression levels (REL). The data are quantified by the method of 2-DDCt.

Intestinal Microflora Characterization

Total DNA is isolated from caecum using Trizol reagent (Life Technologies) and is amplified by PCR, targeting the V3 region of the 16S rRNA gene using the universal bacterial primers HDA1-GC and HDA2 (Table 1). Each reaction mixture (25 µl) contains 4 µl of DNA diluted to 50 ng/µl, deoxynucleoside triphosphate (Sigma-Aldrich) at a concentration of 200 mM, 0.3 µM of each primer, and 0.07 µl of Taq polymerase (Sigma-Aldrich). The following amplification program is used: 94° C. for 5 min, 30 cycles consisting of 94° C. for 30 s, 55° C. for 45 s, and 72° C. for 60 s, and 30 min at 72° C. Denaturing gradient gel electrophoresis (DGGE) is then performed by using DGGE 2401 systems (CBS & Scientific Co.) and 8% polyacrylamide gels with a 35-55% gradient of urea (99.0-100.5%—Sigma-Aldrich) and formamide (99+%—Sigma-Aldrich), which increases in the direction of electrophoresis. Electrophoretic runs are in a Tris-acetate-EDTA buffer (40 mmol/l Tris, 20 mmol/l acetic acid, and 1 mmol/l EDTA) at 60 V and 60° C. for 18 h. Gels were stained with SYBR Safe 16 (Life Technologies) for 30 min, rinsed with deionized water, then scanned and analyzed by using Typhoon 9400 Variable Mode Imager (Amersham Biosciences). Hierarchical clustering is performed by using Permutmatrix 1.9.3.0 (Caraux G, Pinloche S (2005) "PermutMatrix: a graphical environment to arrange gene expression profiles in optimal linear order." *Bioinformatics* 21: 1280-1281).

Weight Loss

Treated and untreated animals will be weighed periodically to measure weight gain or loss of the treated animals compared to the control group.

Statistical Analysis

Results are expressed as means±SEM. Statistical analyses is performed using GraphPad Prism version 5.0 for windows (GraphPad Software, San Diego, Calif.; www.graphpad.com). The level of significance is set at $p<0.05$.

Exemplary test compounds representative of Formulas I, IA, II, III and IV are tested in the above assays as follows. For example:

Biguanides: Formula (I)

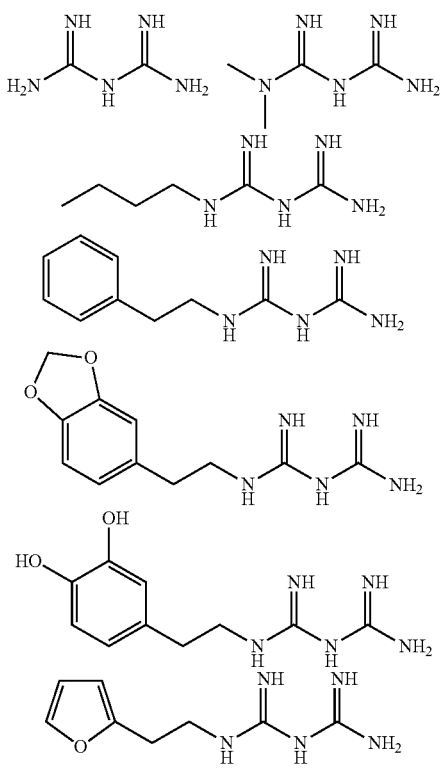

301
-continued
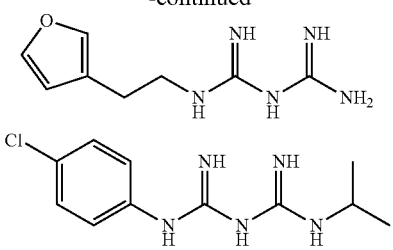
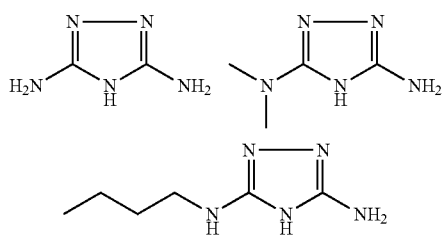
Triazoles: Formula (IA)
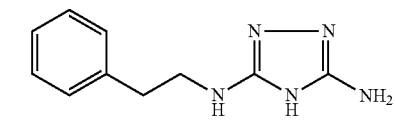
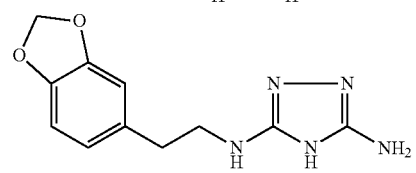
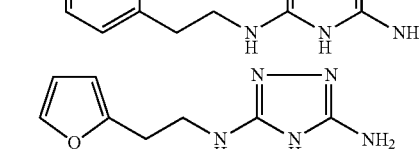
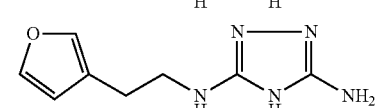
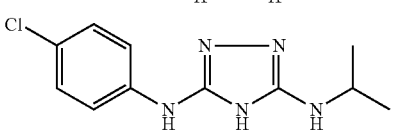
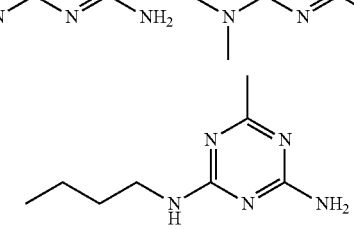
Triazines: Formula (II)
302
-continued
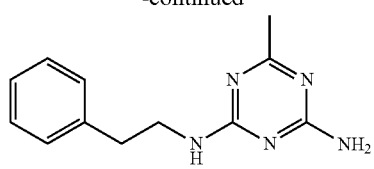
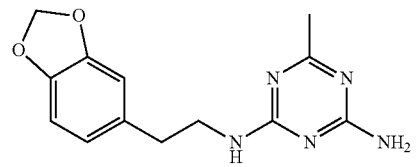
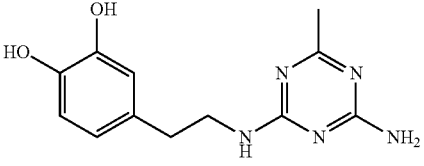
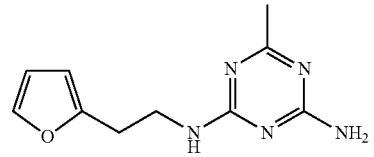
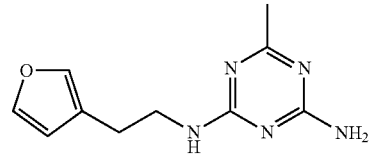
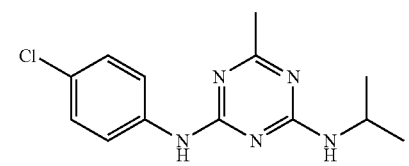
Dihydrotriazines: Formula (III)
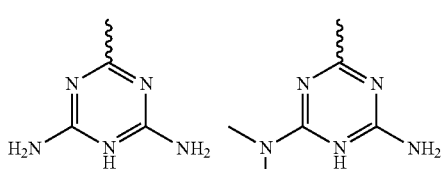
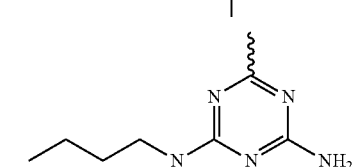
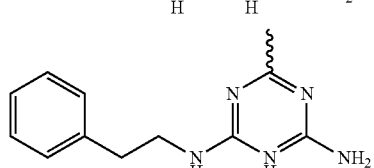
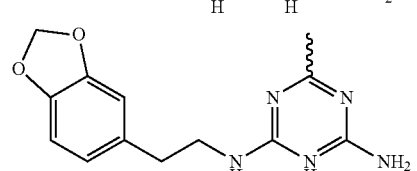

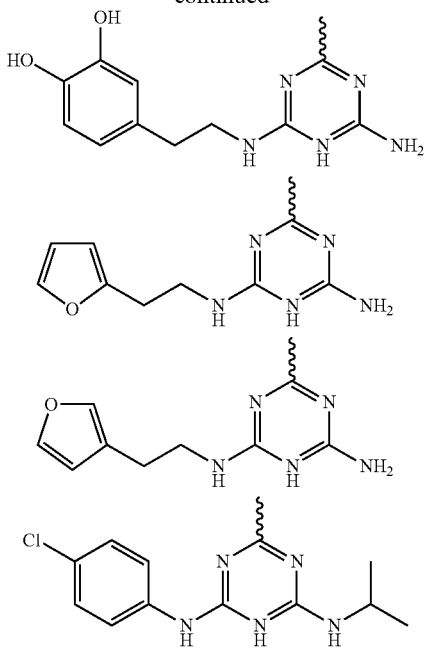

7-ring cyclic biguanides: Formula (IV)

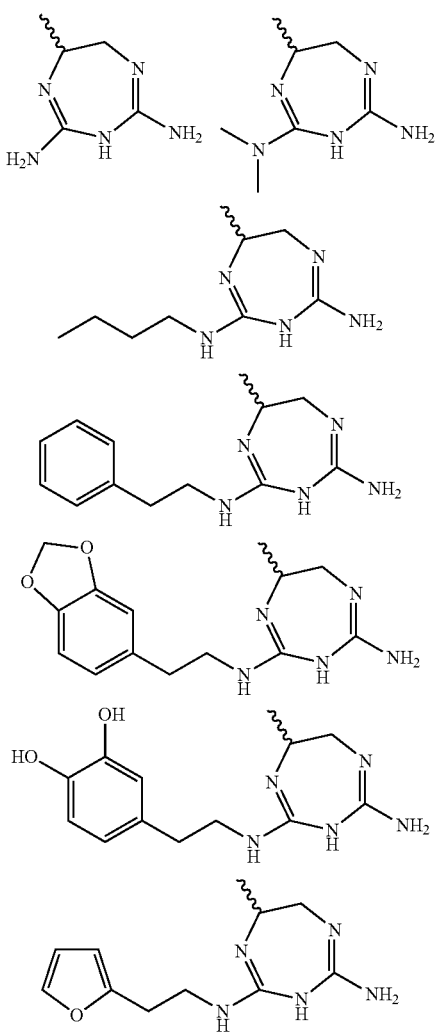

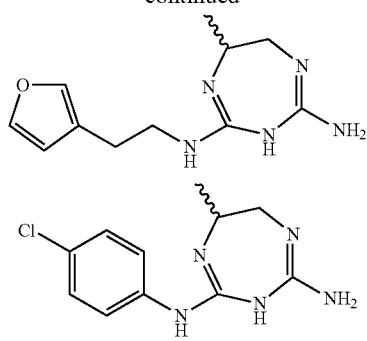

Example 5

A 12-Week, Randomized, Double-Blind, Placebo-Controlled, Parallel-Group, Multicenter Study to Determine the Safety and Efficacy of Twice Daily Administration of EFB0027 in Subjects with Type 2 Diabetes Mellitus The experiments described in Example 5 will (1) compare the effect on glycemic control, as assessed by HbA1c, of EFB0027 administered two times a day (BID) before the morning and evening meals to placebo for 12 weeks in subjects with type 2 diabetes mellitus, (2) assess the safety and tolerability of the range of doses of EFB0027 administered BID for 12 weeks in subjects with type 2 diabetes mellitus, (3) assess dose-dependence of effect on HbA1c of EFB0027 administered BID for 12 weeks in subjects with type 2 diabetes mellitus, and (4) compare EFB0027, EFB0026, a combination of EFB0026 and EFB0027, and placebo administered BID for 12 weeks in subjects with type 2 diabetes mellitus on the following:

Metformin pharmacokinetics (PK)

Change from baseline in HbA1c over time

Proportion of subjects who achieve HbA1c of <7% at 12 weeks

Body weight

Change from baseline in fasting plasma glucose, insulin, triglycerides, peptide YY (PYY), and glucagon-like peptide 1 (GLP-1) over time

Example 5.1: Materials and Methods

Example 5.1.1: Study Design

There will be 8 study visits; one screening visit (Visit 1) followed by 2 lead-in stabilization period visits (Visits 2 and 3) and 5 randomized treatment period visits (Visits 4 through 8).

Subjects will administer EFB0026 500 mg BID (1000 mg/day) for 2 weeks followed by 1000 mg BID (2000 mg/day) for 4 weeks during the single-blind, 6-week lead-in stabilization period.

At Visit 4, each of approximately 250 subjects will be randomized to one of 5 treatment groups in the proportion of 1:1:1:1:1. Randomization is to be stratified by Visit 3 (Week −1) HbA1c.

Treatment Groups

| Treatment Group | N | Treatment* |
|---|---|---|
| A | 50 | Placebo BID |
| B | 50 | EFB0026 500 mg BID |
| C | 50 | EFB0027 500 mg BID |
| D | 50 | EFB0026 1000 mg BID |
| E | 50 | EFB0027 1000 mg BID |
| F | 50 | EFB0026 500 mg plus EFB0027 1000 mg BID |

*EFB0026 = metformin HCl tablets (nonenteric-coated); EFB0027 = metformin HCl tablets with a pH 6.5 enteric coating (enteric-coated)
Treatment groups B and C will include 2 placebo tablets per dose and treatment groups D and E will include 1 placebo tablet per dose to preserve the blind.

At lead-in stabilization period and randomized treatment period visits (Visits 2, 3, 4, 5, 6, 7 and 8):

Subjects will arrive at the study clinic after having fasted overnight for at least 10 hours Subjects will be instructed not to take their morning dose of investigational product (IP) on the days of study visits until after the fasting blood draws are completed. The morning dose will be administered at the study site on the days of study visits (Visits 2 through 7 only)

A lipid panel will be collected at Screening, Day 1 and Week 12 (Visits 1, 3 and 7)

Fasting blood samples (one 6-mL sample and one 2-mL sample) will be collected for measurement of plasma metformin, glucose, insulin, GLP-1 and PYY at all study visits. Triglycerides will also be assessed at visits where a full lipid panel is not scheduled (Visits 2, 3, 5, 6 and 7)

HbA1c will be measured at Screening, Week −6, Week −1, Day 1, and Weeks 4, 8, and 12 (Visits 1, 2, 3, 4, 6, 7 and 8)

If a subject's underlying diabetes is inadequately controlled on randomized treatment and if the subject is experiencing hyperglycemia that is a significant worsening from the baseline condition (as indicated by an HbA1c value ≥10% or increase by more than 1.0% from the Visit 3 value), the subject will be withdrawn from the study and administered appropriate alternate therapy.

Example 5.1.2: Visit Structure

The study will consist of 8 study visits with one screening visit (Visit 1), 2 lead-in stabilization period visits (Visits 2 and 3) and 5 randomized treatment period visits (Visits 4, 5, 6, 7 and 8). Visit 1 procedures may be conducted over >1 day. The interval separating the beginning of Visit 1 procedures and Visit 2 will be ≤28 days. Visits 2 and 3 (Weeks −6 and −1) will be scheduled at −6 weeks±3 days and −1 week±3 days relative to Visit 4 (Day 1). Visits 5, 6, 7 and 8 will be scheduled at 2, 4, 8 and 12 weeks±3 days relative to Visit 4 (Day 1). Subjects may be discharged from the clinic after each visit's procedures are completed. Subjects will have completed the study after finishing Visit 8 procedures.

Example 5.1.3: Study Duration

Total study duration will be between 132 to 163 days depending on the number of intervening days between study visits.

Example 5.1.3: Study Population

Each subject of the study will meet the following criteria:
1. Is 18 to 65 years old at Screening (Visit 1).
2. Is diagnosed with Type 2 Diabetes Mellitus and is treated with diet and exercise alone, metformin alone, DPP-4 inhibitor alone, or a combination regimen of metformin with a DPP-4 inhibitor (stable regimen for a minimum of 2 months at Visit 1).
3. Has an HbA1c 6.5 to 9.0% (inclusive) at Visit 1 and Visit 3.
4. Has serum creatinine below the upper limit of normal at Visit 1 and an estimated creatinine clearance above 80 using the Crockroft and Gault equation (CrCl= [(140−age)×body weight in kg]/(serum creatinine× 72)×(0.85 for females).
5. Has a BMI of 25.0 kg/m$^2$ to 45.0 kg/m$^2$, inclusive, at Visit 1.
6. Has a stable body weight, i.e., not varying by >10% for at least 6 months prior to Visit 1 as documented by the investigator.
7. Is male, or is female and meets all of the following criteria:
    a. Not breastfeeding
    b. Negative pregnancy test result (human chorionic gonadotropin, beta subunit) at Visit 1 (Screening)
    c. Surgically sterile, postmenopausal, or if of childbearing potential, must practice and be willing to continue to practice appropriate birth control during the entire duration of the study
8. Has a physical examination with no clinically significant abnormalities as judged by the investigator.
9. Has a fasting glucose concentration of <240 mg/dL at Visit 1.
10. Either is not treated with or has been on a stable treatment regimen with any of the following medications for a minimum of 3 months prior to Visit 1 (Screening):
    a. Hormone replacement therapy (female subjects)
    b. Oral contraceptives (female subjects)
    c. Antihypertensive agents
    d. Lipid-lowering agents
    e. Thyroid replacement therapy
    f. Antidepressant agents
11. Is willing and able to follow study procedures.
12. Is able to read, understand, and sign the Informed Consent Form (ICF) and an Authorization to Use and Disclose Protected Health Information form (consistent with Health Insurance Portability and Accountability Act of 1996 [HIPAA] legislation, answer the study questions, communicate with the investigator, and understand and comply with protocol requirements.

Subjects who meet any of the following criteria will be excluded:
1. Has a clinically significant medical condition that could potentially affect study participation and/or personal well-being, as judged by the investigator, including but not limited to the following conditions:
    a. Hepatic disease
    b. Renal disease
    c. Gastrointestinal disease
    d. Endocrine disorder except diabetes
    e. Cardiovascular disease
    f. Seizure disorder
    g. Organ transplantation h. Chronic infection (e.g., tuberculosis, human immunodeficiency virus, hepatitis B virus, or hepatitis C virus)
2. Has any chronic disease requiring medication that has been adjusted in the past 90 days (subjects may take acute intermittent over-the-counter medications such as Tylenol, if needed).
3. Has any drug treatment that affects gastric pH (prescription or over-the-counter), including any antacids or medications such as Rolaids or Pepcid within 2 days of Visit 1 (Screening).
4. Has renal disease or renal dysfunction (e.g., as suggested by serum creatinine levels ≥1.5 mg/dL [males], ≥1.4 mg/dL [females] or abnormal creatinine clearance).
5. Has known hypersensitivity or allergies to metformin hydrochloride or any component of study treatment.
6. Has clinical laboratory test (clinical chemistry, hematology, or urinalysis) abnormalities other than those expected in subjects with diabetes and judged by the investigator to be clinically significant at Visit 1 (Screening).
7. Has physical, psychological, or historical finding that, in the investigator's opinion, would make the subject unsuitable for the study.
8. Currently abuses drugs or alcohol or has a history of abuse that in the investigator's opinion would cause the individual to be noncompliant with study procedures.
9. Has donated blood within 2 months of Visit 1 (Screening) or is planning to donate blood during the study.
10. Has used insulin within 3 months of Visit 1 (Screening).
11. Has received GLP-1 receptor agonists and/or thiazolidinedione treatment within 6 months of Visit 1 (Screening).
12. Has received Furosemide, Nifedipine, thiazides or other diuretics, corticosteroids, cationic drugs, or thyroid products within 6 months of Visit 1 (Screening).
13. Has had a major surgery or a blood transfusion within 6 months of Visit 1 (Screening).
14. Has received any investigational drug within one month (or five half-lives of the investigational drug, whichever is greater) of Visit 1 (Screening).
15. Is an immediate family member (spouse, parent, child, or sibling; biological or legally adopted) of personnel directly affiliated with the study at the clinical study site, or is directly affiliated with the study at the clinical study site.
16. Is employed by Elcelyx Therapeutics, Inc (Elcelyx) (that is an employee, temporary contract worker, or designee responsible for the conduct of the study).

Once screened and qualified for entry, subject will be instructed as follows:

Fast for at least 10 hours (no food or beverage except water) prior to each visit Take no new prescription medications or over-the-counter preparations without prior approval of the investigator (who may contact the sponsor for consultation).

Take no anti-diabetic medications during the study other than the investigational product. Discontinue use of any DPP-4 inhibitors or prescribed metformin prior to enrollment (Visit 2)

Take no caffeine before (at least 10 hours) or during study visits

On the days of study visits do not take the dose of investigational product at home before the visit Bring all previously dispensed empty, partially used or unused containers of investigational product to each visit Do not begin a diet or weight loss program during the study Avoid strenuous exercise and alcohol 24 hours prior to each scheduled visit.

Refrain from smoking during study visits (i.e., no smoking until all visit procedures are completed)

Example 5.1.4: Investigational Products

Placebo
EFB0026: 500 mg metformin HCl tablets (nonenteric-coated)
EFB0027: 500 mg metformin HCl tablets with a pH 6.5 enteric coating (enteric-coated)

Example 5.1.5: Study Methods

EFB0026 500 mg BID (1000 mg/day) will be administered for 2 weeks followed by 1000 mg BID (2000 mg/day) for 4 weeks during the lead-in stabilization period. Randomized treatment will be administered BID over 12 weeks. HbA1c, metformin PK, fasting glucose, insulin, GLP-1, PYY, lipids, and body weight will be collected at scheduled time points. Efficacy assessments will be of HbA1c and body weight, pharmacokinetic assessments will be of plasma metformin, and pharmacodynamic assessments will be of fasting glucose, insulin, GLP-1, PYY and lipids. Safety will be assessed through the monitoring of adverse events, by electrocardiogram, and clinical chemistry.

Example 5.1.6: Statistical Considerations

Analysis populations will be selected and described in the Statistical Analysis Plan Study endpoints include $HbA_{1c}$, metformin PK, fasting glucose, insulin, GLP-1, PYY, lipids, and body weight Demographic and baseline characteristics will be summarized descriptively While certain embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating diabetes in a patient in need thereof, comprising administering a therapeutically effective amount of metformin or a salt thereof to said subject in a delayed-release formulation adapted to have an onset of release of said metformin or a salt thereof distal of the duodenum and to minimize the circulating plasma concentration of metformin in the patient, wherein the resulting circulating plasma concentration of said metformin is below about 0.5 μg/mL.

2. The method according to claim 1, wherein the resulting circulating plasma concentration of metformin is below about 0.25 μg/mL.

3. The method according to claim 1, wherein said delayed-release formulation is adapted to provide at least 20% less relative bioavailability of metformin compared to an immediate release composition having the same amount of said metformin or a salt thereof.

4. The method according to claim 1, wherein said delayed-release formulation is adapted to provide at least 30% less relative bioavailability of metformin compared to an immediate release composition having the same amount of said metformin or a salt thereof.

5. The method according to claim 1, wherein said delayed-release formulation is adapted to provide at least 40% less relative bioavailability of metformin compared to an immediate release composition having the same amount of said metformin or a salt thereof.

6. The method according to claim 1, wherein said delayed-release formulation is adapted to provide at least 50% less relative bioavailability of metformin compared to an immediate release composition having the same amount of said metformin or a salt thereof.

7. The method according to claim 1, wherein the daily dose of said metformin or a salt thereof is between about 50 mg and about 2000 mg.

8. The method according to claim 1, wherein said delayed-release formulation comprises an enteric coating formulated to have an onset of release of said metformin or a salt thereof at a pH of about 5.0.

9. The method according to claim 1, wherein delayed-release formulation comprises an enteric coating formulated to have an onset of release of said metformin or a salt thereof at a pH of about 5.5.

10. The method according to claim 1, wherein said delayed-release formulation comprises an enteric coating formulated to have an onset of release of said metformin or a salt thereof at or above about pH 6.0.

11. The method according to claim 1, wherein said delayed-release formulation comprises an enteric coating formulated to have an onset of release of said metformin or a salt thereof at or above about pH 6.5.

12. The method according to claim 1, wherein said delayed-release formulation comprises an enteric coating formulated to have an onset of release of said metformin or a salt thereof at or above about pH 7.0.

13. The method according to claim 1, further comprising co-administering a second antidiabetic agent selected from the group consisting of thiazolidinediones, sulfonylureas, meglitinides, alpha-glucosidase inhibitors, a second DPP-IV inhibitor, incretin mimetics, and SGLT inhibitors.

14. The method according to claim 13, wherein said second antidiabetic agent is an SGLT inhibitor.

15. The method according to claim 13, wherein said second antidiabetic agent is a second DPP-IV inhibitor.

16. The method according to claim 13, wherein said second antidiabetic agent is co-formulated with said metformin or a salt thereof and administered simultaneously in a combined formulation.

17. The method according to claim 16, wherein said combined formulation is provided in the form of a delayed-release component coupled with an immediate release component in a unitary dosage form.

18. The method according to claim 1, further comprising co-administering an antiobesity agent.

19. The method according to claim 18, wherein said antiobesity agent is lorcaserin.

20. The method according to claim 18, wherein said antiobesity agent is phentermine.

21. The method according to claim 18, wherein said antiobesity agent is a combination of lorcaserin and phentermine.

22. The method according to claim 18, wherein said antiobesity agent is a combination of topiramate and phentermine.

23. The method according to claim 18, wherein said antiobesity agent is a combination of bupropion and naltrexone.

24. The method according to claim 18, wherein said antiobesity agent is co-formulated with said metformin or a salt thereof and administered simultaneously in a combined formulation.

25. The method according to claim 18, wherein said combined formulation is provided in the form of a delayed-release component coupled with an immediate release component in a unitary dosage form.

26. The method according to any one of the preceding claims, wherein said metformin or a salt thereof is metformin hydrochloride.

* * * * *